US012590082B2

(12) United States Patent
Zhang et al.

(10) Patent No.: US 12,590,082 B2

(45) Date of Patent: Mar. 31, 2026

(54) FUSED TRICYCLIC DERIVATIVE AND PHARMACEUTICAL APPLICATION THEREOF

(71) Applicant: CHIA TAI TIANQING PHARMACEUTICAL GROUP CO., LTD., Lianyungang (CN)

(72) Inventors: Peng Zhang, Shanghai (CN); Yunfu Luo, Shanghai (CN); Feng Gao, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 517 days.

(21) Appl. No.: 18/027,049

(22) PCT Filed: Sep. 28, 2021

(86) PCT No.: PCT/CN2021/121335

§ 371 (c)(1),
(2) Date: Mar. 17, 2023

(87) PCT Pub. No.: WO2022/063317

PCT Pub. Date: Mar. 31, 2022

(65) Prior Publication Data

US 2023/0322745 A1 Oct. 12, 2023

(30) Foreign Application Priority Data

| | | |
|---|---|---|
| Sep. 28, 2020 | (CN) | 202011040519.4 |
| Dec. 30, 2020 | (CN) | 202011615061.0 |
| Apr. 1, 2021 | (CN) | 202110357594.1 |
| Jun. 10, 2021 | (CN) | 202110648266.7 |
| Sep. 17, 2021 | (CN) | 202111094082.7 |

(51) Int. Cl.

| | |
|---|---|
| ***C07D 409/14*** | (2006.01) |
| ***C07D 413/14*** | (2006.01) |
| ***C07D 487/04*** | (2006.01) |
| ***C07D 491/048*** | (2006.01) |
| ***C07D 491/056*** | (2006.01) |
| ***C07D 491/107*** | (2006.01) |

(52) U.S. Cl.

CPC ......... *C07D 409/14* (2013.01); *C07D 413/14* (2013.01); *C07D 487/04* (2013.01); *C07D 491/048* (2013.01); *C07D 491/056* (2013.01); *C07D 491/107* (2013.01)

(58) Field of Classification Search

CPC .. C07D 409/14; C07D 413/14; C07D 487/04; C07D 491/048; C07D 491/056; C07D 491/107

See application file for complete search history.

(56) References Cited

U.S. PATENT DOCUMENTS

| | | | |
|---|---|---|---|
| 2014/0303127 A1 | 10/2014 | Bosch | |
| 2016/0166566 A1 | 6/2016 | Julia Jane | |
| 2016/0200718 A1 | 7/2016 | Aiguade Bosch | |
| 2019/0185461 A1 | 6/2019 | Wei | |

FOREIGN PATENT DOCUMENTS

| | | | | |
|---|---|---|---|---|
| CN | 103998443 A | 8/2014 | | |
| CN | 104024245 A | 9/2014 | | |
| CN | 105492027 A | 4/2016 | | |
| CN | 109928953 * | 6/2019 | ............. A61P 11/08 | |
| CN | 109928953 A | 6/2019 | | |
| WO | WO 2017012489 A1 | 1/2017 | | |
| WO | 2018150347 A1 | 8/2018 | | |

OTHER PUBLICATIONS

International Search Report in International Patent Application No. PCT/CN2021/121335 mailed Dec. 30, 2021 (10 pages w/English translation).

International Written Opinion in International Patent Application No. PCT/CN2021/121335 mailed Dec. 30, 2021 (10 pages w/English translation).

Singh et al. "Navafenterol (AZD8871) in patients with COPD: a randomized, double-blind, phase I study evaluating safety pharmacodynamics of single doses of this novel, inhaled, long-acting, dual-pharmacology bronchodilator", Respiratory Research 2020, 21(Suppl 1): 102.

Extended European Search Report of PCT No. CN2021121335, mailed Oct. 8, 2024 (9 pages).

(Continued)

*Primary Examiner* — Erich A Leeser

(74) *Attorney, Agent, or Firm* — NIXON PEABODY LLP

(57) ABSTRACT

Disclosed are a fused tricyclic derivative and a pharmaceutical application thereof. Specifically disclosed are a compound represented by formula (III) and a pharmaceutically acceptable salt thereof.

(III)

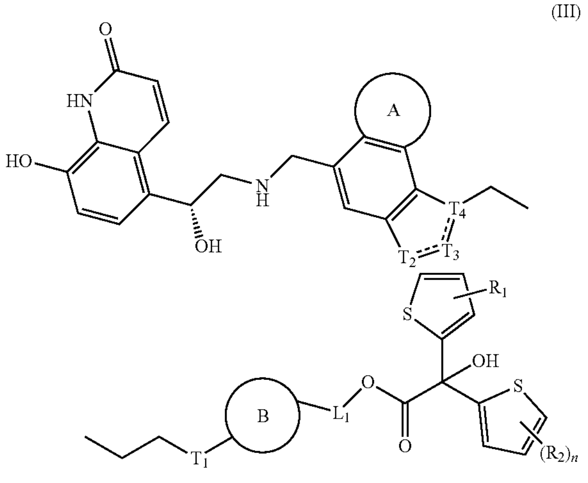

20 Claims, No Drawings

(56) References Cited

OTHER PUBLICATIONS

Aparici et al. "Pharmacological profile of AZD8871 (LAS191351), a novel inhaled dual M3 receptor antagonist/β2-adrenoceptor agonist molecule with long-lasting effects and favorable safety profile." The Journal of Pharmacology and Experimental Therapeutics 370.1, dated May 13, 2019 (50 pages).

* cited by examiner

FUSED TRICYCLIC DERIVATIVE AND PHARMACEUTICAL APPLICATION THEREOF

CROSS-REFERENCE TO RELATED APPLICATIONS

The present application is a U.S. National Stage Entry of International Application No. PCT/CN2021/121335 filed on Sep. 28, 2021, which claims 1) the priority and benefit to Chinese Patent Application No. 202011040519.4 filed with China National Intellectual Property Administration on Sep. 28, 2020, 2) the priority and benefit to Chinese Patent Application No. 202011615061.0 filed with China National Intellectual Property Administration on Dec. 30, 2020, 3) the priority and benefit to Chinese Patent Application No. 202110357594.1 filed with China National Intellectual Property Administration on Apr. 1, 2021, 4) the priority and benefit to Chinese Patent Application No. 202110648266.7 filed with China National Intellectual Property on Jun. 10, 2021, and 5) the priority and benefit to Chinese Patent Application No. 202111094082.7 filed with China National Intellectual Property on Sep. 17, 2021, the contents of which are incorporated herein by reference in their entirety.

TECHNICAL FIELD

The present application relates to a fused tricyclic derivative and pharmaceutical use thereof, in particular to a compound of formula (III) and a pharmaceutically acceptable salt thereof.

BACKGROUND

A single molecule with dual activity at M3 muscarinic receptor and β2 adrenoceptor (MABA) will be more inclined to exhibit a synergistic drug effect on a target in the case of consistent pharmacokinetic properties, and will also offer relevant advantages in formulation as compared to a two-component combination. It will also be easier to formulate with other therapeutic agents (such as inhaled corticosteroids) to provide a triple therapy combination. Therefore, a novel drug having both β2 receptor agonist and muscarinic receptor antagonist activities and suitable for the treatment of respiratory diseases such as asthma and COPD is of high clinical value and interest.

SUMMARY

The present application provides a compound of formula (III) or a pharmaceutically acceptable salt thereof, (III)

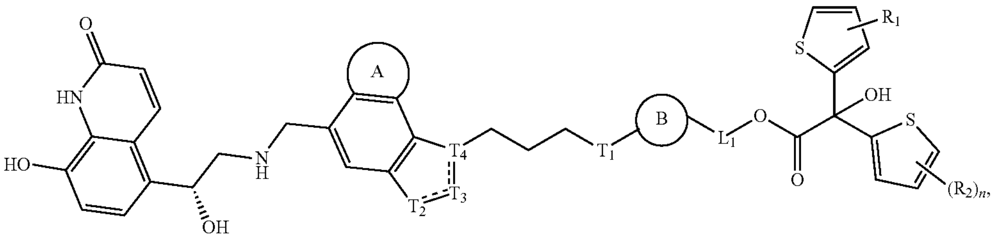

wherein, $R_1$ is selected from the group consisting of H, halogen, $C_{1-4}$ alkyl and phenyl;

$R_2$ is each independently selected from the group consisting of H, halogen and $C_{1-4}$ alkyl;

or two $R_2$, together with the thiophene ring to which they are connected, form benzothiophene;

n is selected from the group consisting of 1 and 2;

$T_1$ is selected from the group consisting of a single bond, —NH— and —N($CH_3$)—;

$L_1$ is selected from the group consisting of a single bond and —$CH_2$—;

the structural unit

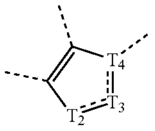

is selected from the group consisting of

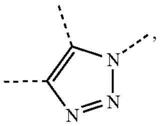,
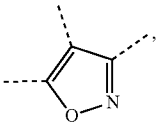,
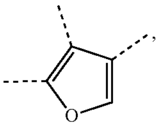,
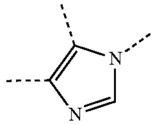
and
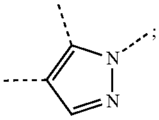;

ring A is selected from the group consisting of the following groups optionally substituted with 1 or 2 $R_b$: $C_{4-6}$ cycloalkenyl, 4- to 6-membered heterocycloalkenyl, 5- to 6-membered heteroaryl,

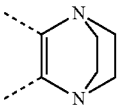,
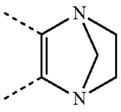, and phenyl;

$R_b$ is each independently selected from the group consisting of —F, —Cl, —Br, —I, —$CH_3$ and —$CH_2CH_3$;

ring B is selected from the group consisting of cyclopentyl, cyclohexyl and 6- to 10-membered heterocycloalkyl, wherein the 6- to 10-membered heterocycloalkyl is optionally substituted with 1 $R_a$;

$R_a$ is selected from the group consisting of —F, —Cl, methyl, —OH and —CN;

wherein "hetero" of the "6- to 10-membered heterocycloalkyl" comprises 1, 2 or 3 heteroatoms or heteroatom groups independently selected from the group consisting of O, S, NH and N, wherein the nitrogen atom is optionally quaternized with methyl halide.

In some embodiments of the present application, $R_1$ is selected from the group consisting of H, —Cl, —Br, methyl, tert-butyl and phenyl.

In some embodiments of the present application, $R_1$ is selected from the group consisting of H, halogen and $C_{1-4}$ alkyl.

In some embodiments of the present application, $R_1$ is selected from the group consisting of H, —Cl, —Br, methyl and tert-butyl.

In some embodiments of the present application, $R_2$ is each independently selected from the group consisting of H, —Cl, —Br, methyl and tert-butyl.

In some embodiments of the present application, $R_2$ is each independently selected from the group consisting of H, halogen and $C_{1-4}$ alkyl.

In some embodiments of the present application, $R_1$ and $R_2$ are both H.

In some embodiments of the present application, the structural unit

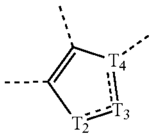

described above is selected from the group consisting of

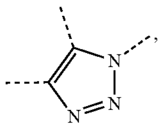,
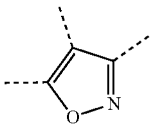
and
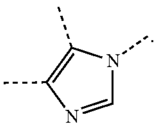.

In some embodiments of the present application, the structural unit

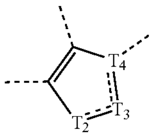

described above is selected from the group consisting of

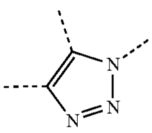
and
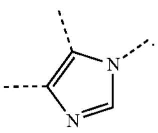.

In some embodiments of the present application, the structural unit

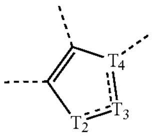

described above is selected from

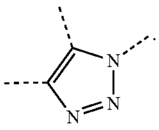

In some embodiments of the present application, $T_1$ is selected from the group consisting of a single bond and $—N(CH_3)—$.

In some embodiments of the present application, ring B is selected from the group consisting of cyclohexyl and 6- to 10-membered heterocycloalkyl, wherein the 6- to 10-membered heterocycloalkyl is optionally substituted with 1 $R_a$.

In some embodiments of the present application, ring B described above is selected from the group consisting of cyclopentyl, cyclohexyl and the following groups optionally substituted with 1 $R_a$: piperidinyl, piperazinyl, morpholinyl, dioxanyl, dithianyl, tetrahydrooxazinyl, tetrahydrothiazinyl, hexahydropyridazinyl, homopiperazinyl, homopiperidinyl, dioxepanyl,

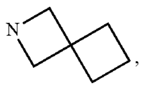,
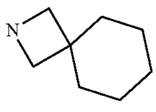,
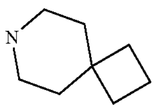
and
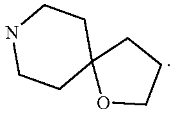.

In some embodiments of the present application, ring B described above is selected from the group consisting of cyclohexyl and the following groups optionally substituted with 1 $R_a$: piperidinyl, piperazinyl,

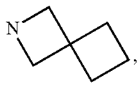,
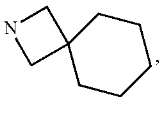,
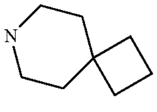
and
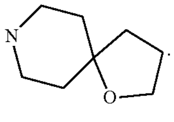.

In some embodiments of the present application, ring B described above is selected from the group consisting of cyclohexyl and the following groups optionally substituted with 1 $R_a$:

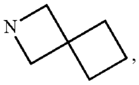,
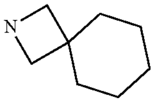,
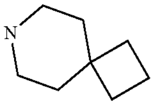
and
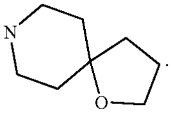.

In some embodiments of the present application, ring B described above is selected from cyclohexyl. In some embodiments of the present application, ring B described above is selected from

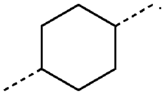.

In some embodiments of the present application, ring B described above is selected from the group consisting of

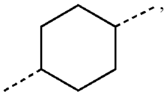,
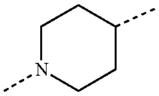,
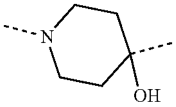,
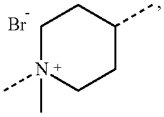,
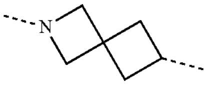,
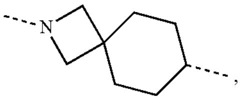,
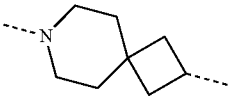
and
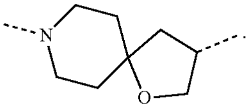.

In some embodiments of the present application, ring B described above is selected from the group consisting of

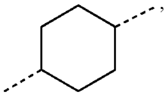,
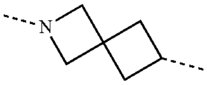,
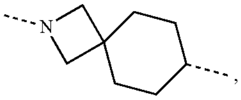,
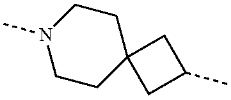
and
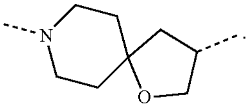.

In some embodiments of the present application, the structural unit

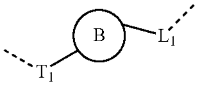

described above is selected from the group consisting of

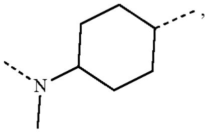,
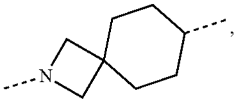,
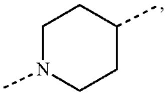,
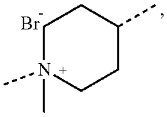,
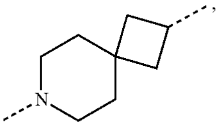,
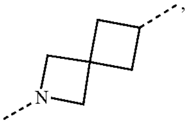,
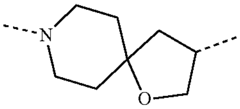
and
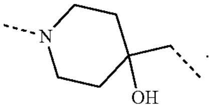.

In some embodiments of the present application, the structural unit

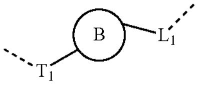

described above is selected from the group consisting of

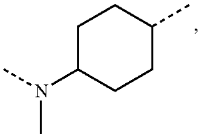,
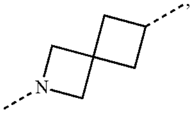,
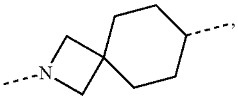,
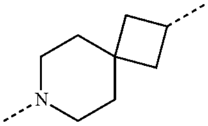
and
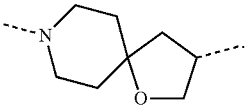.

In some embodiments of the present application, the structural unit

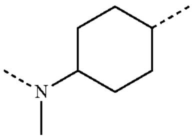

described above is selected from

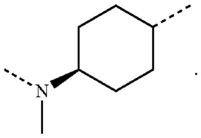

In some embodiments of the present application, the structural unit

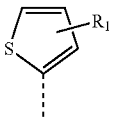

described above is selected from the group consisting of

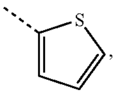, 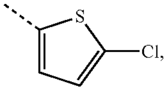, 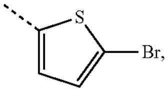, 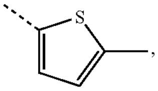, 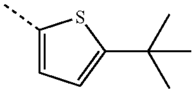 and 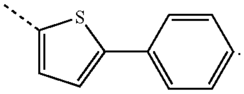.

In some embodiments of the present application, the structural unit

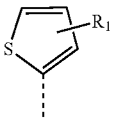

described above is selected from the group consisting of

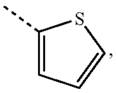, 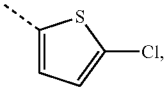, 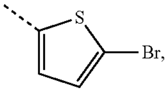, 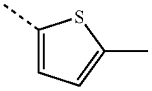 and 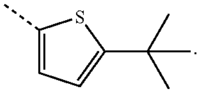.

In some embodiments of the present application, the structural unit

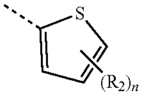

described above is selected from the group consisting of

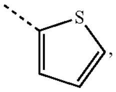, 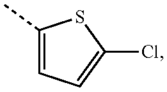, 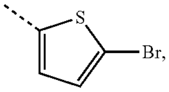, 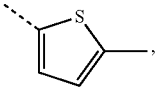, 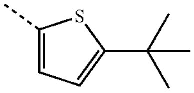 and 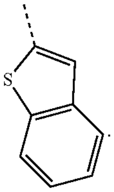.

In some embodiments of the present application, the structural unit

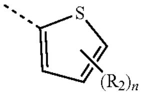

described above is selected from the group consisting of

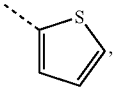, 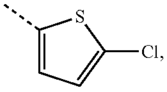, 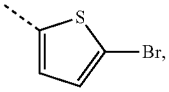, 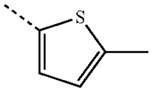 and 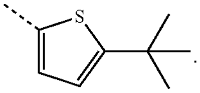.

In some embodiments of the present application, $R_b$ is each independently selected from the group consisting of —F, —Cl, —Br, —I and $—CH_3$.

In some embodiments of the present application, $R_b$ is selected from $—CH_3$.

In some embodiments of the present application, $R_a$ is selected from the group consisting of —F, $—CH_3$, —OH and —CN.

In some embodiments of the present application, $R_a$ is selected from the group consisting of $—CH_3$ and —OH.

In some embodiments of the present application, ring A described above is selected from the group consisting of $C_{4-6}$ cycloalkenyl, 4- to 6-membered heterocycloalkenyl, 5- to 6-membered heteroaryl,

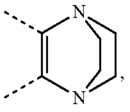, 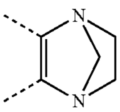

and phenyl, wherein the $C_{4-6}$ cycloalkenyl, 4- to 6-membered heterocycloalkenyl, and 5- to 6-membered heteroaryl are optionally substituted with 1 or 2 $R_b$.

In some embodiments of the present application, ring A described above is selected from the group consisting of the following groups optionally substituted with 1 or 2 $R_b$:

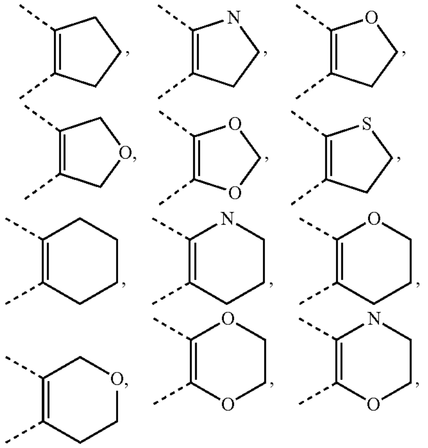

pyrrolyl, thienyl, furanyl, pyrazolyl, imidazolyl, oxazolyl, thiazolyl, triazolyl, pyridinyl, pyrimidinyl, pyrazinyl, pyridazinyl,

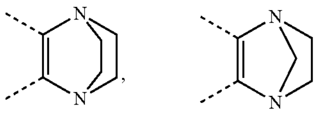

and phenyl.

In some embodiments of the present application, ring A described above is selected from the group consisting of the following groups optionally substituted with 1 or 2 $R_b$:

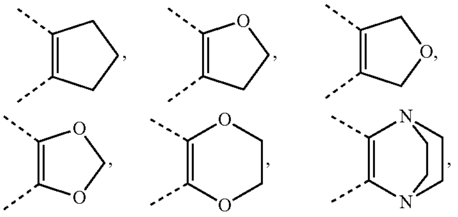

pyrazolyl and phenyl.

In some embodiments of the present application, ring A described above is selected from the group consisting of

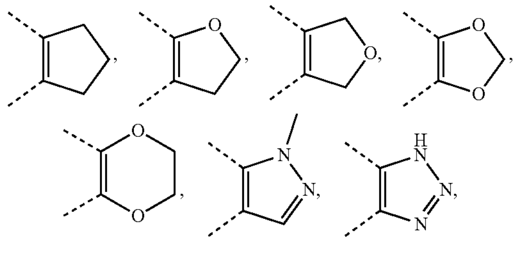

-continued

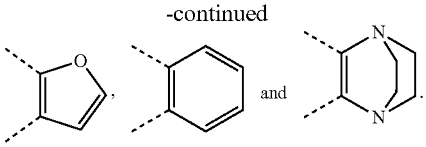

In some embodiments of the present application, ring A described above is selected from the group consisting of

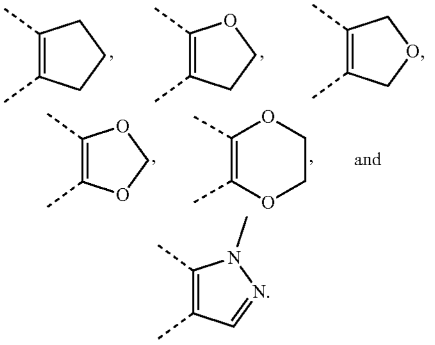

In some embodiments of the present application, ring A described above is selected from the group consisting of

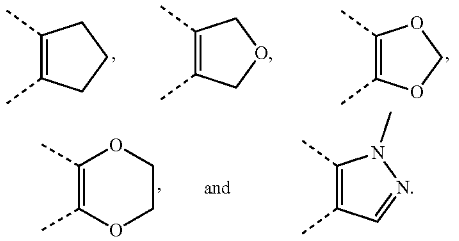

In some embodiments of the present application, ring A described above is selected from the group consisting of

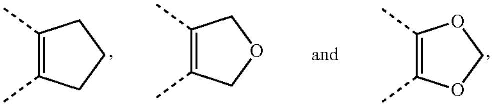

In some embodiments of the present application, the heterocycloalkyl, heterocycloalkenyl or heteroaryl contains 1, 2 or 3 heteroatoms selected from the group consisting of N, O and S.

In some embodiments of the present application, the heterocycloalkyl, heterocycloalkenyl or heteroaryl contains 1 or 2 heteroatoms selected from the group consisting of N and 0.

In some embodiments of the present application, the 6- to 10-membered heterocycloalkyl comprises a monocyclic ring, a spiro ring, or a bridged ring.

In some embodiments of the present application, the 6- to 10-membered heterocycloalkyl comprises a monocyclic ring or a spiro ring.

In some embodiments of the present application, the compound described above is selected from the group consisting of structures of (III-1), (III-2), (III-3), (IV-1), (IV-2) and (V-1), (III-1)
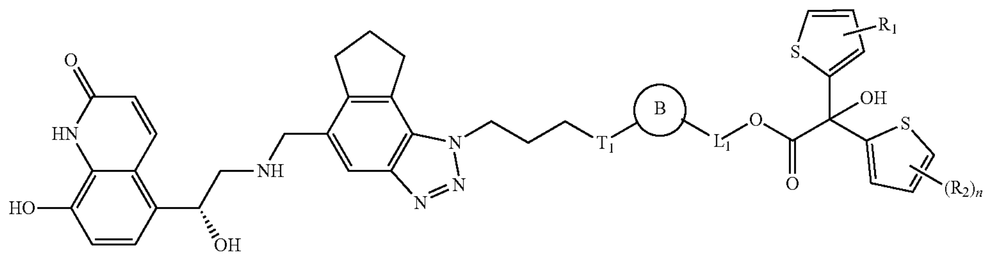
(III-2)
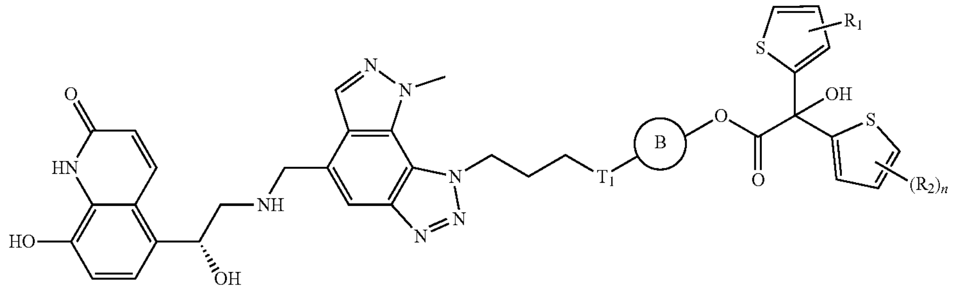
(III-3)
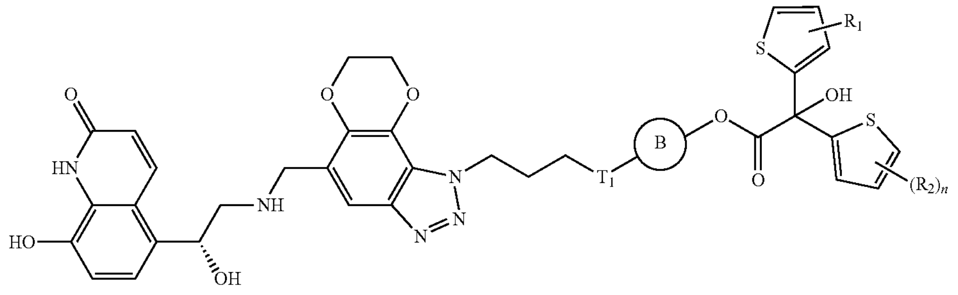
(IV-1)
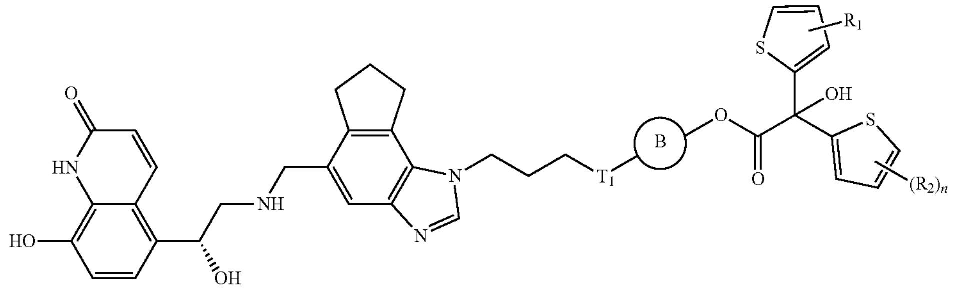
(IV-2)
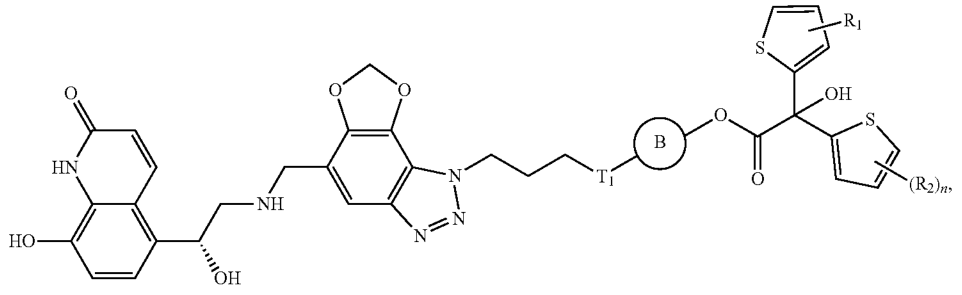

-continued (V-1)

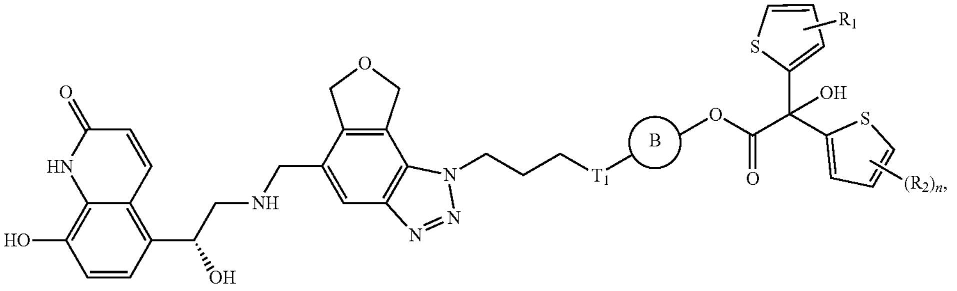

wherein, $R_1$, $R_2$, $T_1$, n, $L_1$ and ring B are as defined herein.

The present application provides a compound of formula (II) or a pharmaceutically acceptable salt thereof, (II)

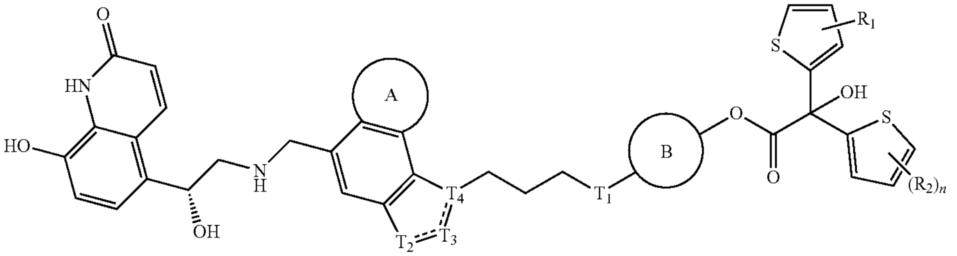

wherein, $R_1$ is selected from the group consisting of H, halogen and $C_{1-4}$ alkyl;

$R_2$ is each independently selected from the group consisting of H, halogen and $C_{1-4}$ alkyl;

n is selected from the group consisting of 1 and 2;

$T_1$ is selected from the group consisting of a single bond, —NH— and —N($CH_3$)—; the structural unit

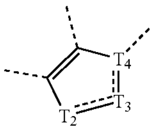

is selected from the group consisting of

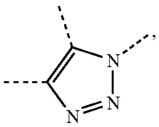,
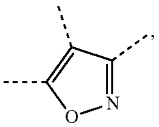,
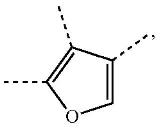,
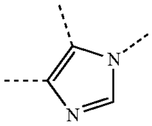
and
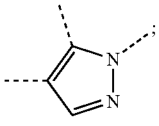;

ring A is selected from the group consisting of

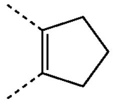,
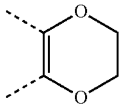,
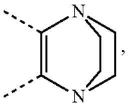,
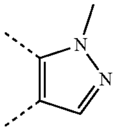

and phenyl;

ring B is selected from the group consisting of cyclohexyl, piperidinyl,

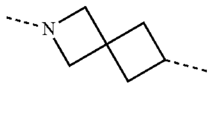
and
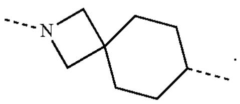.

In some embodiments of the present application, provided is the compound or the pharmaceutically acceptable salt thereof described above, wherein the compound is selected from a structure of formula (II-1), (II-1)

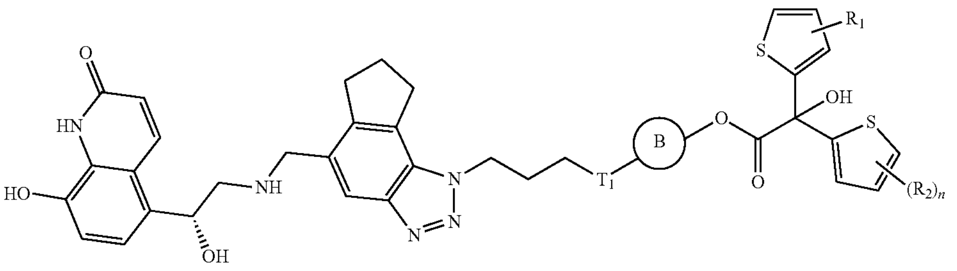

wherein, $R_1$, $R_2$, $T_1$, n and ring B are as defined herein.

In some embodiments of the present application, $R_1$ described above is selected from the group consisting of H, —Cl, —Br and tert-butyl.

In some embodiments of the present application, $R_2$ described above is each independently selected from the group consisting of H, —Cl, —Br, and tert-butyl.

Some other embodiments of the present application are derived from any combination of the variables as described above.

The present application also provides compounds as shown below or pharmaceutically acceptable salts thereof:

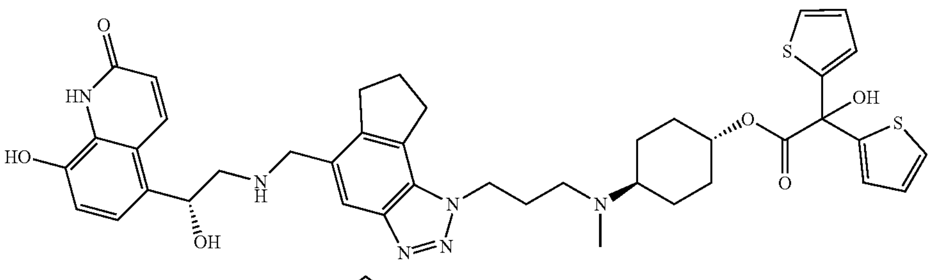
,

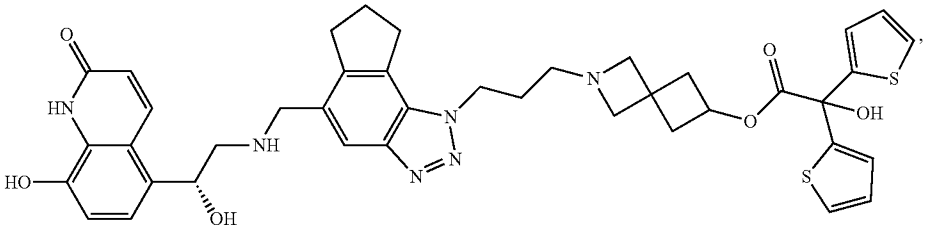
,

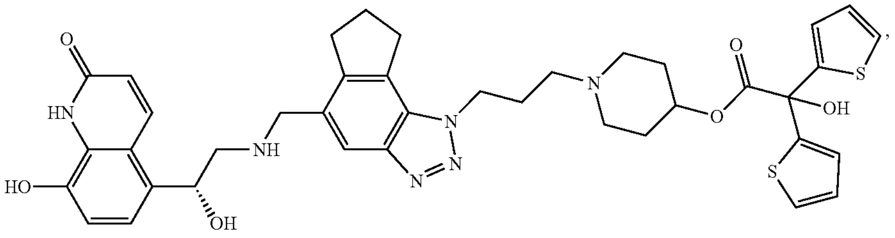
,

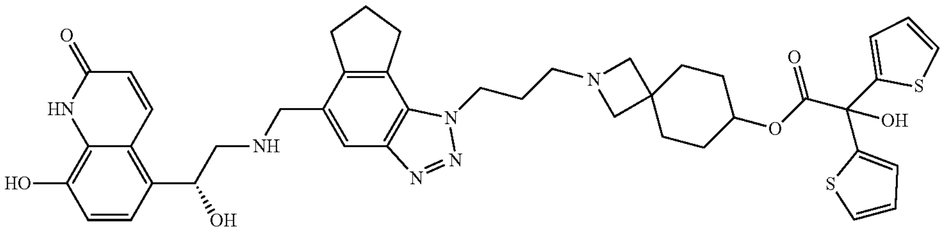
,

-continued
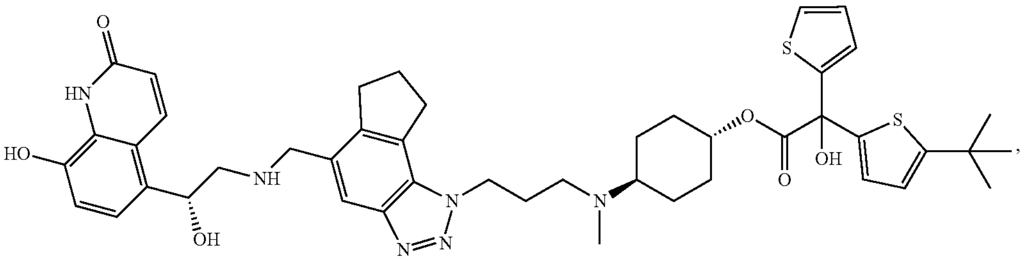
,
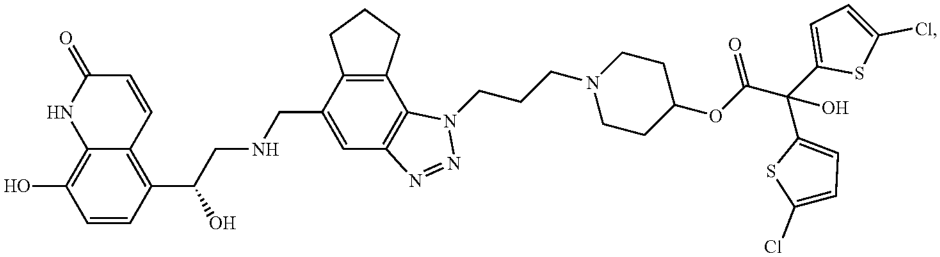
,
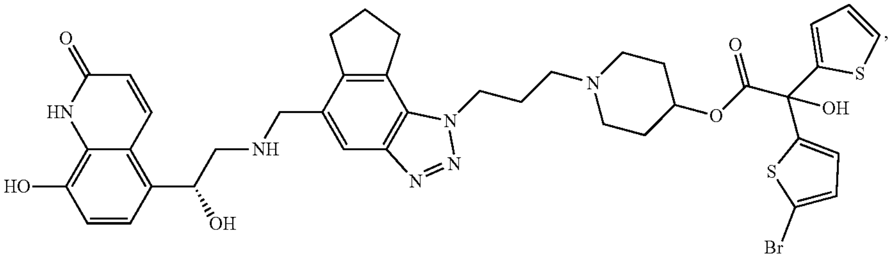
,
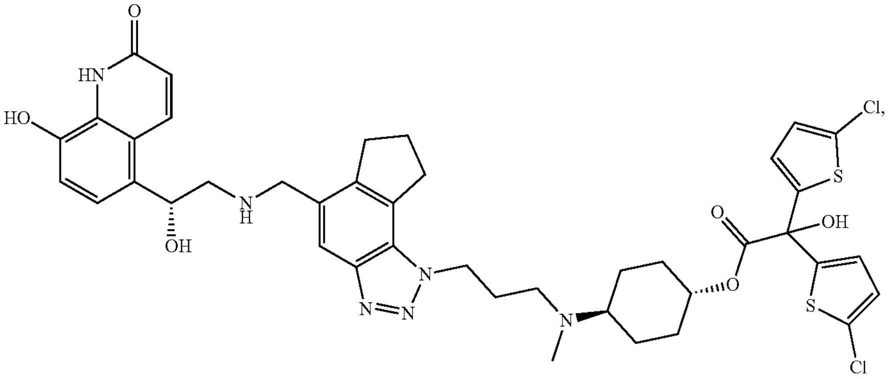
,
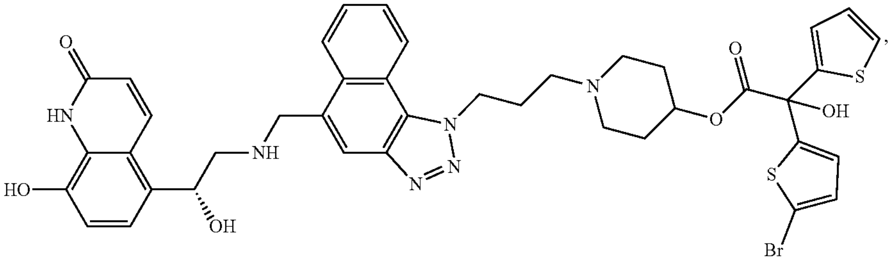
,
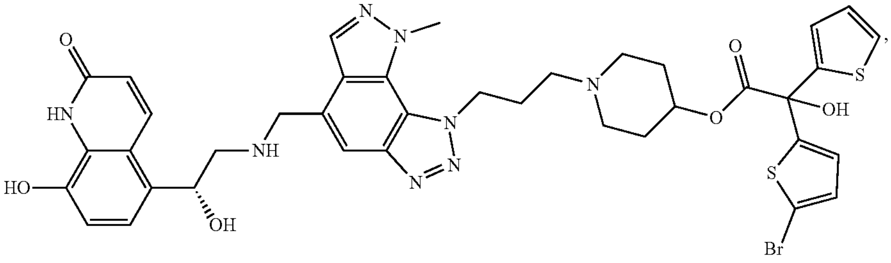
, -continued
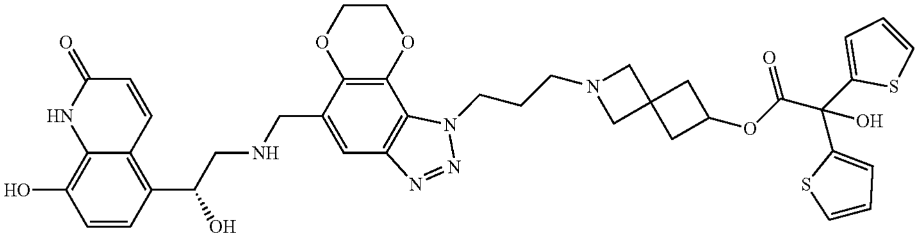
,
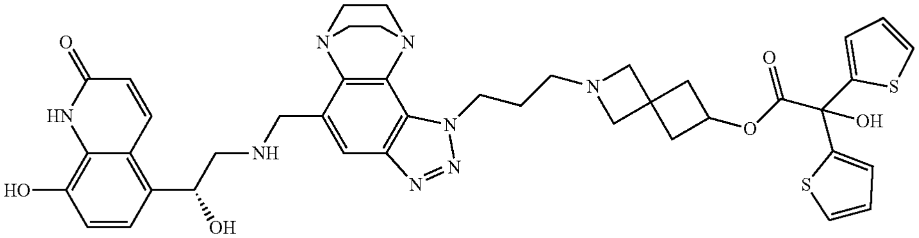
,
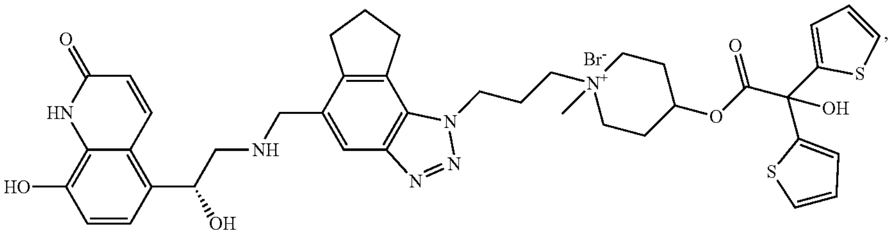
,
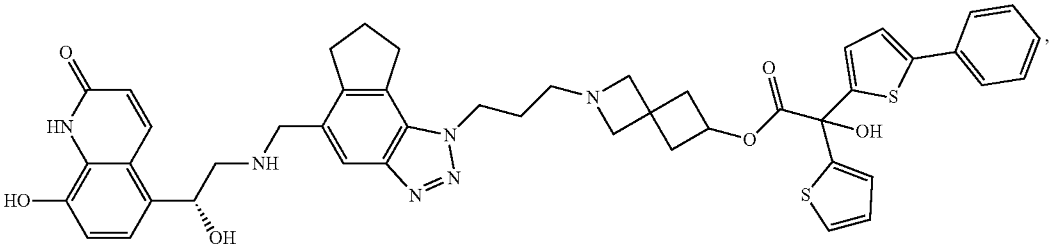
,
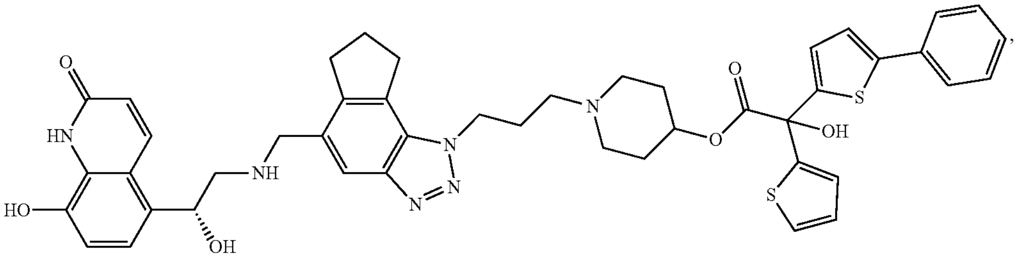
,
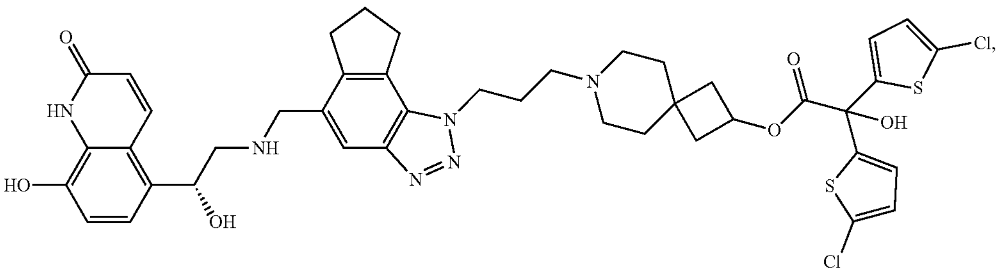
, -continued
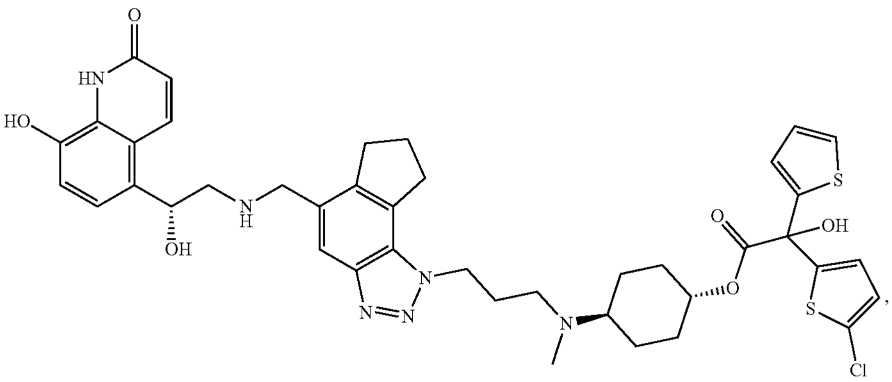
,
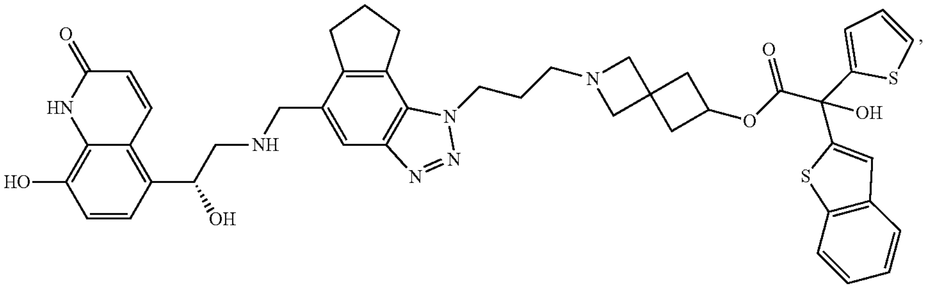
,
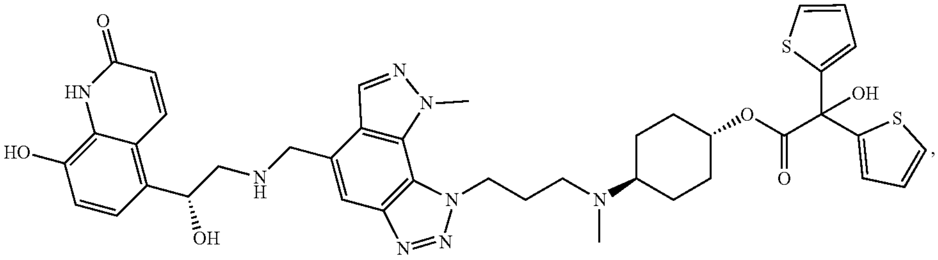
,
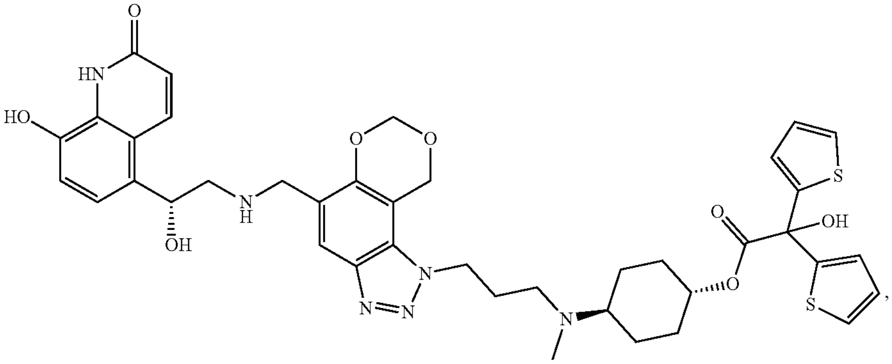
,
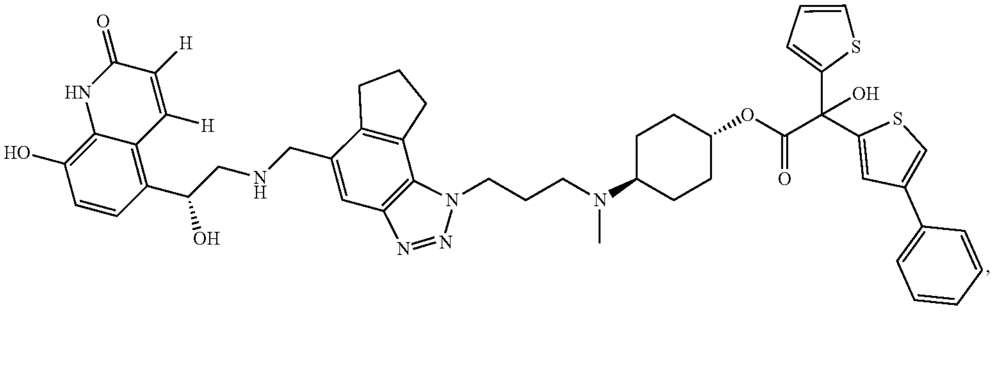
, -continued
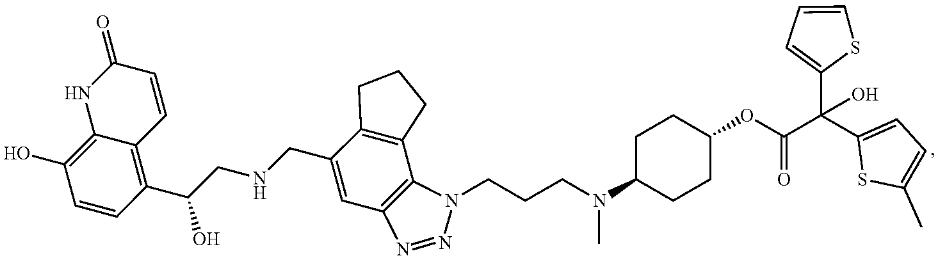
,
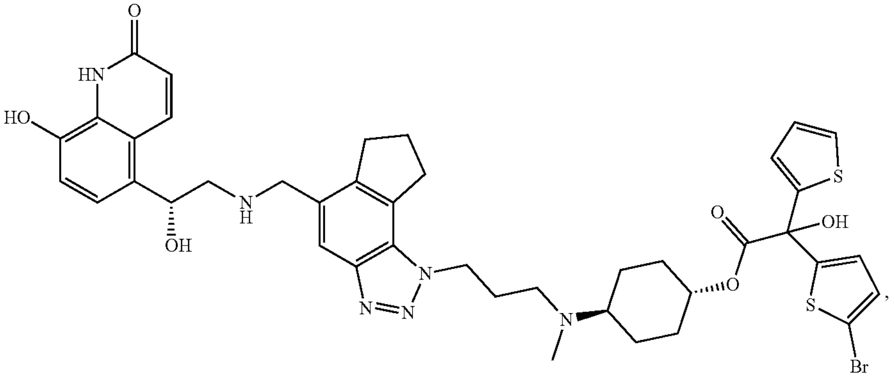
,
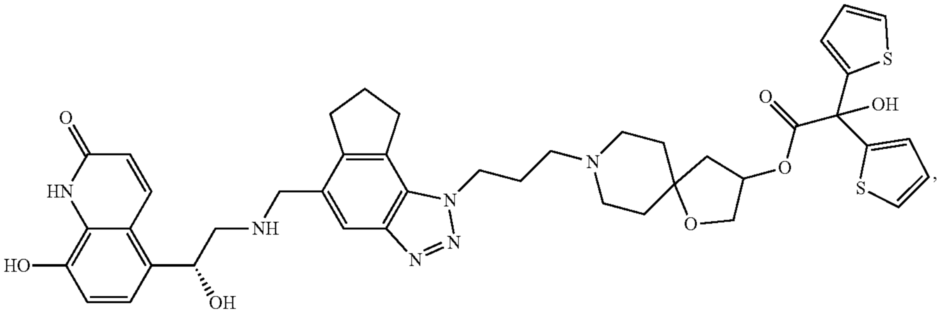
,
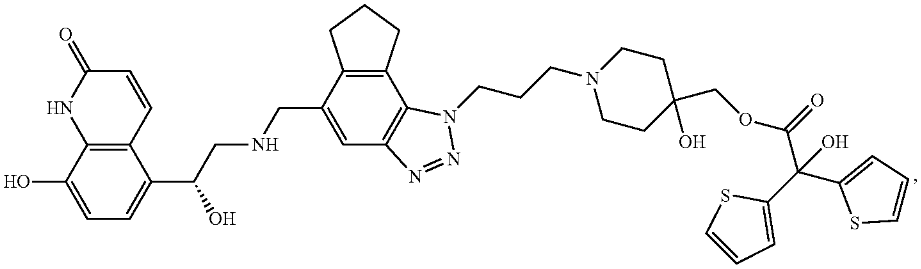
,
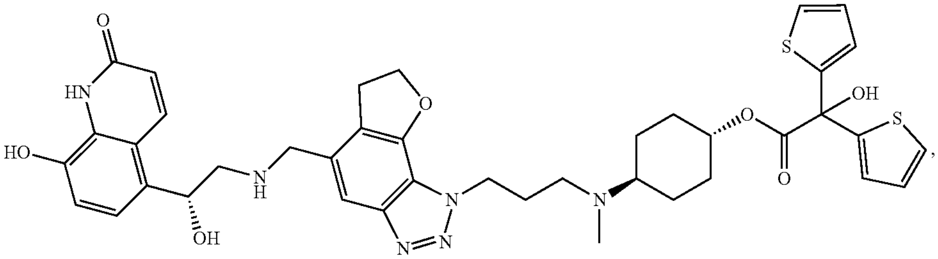
, -continued
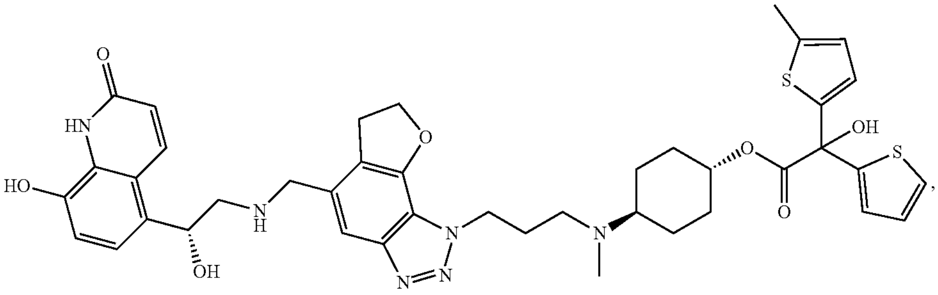
,
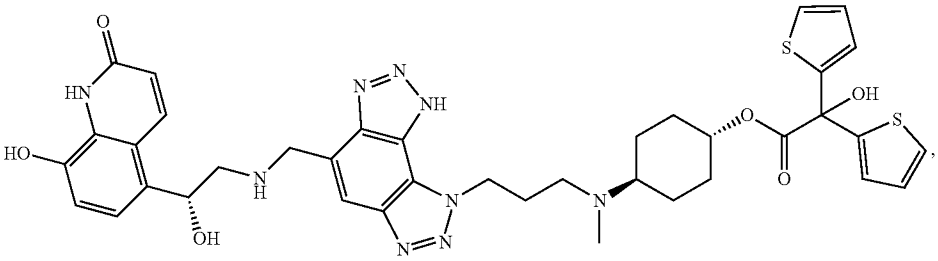
,
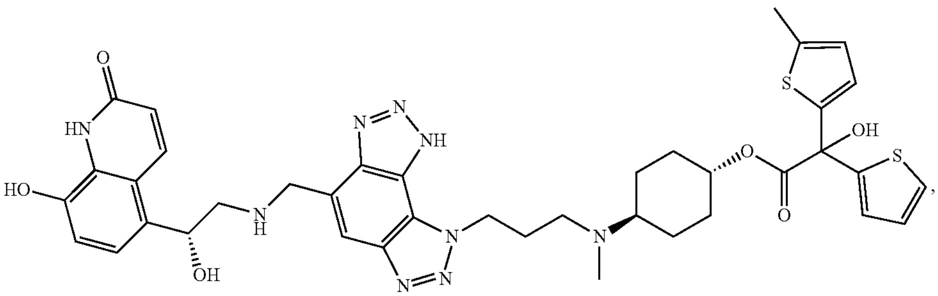
,
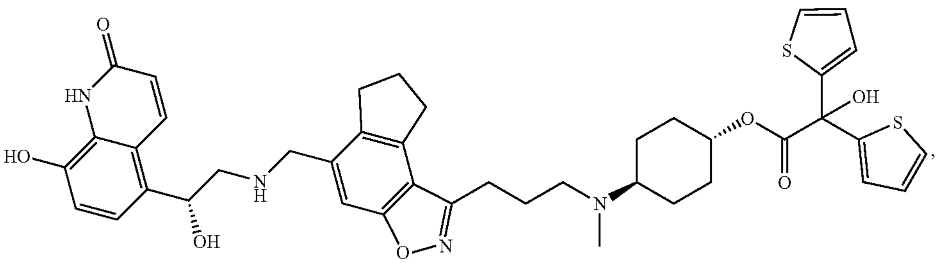
,
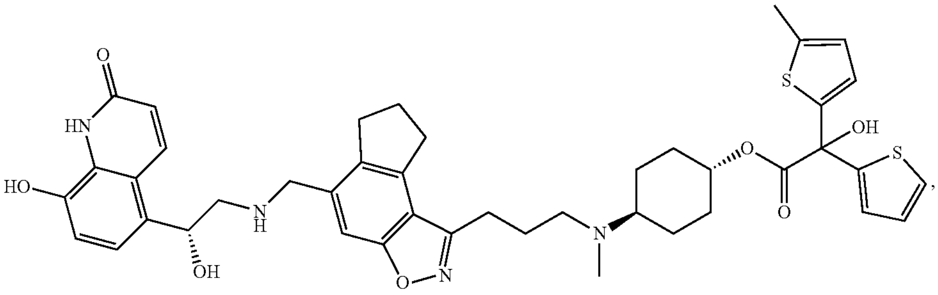
,
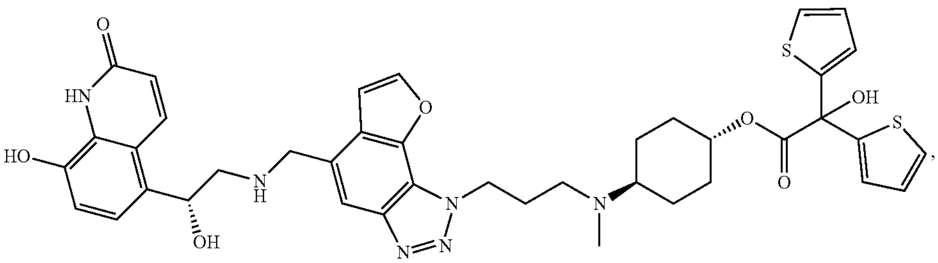
, -continued
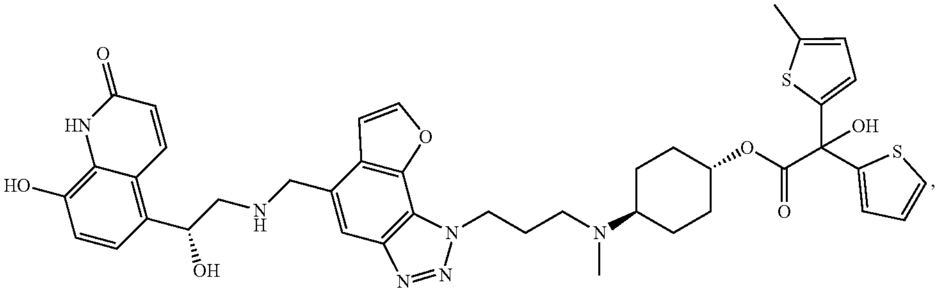,
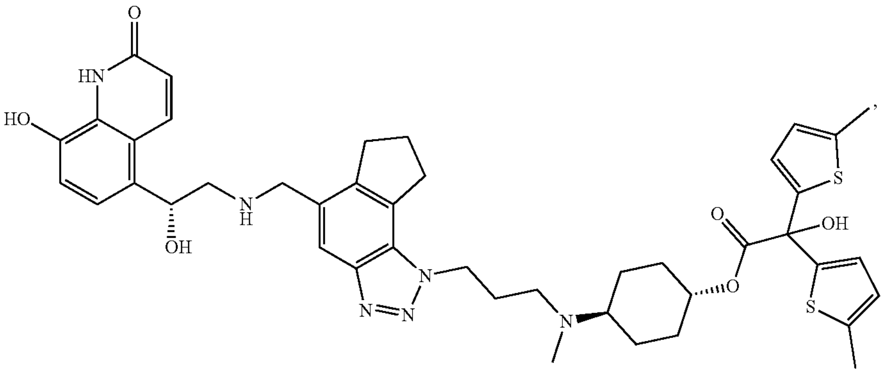,
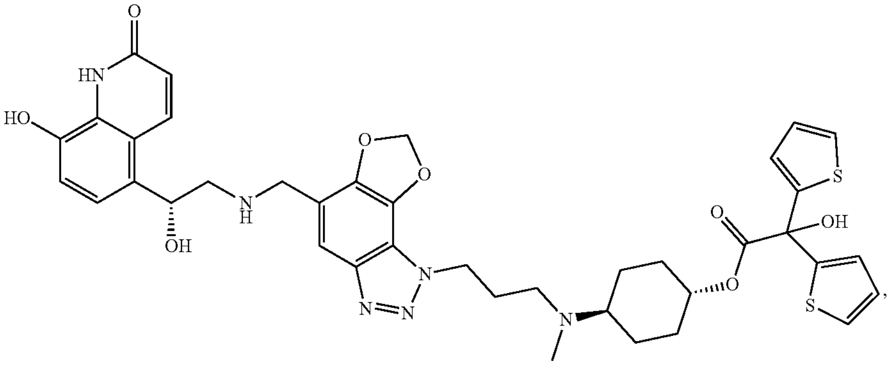,
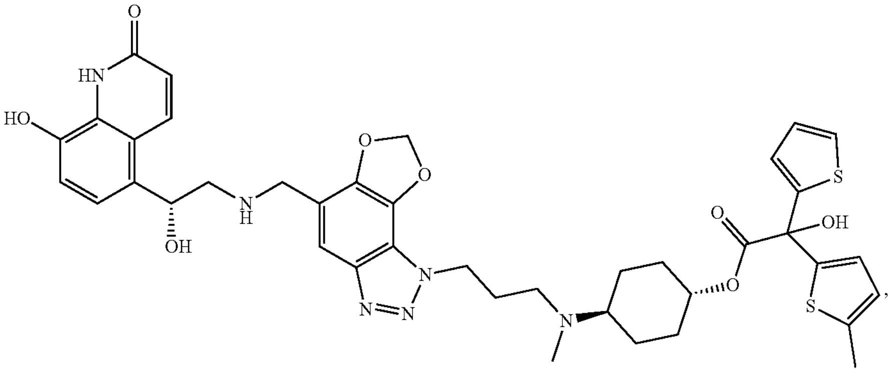,
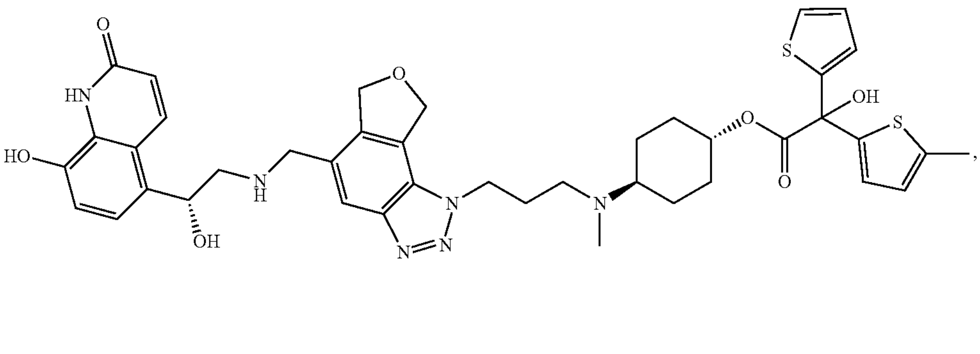, -continued
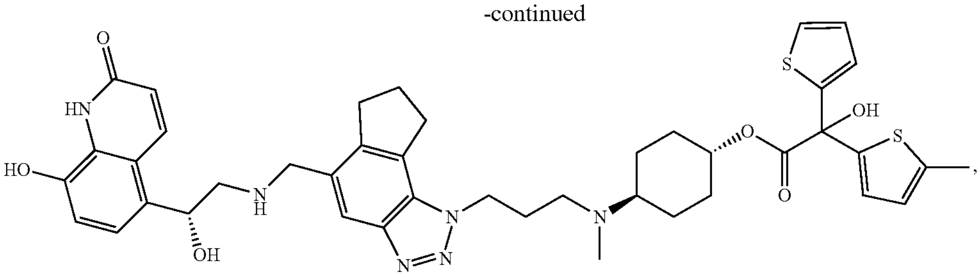
,
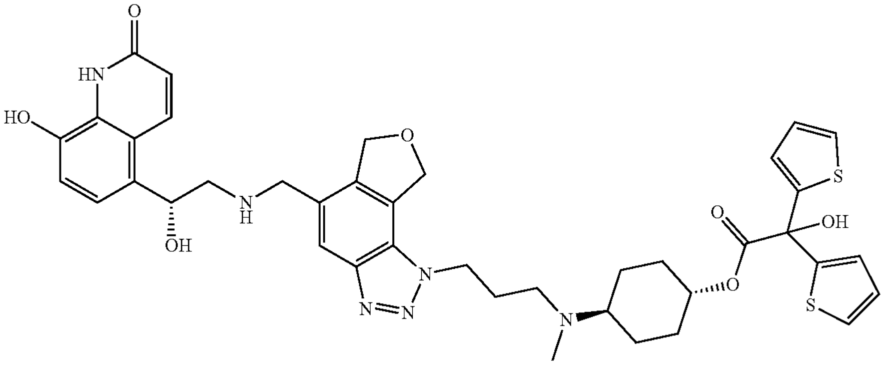
and
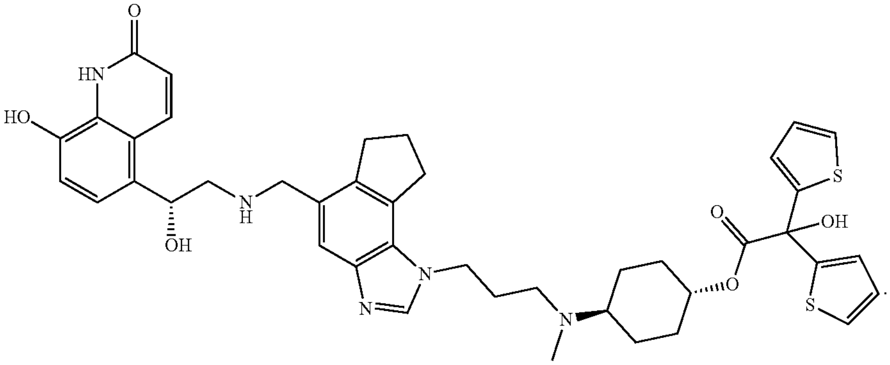
.
The present application also provides compounds as shown below or pharmaceutically acceptable salts thereof:
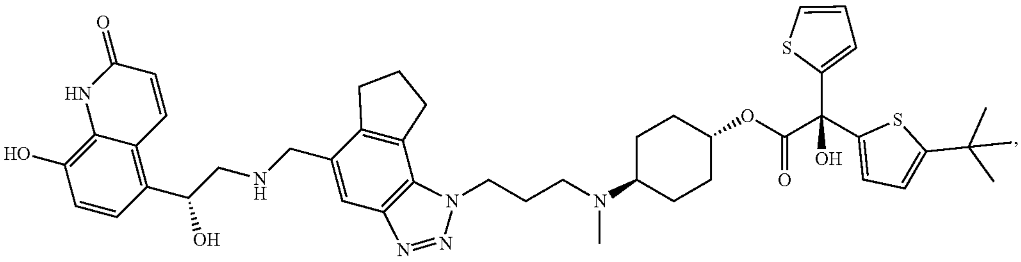
,
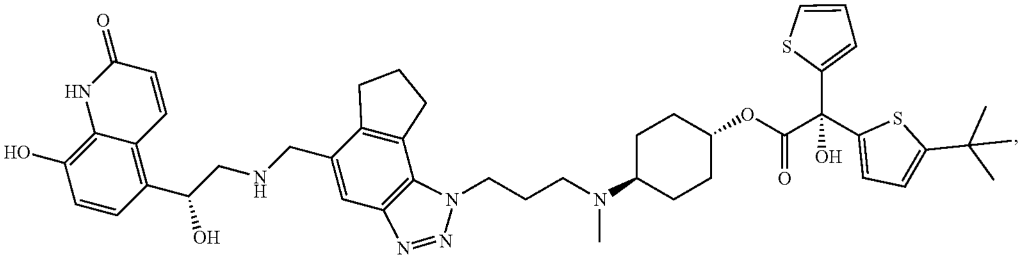
, -continued
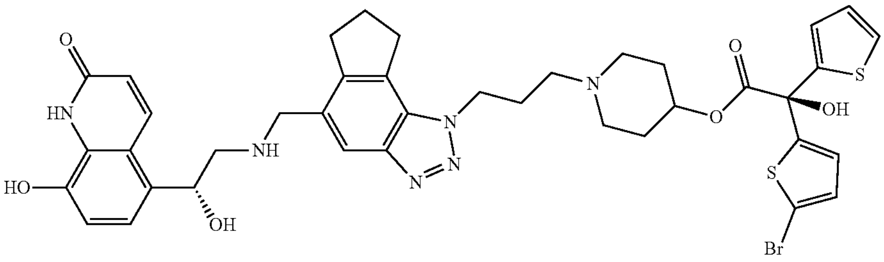
,
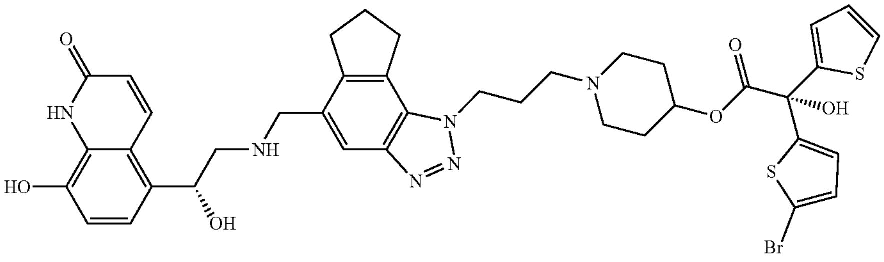
,
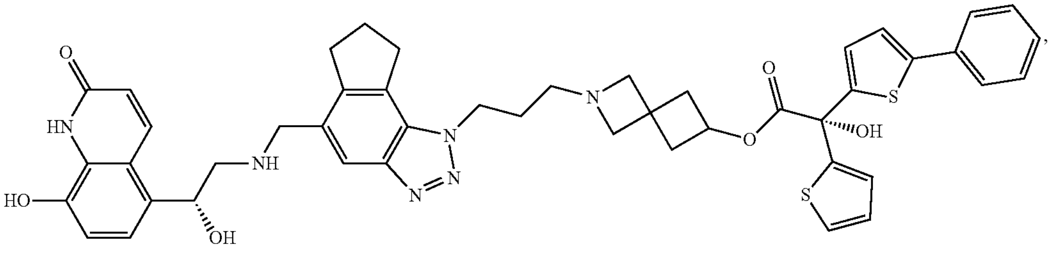
,
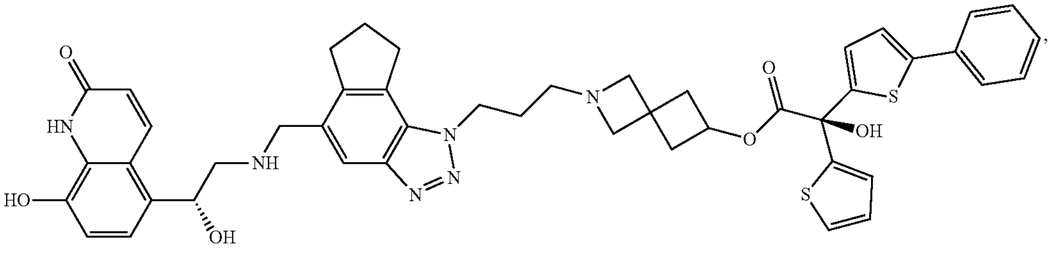
,
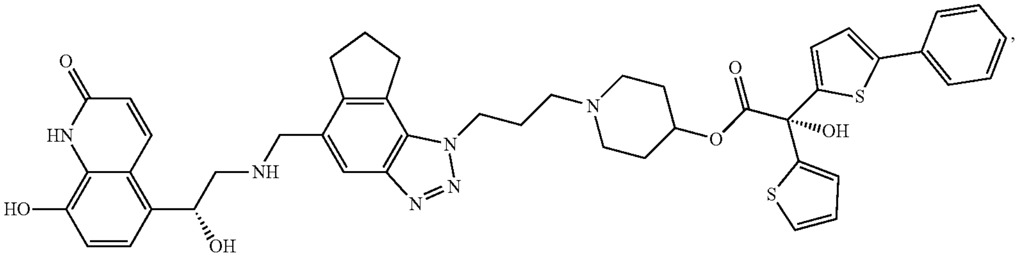
,
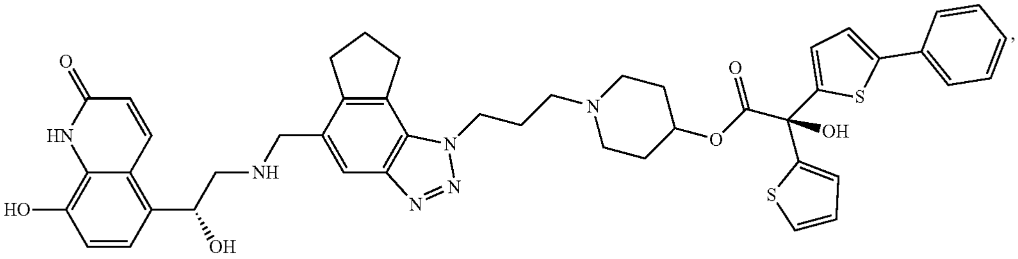
, -continued
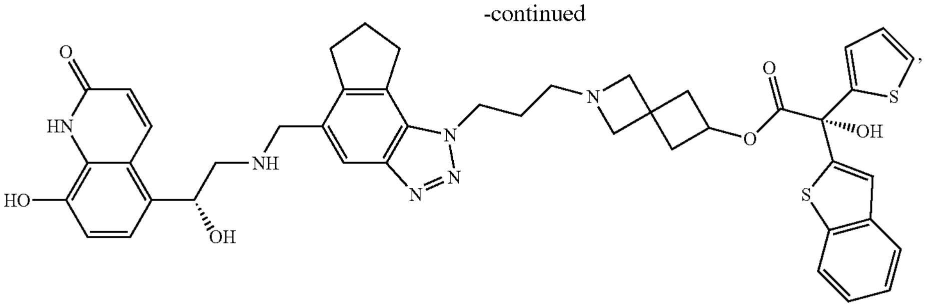
,
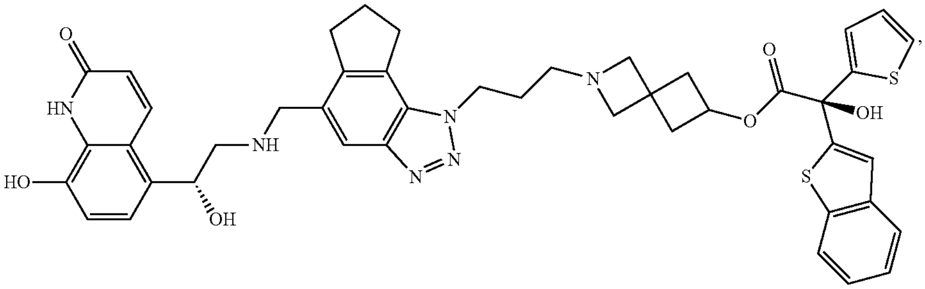
,
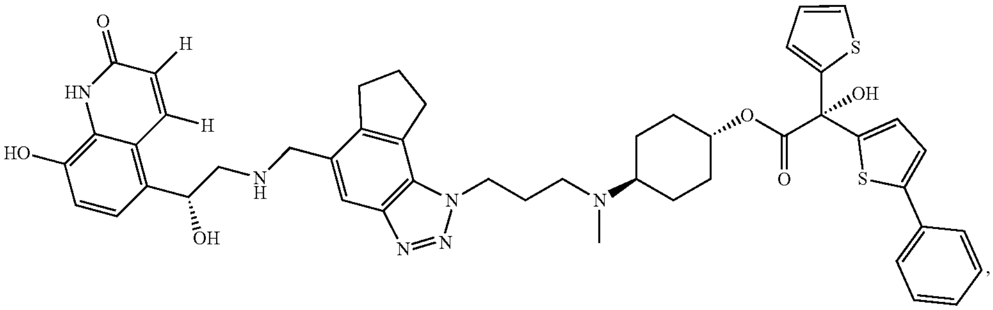
,
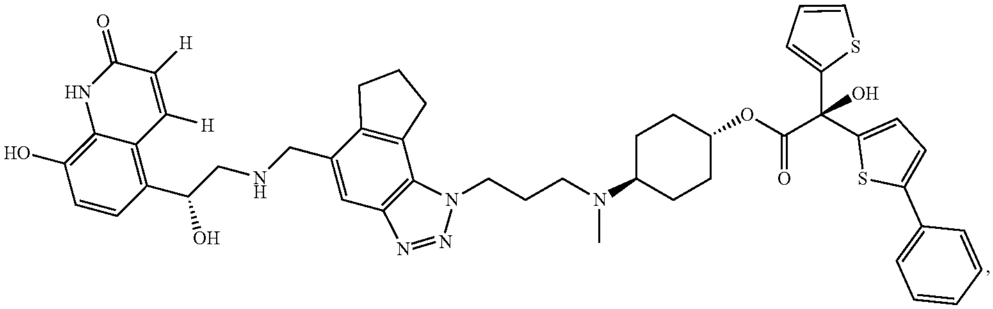
,
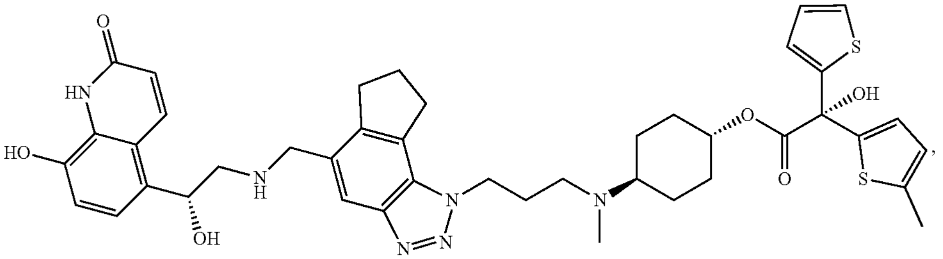
,
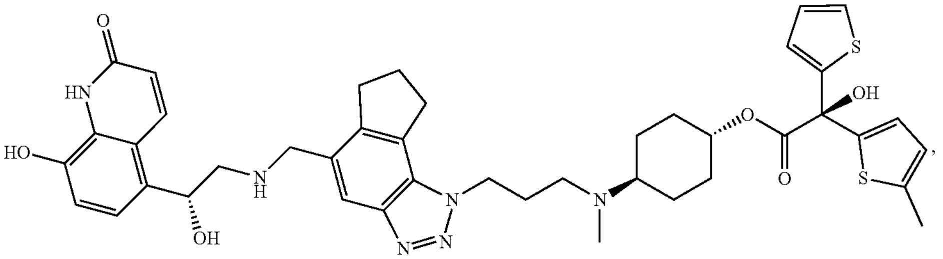
, -continued
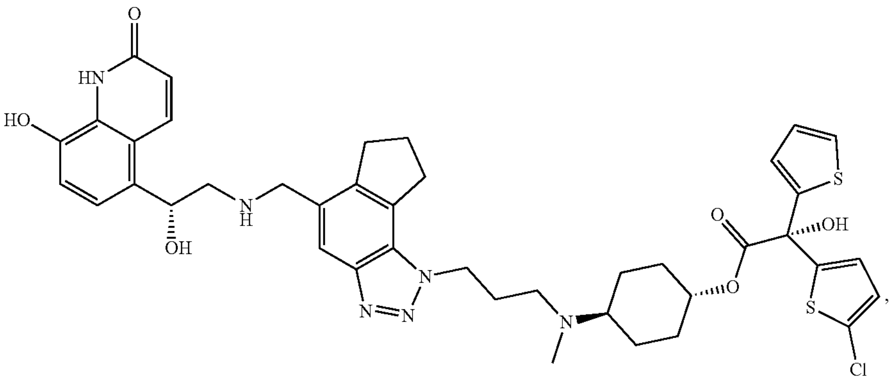
,
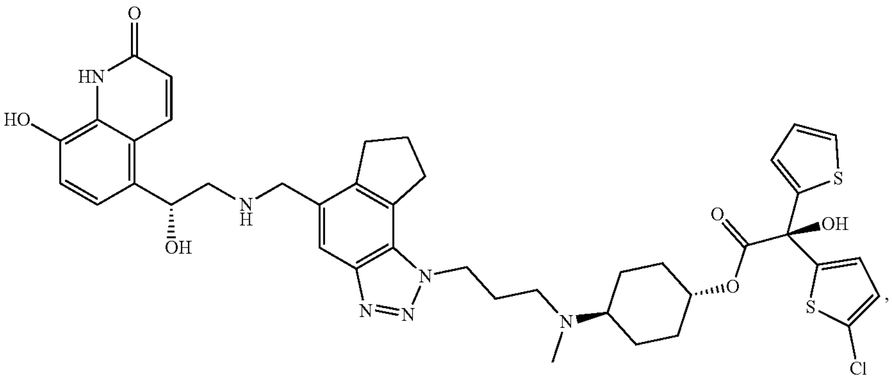
,
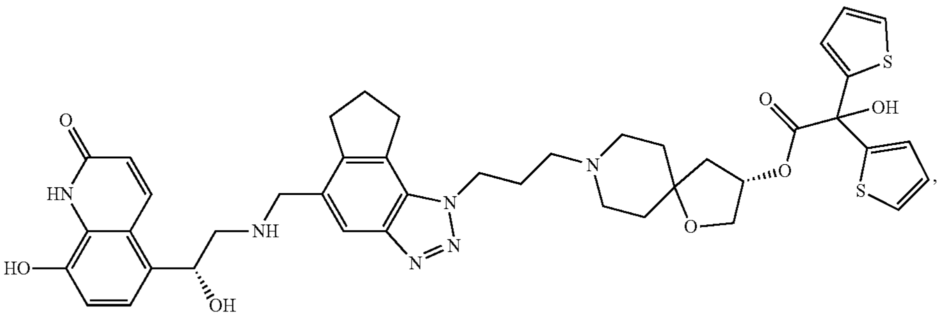
,
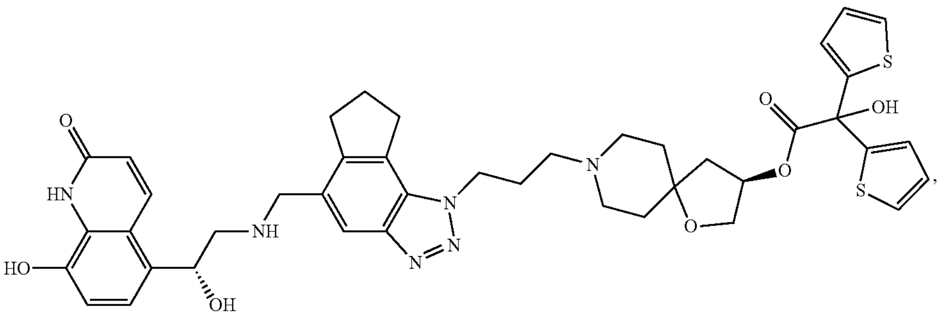
, -continued
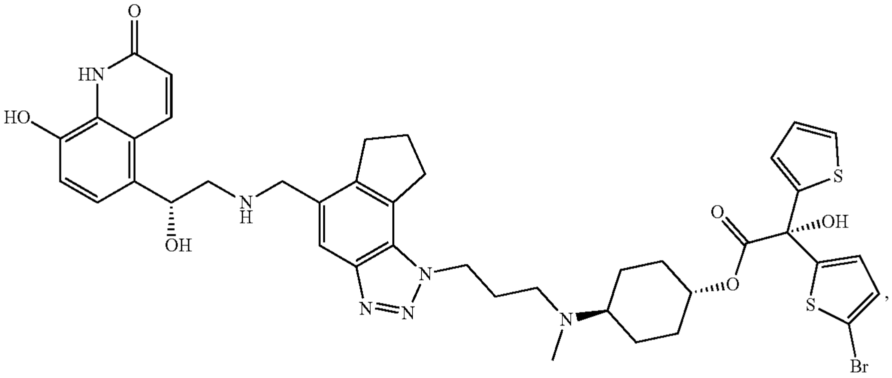
,
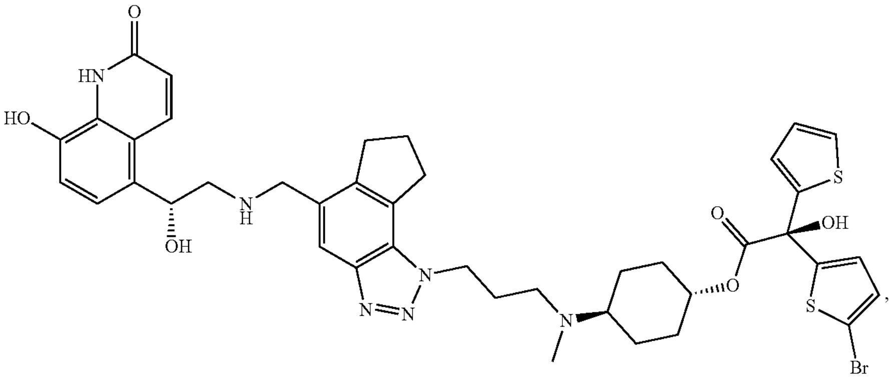
,
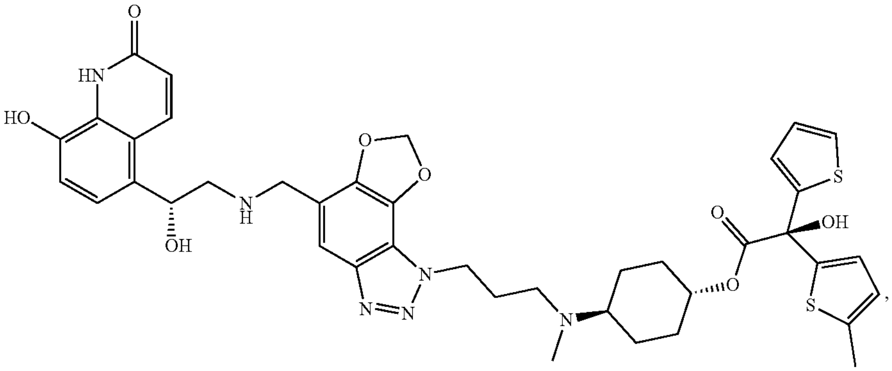
,
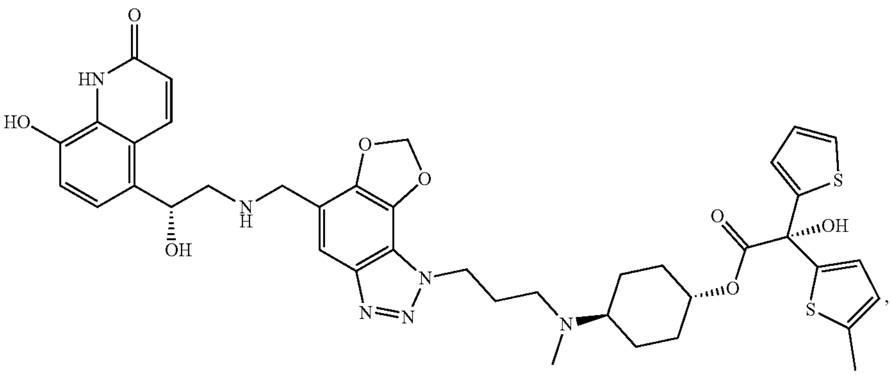
, -continued

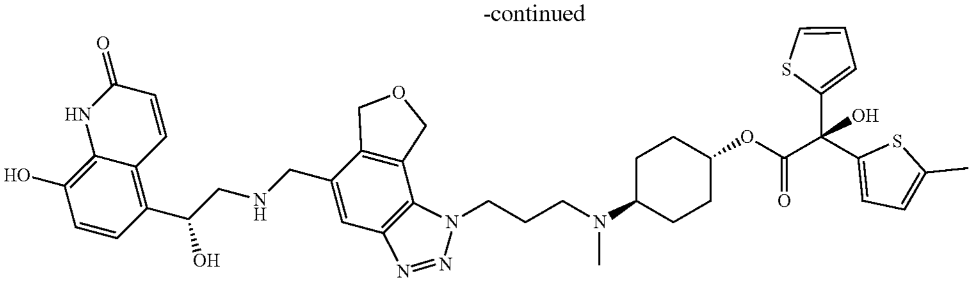

,

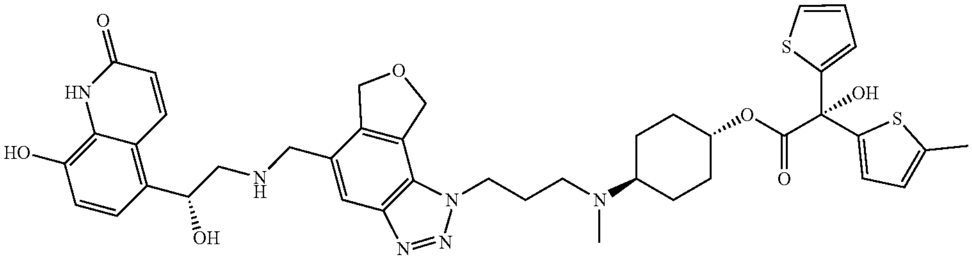

,

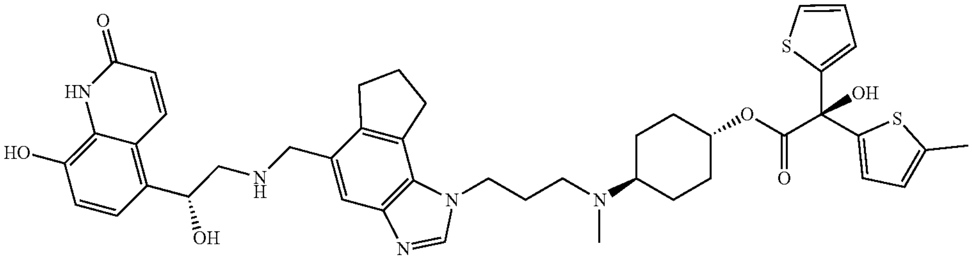

,

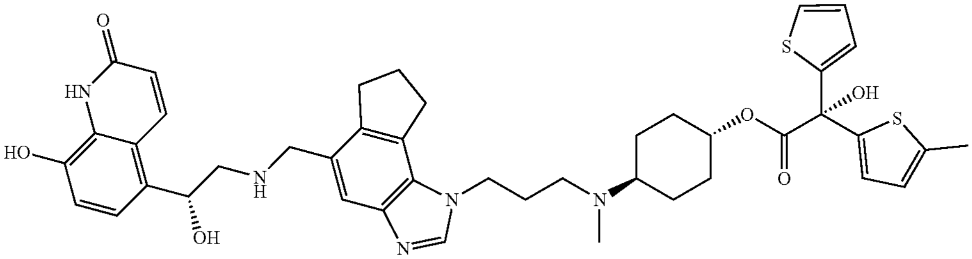

.

The present application also provides a pharmaceutical composition comprising the compound or the pharmaceutically acceptable salt thereof described above. Further, the pharmaceutical composition may comprise a pharmaceutically acceptable excipient.

The present application also provides use of the compound or the pharmaceutically acceptable salt thereof described above in preparing a medicament for treating chronic obstructive pulmonary disease (COPD).

The present application also provides use of the compound or the pharmaceutically acceptable salt thereof described above or the pharmaceutical composition described above in preparing a medicament for treating chronic obstructive pulmonary disease (COPD).

The present application also provides use of the compound or the pharmaceutically acceptable salt thereof described above or the pharmaceutical composition described above in treating chronic obstructive pulmonary disease (COPD).

The present application also provides the compound or the pharmaceutically acceptable salt thereof described above or the pharmaceutical composition described above for use in treating chronic obstructive pulmonary disease (COPD).

The present application also provides a method for treating chronic obstructive pulmonary disease (COPD), which comprises administering to a subject in need thereof a therapeutically effective amount of the compound or the pharmaceutically acceptable salt thereof described above or the pharmaceutical composition described above.

Technical Effects

The compound of the present application has good dual activity of antagonism of M3 muscarinic receptor and agonism of β2-adrenergic receptor, and has certain selectivity relative to the activity of β1. Compared with the reference compound AZD8871, the compound has a faster clearance rate after administration by intravenous injection, and has longer half-life, higher exposure and higher bioavailability after intra-tracheal administration with a nebulizer needle.

Definitions and Description

Unless otherwise stated, the following terms and phrases used herein are intended to have the following meanings. A particular term or phrase, unless otherwise specifically defined, should not be considered as uncertain or unclear, but construed according to its common meaning. When referring to a trade name herein, it is intended to refer to its corresponding commercial product or its active ingredient.

The term "pharmaceutically acceptable" is used herein for those compounds, materials, compositions and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound of the present application, which is prepared from the compound having particular substituents discovered by the present application and a relatively non-toxic acid or base. When the compound of the present application contains a relatively acidic functional group, a base addition salt can be obtained by making such a compound in contact with a sufficient amount of a base in a pure solution or a suitable inert solvent. When the compound of the present application contains a relatively basic functional group, an acid addition salt can be obtained by making such a compound in contact with a sufficient amount of an acid in a pure solution or a suitable inert solvent. Certain particular compounds of the present application contain both basic and acidic functional groups that allow the compounds to be converted into either base or acid addition salts.

The pharmaceutically acceptable salts of the present application can be synthesized from a parent compound having an acidic or basic group using conventional chemical methods. In general, such salts are prepared subjecting the free acid or base form of the compound to a reaction with a stoichiometric amount of the appropriate base or acid in water or an organic solvent or a mixture thereof.

Unless otherwise stated, the term "isomer" is intended to include geometric isomers, cis-trans isomers, stereoisomers, enantiomers, optical isomers, diastereoisomers and tautomers.

The compounds of the present application can occur in the form of a particular geometric isomer or stereoisomer. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. Substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers in which molecules each have two or more chiral centers and are not mirror images of each other.

Unless otherwise stated, "(+)" represents dextrorotation, "(−)" represents levorotation, and "(±)" represents racemization.

Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ).

Unless otherwise stated, the term "enriched with one isomer", "isomer enriched", "enriched with one enantiomer", or "enantiomer enriched" means that the content of one of the isomers or enantiomers is less than 100% and more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise stated, the term "isomeric excess" or "enantiomeric excess" refers to the difference between the relative percentages of two isomers or enantiomers. For example, if the content of one of the isomers or enantiomers is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. An enantiomer of a certain compound of the present application can be prepared by asymmetric synthesis or derivatization using a chiral additive, wherein the resulting diastereoisomeric mixture is separated and the auxiliary group is cleaved so as to provide the desired pure enantiomer. Alternatively, when the molecule contains a basic functional group (such as amino) or an acidic functional group (such as carboxyl), it reacts with an appropriate optically active acid or base to form a salt of the diastereoisomer, which is then subjected to diastereoisomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate generated from amines).

The compound of the present application may contain an unnatural proportion of atomic isotope at one or more of the atoms that constitute the compound. For example, the compound may be labeled with a radioisotope, such as tritium ($^{3}H$), iodine-125 ($^{125}I$), or C-14 ($^{14}C$). For another example, hydrogen can be substituted with deuterium to form a deuterated drug, and the bond formed by deuterium and carbon is firmer than that formed by common hydrogen and carbon. Compared with an un-deuterated drug, the deuterated drug has the advantages of reduced toxic side effects, increased stability, enhanced efficacy, prolonged biological half-life and the like. All isotopic variations of the compound described herein, whether radioactive or not, are encompassed within the scope of the present application.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$ alkyl, $C_{1-3}$ alkyl, $C_{2-3}$ alkyl, and the like, and may be monovalent (e.g., methyl), divalent (e.g., methylene) or polyvalent (e.g., methenyl). Examples of $C_{1-4}$ alkyl include, but are not limited to, methyl (Me), ethyl (Et), propyl (including n-propyl and isopropyl), butyl (including n-butyl, isobutyl, s-butyl, t-butyl), and the like.

Unless otherwise specified, "$C_{4-6}$ cycloalkyl" refers to a saturated cyclic hydrocarbon group consisting of 4 to 6 carbon atoms, including monocyclic and bicyclic systems.

The $C_{4-6}$ cycloalkyl includes $C_{4-5}$ cycloalkyl, $C_{5-6}$ cycloalkyl, and the like, and may be monovalent, divalent or polyvalent. Examples of $C_{4-6}$ cycloalkyl include, but are not limited to, cyclobutyl, cyclopentyl, cyclohexyl, and the like.

Unless otherwise specified, the term "$C_{4-6}$ cycloalkenyl" refers to an incompletely saturated cyclic hydrocarbon group consisting of 4 to 6 carbon atoms, which is a monocyclic or bicyclic ring system. The $C_{4-6}$ cycloalkenyl includes $C_{4-5}$ cycloalkenyl, $C_{5-6}$ cycloalkenyl, and the like, and may be monovalent, divalent or polyvalent. Non-limiting examples of $C_{4-6}$ cycloalkenyl include, but are not limited to, cyclopentenyl, cyclopentadienyl, cyclohexenyl, cyclohexadienyl, and the like.

Unless otherwise specified, the term "4- to 6-membered heterocycloalkyl", by itself or in combination with other terms, refers to a saturated cyclic group consisting of 4 to 6 ring atoms, of which 1, 2, 3 or 4 are heteroatoms independently selected from the group consisting of O, S and N, and the rest are carbon atoms, wherein the nitrogen atom is optionally quaternized, and the nitrogen and sulfur heteroatoms can be optionally oxidized (i.e., NO and $S(O)_p$, wherein p is 1 or 2). It includes monocyclic and bicyclic systems, wherein the bicyclic system includes spirocyclic, fused, and bridged rings. Furthermore, with respect to the "4- to 6-membered heterocycloalkyl", a heteroatom may occupy the position where the heterocycloalkyl is connected to the rest of the molecule. The 4- to 6-membered heterocycloalkyl includes 5- to 6-membered heterocycloalkyl, 4-membered heterocycloalkyl, 5-membered heterocycloalkyl, 6-membered heterocycloalkyl, and the like. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, and the like), tetrahydrofuranyl (including tetrahydrofuran-2-yl, and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1,2-oxazinyl, 1,2-thiazinyl, hexahydropyridazinyl, and the like.

Unless otherwise specified, the term "4- to 6-membered heterocycloalkenyl" refers to a partially unsaturated (but not fully unsaturated heteroaryl) non-aromatic ring consisting of 4 to 6 ring atoms, 1, 2, 3 or 4 of which are heteroatoms independently selected from the group consisting of O, S and N, and the rest are carbon atoms, wherein the nitrogen atoms are optionally quaternized, and the nitrogen and sulfur heteroatoms can be optionally oxidized (i.e., NO and $S(O)_p$, wherein p is 1 or 2). It includes monocyclic and bicyclic systems, wherein the bicyclic system includes spirocyclic, fused, and bridged rings. Furthermore, with respect to the "4- to 6-membered heterocycloalkenyl", a heteroatom may occupy the position where the heterocycloalkenyl is connected to the rest of the molecule. The 4- to 6-membered heterocycloalkenyl includes 4-membered heterocycloalkenyl, 5-membered heterocycloalkenyl, 6-membered heterocycloalkenyl, and the like. Examples of 4- to 6-membered heterocycloalkenyl include, but are not limited to, dihydropyrrolyl, dihydrofuranyl, dihydropyridinyl, tetrahydropyridinyl, dihydropyranyl, and the like.

Unless otherwise specified, the terms "5- to 6-membered heteroaromatic ring" and "5- to 6-membered heteroaryl" are used interchangeably herein, and the term "5- to 6-membered heteroaryl" refers to a monocyclic group consisting of 5 to 6 ring atoms with a conjugated pi-electron system, of which 1, 2, 3 or 4 ring atoms are heteroatoms independently selected from the group consisting of O, S and N, and the rest are carbon atoms. The nitrogen atom is optionally quaternized, and the nitrogen and sulfur heteroatoms are optionally oxidized (i.e., NO and $S(O)_p$, wherein p is 1 or 2). The 5- to 6-membered heteroaryl can be connected to the rest of the molecule through a heteroatom or a carbon atom. The 5- to 6-membered heteroaryl includes 5-membered heteroaryl and 6-membered heteroaryl. Examples of the 5- to 6-membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (including 1H-1,2,3-triazolyl, 2H-1,2,3-triazolyl, 1H-1,2,4-triazolyl, 4H-1,2,4-triazolyl, and the like), tetrazolyl, isoxazolyl (including 3-isoxazolyl, 4-isoxazolyl, 5-isoxazolyl, and the like), thiazolyl (including 2-thiazolyl, 4-thiazolyl, 5-thiazolyl, and the like), furanyl (including 2-furanyl, 3-furanyl, and the like), thienyl (including 2-thienyl, 3-thienyl, and the like), pyridinyl (including 2-pyridinyl, 3-pyridinyl, 4-pyridinyl, and the like), pyrazinyl, or pyrimidinyl (including 2-pyrimidinyl, 4-pyrimidinyl, and the like).

Unless otherwise specified, the term "6- to 10-membered heterocycloalkyl", by itself or in combination with other terms, refers to a saturated cyclic group consisting of 6 to 10 ring atoms, of which 1, 2, 3, or 4 ring atoms are heteroatoms independently selected from the group consisting of O, S, and N, and the rest are carbon atoms, wherein the nitrogen atom is optionally quaternized, and the nitrogen and sulfur heteroatoms can be optionally oxidized (i.e., NO and $S(O)_p$, wherein p is 1 or 2). It includes monocyclic, bicyclic and tricyclic systems, wherein the bicyclic and tricyclic systems include spirocyclic, fused and bridged rings. In addition, with respect to the "6- to 10-membered heterocycloalkyl", a heteroatom may occupy the position where the heterocycloalkyl is connected to the rest of the molecule. The 6- to 10-membered heterocycloalkyl includes 6- to 7-membered heterocycloalkyl, 6- to 8-membered heterocycloalkyl, 6- to 9-membered heterocycloalkyl, 6-membered heterocycloalkyl, 7-membered heterocycloalkyl, 8-membered heterocycloalkyl, 9-membered heterocycloalkyl, 10-membered heterocycloalkyl, and the like. Examples of 6- to 10-membered heterocycloalkyl include, but are not limited to, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1,2-oxazinyl, 1,2-thiazinyl, hexahydropyridazinyl, homopiperazinyl, homopiperidinyl, dioxepanyl, or the like. Unless otherwise specified, the term "halo" or "halogen", by itself or as part of another substituent, refers to a fluorine, chlorine, bromine or iodine atom.

The carbon atom with "*" can be a chiral carbon atom present in a form of a single (R) or (S) enantiomer or in a form enriched in one enantiomer.

The term "optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted with substituents, wherein the substituents may include deuterium and hydrogen variants, as long as the valence of the specific atom is normal and the substituted compound is stable. When the substituent is an oxygen (i.e., =O), it means that two hydrogen atoms are substituted. Substitution with oxygen does not occur on aromatic groups. The term "optionally substituted" means that an atom can be substituted with a substituent or not. Unless otherwise specified, the type and number of the substituent may be arbitrary as long as being chemically achievable.

When any variable (e.g., R) occurs more than once in the composition or structure of a compound, the variable is independently defined in each case. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

When the number of a connecting group is 0, for example, $-(CRR)_0-$, it means that the connecting group is a single bond.

When the number of a substituent is 0, it means that there is no such a substituent in a structure. For example, $-A-(R)_0$ means that the structure is actually -A.

When a substituent is absent, it means that there is no such a substituent in a structure. For example, when X is absent in A-X, it means that the structure is actually A.

When one of variables is selected from a single bond, it means that the two groups which it connects are connected directly. For example, in A-L-Z, when L represents a single bond, it means that the structure is actually A-Z.

When a bond of a substituent is cross-connected to two or more atoms on a ring, the substituent can be bonded to any atom on the ring. For example, structural unit

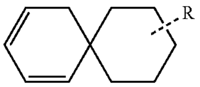 or 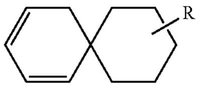

represents that the substitution of substituent R may occur in any one position on cyclohexyl or cyclohexadienyl. When it is not specified by which atom the listed substituent is connected to the group to be substituted, the substituent can be bonded via its any atom. For example, pyridinyl as a substituent can be connected to the group to be substituted via any carbon atom on the pyridine ring.

When the direction for connection of the listed connecting group is not specified, the direction for connection is arbitrary. For example, when the connecting group L contained in

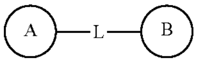

is -M-W—, -M-W— can either connect ring A and ring B in a direction same as left-to-right reading order to form

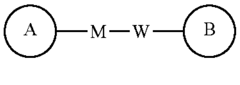, or connect ring A and ring B in a direction opposite to the left-to-right reading order to form

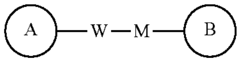.

A combination of the connecting group, a substituent and/or a variant thereof is permissible only if the combination can result in a stable compound.

Unless otherwise specified, when a group has one or more connectable sites, any one or more of the sites of the group may be connected to other groups by chemical bonds. When there is no designated connecting mode for a chemical bond and H atoms are present at a connectable site, the number of the H atoms at the connectable site is correspondingly reduced based on the number of the connected chemical bonds, and a group with a corresponding valence number is thus formed. The chemical bond that connect the site and another group may be represented by a straight solid bond (  ), a straight dashed bond (  ), or a wavy line (  ).

For example, the straight solid bond in $-OCH_3$ refers to being connected to another group via the oxygen atom in the group; the straight dashed bond in

refers to being connected to another group via two ends of the nitrogen atom in the group; the wavy line in

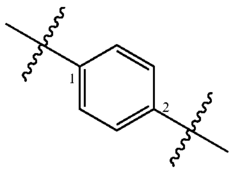 [SMILES: *c1ccc(*)cc1]

refers to being connected to another group via the carbon atoms at positions 1 and 2 in the phenyl group;

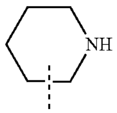

means that any connectable site on the piperidinyl can be connected to another group via 1 bond in at least 4 connecting modes:

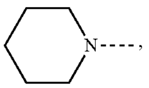, 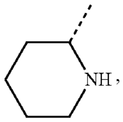, 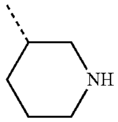 and

-continued

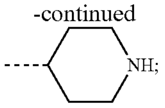

even if —N— is connected with an H atom,

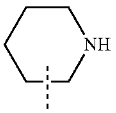

includes the connection mode of

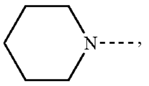

but when 1 bond is connected to a site, the number of H at that site is correspondingly reduced by 1 and a monovalent piperidinyl is thus formed.

Unless otherwise specified, the number of atoms on a ring is generally defined as the member number of the ring. For example, "5- to 7-membered ring" refers to a "ring" on which 5 to 7 atoms are arranged in a circle. The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethoxycarbonyl, such as carbobenzoxy (Cbz) and 9-fluorenylmethoxycarbonyl (Fmoc); arylmethyl, such as benzyl (Bn), trityl (Tr), 1,1-di-(4'-methoxyphenyl) methyl; and silyl, such as trimethylsilyl (TMS) and tert-butyldimethylsilyl (TBS). The term "hydroxy protecting group" refers to a protecting group suitable for preventing side reactions of the hydroxy group. Representative hydroxy protecting groups include, but are not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); and silyl, such as trimethylsilyl (TMS) and tert-butyldimethylsilyl (TBS).

The compounds of the present application can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The compound of the present application may be structurally confirmed by conventional methods well known to those skilled in the art; if the present application relates to the absolute configuration of the compound, this absolute configuration may be confirmed by means of conventional techniques in the art. For example, in the single crystal X-ray diffraction (SXRD) method, intensity data of diffraction of the single crystal grown are collected with a Bruker D8 venture diffractometer, the light source is CuKα radiation, and the scanning mode is φ/ω scanning; after related data are collected, the direct method (Shelxs97) is further employed to analyze the crystal structure, and thus the absolute configuration can be confirmed.

The solvents used in the present invention are commercially available. The following abbreviations are used in the present application: aq. and $H_2O$ represent water; eq represents equivalent; Boc represents tert-butyloxycarbonyl; PE represents petroleum ether; ACN represents acetonitrile; EtOAc represents ethyl acetate; EtOH represents ethanol; MeOH represents methanol; TBS represents tert-butyl dimethylsilyl; HPLC represents high performance liquid chromatography; LCMS represents liquid chromatography-mass spectrometry; r.t. represents room temperature; mp represents melting point; ° C. represents Celsius degree; h represents hour; mL represents milliliter; mM represents millimoles per liter; mmol represents millimoles; mol represents micromole; HNMR represents nuclear magnetic hydrogen spectroscopy; MS represents mass spectrometry; min represents minutes; and pH represents the negative logarithm of the molar concentration of hydrogen ions.

Compounds are named according to conventional nomenclature rules in the art or using ChemDraw® software, and supplier's catalog names are given for commercially available compounds.

DETAILED DESCRIPTION

The present application is described in detail below by way of examples, which, however, are not intended to disadvantageously limit the scope of the present application in any way. The present application has been described in detail herein and specific embodiments have also been disclosed, it will be apparent to those skilled in the art that various changes and modifications can be made to the specific embodiments without departing from the spirit and scope of the present application. All reagents used in the present application are commercially available and can be used without further purification.

Example 1

1

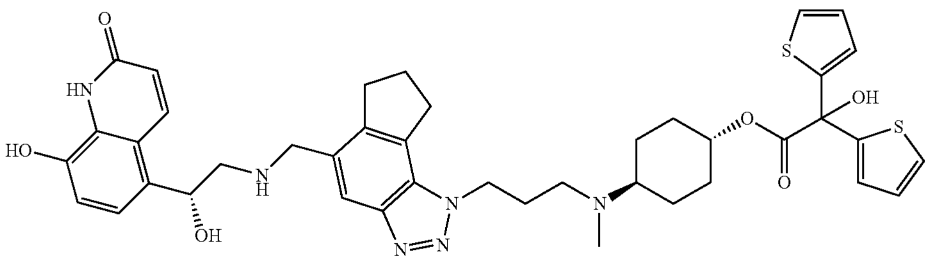

Synthetic Route:
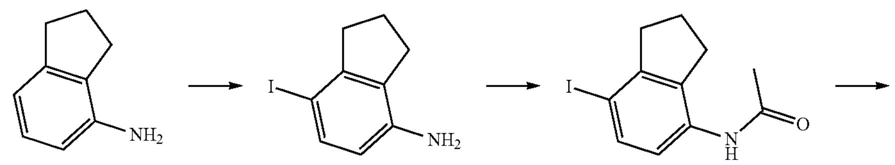
1-1 1-2 1-3
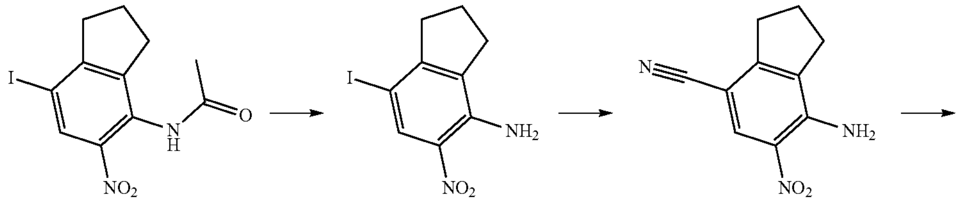
1-4 1-5 1-6
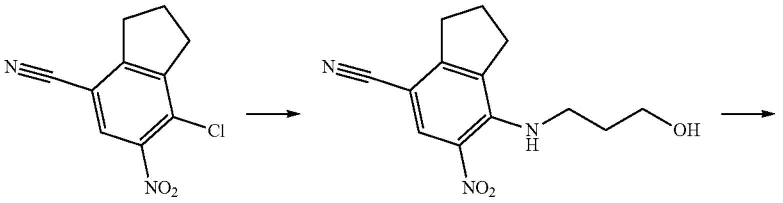
1-7 1-8
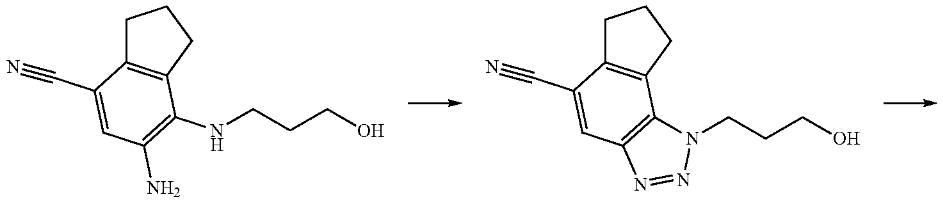
1-9 1-10
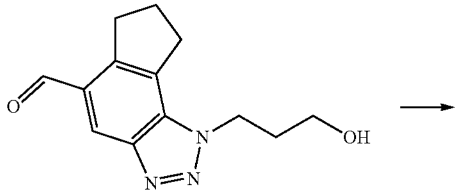
1-11
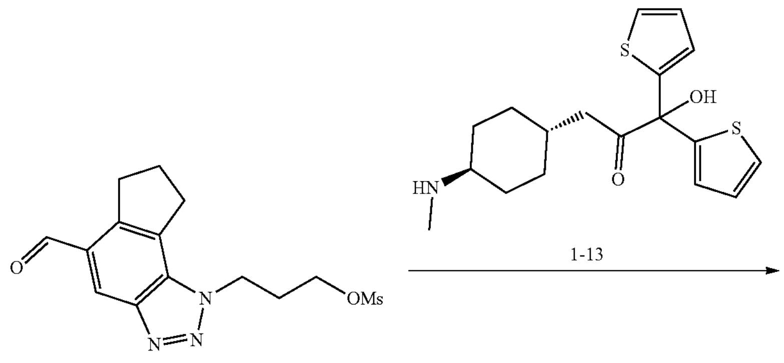
1-13
1-12

-continued
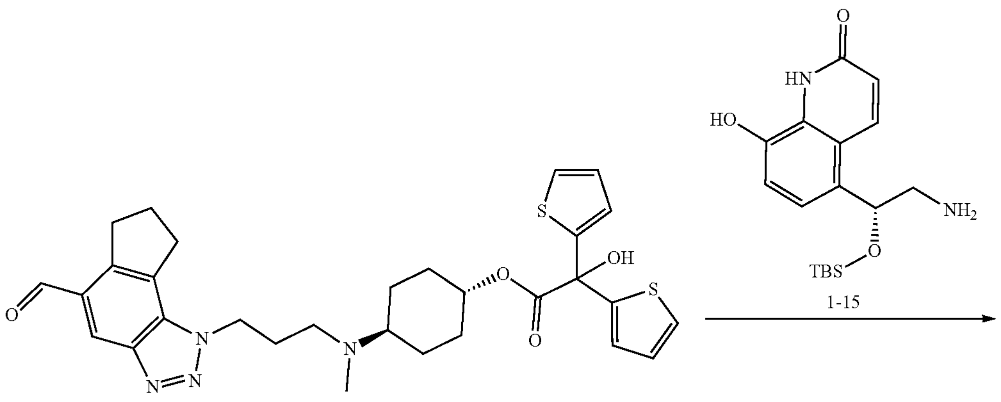
1-15
1-14
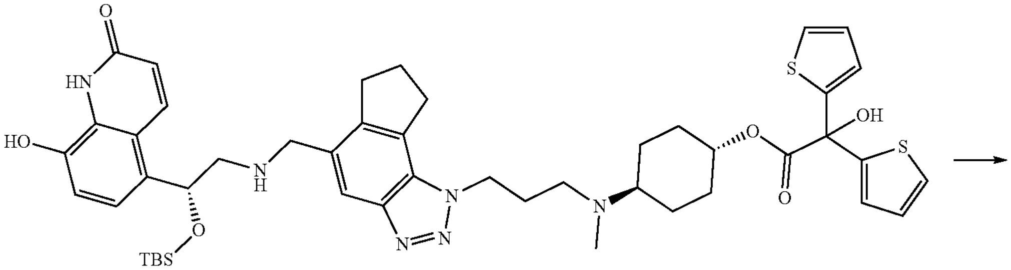
1-16
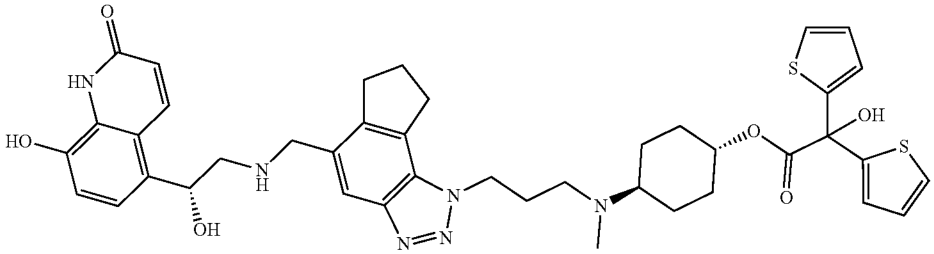
1
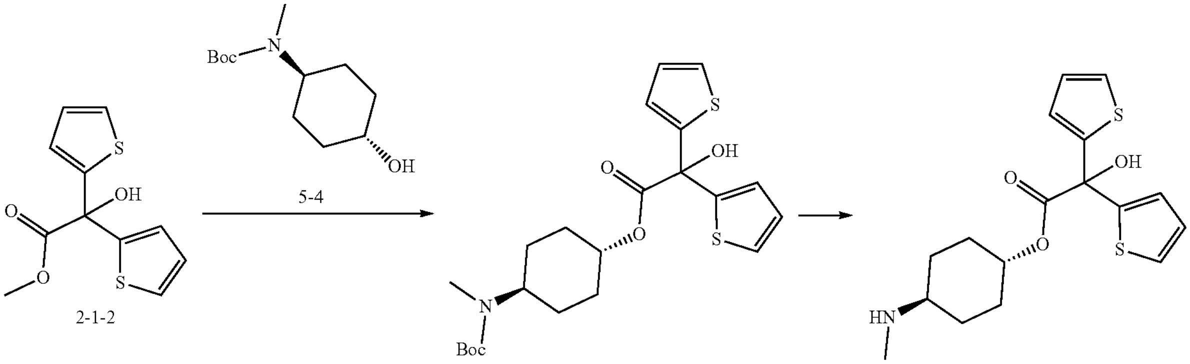
5-4
2-1-2
1-13′
1-13

-continued

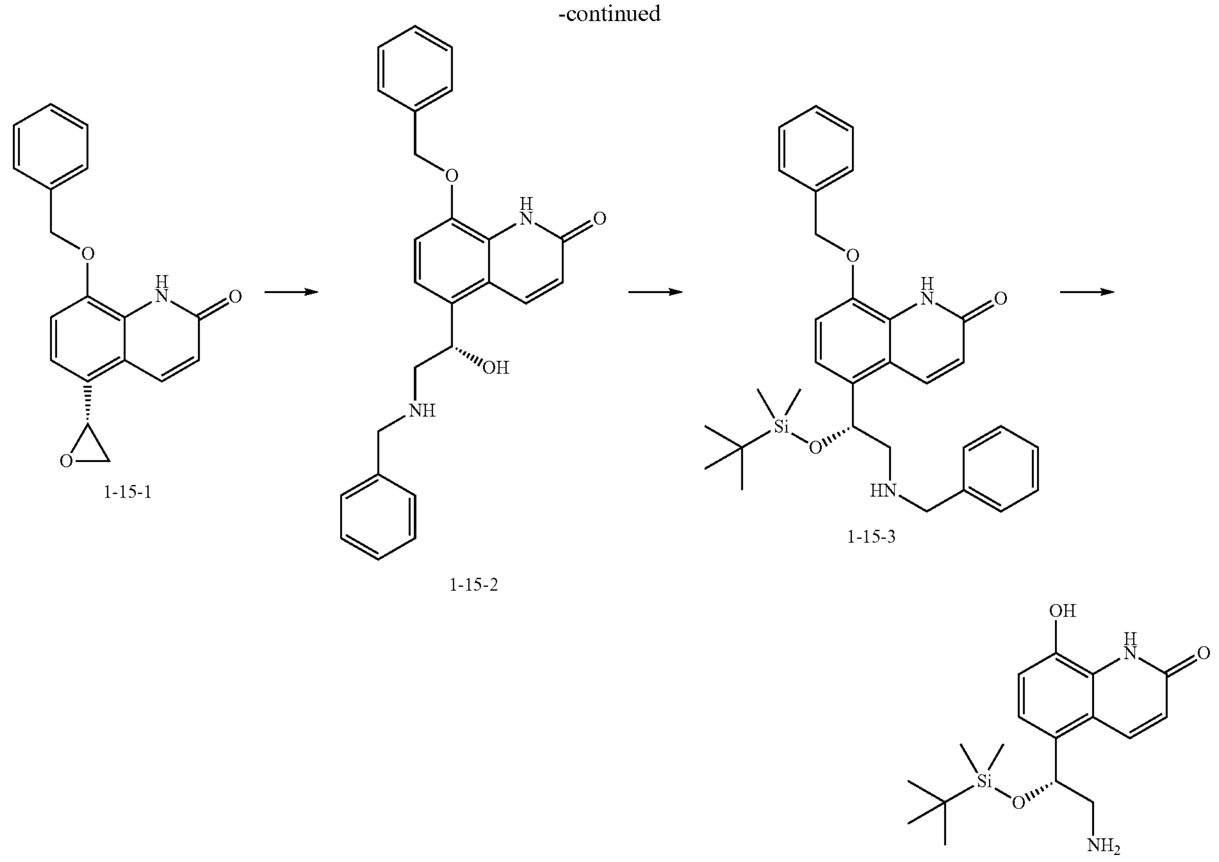

1-15-1 1-15-2 1-15-3 1-15

Step 1: Synthesis of Compound 1-2

Compound 1-1 (15 g) was dissolved in acetic acid (75 mL) and water (75 mL), and sodium perborate (17.33 g) was added under stirring. The mixture was cooled to 0° C. and a solution of potassium iodide (18.70 g) in water (150 mL) was slowly added dropwise. The mixture was heated to room temperature (25° C.) and stirred for 0.5 h. After the reaction was completed, the reaction solution was filtered, and the filter cake was washed with 500 mL of water. The solid was collected and concentrated to dryness under reduced pressure to give compound 1-2, which was directly used in the next step.

$^1$H NMR (400 MHz, $CDCl_3$) δ: 7.32 (d, J=8.4 Hz, 1H), 6.30 (d, J=8.4 Hz, 1H), 3.65 (s, 2H), 2.92-2.84 (m, 4H), 2.18-2.05 (m, 2H).

MS-ESI calcd. $[M+H]^+$ 260, found 260.0.

Step 2: Synthesis of Compound 1-3

Compound 1-2 (26.5 g) was dissolved in tetrahydrofuran (250 mL), and acetic anhydride (15.66 g) and diisopropylethylamine (26.44 g) were added. The mixture was heated to 45° C. and stirred for 16 h. After the reaction was completed, the reaction solution was diluted with 500 mL of ethyl acetate, washed with 500 mL of water and 500 mL of saturated brine sequentially, dried over anhydrous sodium sulfate, filtered, and concentrated to dryness under reduced pressure to give compound 1-3, which was directly used in the next step.

MS-ESI calcd. $[M+H]^+$ 302, found 302.0.

Step 3: Synthesis of Compound 1-4

To a suspension of compound 1-3 (5 g) in acetic anhydride (50 mL) was added concentrated nitric acid (2.41 g, purity: 65%) at 0° C. The mixture was stirred at 0-25° C. for 2 h. After the reaction was completed, the reaction solution was filtered, and the filter cake was washed with 50 mL of petroleum ether. The solid was collected and concentrated to dryness under reduced pressure to give compound 1-4, which was directly used in the next step.

$^1$H NMR (400 MHz, $CDCl_3$) δ: 8.69 (s, 1H), 8.26 (s, 1H), 3.06-2.97 (m, 4H), 2.26-2.21 (m, 3H), 2.14 (t, J=7.6 Hz, 2H).

MS-ESI calcd. $[M+H]^+$ 347, found 346.9.

Step 4: Synthesis of Compound 1-5

Compound 1-4 (14.5 g) was dissolved in ethanol (400 mL), and hydrochloric acid solution (6 M, 139.64 mL) was added. The mixture was heated to 85° C. and stirred for 72 h. After the reaction was completed, the reaction solution was concentrated under reduced pressure to remove most of ethanol and filtered. The precipitated solid was collected and concentrated to dryness reduced pressure to give compound 1-5, which was directly used in the next step.

$^1$H NMR (400 MHz, $CDCl_3$) δ: 8.38 (s, 1H), 5.96 (s, 2H), 3.03-2.83 (m, 4H), 2.28-2.09 (m, 2H).

MS-ESI calcd. $[M+H]^+$ 305, found 304.9.

Step 5: Synthesis of Compound 1-6

Compound 1-5 (8.5 g) was dissolved in dimethyl sulfoxide (100 mL), and cuprous oxide (799.95 mg) and acetyl nitrile (3.86 g) were added. The mixture was heated to 130° C. and stirred for 4 h. After the reaction was completed, the reaction solution was cooled to room temperature and poured into 750 mL of water, and the resulting mixture was extracted with ethyl acetate (350 mL×2). The organic phases were combined, washed with saturated brine (350 mL×1), dried over anhydrous sodium sulfate, filtered and concentrated under reduced pressure, and the residue was separated and purified by flash silica gel column chromatography (eluent: ethyl acetate/petroleum ether, 0-30%) to give compound 1-6.

$^1$H NMR (400 MHz, $CDCl_3$) δ: 8.38 (s, 1H), 6.37 (s, 2H), 3.15 (t, J=7.6 Hz, 2H), 2.84 (t, J=7.6 Hz, 2H), 2.35-2.26 (m, 2H).

Step 6: Synthesis of Compound 1-7

A mixture of cuprous chloride (6.25 g) and acetonitrile (470 mL) was heated to 65° C., tert-butyl nitrite (5.99 g) was added in one portion, and compound 1-6 (4.72 g) was added in portions. The mixture was stirred at 65° C. for 0.5 h. After the reaction was completed, the reaction solution was cooled to room temperature and concentrated to dryness under reduced pressure. Ethyl acetate (500 mL) and hydrochloric acid solution (6 M, 200 mL) were added to the residue, followed by liquid separation. The organic phase was washed with saturated brine (500 mL), dried over anhydrous sodium sulfate, filtered and concentrated under reduced pressure, and the residue was separated and purified by flash silica gel column chromatography (eluent: ethyl acetate/petroleum ether, 0-10%) to give compound 1-7.

$^1$H NMR (400 MHz, $CDCl_3$) δ: 8.01 (s, 1H), 3.28 (t, J=7.6 Hz, 2H), 3.16 (t, J=7.6 Hz, 2H), 2.31 (t, J=7.6 Hz, 2H).

Step 7: Synthesis of Compound 1-8

Compound 1-7 (3.74 g) was dissolved in tetrahydrofuran (150 mL), and triethylamine (4.25 g) and 3-aminopropanol (3.79 g) were added. The mixture was heated to 65° C. and stirred for 16 h. After the reaction was completed, the reaction solution was cooled to room temperature and poured into 300 mL of water, and the resulting mixture was extracted with ethyl acetate (300 mL). The organic phase was washed with saturated brine (300 mL×1), dried over anhydrous sodium sulfate, filtered and concentrated under reduced pressure, and the residue was separated and purified by flash silica gel column chromatography (eluent: dichloromethane, 100%) to give compound 1-8.

$^1$H NMR (400 MHz, $CDCl_3$) δ: 8.66 (s, 1H), 8.37 (s, 1H), 3.90-3.75 (m, 4H), 3.29 (t, J=7.2 Hz, 2H), 3.04 (t, J=7.6 Hz, 2H), 2.23-2.13 (m, 2H), 1.96-1.88 (m, 2H), 1.47 (t, J=4.4 Hz, 1H).

MS-ESI calcd. $[M+H]^+$ 262, found 261.9.

Step 8: Synthesis of Compound 1-9

Compound 1-8 (2.35 g) was dissolved in a mixed solution of methanol, tetrahydrofuran and water (135 mL, volume ratio: 1/1/1), and reduced iron powder (3.01 g) and ammonium chloride (2.41 g) were added. The mixture was heated to 70° C. and stirred for 2 h. After the reaction was completed, the reaction solution was filtered, and the filtrate was collected, concentrated to dryness under reduced pressure, and separated and purified by flash silica gel column chromatography (eluent: ethyl acetate/petroleum ether, 0-50%) to give compound 1-9.

$^1$H NMR (400 MHz, $CDCl_3$) δ: 6.79 (s, 1H), 3.91-3.81 (m, 2H), 3.41 (s, 2H), 3.05-2.92 (m, 4H), 2.16-2.08 (m, 2H), 1.88-1.79 (m, 2H).

MS-ESI calcd. $[M+H]^+$ 232, found 232.0.

Step 9: Synthesis of Compound 1-10

Compound 1-9 (2 g) was dispersed in hydrochloric acid solution (6 M, 14.41 mL), and the system was cooled to 0° C. A solution of sodium nitrite (894.97 mg) in water (8 mL) was slowly added dropwise at 0° C. The mixture was stirred at 0-25° C. for 1 h. After the reaction was completed, the reaction solution was subjected to liquid separation in ethyl acetate (200 mL) and water (200 mL). The organic phase was washed with saturated brine (100 mL), dried over anhydrous sodium sulfate, filtered and concentrated to dryness under reduced pressure to give compound 1-10, which was directly used in the next step.

MS-ESI calcd. $[M+H]^+$ 243, found 243.0.

Step 10: Synthesis of Compound 1-11

Compound 1-10 (2 g) was dissolved in formic acid solution (80 mL, purity: 75%), and nickel-aluminum alloy (3.54 g) was added. The mixture was heated to 90° C. and stirred for 16 h. The reaction solution was filtered, and the filtrate was collected and concentrated to dryness under reduced pressure. 200 mL of ethanol was added, and an aqueous sodium hydroxide solution (2 M, 41.28 mL) was added under stirring. The mixture was stirred at 25° C. for 1 h. After the reaction was completed, the reaction solution was cooled in an ice bath, adjusted to pH 6-7 with 2 N hydrochloric acid solution, concentrated under reduced pressure to remove most of methanol, and extracted with ethyl acetate (250 mL×2). The organic phase was washed with saturated brine (200 mL), dried over anhydrous sodium sulfate, filtered and concentrated to dryness under reduced pressure to give compound 1-11, which was directly used in the next step.

MS-ESI calcd. $[M+H]^+$ 246, found 246.0.

Step 11: Synthesis of Compound 1-12

Compound 1-11 (250 mg) was dissolved in dichloromethane (20 mL), and triethylamine (309.41 mg) and methanesulfonyl chloride (233.51 mg) were added. The mixture was stirred at 25° C. for 0.5 h. Two reactions were set up in parallel. After the reaction was completed, the reaction solution was subjected to liquid separation in dichloromethane (200 mL) and water (200 mL). The organic phase was washed with saturated brine (100 mL), dried over anhydrous sodium sulfate, filtered, concentrated to dryness under reduced pressure, and separated and purified by flash silica gel column chromatography (eluent: methanol/dichloromethane, 0-2%) to give compound 1-12.

MS-ESI calcd. $[M+H]^+$ 324, found 324.0.

Step 12: Synthesis of Compound 1-13'

Compound 2-1-2 (11.09 g) dissolved in anhydrous toluene (100 mL) was added to compound 5-4 (10 mg) dissolved in anhydrous toluene (100 mL), followed by the addition of sodium hydride (872 mg, purity: 60%). The mixture was stirred at 155° C. for 2 h. The reaction solution was cooled to room temperature, and the reaction was quenched with 4% aqueous sodium bicarbonate solution (200 mL). The resulting mixture was extracted with ethyl acetate (200 mL×2). The organic phases were combined, washed with saturated brine (200 mL), dried over anhydrous sodium sulfate, filtered and concentrated under reduced pressure, and the residue was separated and purified by silica gel column chromatography (petroleum ether/ethyl acetate, 20:1-6:1) to give compound 1-13'.

MS-ESI calcd. $[M+H-18]^+$ 434, found 434.1.

Step 13: Synthesis of Compound 1-13

Compound 1-13' (400 mg) was dissolved in ethyl acetate (4 mL), and a solution of hydrogen chloride in ethyl acetate (6.64 mL, 4 M) was added. The mixture was stirred at 25° C. for 2 h. The reaction solution was adjusted to about pH 8 with a saturated aqueous sodium carbonate solution and extracted with ethyl acetate (30 mL×3). The organic phases were combined, washed with saturated brine (100 mL), dried over anhydrous sodium sulfate, filtered and concentrated under reduced pressure to give crude compound 1-13.

MS-ESI calcd. $[M+H]^+$ 352, found 352.1.

Step 14: Synthesis of Compound 1-14

Compound 1-13 (200 mg) was dissolved in acetonitrile (20 mL), and diisopropylethylamine (220.62 mg), potassium iodide (141.69 mg) and compound 1-12 (184.00 mg) were added. The mixture was heated to 90° C. and stirred for 16 h. After the reaction was completed, the reaction solution was concentrated to dryness under reduced pressure, and separated and purified by flash silica gel column chromatography (eluent: methanol/dichloromethane, 0-5%) to give compound 1-14.

MS-ESI calcd. $[M+H]^+$ 579, found 579.2.

Step 15: Synthesis of Acetate Salt of Compound 1-15

Compound 1-15-1 (2 g) was added to benzylamine (4.92 g). The mixture was stirred at 150° C. for 0.5 h under microwave irradiation. The reaction was quenched with water (40 mL), and the resulting mixture was extracted with ethyl acetate (40 mL×3). The organic phases were combined, washed with saturated brine (80 mL), dried over anhydrous sodium sulfate, filtered and concentrated under reduced pressure, and the residue was separated and purified by silica gel column chromatography (petroleum ether/ethyl acetate, 10:1-0:1, dichloromethane/methanol: 20:1-10:1) to give compound 1-15-2. MS-ESI calcd. $[M+H]^+$ 401, found 401.1.

Compound 1-15-2 (50 mg) was dissolved in DCM (1 mL), and 2,6-dimethylpyridine (26.8 mg) and tert-butyldimethylsilyl trifluoromethanesulfonate (36.30 mg) were added at 0° C. The mixture was stirred at 20° C. for 2 h. The reaction was quenched with water (2 mL), and the resulting mixture was extracted with dichloromethane (2 mL×2). The organic phases were combined, washed with saturated brine (2 mL), dried over anhydrous sodium sulfate, filtered and concentrated under reduced pressure to give crude compound 1-15-3. MS-ESI calcd. $[M+H]^+$ 515, found 515.2.

Compound 1-15-3 (10 g) was dissolved in methanol (100 mL), and acetic acid (1.67 mL) and $Pd(OH)_2$ (2 g, 20%) were added. The mixture was stirred at 20° C. for 16 h under hydrogen atmosphere (15 psi). The reaction solution was filtered and concentrated under reduced pressure to give an acetate salt of crude compound 1-15.

MS-ESI calcd. $[M+H]^+$ 335, found 334.9.

Step 16: Synthesis of Compound 1-16

Compound 1-14 (325 mg) and compound 1-15 (187.83 mg) were dissolved in methanol (10 mL) and tetrahydrofuran (8 mL), and 4A molecular sieve (300 mg), diisopropylethylamine (217.73 mg) and sodium triacetoxyborohydride (595.09 mg) were added. The mixture was stirred at 25° C. for 3 h, and sodium triacetoxyborohydride (595.09 mg) was added. The mixture was stirred at 25° C. for 16 h, and sodium triacetoxyborohydride (595.09 mg) was added. The mixture was stirred at 25° C. for 3 h. The reaction solution was concentrated to dryness, and 10 mL of water was added. The resulting mixture was extracted with dichloromethane (20 mL×2). The organic phase was washed with saturated brine (20 mL), dried over anhydrous sodium sulfate, filtered, concentrated to dryness under reduced pressure, and separated and purified by flash silica gel column chromatography (eluent: methanol/dichloromethane, 0-10%) to give compound 1-16.

MS-ESI calcd. $[M+H]^+$ 897, found 897.5.

Step 17: Synthesis of Trifluoroacetate Salt of Compound 1

Compound 1-16 (213 mg) was dissolved in tetrahydrofuran (5 mL), and triethylamine trihydrofluoride (191.35 mg) was added. The mixture was stirred at 25° C. for 16 h. After the reaction was completed, the reaction solution was concentrated to dryness under reduced pressure, and separated by high performance liquid chromatography (column: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid), gradient elution method: acetonitrile, from 17% to 57% in 8 min) to give a trifluoroacetate salt of compound 1.

$^1H$ NMR (400 MHz, DMSO-$d_6$) δ: 10.86-10.34 (m, 2H), 9.87 (s, 1H), 9.43-9.01 (m, 2H), 8.15 (d, J=9.6 Hz, 1H), 8.07 (s, 1H), 7.47 (d, J=4.0 Hz, 2H), 7.31 (s, 1H), 7.15 (d, J=7.6 Hz, 1H), 7.07 (s, 2H), 7.03-6.76 (m, 3H), 6.53 (d, J=9.6 Hz, 1H), 6.28 (s, 1H), 5.42 (d, J=8.0 Hz, 1H), 4.78 (s, 3H), 4.38 (s, 2H), 3.36 (s, 4H), 3.19 (s, 2H), 3.09 (s, 2H), 2.71 (s, 3H), 2.54 (s, 1H), 2.32 (s, 2H), 2.22 (s, 2H), 1.99 (s, 4H), 1.64 (d, J=7.6 Hz, 2H), 1.46 (d, J=10.8 Hz, 2H).

MS-ESI calcd. $[M+H]^+$ 783, found 783.4.

Example 2

2

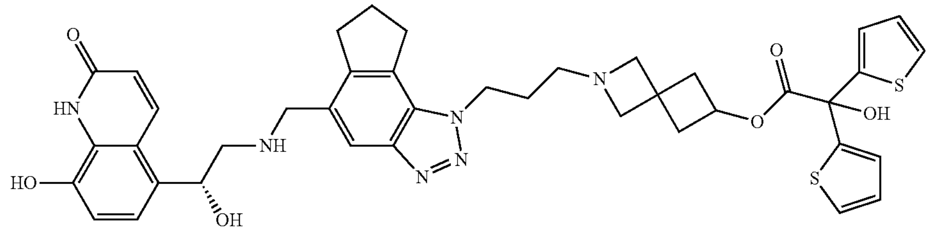

Synthetic Route:

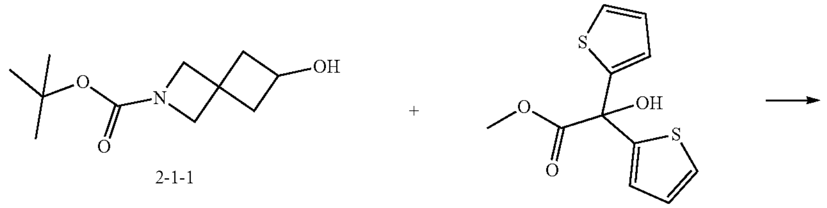

2-1-1

2-1-2

-continued

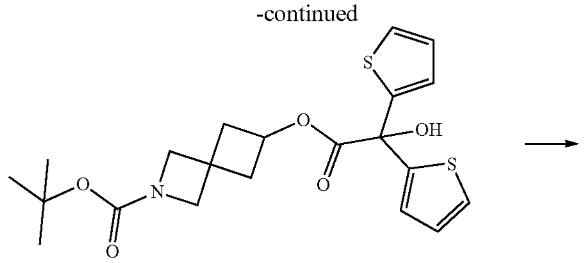

2-1

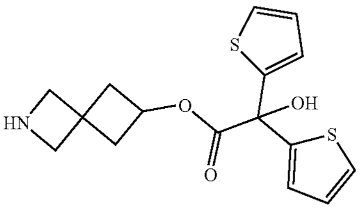

2-2

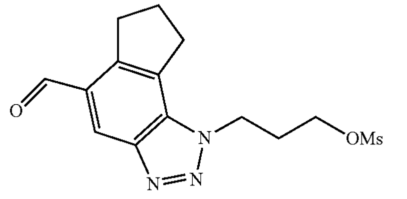

1-12

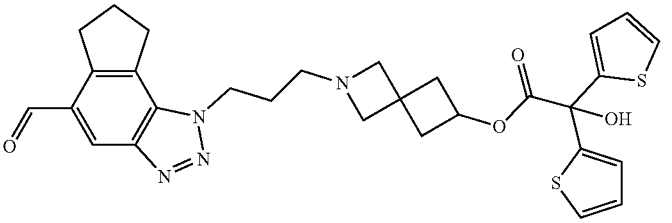

2-3

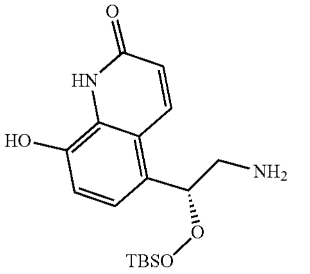

1-15

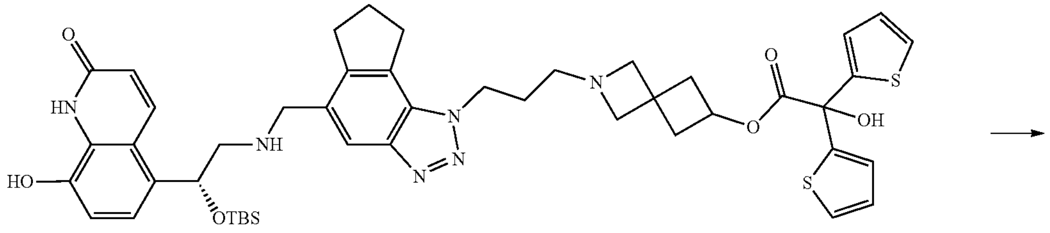

2-5

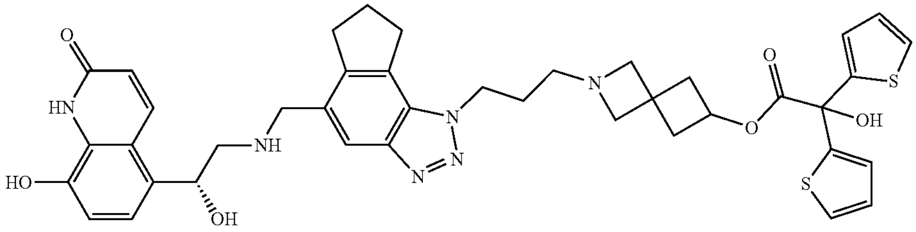

2

Step 1: Synthesis of Compound 2-1

Compound 2-1-1 (1.80 g) and 2-1-2 (2.79 g) were dissolved in anhydrous toluene (50 mL), and sodium hydride (168 mg, purity: 60%) was added in portions at room temperature. The mixture was heated to 130° C. and stirred for 14 h. The reaction solution was cooled to room temperature, and water (20 mL) was added to quench the reaction. The resulting mixture was extracted with ethyl acetate (50 mL×2). The organic phases were combined, washed with saturated brine (100 mL), dried over anhydrous sodium sulfate, filtered and concentrated under reduced pressure, and the residue was separated and purified by silica gel column chromatography (petroleum ether/ethyl acetate, 1:0-5:1) to give compound 2-1.

MS-ESI calcd. $[M+H-18]^+$ 418, found 418.

Step 2: Synthesis of Compound 2-2

Compound 2-1 (1.10 g) was dissolved in dioxane (2 mL), and hydrochloric acid/dioxane solution (10 mL, 4 M) was added. The mixture was stirred at room temperature for 0.5 h. The reaction solution was adjusted to about pH 7 with a saturated aqueous sodium carbonate solution and extracted with ethyl acetate (40 mL). The organic phase was discarded, and the aqueous phase was further adjusted to about pH 10 with a saturated aqueous sodium carbonate solution and extracted with dichloromethane/methanol=10:1 (30 mL×4). The organic phases were combined, dried over anhydrous sodium sulfate and concentrated under reduced pressure to give crude compound 2-2.

MS-ESI calcd. $[M+H]^+$ 336, found 336.

Step 3: Synthesis of Compound 2-3

Compound 2-2 (135 mg) was dissolved in acetonitrile (10 mL), and diisopropylethylamine (156.04 mg), potassium iodide (167.02 mg) and compound 1-12 (130.14 mg) were added. The mixture was heated to 90° C. and stirred for 16 h. After the reaction was completed, the reaction solution was poured into 30 mL of water, and the resulting mixture was extracted with dichloromethane (50 mL×2). The organic phases were combined, washed with saturated brine (50 mL), dried over anhydrous sodium sulfate, filtered, concentrated to dryness under reduced pressure, and separated and purified by preparative thick-layer chromatography (eluent: methanol/dichloromethane=1/20) to give compound 2-3.

MS-ESI calcd. $[M+H]^+$ 563, found 563.3.

Step 4: Synthesis of Compound 2-5

Compound 2-3 (115 mg) and compound 1-15 (68.36 mg) were dissolved in methanol (5 mL) and tetrahydrofuran (4 mL), and 4A molecular sieve (150 mg) and sodium triacetoxyborohydride (216.57 mg) were added. The mixture was stirred at 25° C. for 16 h, and sodium triacetoxyborohydride (216.57 mg) was added. The mixture was stirred at 25° C. for 71 h. The reaction solution was concentrated to dryness, and 10 mL of water was added. The resulting mixture was extracted with dichloromethane (20 mL×2). The organic phase was washed with saturated brine (20 mL), dried over anhydrous sodium sulfate, filtered, concentrated to dryness under reduced pressure, and separated and purified by preparative thick-layer chromatography (eluent: methanol/dichloromethane=1/20) to give compound 2-5.

MS-ESI calcd. $[M+H]^+$ 881, found 881.4.

Step 5: Synthesis of Formate Salt of Compound 2

Compound 2-5 (96 mg) was dissolved in tetrahydrofuran (5 mL), and triethylamine trihydrofluoride (87.81 mg) was added. The mixture was stirred at 25° C. for 16 h. After the reaction was completed, the reaction solution was concentrated to dryness under reduced pressure, and separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 2.

$^1H$ NMR (400 MHz, DMSO-$d_6$) δ: 10.77-9.94 (m, 1H), 8.21 (s, 2H), 8.13 (d, J=10.0 Hz, 1H), 7.78 (s, 1H), 7.46 (d, J=4.4 Hz, 2H), 7.06 (d, J=3.6 Hz, 3H), 7.00-6.95 (m, 2H), 6.91 (d, J=8.4 Hz, 1H), 6.42 (d, J=9.6 Hz, 1H), 5.14 (s, 1H), 4.91 (t, J=6.8 Hz, 1H), 4.67 (t, J=6.4 Hz, 2H), 3.91 (s, 6H), 3.29 (t, J=6.8 Hz, 2H), 3.22 (s, 2H), 3.17 (s, 1H), 3.14 (s, 2H), 2.94 (t, J=7.2 Hz, 2H), 2.87-2.76 (m, 2H), 2.54 (s, 1H), 2.41 (t, J=6.4 Hz, 2H), 2.21-2.07 (m, 4H), 1.90-1.81 (m, 2H).

MS-ESI calcd. $[M+H]^+$ 767, found 767.4.

Example 3

3

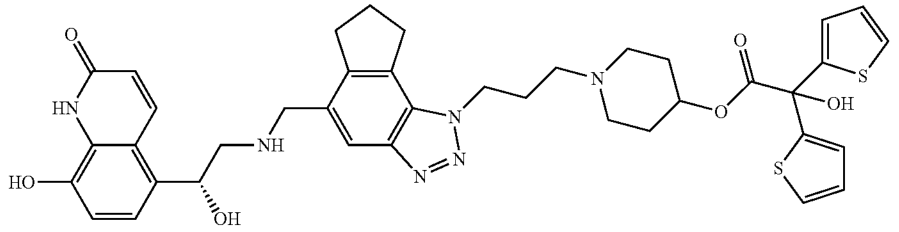

Synthetic Route:

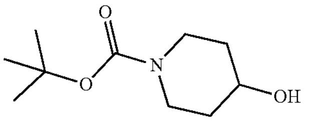

3-1-1

+

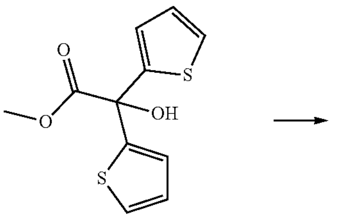

2-1-2

-continued

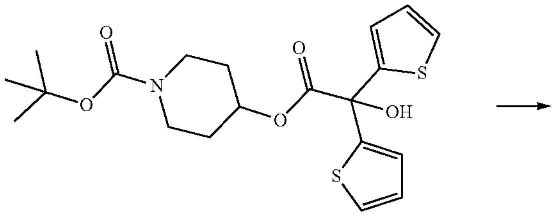

3-1

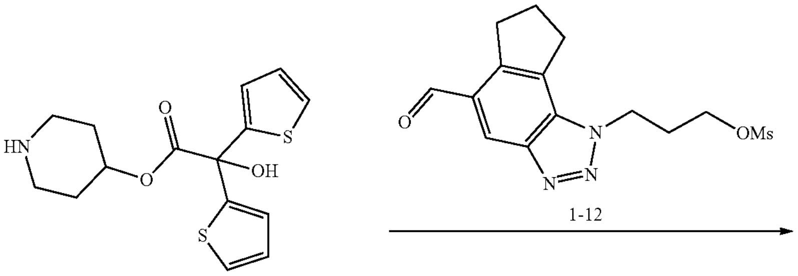

1-12

3-2

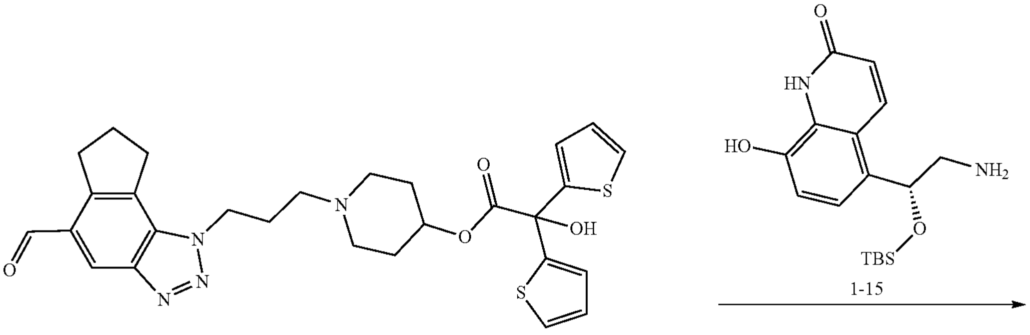

1-15

3-3

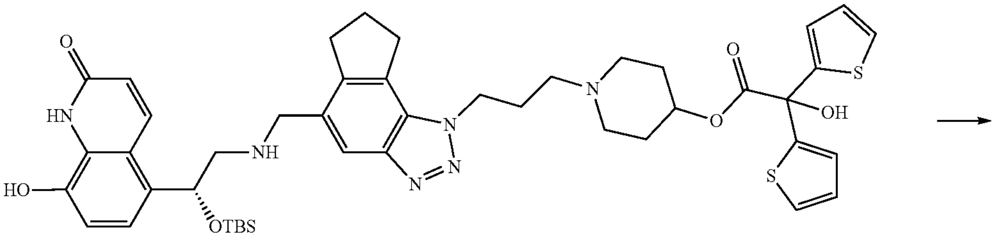

3-5

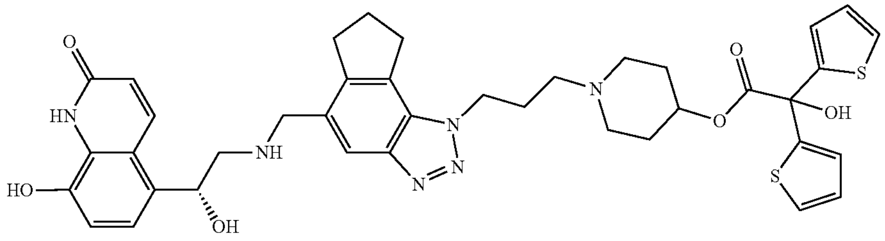

3

Step 1: Synthesis of Compound 3-1

Compound 3-1-1 (1 g) and compound 2-1-2 (1.26 g) were dissolved in toluene (20 mL), and 4-dimethylaminopyridine (607.01 mg) was added. The mixture was heated to 120° C. and stirred for 16 h. After the reaction was completed, the reaction solution was cooled to room temperature and poured into 50 mL of saturated aqueous ammonium chloride solution to quench the reaction. The resulting mixture was extracted with ethyl acetate (50 mL×2). The organic phases were combined, washed with saturated brine (50 mL), dried over anhydrous sodium sulfate, filtered and concentrated to dryness under reduced pressure, and separated and purified by flash silica gel column chromatography (eluent: ethyl acetate/petroleum ether, 0-30%) to give compound 3-1.

Step 2: Synthesis of Compound 3-2

Compound 3-1 (681 mg) was dissolved in ethyl acetate (5 mL), and hydrogen chloride/ethyl acetate solution (4 M, 12.06 mL) was added. The mixture was stirred at 25° C. for 2 h. After the reaction was completed, the reaction solution was diluted with 100 mL of ethyl acetate, adjusted to pH 7-8 with sodium carbonate solution, and subjected to liquid separation. The organic phase was washed with saturated brine (100 mL), dried over anhydrous sodium sulfate, filtered, and concentrated to dryness under reduced pressure. The residue was slurried with 5 mL of ethyl acetate and filtered, and the solid was collected and concentrated to dryness under reduced pressure to give compound 3-2.

MS-ESI calcd. $[M+H]^+$ 324, found 324.0.

Step 3: Synthesis of Compound 3-3

Compound 3-2 (100 mg) was dissolved in acetonitrile (10 mL), and diisopropylethylamine (119.88 mg), potassium iodide (128.31 mg) and compound 1-12 (99.98 mg) were added. The mixture was heated to 90° C. and stirred for 16 h. After the reaction was completed, the reaction solution was poured into 30 mL of water, and the resulting mixture was extracted with dichloromethane (50 mL×2). The organic phases were combined, washed with saturated brine (50 mL), dried over anhydrous sodium sulfate, filtered, concentrated to dryness under reduced pressure, and separated and purified by preparative thick-layer chromatography (eluent: methanol/dichloromethane=1/20) to give compound 3-3.

MS-ESI calcd. $[M+H]^+$ 551, found 551.3.

Step 4: Synthesis of Compound 3-5

Compound 3-3 (121 mg) and compound 1-15 (73.49 mg) were dissolved in methanol (5 mL) and tetrahydrofuran (4 mL), and 4A molecular sieve (150 mg) and sodium triacetoxyborohydride (232.84 mg) were added. The mixture was stirred at 25° C. for 16 h, and sodium triacetoxyborohydride (232.84 mg) was added. The mixture was stirred at 25° C. for 71 h. The reaction solution was concentrated to dryness, and 10 mL of water was added. The resulting mixture was extracted with dichloromethane (20 mL×2). The organic phase was washed with saturated brine (20 mL), dried over anhydrous sodium sulfate, filtered, concentrated to dryness under reduced pressure, and separated and purified by preparative thick-layer chromatography (eluent: methanol/dichloromethane=1/20) to give compound 3-5.

MS-ESI calcd. $[M+H]^+$ 869, found 869.4.

Step 5: Synthesis of Formate Salt of Compound 3

Compound 3-5 (130 mg) was dissolved in tetrahydrofuran (5 mL), and triethylamine trihydrofluoride (120.56 mg) was added. The mixture was stirred at 25° C. for 16 h. After the reaction was completed, the reaction solution was concentrated to dryness under reduced pressure, and separated by high performance liquid chromatography (column: Welch Xtimate C18, length×inner diameter: 100 mm×40 mm, 3 μm); preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 10% to 50% in 8 min) to give a formate salt of compound 3.

$^1H$ NMR (400 MHz, DMSO-$d_6$) δ: 10.51 (s, 2H), 10.08-9.66 (m, 1H), 9.18 (d, J=19.2 Hz, 2H), 8.23-8.05 (m, 2H), 7.46 (s, 3H), 7.25-7.06 (m, 3H), 6.98 (d, J=7.2 Hz, 3H), 6.53 (d, J=9.2 Hz, 1H), 6.25 (s, 1H), 5.41 (d, J=9.2 Hz, 1H), 5.20-4.90 (m, 1H), 4.80 (s, 2H), 4.38 (s, 2H), 3.53-3.32 (m, 5H), 3.22-3.09 (m, 6H), 2.73 (s, 1H), 2.33-2.20 (m, 3H), 2.10 (s, 1H), 2.06-1.85 (m, 3H), 1.75 (s, 1H).

MS-ESI calcd. $[M+H]^+$ 756, found 756.1.

Example 4

4

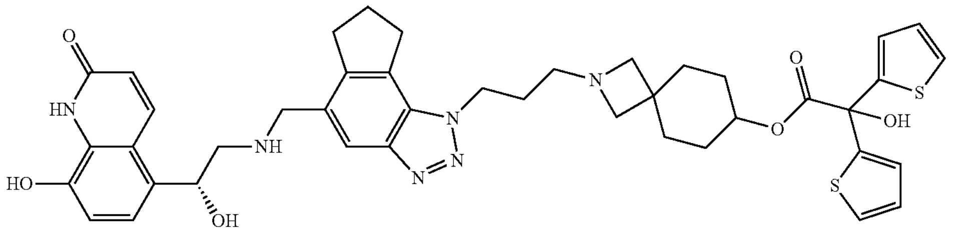

Synthetic Route:

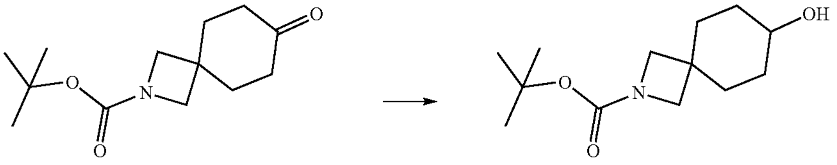

+

4-1-1 4-1-2

-continued
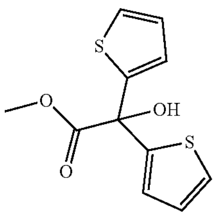
2-1-2
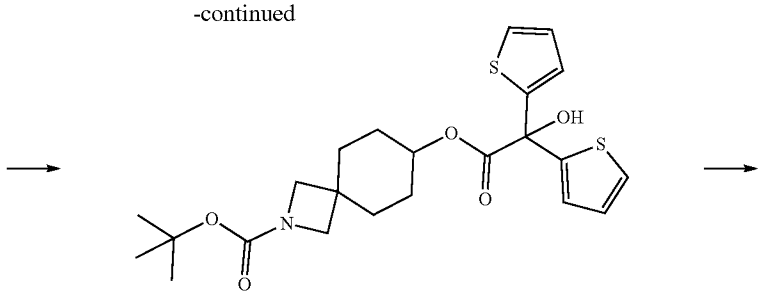
4-1-4
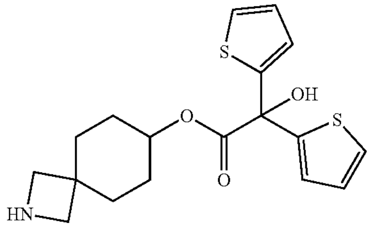
4-2
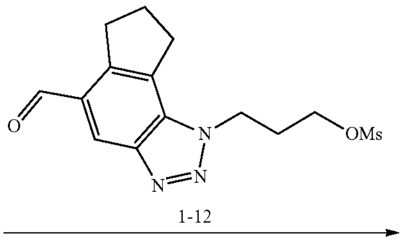
1-12
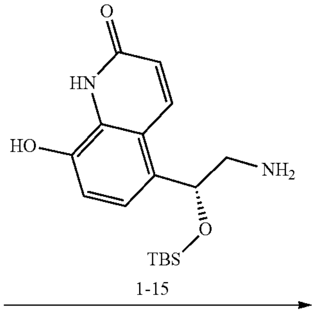
1-15
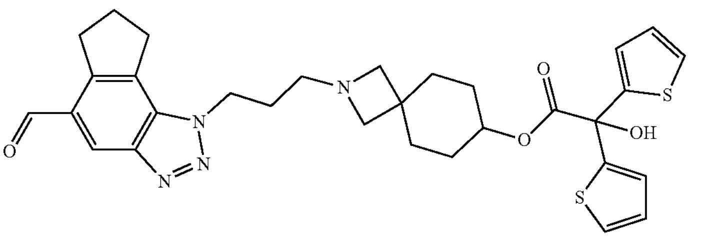
4-3
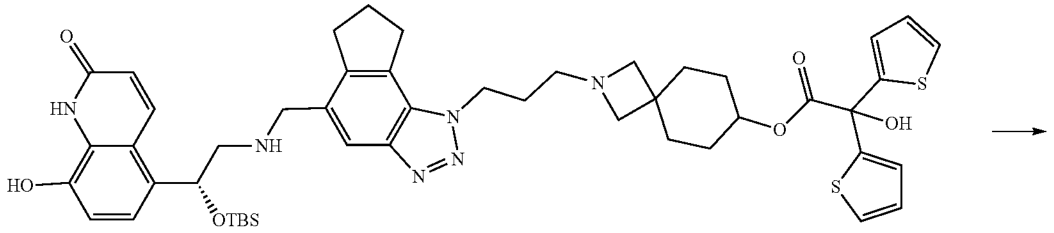
4-5
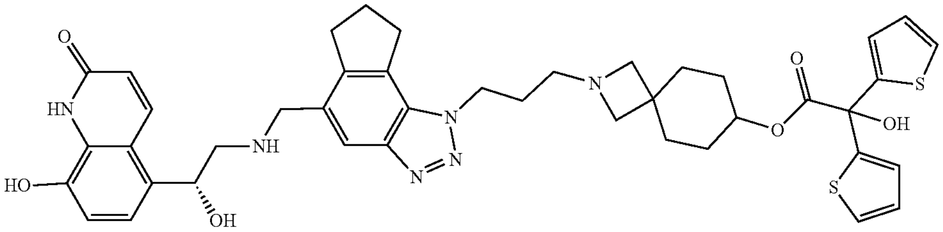
4
Step 1: Synthesis of Compound 4-1-2
Compound 4-1-1 (250 mg) was dissolved in methanol (4 mL), and sodium borohydride (118 mg) was added at 0° C. The mixture was stirred at 0° C. for 0.5 h. Water (5 mL) was added to quench the reaction, and the resulting mixture was extracted with ethyl acetate (10 mL×2). The organic phases were combined, dried over anhydrous sodium sulfate, filtered and concentrated under reduced pressure to give crude compound 4-1-2.

$^1$H NMR (400 MHz, $CD_3OD$) δ: 3.60-3.54 (m, 4H), 3.32-3.30 (m, 1H), 1.90-1.77 (m, 4H), 1.58-1.48 (m, 2H), 1.43 (s, 9H), 1.36-1.26 (m, 2H).

Step 2: Synthesis of Compound 4-1-4

Compound 4-1-2 (161 mg) and compound 2-1-2 (170 mg) were dissolved in anhydrous toluene (4 mL), and potassium tert-butoxide (45 mg) and anhydrous magnesium sulfate (161 mg) were added in portions at room temperature. The mixture was heated to 120° C. and stirred for 2 h. The reaction solution was cooled to room temperature, and sodium hydride (13 mg, purity: 60%) was added. The resulting mixture was heated to 120° C. and stirred for 2 h. The reaction solution was cooled to room temperature and added to a saturated aqueous ammonium chloride solution (10 mL) in an ice bath to quench the reaction. The resulting mixture was extracted with ethyl acetate (10 mL×2). The organic phases were combined, washed with saturated brine (20 mL), dried over anhydrous sodium sulfate, filtered and concentrated under reduced pressure, and the residue was separated and purified by silica gel column chromatography (petroleum ether/ethyl acetate, 1:0-5:1) to give compound 4-1-4.

MS-ESI calcd. $[M+H-18-56]^+$ 390, found 390.

Step 3: Synthesis of Compound 4-2

Compound 4-1-4 (200 mg) was dissolved in dioxane solution (2 mL), and an aqueous formic acid solution (4 mL, concentration: 75%) was added. The mixture was stirred at 60° C. for 14 h. The reaction solution was concentrated under reduced pressure, and a saturated aqueous sodium carbonate solution (10 mL) was added to the residue. The resulting mixture was extracted with ethyl acetate (20 mL×4). The organic phases were combined, dried over anhydrous sodium sulfate, and concentrated under reduced pressure to give crude compound 4-2 (150 mg, colorless oil, purity: 85%).

MS-ESI calcd. $[M+H]^+$ 364, found 364.

Step 4: Synthesis of Compound 4-3

Compound 1-12 (62 mg) was dissolved in acetonitrile (10 mL), and diisopropylethylamine (74.34 mg), potassium iodide (47.74 mg) and compound 4-2 (69.69 mg) were added. The mixture was heated to 90° C. and stirred for 16 h. After the reaction was completed, the reaction solution was concentrated to dryness under reduced pressure, and separated and purified by flash silica gel column chromatography (eluent: ethyl acetate/petroleum ether, 0-50%; methanol/dichloromethane, 0-5%) to give compound 4-3.

MS-ESI calcd. $[M+H]^+$ 591, found 591.2.

Step 5: Synthesis of Compound 4-5

Compound 4-3 (40 mg) and compound 1-15 (22.65 mg) were dissolved in methanol (2.5 mL) and tetrahydrofuran (2 mL), and 4A molecular sieve (50 mg) and sodium triacetoxyborohydride (71.75 mg) were added. The mixture was stirred at 25° C. for 16 h, and sodium triacetoxyborohydride (71.75 mg) was added. The mixture was stirred at 25° C. for 24 h. The reaction solution was concentrated to dryness, and 10 mL of water was added. The resulting mixture was extracted with dichloromethane (20 mL×2). The organic phase was washed with saturated brine (20 mL), dried over anhydrous sodium sulfate, filtered, concentrated to dryness under reduced pressure, and separated and purified by flash silica gel column chromatography (eluent: methanol/dichloromethane, 0-2%) to give compound 4-5.

MS-ESI calcd. $[M+H]^+$ 909, found 909.5.

Step 6: Synthesis of Formate Salt of Compound 4

Compound 4-5 (35 mg) was dissolved in tetrahydrofuran (5 mL), and triethylamine trihydrofluoride (31.03 mg) was added. The mixture was stirred at 25° C. for 16 h. After the reaction was completed, the reaction solution was concentrated to dryness under reduced pressure, and separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 4.

$^1$H NMR (400 MHz, DMSO-$d_6$) δ: 10.32 (s, 1H), 8.20 (s, 1H), 8.13 (d, J=9.6 Hz, 1H), 7.76 (s, 1H), 7.46 (d, J=4.4 Hz, 2H), 7.27 (s, 1H), 7.11-7.04 (m, 3H), 7.00-6.94 (m, 2H), 6.90 (d, J=8.0 Hz, 1H), 6.41 (d, J=9.6 Hz, 1H), 5.12 (s, 1H), 4.78 (s, 1H), 4.68 (s, 2H), 3.88 (s, 2H), 3.30 (d, J=6.8 Hz, 2H), 2.97 (d, J=3.2 Hz, 4H), 2.95-2.74 (m, 6H), 2.54 (s, 2H), 2.22-2.13 (m, 2H), 1.89 (s, 2H), 1.62 (s, 4H), 1.54-1.34 (m, 4H).

MS-ESI calcd. $[M+H]^+$ 795, found 795.5.

Example 5 and Example 6

5 or 6

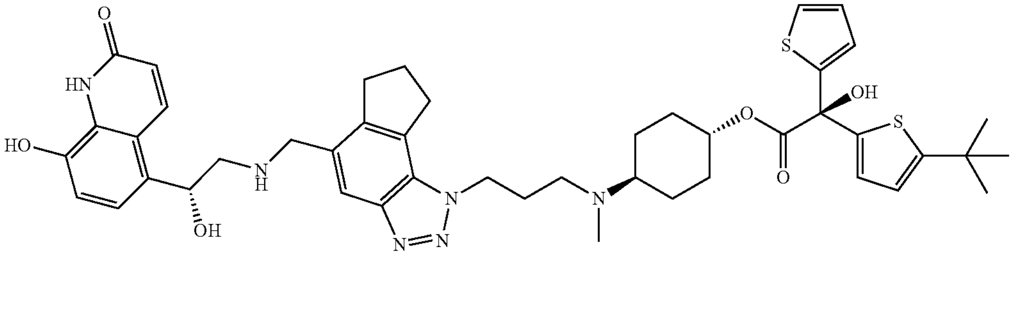

-continued
5 or 6
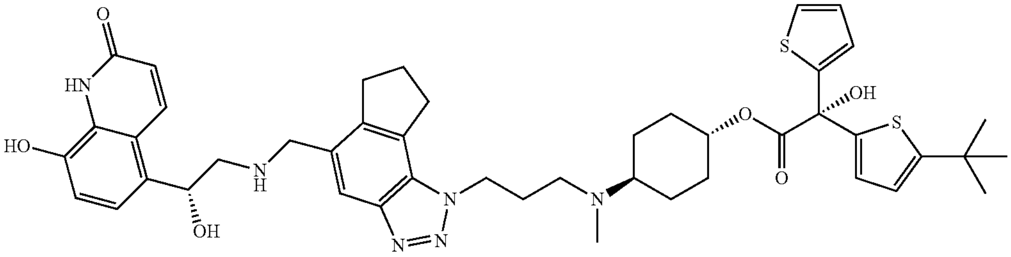
Synthetic Route:
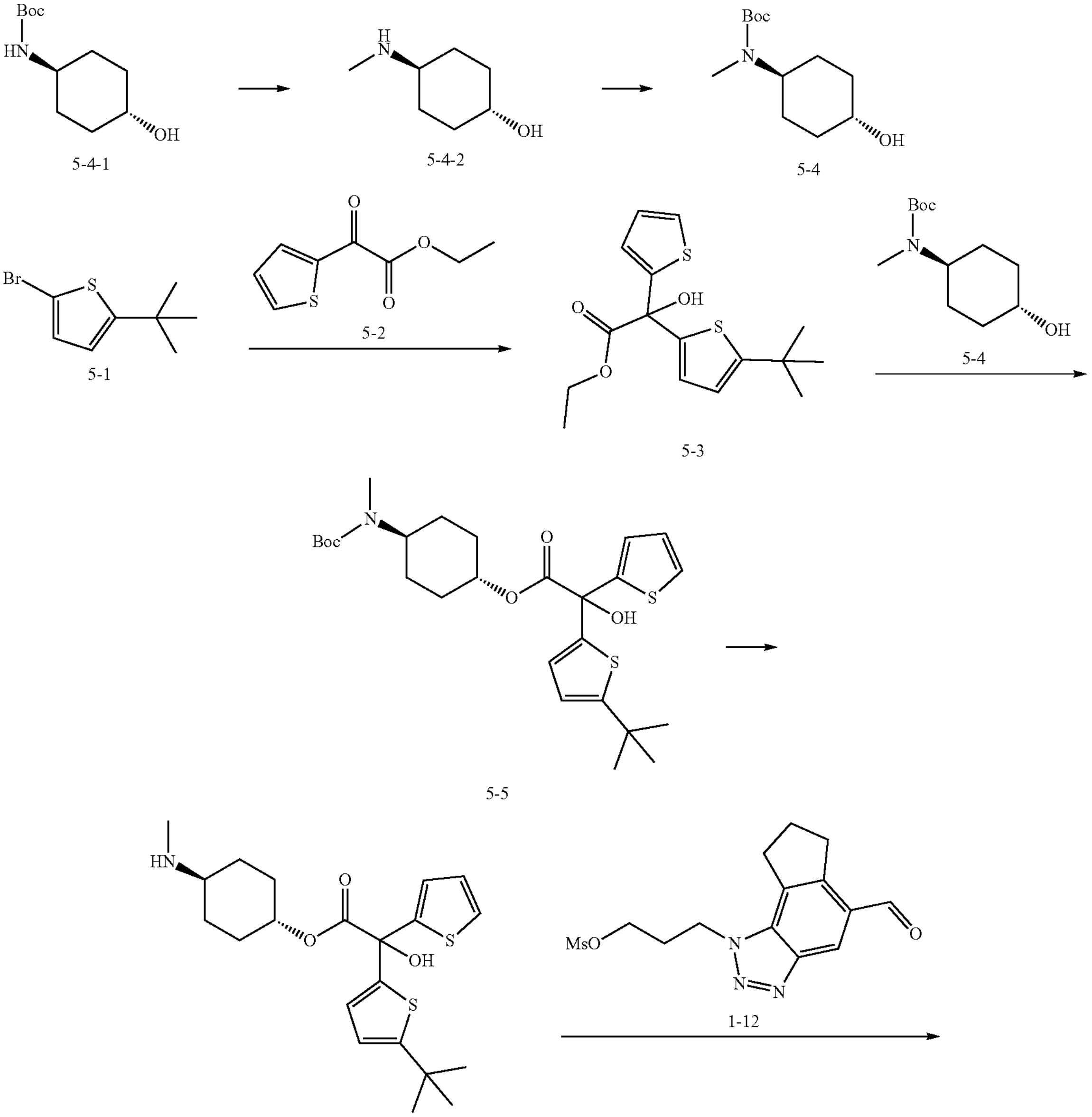
5-4-1
5-4-2
5-4
5-1
5-2
5-3
5-4
5-5
5-6
1-12

-continued
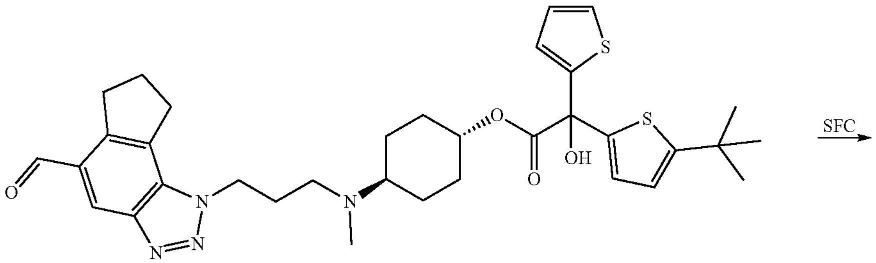
5-7
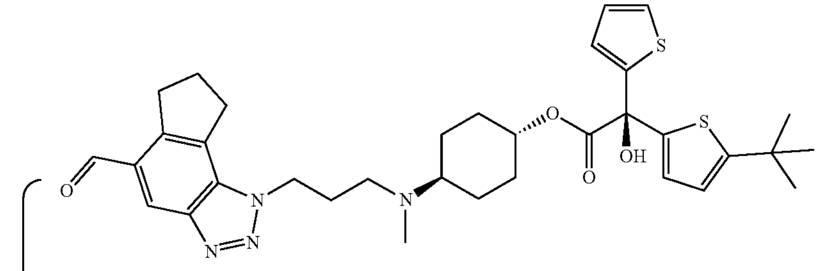
5-7A or 5-7B
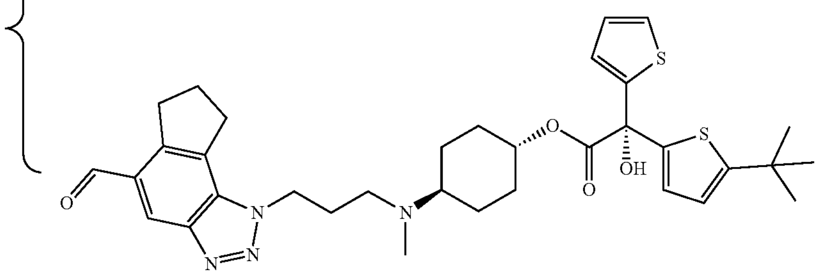
5-7A or 5-7B
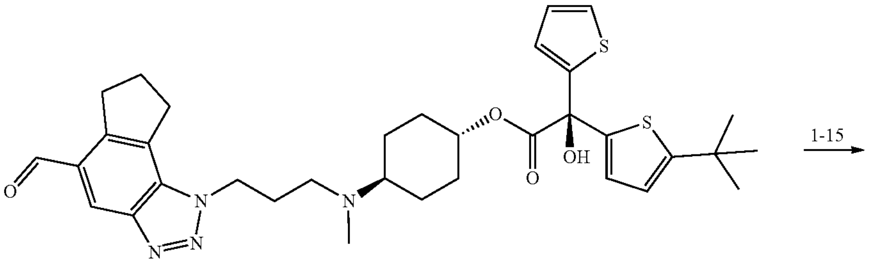
5-7A or 5-7B
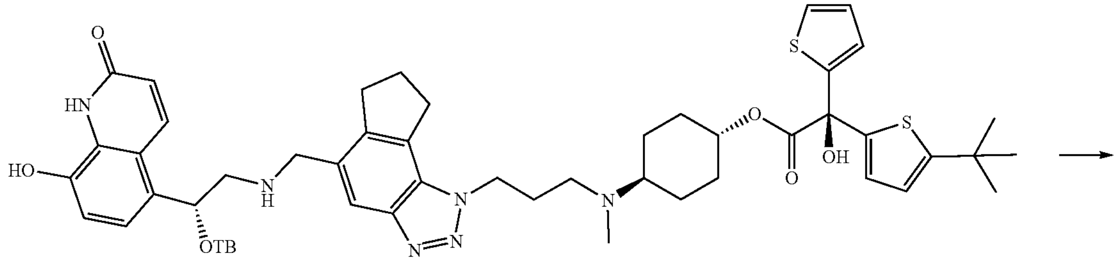
5-8 or 6-1

-continued

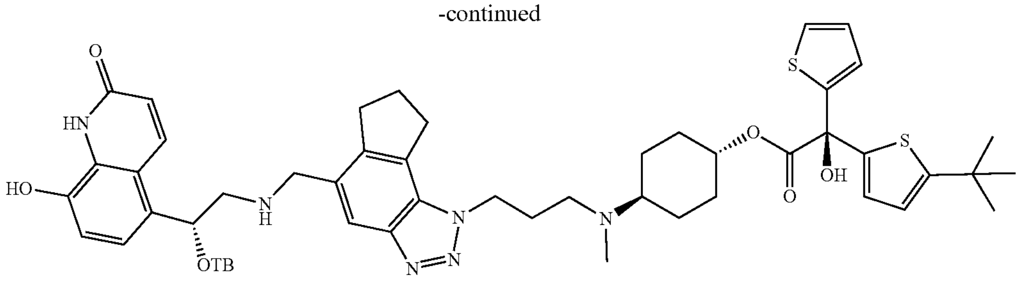

5 or 6

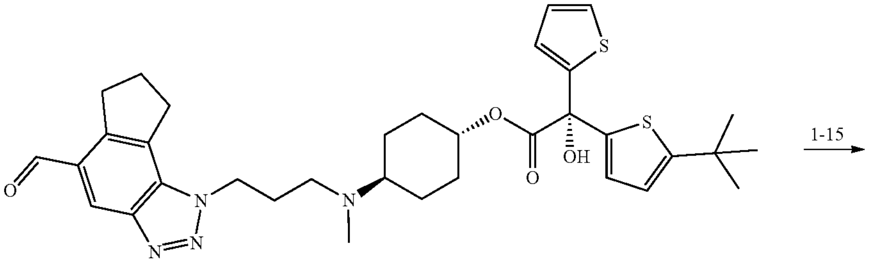

5-7A or 5-7B

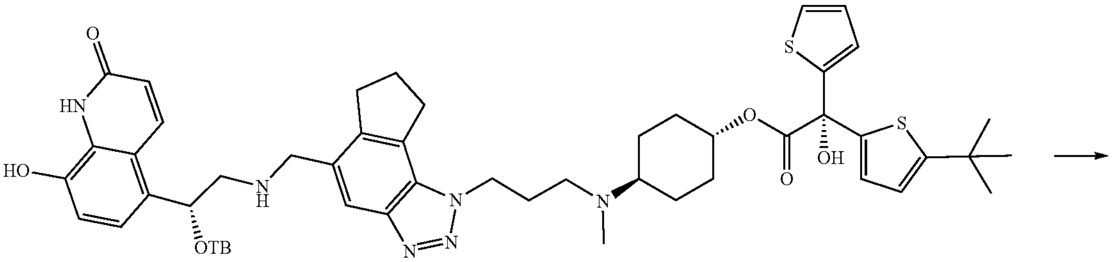

5-8 or 6-1

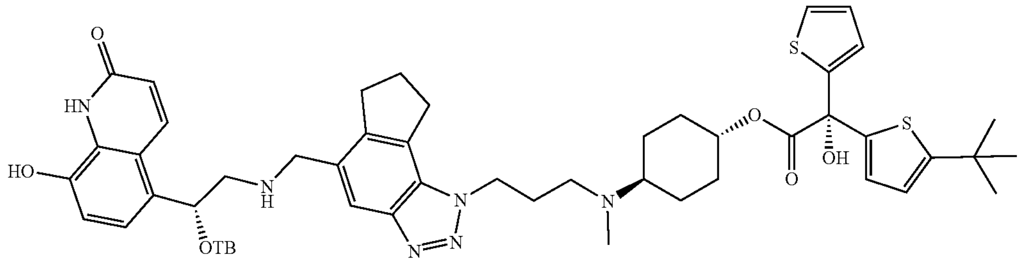

5 or 6

Step 1: Synthesis of Compound 5-4-2

Lithium aluminum hydride (9.70 g) was dissolved in tetrahydrofuran (500 mL), and compound 5-4-1 (11.0 g) was added in portions at 0° C. The mixture was heated to 75° C. and stirred for 14 h. Water (10 mL) was carefully and slowly added dropwise to the reaction solution at 0° C. to quench the reaction, and 4 N aqueous sodium hydroxide solution (10 mL) was added, followed by the addition of water (20 mL). The resulting mixture was filtered, and the filtrate was dried over anhydrous sodium sulfate, filtered and concentrated under reduced pressure. The residue was slurried with petroleum ether (80 mL) at room temperature for 20 min, filtered and concentrated under reduced pressure to give compound 5-4-2.

$^1$H NMR (400 MHz, $CDCl_3$) δ: 3.63-3.56 (m, 1H), 2.40 (s, 3H), 2.34-2.32 (m, 1H), 1.97-1.92 (m, 4H), 1.35-1.25 (m, 2H), 1.15-1.08 (m, 2H).

Step 2: Synthesis of Compound 5-4

Compound 5-4-2 (4.1 g) was dissolved in dichloromethane (30 mL) and isopropanol (30 mL), and di-tert-butyl dicarbonate (9.70 g) was added at room temperature. The mixture was stirred at room temperature for 15 h. Water (50 mL) was added to the reaction solution, and the resulting mixture was extracted with dichloromethane (50 mL×2). The organic phases were combined, dried over anhydrous sodium sulfate and concentrated under reduced pressure to give crude compound 5-4.

$^1$H NMR (400 MHz, $CDCl_3$) δ: 4.05-3.74 (m, 1H), 3.58-3.52 (m, 1H), 2.70 (s, 3H), 2.05-1.98 (m, 2H), 1.82-1.78 (m, 2H), 1.72-1.66 (m, 2H), 1.52 (s, 9H), 1.44-1.36 (m, 2H).

Step 3: Synthesis of Compound 5-3

Compound 5-1 (0.677 g) was dissolved in tetrahydrofuran (60 mL), and n-butyllithium (1.22 mL, concentration: 2.5 M) was added at −70° C. The mixture was vacuumized and purged with nitrogen three times, and stirred at −70° C. for 20 min. Compound 5-2 (0.569 g) dissolved in 6 mL of tetrahydrofuran was added to the reaction solution, and the resulting mixture was reacted at −70° C. for 1 h. The reaction was quenched with 20 mL of aqueous ammonium chloride solution at −70° C., and 20 mL of water was added. The resulting mixture was extracted with 60 mL of ethyl acetate in three times. Finally, the organic phase was dried over anhydrous sodium sulfate and concentrated under reduced pressure. After concentration, the residue was separated and purified by silica gel column chromatography (petroleum ether/ethyl acetate, 1:0-5:1) to give compound 5-3.

MS-ESI calcd. $[M+H-18]^+$ 306.9, found 306.9.

Step 4: Synthesis of Compound 5-5

Compound 5-3 (200 mg) was dissolved in toluene (2.5 mL), and sodium hydride (40.19 mg, purity: 60%) and compound 5-4 (212 mg) were added. The mixture was vacuumized and purged with nitrogen three times, and reacted at 120° C. for 12 h. The reaction was quenched with 5 mL of saturated aqueous ammonium chloride, solution and 5 mL of water was added. The resulting mixture was extracted with 30 mL of ethyl acetate in three times. The organic phase was dried over anhydrous sodium sulfate and concentrated under reduced pressure. After concentration, the residue was separated and purified by silica gel column chromatography (petroleum ether/ethyl acetate, 1:0-5:1) to give compound 5-5.

MS-ESI calcd. $[M+H-18]^+$ 490, found 490.

Step 5: Synthesis of Compound 5-6

Compound 5-5 (245 mg) was dissolved in 1,4-dioxane (2 mL), and the solution was vacuumized and purged with nitrogen three times, followed by the addition of HCl/dioxane (6.45 mL, concentration: 4 M) under nitrogen atmosphere. The mixture was reacted at 25° C. for 1 h to give crude product 5-6. Purification was not required in this reaction, and TLC or mass spectrometry was performed to determine that the starting material was consumed completely. The product would be directly used in the next step if its content exceeded 85% in the reaction solution.

MS-ESI calcd. $[M+H]^+$ 408, found 408.

Step 6: Synthesis of Compound 5-7

Compound 5-6 (70 mg) was dissolved in acetonitrile (7 mL), and the solution was vacuumized and purged with nitrogen three times, followed by the addition of compound 1-12 (55 mg), DIPEA (66 mg) and KI (42 mg) under nitrogen atmosphere. The resulting mixture was stirred at 90° C. for 16 h. After the reaction was completed, the reaction solution was concentrated under reduced pressure, and the residue was separated and purified by silica gel column chromatography (dichloromethane/methanol, 1:0-10:1) to give compound 5-7.

MS-ESI calcd. $[M+H]^+$ 634, found 634.

Step 7: Preparation of Compounds 5-7A and 5-7B

Compound 5-7 (253 mg) was separated and purified by chiral liquid chromatography to give compound 5-7A and compound 5-7B.

SFC separation method (chromatographic column: AS-3 150 mm×4.6 mm, 3 μm; mobile phase: A: carbon dioxide; B: ethanol (containing 0.05% ammonium hydroxide) 40%-40%, flow rate: 2.5 mL/min; column temperature: 40° C.).

The retention time of compound 5-7A in the chiral high-performance liquid chromatographic column was 5.656 min.

The retention time of compound 5-7B in the chiral high-performance liquid chromatographic column was 6.234 min.

Step 8: Synthesis of Compound 5-8

Compound 5-7A (50 mg) and compound 1-15 (34.5 mg) were dissolved in anhydrous methanol (3 mL) and anhydrous tetrahydrofuran (1.5 mL), and DIEA (22.6 mg) and $NaBH(OAc)_3$ (92 mg) were added. The mixture was reacted at 20° C. for 12 h, and $NaBH(OAc)_3$ (92 mg) was added. The mixture was reacted for another 8 h, and $NaBH(OAc)_3$ (92 mg) was added. The mixture was reacted for another 14 h. An aqueous $Na_2CO_3$ solution (5 mL, concentration: 4%) was added to the reaction solution, and the resulting mixture was extracted with ethyl acetate (60 mL) in three times. The resulting liquid was dried and concentrated, and the residue was collected to give product 5-8, which was directly used in the next reaction without purification.

MS-ESI calcd. $[M+H]^+$ 953, found 953.

Step 9: Synthesis of Formate Salt of Compound 5

Compound 5-8 (67 mg) was dissolved in anhydrous tetrahydrofuran (2 mL), and triethylamine trihydrofluoric acid (80 mg) was added. The mixture was reacted at 25° C. for 16 h. The reaction solution was concentrated under reduced pressure, and 1 mL of DMSO and 1 mL of acetonitrile were added. The mixture was separated by high performance liquid chromatography (formic acid method, preparative column: Phenomenex Gemini-NX C18, length×inner diameter: 75×30 mm, 3 μm; preparation method: the crude product was dissolved in dimethyl sulfoxide and filtered through a 0.45 μm filter membrane to give a sample solution; mobile phase system: acetonitrile/water (0.225% formic acid); gradient elution method: acetonitrile, from 15% to 35% in 7 min) to give a formate salt of compound 5.

MS-ESI calcd. $[M+H]^+$ 839, found 839.

$^1H$ NMR (400 MHz, DMSO-$d_6$) δ: 10.32 (s, 1H), 8.18 (s, 2H), 8.16-8.11 (m, 1H), 7.77 (s, 1H), 7.48-7.43 (m, 1H), 7.15-7.03 (m, 3H), 7.00-6.95 (m, 1H), 6.94-6.89 (m, 1H), 6.85-6.82 (m, 1H), 6.73-6.69 (m, 1H), 6.46-6.40 (m, 1H), 5.12 (s, 1H), 4.77-4.60 (m, 4H), 3.89 (s, 2H), 2.99-2.90 (m, 2H), 2.90-2.76 (m, 3H), 2.47-2.43 (m, 3H), 2.33 (s, 1H), 2.24-2.09 (m, 5H), 2.08-1.94 (m, 3H), 1.90 (s, 2H), 1.68 (s, 2H), 1.46-1.31 (m, 5H), 1.30 (s, 9H).

The formate salt of compound 6 was prepared in a 2-step reaction with compound 5-7B as the starting material by referring to the synthetic route of the formate salt of compound 5.

Formate salt of compound 6: $^1H$ NMR (400 MHz, DMSO-$d_6$) δ: 10.26 (s, 1H), 8.15 (s, 1H), 8.14-8.10 (m, 1H), 7.72 (s, 1H), 7.46-7.42 (m, 1H), 7.12-7.03 (m, 4H), 6.99-6.94 (m, 1H), 6.91-6.87 (m, 1H), 6.85-6.80 (m, 1H), 6.72-6.69 (m, 1H), 6.43-6.38 (m, 1H), 5.08 (s, 1H), 4.74-4.64 (m, 3H), 3.83 (s, 2H), 2.97-2.90 (m, 2H), 2.79-2.74 (m, 1H), 2.66 (s, 2H), 2.42-2.42 (m, 1H), 2.32 (s, 2H), 2.23-2.08 (m, 7H), 2.03-1.92 (m, 3H), 1.89 (s, 2H), 1.65 (s, 2H), 1.33 (s, 5H), 1.29 (s, 9H);

MS-ESI calcd. $[M+H]^+$ 839, found 839.

Example 7
7
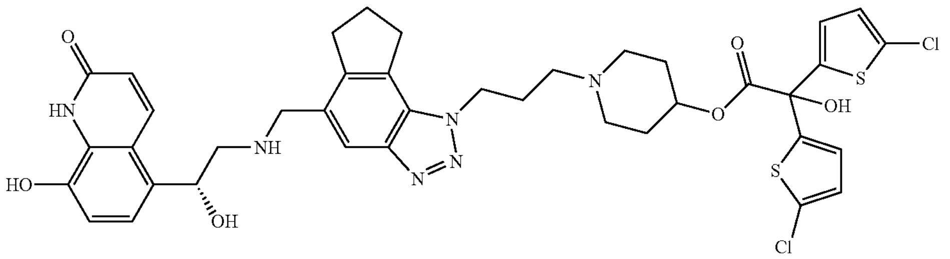
Synthetic Route:
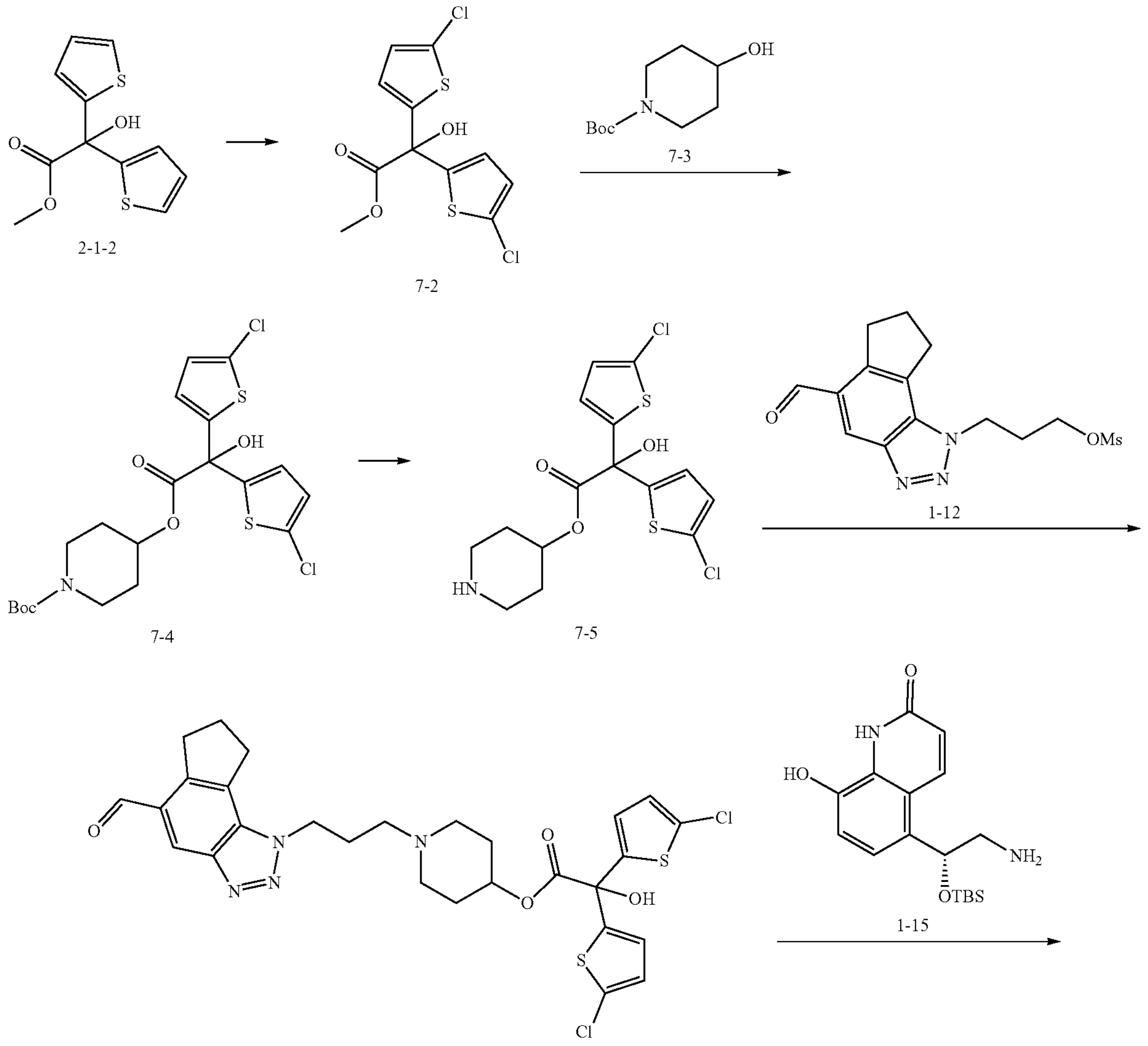
2-1-2
7-2
7-3
7-4
7-5
1-12
7-6
1-15

-continued

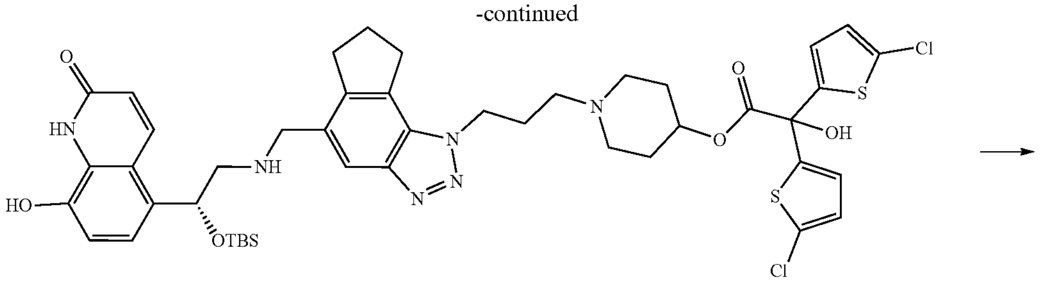

7-7

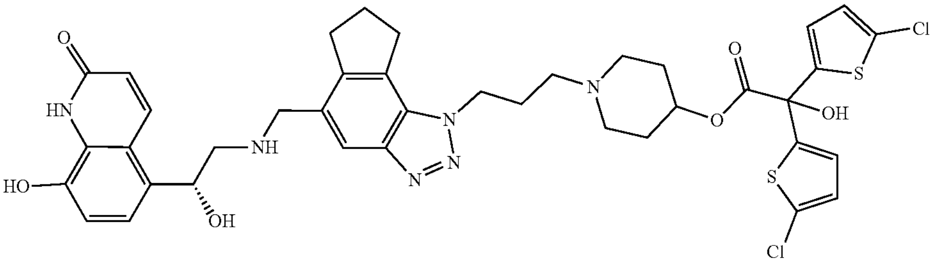

7

Step 1: Synthesis of Compound 7-2

Compound 2-1-2 (2.5 g) was dissolved in dichloromethane (7 mL), and the solution was vacuumized and purged with nitrogen three times, followed by the addition of NCS (2.36 g) at 25° C. Then, the mixture was stirred at 25° C. for 12 h. The reaction solution was distilled under reduced pressure and separated by high performance liquid chromatography to give compound 7-2.

MS-ESI calcd. $[M+H-18]^+$ 305, found 305.

Step 2: Synthesis of Compound 7-4

Compound 7-2 (500 mg) was dissolved in toluene (5 mL), and sodium hydride (61.88 mg, purity: 60%) and 7-3 (311.34 mg) were added. The mixture was vacuumized and purged with nitrogen three times, and reacted at 120° C. for 12 h. The reaction was quenched with 10 mL of saturated aqueous ammonium chloride solution, and 10 mL of water was added. The resulting mixture was extracted with 600 mL of ethyl acetate in three times. The organic phase was dried over anhydrous sodium sulfate and concentrated under reduced pressure. After concentration, the residue was separated and purified by silica gel column chromatography (petroleum ether/ethyl acetate, 1:0-5:1) to give compound 7-4.

MS-ESI calcd. $[M+H-18]^+$ 474, found 474.

Step 3: Synthesis of Compound 7-5

Compound 7-4 (0.596 g) was dissolved in 1,4-dioxane (2 mL), and the solution was vacuumized and purged with nitrogen three times, followed by the addition of HCl/dioxane (18.15 mL, concentration: 4 M) under nitrogen atmosphere. The mixture was reacted at 25° C. for 1 h to give crude product 7-5. Purification was not required in this reaction, and TLC or mass spectrometry was performed to determine that the starting material was consumed completely. The product would be directly used in the next step if its content exceeded 85% in the reaction solution.

MS-ESI calcd. $[M+H]^+$ 392.3, found 391.8.

Step 4: Synthesis of Compound 7-6

Compound 7-5 (200 mg) was dissolved in acetonitrile (20 mL), and the solution was vacuumized and purged with nitrogen three times, followed by the addition of compound 1-12 (164.85 mg), DIPEA (197.66 mg) and KI (800 mg) under nitrogen atmosphere. The resulting mixture was stirred at 90° C. for 16 h. After the reaction was completed, the reaction solution was concentrated under reduced pressure, and the residue was separated and purified by silica gel column chromatography (dichloromethane/methanol, 1:0-10:1) to give compound 7-6.

MS-ESI calcd. $[M+H]^+$ 619, found 619.

Step 5: Synthesis of Compound 7-7

Compound 7-6 (210 mg) and compound 1-15 (148.58 mg) were dissolved in anhydrous methanol (4 mL) and anhydrous tetrahydrofuran (2 mL), and DIEA (97.34 mg) and $NaBH(OAc)_3$ (399.08 mg) were added. The mixture was reacted at 20° C. for 12 h, and $NaBH(OAc)_3$ (399.08 mg) was added. The mixture was reacted for another 8 h, and $NaBH(OAc)_3$ (399.08 mg) was added. The mixture was reacted for another 14 h. An aqueous $Na_2CO_3$ solution (5 mL, concentration: 4%) was added to the reaction solution, and the resulting mixture was extracted with ethyl acetate (60 mL) in three times. The resulting liquid was dried and concentrated, and the residue was collected to give product 7-7, which was directly used in the next reaction without purification.

MS-ESI calcd. $[M+H]^+$ 938, found 938.

Step 6: Synthesis of Trifluoroacetate Salt of Compound 7

Compound 7-7 (350 mg) was dissolved in anhydrous tetrahydrofuran (6 mL), and triethylamine trihydrofluoric acid (350 mg) was added. The mixture was reacted at 25° C. for 16 h. The reaction solution was concentrated under reduced pressure, and 1 mL of DMSO and 1 mL of acetonitrile were added. The mixture was separated and purified by high performance liquid chromatography (formic acid method, preparative column: Welch Xtimate C18, length×inner diameter: 100×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 28% to 58% in 8 min) to give a trifluoroacetate salt of compound 7.

MS-ESI calcd. $[M+H]^+$ 823, found 823.

$^1H$ NMR (400 MHz, DMSO-$d_6$) δ: 10.61 (s, 1H), 10.48 (s, 1H), 10.33-10.01 (m, 1H), 9.39-9.16 (m, 2H), 8.16 (s, 1H), 8.08 (s, 1H), 7.82 (s, 1H), 7.25-7.07 (m, 1H), 7.02-7.00 (m, 2H), 6.99-6.91 (m, 2H), 6.59-6.48 (m, 1H), 5.50-5.37 (m, 1H), 5.20-4.97 (m, 1H), 4.81 (s, 2H), 4.39 (s, 2H), 3.58-3.50 (m, 1H), 3.49-3.44 (m, 1H), 3.39-3.34 (m, 2H), 3.29-3.11 (m, 6H), 2.38-2.18 (m, 6H), 2.14-1.93 (m, 4H), 1.80 (s, 2H).
Example 8 and Example 9
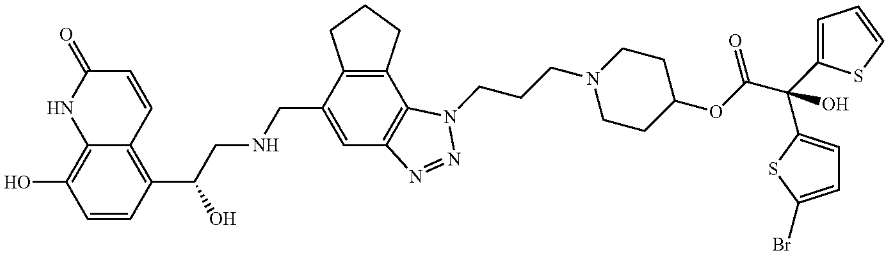
8 or 9
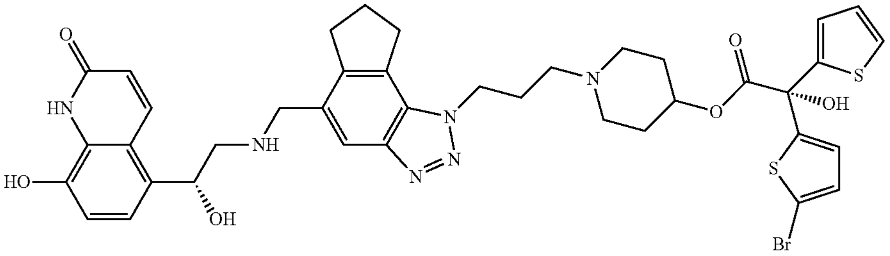
8 or 9
Synthetic Route:
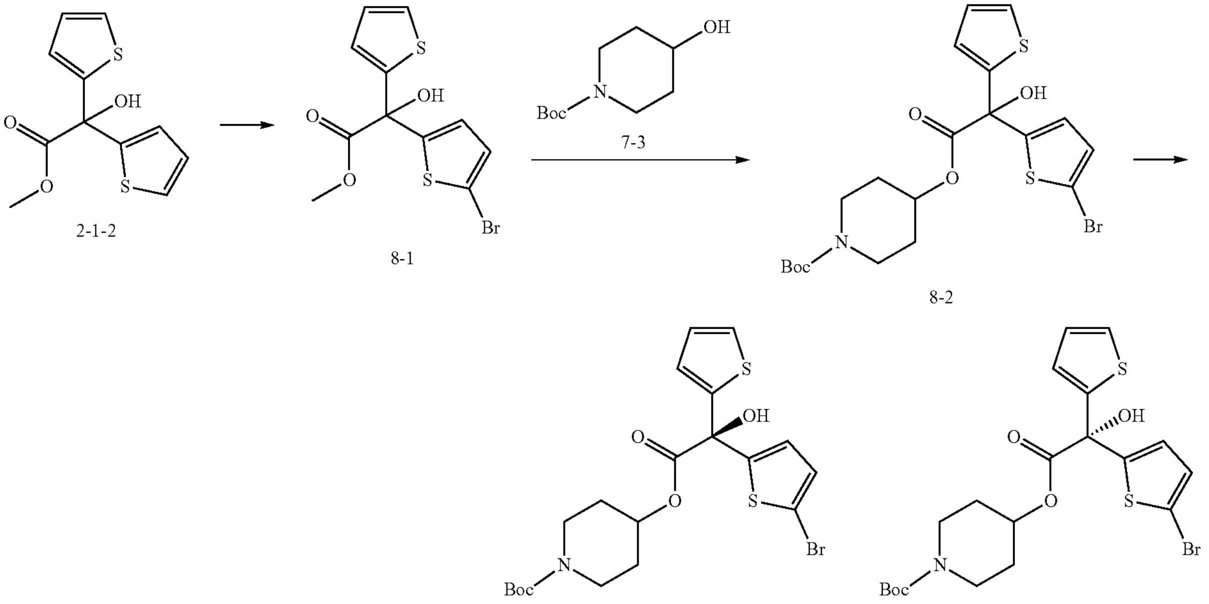
2-1-2
8-1
7-3
8-2
8-2A or 8-2B
8-2A or 8-2B -continued
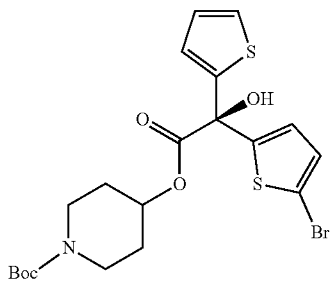
8-2A or 8-2B
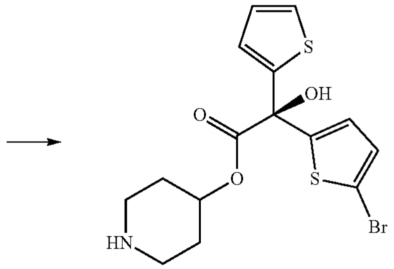
8-3 or 9-1
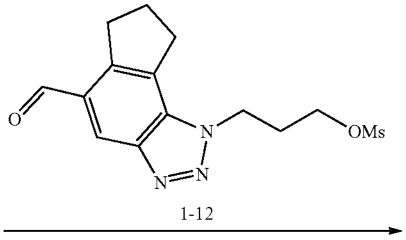
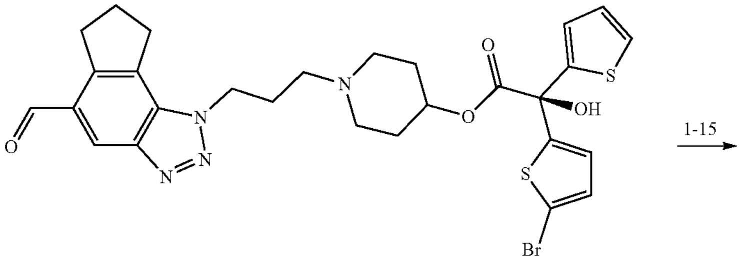
8-4 or 9-2
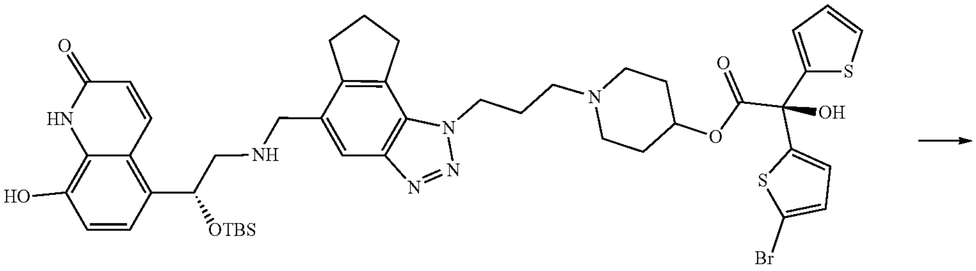
8-5 or 9-3
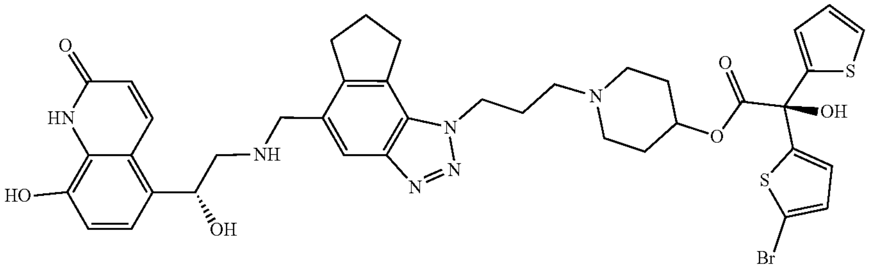
8 or 9
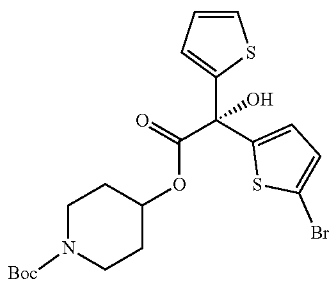
8-2A or 8-2B
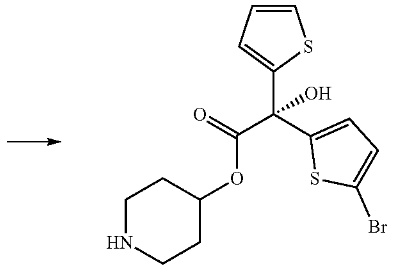
8-3 or 9-1
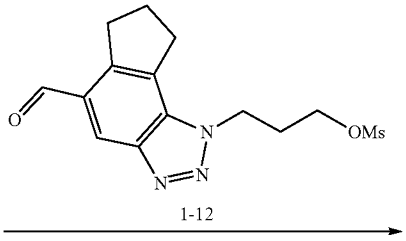

-continued

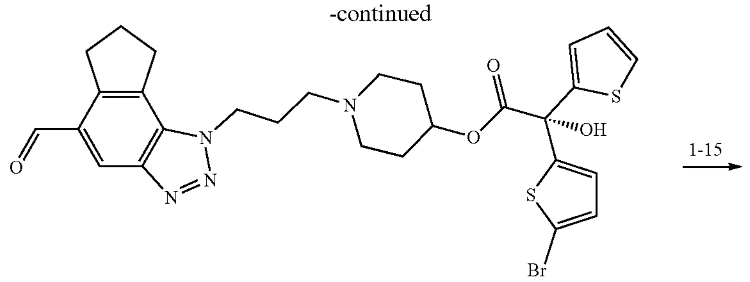

8-4 or 9-2

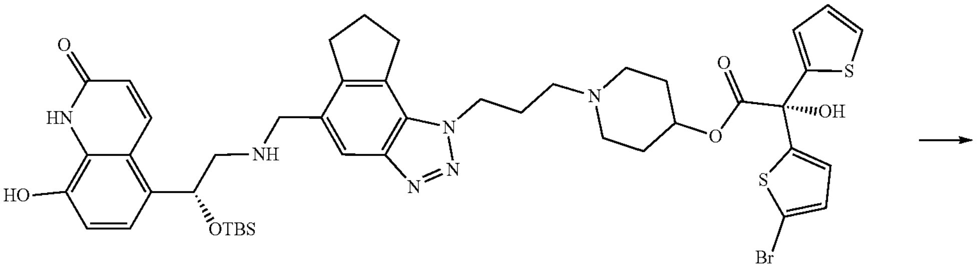

8-5 or 9-3

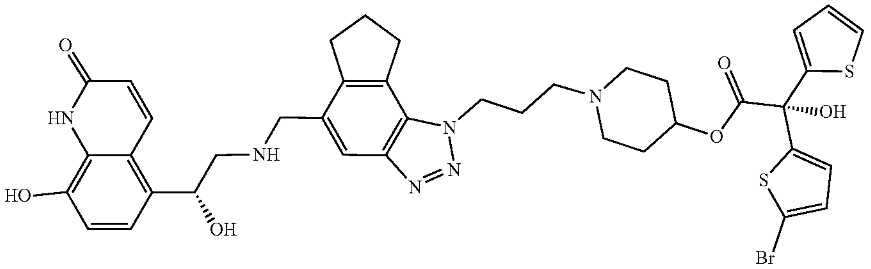

8 or 9

Step 1: Synthesis of Compound 8-1

Compound 2-1-2 (2 g) was dissolved in anhydrous dichloromethane (45 mL), and N-bromosuccinimide (2.10 g) was added. The mixture was stirred at 25° C. for 36 h. The reaction solution was concentrated under reduced pressure, and the residue was separated and purified by high performance liquid chromatography to give compound 8-1.

MS-ESI calcd. $[M+H-18]^+$ 314, 316, found 314.6.

Step 2: Synthesis of Compound 8-2

Compound 8-1 (1.18 g) and compound N-Boc-4-hydroxypiperidine (1.32 mg) were dissolved in anhydrous toluene (13 mL), and sodium hydride (141.6 mg, purity: 60%) was added in portions at room temperature. The mixture was heated to 120° C. and stirred for 18 h. The reaction solution was cooled to 0° C., and a saturated aqueous ammonium chloride solution (20 mL) was added to quench the reaction. The resulting mixture was extracted with ethyl acetate (30 mL×3). The organic phases were combined, washed with saturated brine (30 mL), dried over anhydrous sodium sulfate, filtered and concentrated under reduced pressure, and the residue was separated and purified by silica gel column chromatography (petroleum ether/ethyl acetate, 1:0-5:1) to give compound 8-2.

$^1H$ NMR (400 MHz, $CDCl_3$) δ ppm: 7.31-7.29 (dd, J=5.02 Hz, 1H), 7.18-7.16 (m, 1H), 6.99-6.97 (dd, J=5.02 Hz, 1H), 6.94 (s, 2H), 5.14-5.10 (m, 1H), 3.47 (m, 1H), 3.46-3.43 (m, 2H), 3.39-3.32 (m, 2H), 1.89-1.85 (m, 2H), 1.74-1.67 (m, 2H), 1.46 (s, 9H).

MS-ESI calcd. $[M+H-18]^+$ 484, 486, found 485.9.

Step 3: Preparation of Compounds 8-2A and 8-2B

Compound 8-2 (550 mg) was separated and purified by chiral liquid chromatography to give compound 8-2A and compound 8-2B.

SFC separation method (chromatographic column: DAICEL CHIRALCEL OJ (250 mm×30 mm, 10 μm); mobile phase: A: carbon dioxide, B: ethanol (containing 0.1% ammonium hydroxide): 45%-45%, flow rate: 70 mL/min, column temperature: 40° C.).

The retention time of compound 8-2A: 3.212 min; MS-ESI calcd. $[M+H]^+$ 484, 486, found 485.8.

The retention time of compound 8-2B: 3.919 min; MS-ESI calcd. $[M+H]^+$ 484, 486, found 485.8.

Step 4: Synthesis of Compound 8-3

Compound 8-2A (180 mg) was dissolved in dioxane (2 mL), and hydrochloric acid/dioxane solution (8 mL, 4 M) was added. The mixture was stirred at 25° C. for 2 h. The reaction solution was adjusted to about pH 8 with a saturated aqueous sodium carbonate solution and extracted with ethyl acetate (30 mL×3). The organic phases were combined, washed with saturated brine (20 mL), dried over anhydrous sodium sulfate, filtered and concentrated under reduced pressure to give crude compound 8-3.

MS-ESI calcd. $[M+H]^+$ 402, 404, found 403.9.

Step 5: Synthesis of Compound 8-4

Compound 8-3 (140 mg) was dissolved in acetonitrile (5 mL), and compound 1-12 (112 mg), N,N-diisopropylethylamine (134.9 mg) and potassium iodide (231 mg) were added at room temperature. The mixture was stirred at 90°

C. for 18 h. The reaction solution was concentrated under reduced pressure, and the residue was separated and purified by silica gel column chromatography (dichloromethane/methanol, 1:0-20:1) to give compound 8-4.

MS-ESI calcd. $[M+H]^+$ 629, 631, found 629.

Step 6: Synthesis of Compound 8-5

Compound 8-4 (100 mg) and compound 1-15 (53.1 mg, acetate) were dissolved in anhydrous methanol (4 mL) and anhydrous tetrahydrofuran (2 mL), and N,N-diisopropylethylamine (82.1 mg) and sodium triacetoxyborohydride (134.6 mg) were added. The mixture was stirred at 25° C. for 24 h, and sodium triacetoxyborohydride (134.6 mg) was added. The mixture was stirred for another 24 h, and sodium triacetoxyborohydride (134.6 mg) was added. The mixture was stirred for another 24 h. A saturated aqueous sodium bicarbonate solution (15 mL) was added to quench the reaction, and the resulting mixture was extracted with ethyl acetate (30 mL×3). The organic phases were combined, washed with water (20 mL×2), dried over anhydrous sodium sulfate, filtered and concentrated under reduced pressure to give crude compound 8-5.

MS-ESI calcd. $[M+H]^+$ 947, 949, found 949.4.

Step 7: Synthesis of Trifluoroacetate Salt of Compound 8

Compound 8-5 (130 mg) was dissolved in anhydrous tetrahydrofuran (4 mL), and triethylamine trihydrofluoride (130 mg) was added. The mixture was stirred at room temperature for 18 h. The reaction solution was concentrated under reduced pressure, and the residue was separated and purified by high performance liquid chromatography (column: Welch Xitimate C18, length×inner diameter: 100 mm×40 mm×3 μm; preparation method: the crude product was dissolved in dimethyl sulfoxide and filtered through a 0.45 μm filter membrane to give a sample solution; mobile phase system: acetonitrile/water (containing 0.75% trifluoroacetic acid), gradient elution method: acetonitrile, from 23% to 53% in 8 min) to give a trifluoroacetate salt of compound 8.

$^{1}$H NMR (400 MHz, DMSO-$d_6$) δ ppm: 10.52-10.50 (m, 2H), 9.99-9.86 (m, 1H), 9.23-9.13 (m, 2H), 8.15-8.08 (m, 2H), 7.59-7.48 (m, 2H), 7.15-7.13 (m, 1H), 7.10-7.08 (m, 1H), 6.99-6.97 (m, 2H), 6.54-6.52 (m, 1H), 6.25 (s, 1H), 5.43-5.41 (m, 1H), 5.13-4.97 (m, 1H), 4.80 (s, 2H), 4.37 (s, 2H), 3.14-3.07 (m, 8H), 2.80 (s, 2H), 2.33 (s, 3H), 2.24-2.22 (m, 3H), 2.10-1.95 (m, 4H), 1.79 (s, 2H).

MS-ESI calcd. $[M+H]^+$ 833, 835, found 835.

The trifluoroacetate salt of compound 9 was prepared in a 4-step reaction with compound 8-2B as the starting material by referring to the synthetic route of the trifluoroacetate salt of compound 8.

Trifluoroacetate Salt of Compound 9:

$^{1}$H NMR (400 MHz, DMSO-$d_6$) δ ppm: 10.50 (s, 2H), 9.87-9.73 (m, 1H), 9.14 (s, 2H), 8.14-8.08 (m, 2H), 7.59-7.48 (m, 2H), 7.15-7.09 (m, 3H), 6.99-6.91 (m, 3H), 6.21 (s, 1H), 5.42-5.40 (m, 1H), 5.13-4.97 (m, 1H), 4.80 (s, 2H), 4.38 (s, 2H), 3.38-3.34 (m, 1H), 3.15-3.07 (m, 8H), 2.80 (s, 1H), 2.67-2.56 (m, 1H), 2.33-2.21 (m, 5H), 2.11 (m, 1H), 2.10-1.95 (m, 3H), 1.77 (s, 1H);

MS-ESI calcd. $[M+H]^+$ 833, 835, found 835.

Example 10

10

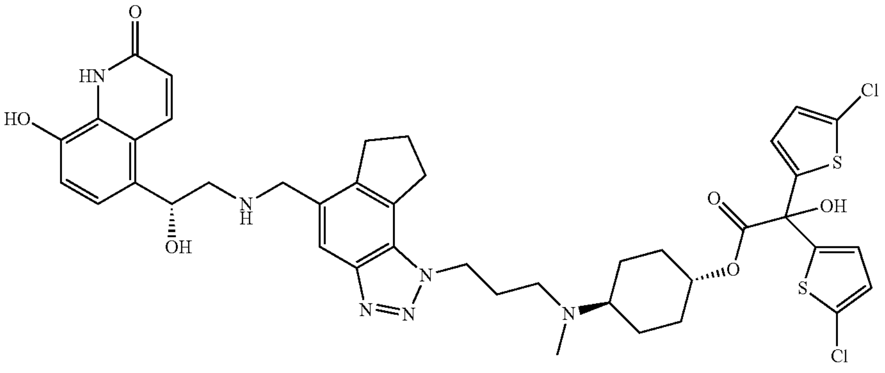

Synthetic Route:

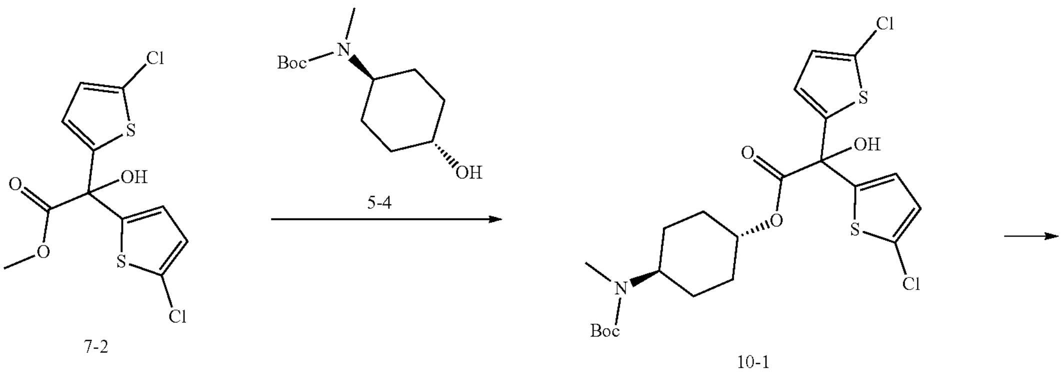

7-2

10-1

-continued

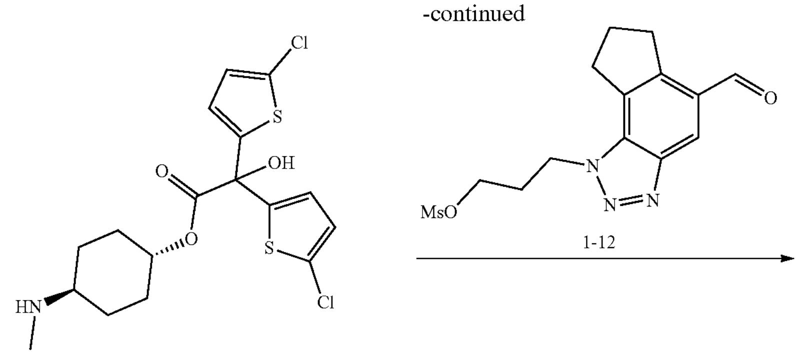

10-2

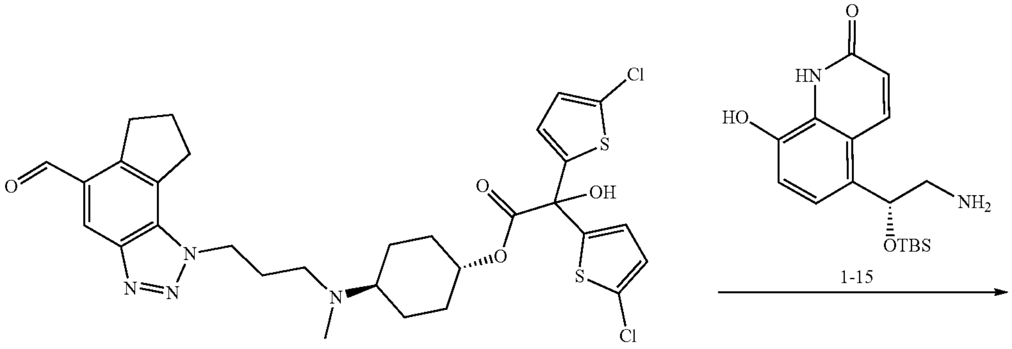

10-3

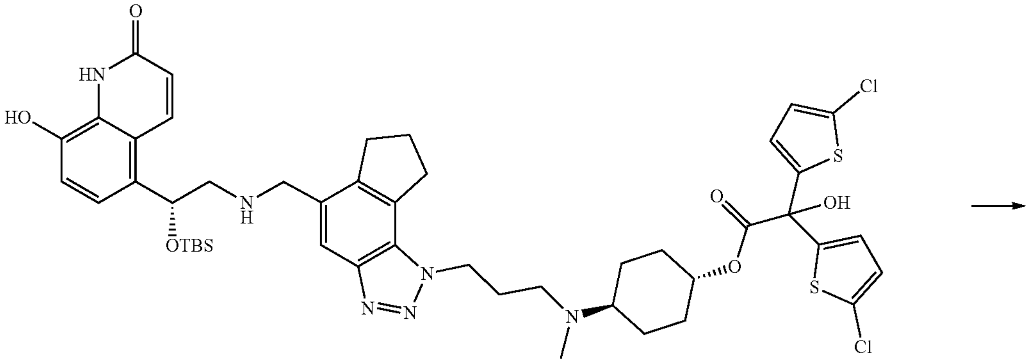

10-4

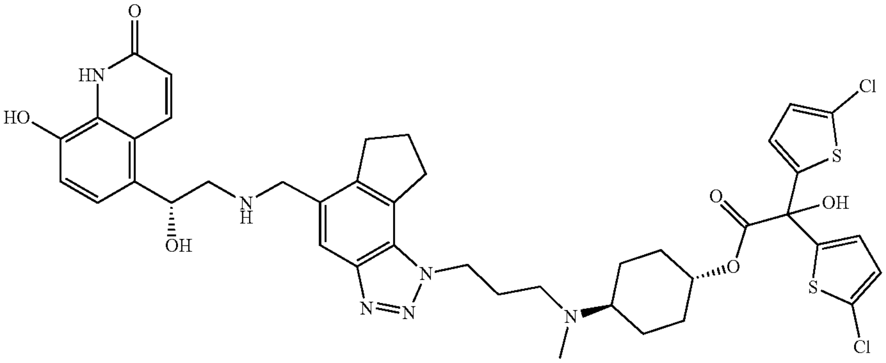

10-5

Step 1: Synthesis of Compound 10-1

Compound 7-2 (474 mg) and compound 5-4 (370 mg) were dissolved in anhydrous toluene (5 mL), and sodium hydride (58.6 mg, purity: 60%) was added in portions at room temperature. The mixture was heated to 120° C. and stirred for 18 h. The reaction solution was cooled to 0° C., and a saturated aqueous ammonium chloride solution (20 mL) was added to quench the reaction. The resulting mixture was extracted with ethyl acetate (30 mL×3). The organic phases were combined, washed with saturated brine (30 mL), dried over anhydrous sodium sulfate, filtered and concentrated under reduced pressure, and the residue was separated and purified by silica gel column chromatography (petroleum ether/ethyl acetate, 1:0-5:1) to give compound 10-1.

$^1$H NMR (400 MHz, $CDCl_3$) δ ppm: 6.93-6.92 (m, 2H), 6.80-6.78 (m, 2H), 4.88-4.80 (m, 1H), 4.79-4.69 (m, 1H), 2.71 (s, 3H), 2.09 (s, 2H), 1.77 (s, 2H), 1.59-1.54 (m, 4H), 1.47 (s, 9H).

MS-ESI calcd. $[M+H-18]^+$ 502, found 501.9.

Step 2: Synthesis of Compound 10-2

Compound 10-1 (286 mg) was dissolved in anhydrous dioxane (1 mL), and hydrochloric acid/dioxane solution (10 mL, 4 M) was added. The mixture was stirred at 25° C. for 2 h. The reaction solution was adjusted to about pH 8 with a saturated aqueous sodium carbonate solution and extracted with ethyl acetate (30 mL×3). The organic phases were combined, washed with saturated brine (20 mL), dried over anhydrous sodium sulfate, filtered and concentrated under reduced pressure to give crude compound 10-2.

MS-ESI calcd. $[M+H]^+$ 420, found 419.8.

Step 3: Synthesis of Compound 10-3

Compound 10-2 (212 mg) was dissolved in acetonitrile (8 mL), and compound 1-12 (163 mg), N,N-diisopropylethylamine (195 mg) and potassium iodide (334.8 mg) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 10-3.

MS-ESI calcd. $[M+H]^+$ 647, found 646.9.

Step 4: Synthesis of Compound 10-4

Compound 10-3 (210 mg) and compound 1-15 (108 mg, acetate) were dissolved in anhydrous methanol (4 mL) and anhydrous tetrahydrofuran (2 mL), and N,N-diisopropylethylamine (125 mg) and sodium triacetoxyborohydride (206 mg) were added. The mixture was stirred at 25° C. for 24 h, and sodium triacetoxyborohydride (206 mg) was added. The mixture was stirred for another 12 h, and sodium triacetoxyborohydride (206 mg) was added. The mixture was stirred for another 12 h. A saturated aqueous sodium bicarbonate solution (30 mL) was added to quench the reaction, and the resulting mixture was extracted with ethyl acetate (30 mL×3). The organic phases were combined, dried over anhydrous sodium sulfate, filtered and concentrated under reduced pressure to give crude compound 10-4.

MS-ESI calcd. $[M+H]^+$ 965, found 965.2.

Step 5: Synthesis of Trifluoroacetate Salt of Compound 10

Compound 10-4 (210 mg) was dissolved in anhydrous tetrahydrofuran (5 mL), and triethylamine trihydrofluoride (203.9 mg) was added. The mixture was stirred at room temperature for 18 h. The reaction solution was concentrated under reduced pressure, and the residue was separated and purified by high performance liquid chromatography (column: Welch Xtimate C18, length×inner diameter: 100 mm×40 mm, 3 μm); preparation method: the crude product was dissolved in dimethyl sulfoxide and filtered through a 0.45 μm filter membrane to give a sample solution; mobile phase system: acetonitrile/water (containing 0.075% trifluoroacetic acid), gradient elution method: acetonitrile, from 30% to 60% in 8 min) to give a trifluoroacetate salt of compound 10.

$^1$H NMR (400 MHz, DMSO-$d_6$) δ ppm: 10.57-10.50 (m, 2H), 9.90 (s, 1H), 9.29-9.17 (m, 2H), 8.16-8.13 (m, 1H), 8.08 (m, 1H), 7.73 (m, 1H), 7.18-7.14 (m, 1H), 7.01-6.97 (m, 3H), 6.95-6.94 (m, 2H), 6.54-6.51 (m, 1H), 6.27 (s, 1H), 5.44-5.41 (m, 1H), 4.80-4.73 (m, 3H), 4.38 (s, 1H), 3.38-3.34 (m, 4H), 3.20-3.07 (m, 5H), 2.71-2.70 (m, 3H), 2.54 (s, 1H), 2.35-2.20 (m, 4H), 2.00 (s, 4H), 1.68-1.60 (m, 2H), 1.53-1.44 (m, 2H). MS-ESI calcd. $[M+H]^+$ 851, found 851.2.

Example 11

11

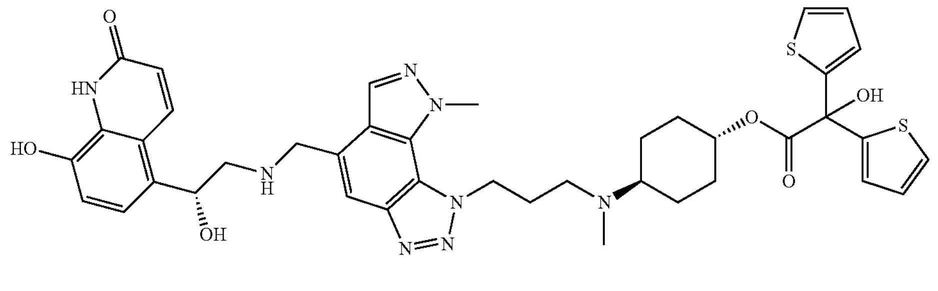

Synthetic Route:

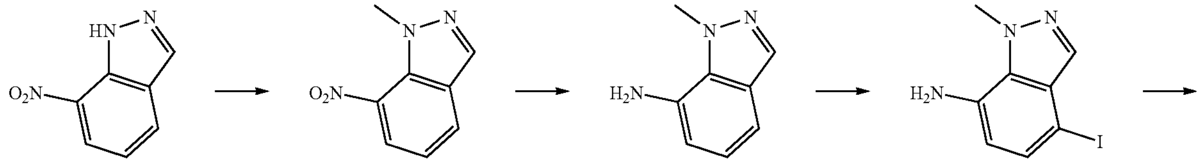

11-1 11-2 11-3 11-4

-continued
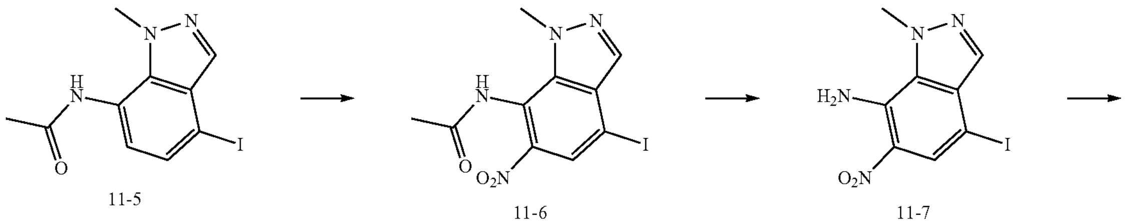
11-5 11-6 11-7
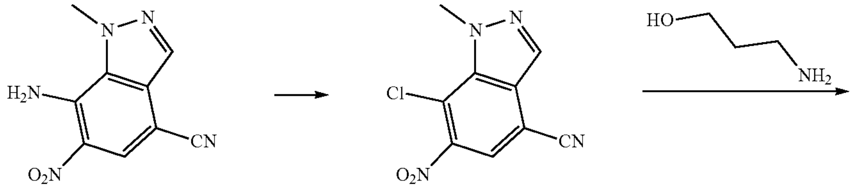
11-8 11-9
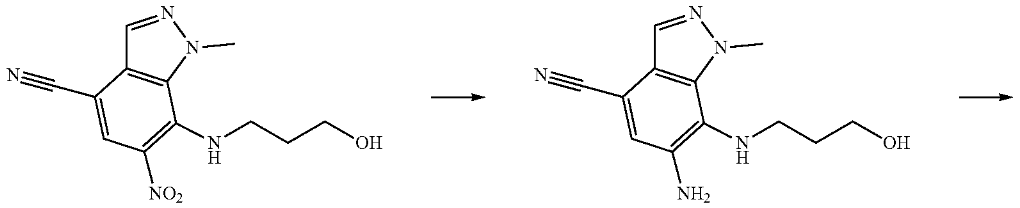
11-10 11-11
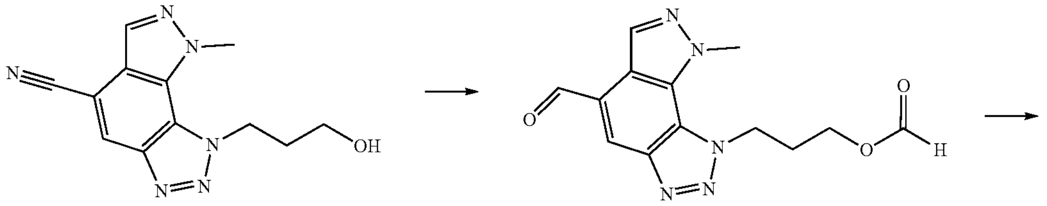
11-12 11-13
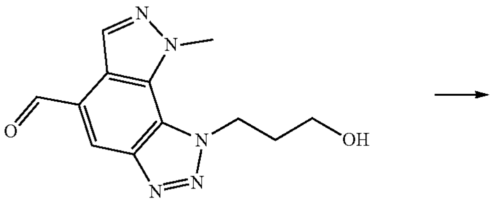
11-14
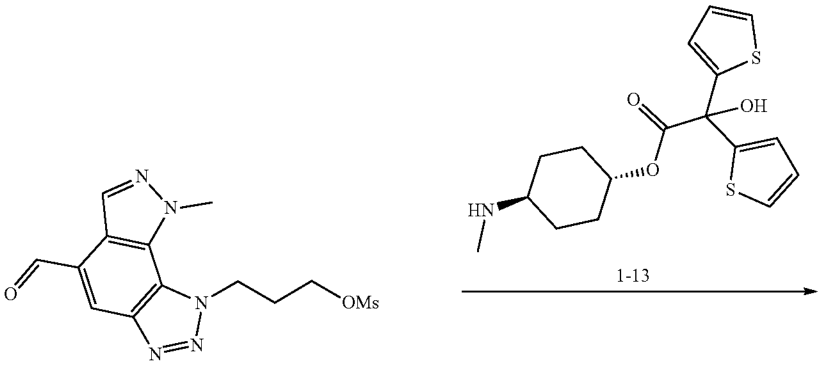
11-15

-continued

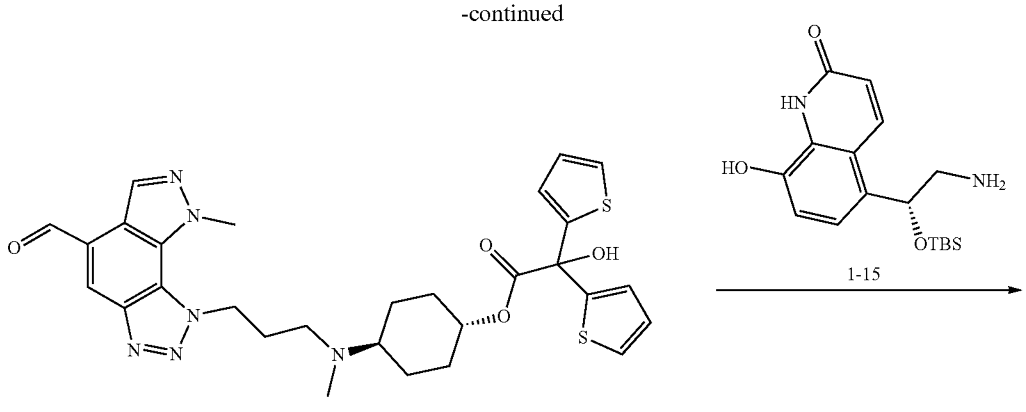

11-16

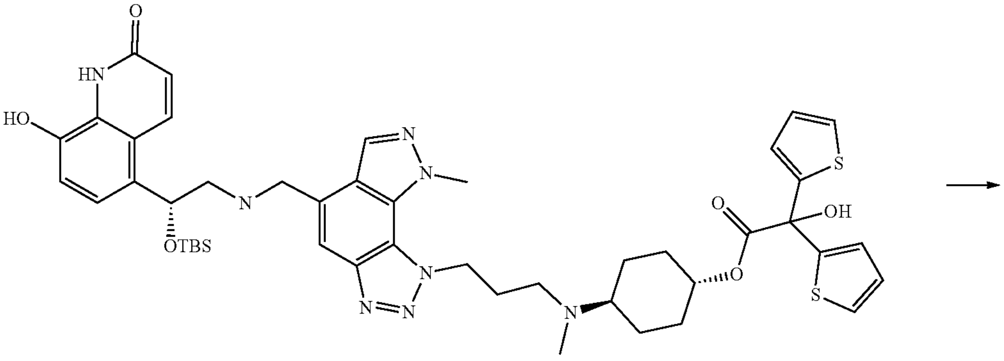

11-17

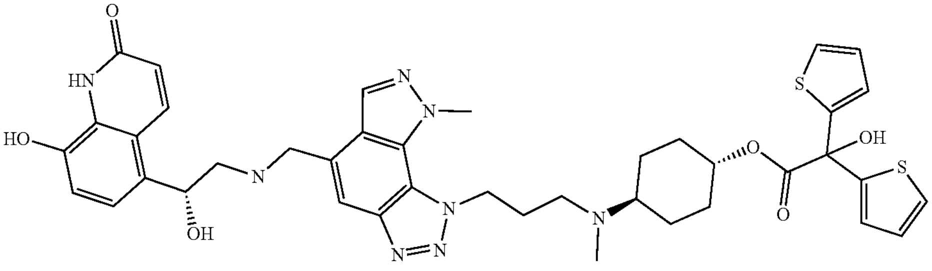

11

Step 1: Synthesis of Compound 11-2

Compound 11-1 (14 g) was dissolved in acetone (150 mL), and potassium hydroxide (7.22 g) and potassium iodide (12.18 g) were added at 0° C. The mixture was stirred at 0° C. for 2 h. After the reaction was completed, 200 mL of a saturated aqueous ammonium chloride solution was added to the reaction solution to quench the reaction, and the resulting mixture was concentrated under reduced pressure to remove most of acetone. The residue was stirred at room temperature for 0.5 h and filtered, and the solid was collected, washed with 500 mL of water, concentrated to dryness under reduced pressure, and separated and purified by flash silica gel column chromatography (eluent: ethyl acetate/petroleum ether, 0-50%) to give compound 11-2.

$^1$H NMR (400 MHz, $CDCl_3$) δ: 8.16 (s, 1H), 8.14 (d, J=8.0 Hz, 1H), 8.04 (d, J=8.0 Hz, 1H), 7.26-7.21 (m, 1H), 4.27 (s, 3H).

MS-ESI calcd. $[M+H]^+$ 178, found 178.0.

Step 2: Synthesis of Compound 11-3

Compound 11-2 (9.33 g) was dissolved in a mixed solution of methanol, tetrahydrofuran and water (300 mL, volume ratio: 1/1/1), and reduced iron powder (17.65 g) and ammonium chloride (14.09 g) were added. The mixture was heated to 70° C. and stirred for 2 h. After the reaction was completed, the reaction solution was filtered, and the filtrate was collected, concentrated to dryness under reduced pressure, and separated and purified by flash silica gel column chromatography (eluent: ethyl acetate/petroleum ether, 0-60%) to give compound 11-3.

MS-ESI calcd. $[M+H]^+$ 148, found 147.9.

Step 3: Synthesis of Compound 11-4

Compound 11-3 (1 g) was dissolved in acetic acid (5 mL) and water (5 mL), and sodium perborate (1.05 g) was added under stirring. The mixture was cooled to 0° C. and a solution of potassium iodide (1.13 g) in water (10 mL) was slowly added dropwise. The mixture was heated to room temperature (25° C.) and stirred for 0.5 h. After the reaction was completed, the reaction solution was filtered, and the filter cake was washed with 100 mL of water. The solid was collected, concentrated to dryness under reduced pressure, and separated and purified by flash silica gel column chromatography (eluent: ethyl acetate/petroleum ether, 0-40%) to give compound 11-4.

MS-ESI calcd. $[M+H]^+$ 274, found 273.8.

Step 4: Synthesis of Compound 11-5

Compound 11-4 (7.8 g) was dissolved in tetrahydrofuran (100 mL), and acetic anhydride (4.37 g) and diisopropylethylamine (4.52 g) were added. The mixture was heated to 45° C. and stirred for 16 h. After the reaction was completed, the reaction solution was concentrated to dryness under reduced pressure, slurried with 50 mL of petroleum ether for 0.5 h and filtered. The solid was collected, concentrated to dryness under reduced pressure to give compound 11-5, which was directly used in the next step.

$^1$H NMR (400 MHz, DMSO-$d_6$) δ: 9.92 (s, 1H), 7.84 (s, 1H), 7.50 (d, J=7.6 Hz, 1H), 6.93 (d, J=7.6 Hz, 1H), 4.09 (s, 3H), 2.12 (s, 3H).

MS-ESI calcd. $[M+H]^+$ 316, found 315.9.

Step 5: Synthesis of Compound 11-6

To a suspension of compound 11-5 (4.25 g) in acetic acid (75 mL) was added concentrated nitric acid (1.96 g, purity: 65%) at 0° C. The mixture was stirred at 45° C. for 16 h. After the reaction was completed, the reaction solution was concentrated to 10 mL and filtered. The solid was collected, concentrated to dryness under reduced pressure, and separated and purified by flash silica gel column chromatography (eluent: methanol/dichloromethane, 0-3%) to give compound 11-6.

MS-ESI calcd. $[M+H]^+$ 361, found 361.0.

Step 6: Synthesis of Compound 11-7

Compound 11-6 (3.24 g) was dissolved in ethanol (120 mL), and hydrochloric acid solution (6 M, 29.99 mL) was added. The mixture was heated to 85° C. and stirred for 16 h. After the reaction was completed, the reaction solution was concentrated under reduced pressure to remove most of ethanol and filtered. The precipitated solid was collected, concentrated to dryness under reduced pressure, and separated and purified by flash silica gel column chromatography (eluent: ethyl acetate/petroleum ether, 0-30%) to give compound 11-7.

MS-ESI calcd. $[M+H]^+$ 319, found 319.0.

Step 7: Synthesis of Compound 11-8

Compound 11-7 (1.23 g) was dissolved in N,N-dimethylformamide (25 mL), and tris(dibenzylideneacetone)dipalladium (177.06 mg), 2-dicyclohexylphosphine-2',4',6'-triisopropylbiphenyl (184.35 mg) and zinc cyanide (544.93 mg) were added under nitrogen atmosphere. The mixture was heated to 80° C. under nitrogen atmosphere and stirred for 16 h. After the reaction was completed, the reaction solution was cooled to room temperature and poured into 500 mL of water, and the resulting mixture was extracted with ethyl acetate (500 mL×2). The organic phases were combined, washed with saturated brine (500 mL×1), dried over anhydrous sodium sulfate, filtered and concentrated under reduced pressure, and the residue was separated and purified by flash silica gel column chromatography (eluent: ethyl acetate/petroleum ether, 0-30%) to give compound 11-8.

$^1$H NMR (400 MHz, DMSO-$d_6$) δ: 8.36 (br s, 2H), 8.32 (s, 1H), 8.12 (s, 1H), 4.44 (s, 3H).

Step 8: Synthesis of Compound 11-9

A mixture of cuprous chloride (1.80 g) and acetonitrile (250 mL) was heated to 65° C., tert-butyl nitrite (1.72 g) was added in one portion, and compound 11-8 (1.45 g) was added in portions. The mixture was stirred at 65° C. for 0.5 h. After the reaction was completed, the reaction solution was cooled to room temperature and concentrated to dryness under reduced pressure. Ethyl acetate (500 mL) and hydrochloric acid solution (6 M, 100 mL) were added to the residue, followed by liquid separation. The organic phase was washed with saturated brine (250 mL), dried over anhydrous sodium sulfate, filtered and concentrated to dryness under reduced pressure to give compound 11-9, which was directly used in the next step.

Step 9: Synthesis of Compound 11-10

Compound 11-9 (1.6 g) was dissolved in tetrahydrofuran (150 mL), and triethylamine (1.71 g) and 3-aminopropanol (1.52 g) were added. The mixture was heated to 65° C. and stirred for 16 h. After the reaction was completed, the reaction solution was cooled to room temperature and poured into 150 mL of water, and the resulting mixture was extracted with ethyl acetate (150 mL). The organic phase was washed with saturated brine (150 mL×1), dried over anhydrous sodium sulfate, filtered and concentrated under reduced pressure, and the residue was separated and purified by flash silica gel column chromatography (eluent: ethyl acetate/petroleum ether, 0-50%) to give compound 11-10.

MS-ESI calcd. $[M+H]^+$ 276, found 276.0.

Step 10: Synthesis of Compound 11-11

Compound 11-10 (1.15 g) was dissolved in ethanol (100 mL), and wet palladium on carbon (5 mg, purity: 10%) was added. The mixture was stirred at 25° C. for 16 h under hydrogen (15 psi) atmosphere. After the reaction was completed, the reaction solution was filtered, and the filter cake was washed with 50 mL of ethanol. The filtrate was collected and concentrated to dryness under reduced pressure to give compound 11-11.

MS-ESI calcd. $[M+H]^+$ 246, found 246.2.

Step 11: Synthesis of Compound 11-12

Compound 11-11 (1 g) was dispersed in hydrochloric acid solution (6 M, 6.79 mL), and the system was cooled to 0° C. A solution of sodium nitrite (421.97 mg) in water (6 mL) was slowly added dropwise at 0° C. The mixture was stirred at 0-25° C. for 1 h. After the reaction was completed, the reaction solution was subjected to liquid separation in ethyl acetate (100 mL) and water (100 mL). The organic phase was washed with saturated brine (100 mL), dried over anhydrous sodium sulfate, filtered and concentrated to dryness under reduced pressure to give compound 11-12, which was directly used in the next step.

MS-ESI calcd. $[M+H]^+$ 257, found 257.2.

Step 12: Synthesis of Compound 11-13

Compound 11-12 (745.00 mg) was dissolved in formic acid solution (100 mL, purity: 75%), and nickel-aluminum alloy (1.25 g) was added. The mixture was heated to 90° C. and stirred for 16 h. The reaction solution was filtered, and the filtrate was collected and concentrated to dryness under reduced pressure to give compound 11-13, which was directly used in the next step.

MS-ESI calcd. $[M+H]^+$ 288, found 288.1.

Step 13: Synthesis of Compound 11-14

Compound 11-13 (835 mg) was dissolved in 60 mL of ethanol and an aqueous sodium hydroxide solution (1 M, 14.53 mL) was added under stirring. The mixture was stirred at 15° C. for 1 h. After the reaction was completed, the reaction solution was cooled in an ice bath, adjusted to pH 6-7 with 2 N hydrochloric acid solution, concentrated under reduced pressure to remove most of methanol, and extracted with ethyl acetate (100 mL×2). The organic phase was washed with saturated brine (100 mL), dried over anhydrous sodium sulfate, filtered and concentrated to dryness under reduced pressure to give compound 11-14, which was directly used in the next step.

MS-ESI calcd. $[M+H]^+$ 260, found 259.9.

Step 14: Synthesis of Compound 11-15

Compound 11-14 (450 mg) was dissolved in dichloromethane (25 mL), and triethylamine (878.17 mg) and methanesulfonyl chloride (409.00 mg) were added. The mixture was stirred at 25° C. for 0.5 h. Two reactions were set up in parallel. After the reaction was completed, the reaction solution was subjected to liquid separation in dichloromethane (250 mL) and water (250 mL). The organic phase was washed with saturated brine (250 mL), dried over anhydrous sodium sulfate, filtered, concentrated to dryness under reduced pressure, and separated and purified by flash silica gel column chromatography (eluent: methanol/dichloromethane, 0-10%) to give compound 11-15.

MS-ESI calcd. $[M+H]^+$ 338, found 338.1.

Step 15: Synthesis of Compound 11-16

Compound 1-13 (100 mg) was dissolved in acetonitrile (10 mL), and diisopropylethylamine (110.31 mg), potassium iodide (141.69 mg) and compound 11-15 (95.98 mg) were added. The mixture was heated to 90° C. and stirred for 16 h. After the reaction was completed, the reaction solution was poured into 50 mL of water, and the resulting mixture was extracted with dichloromethane (50 mL×2), followed by liquid separation. The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-10%) to give compound 11-16.

MS-ESI calcd. $[M+H]^+$ 593, found 593.2.

Step 16: Synthesis of Compound 11-17

Compound 11-16 (107 mg) and compound 1-15 (60.38 mg) were dissolved in methanol (5 mL) and tetrahydrofuran (4 mL), and sodium triacetoxyborohydride (191.30 mg) was added. The mixture was stirred at 25° C. for 40 h, and sodium triacetoxyborohydride (191.30 mg) was added. The mixture was stirred at 25° C. for 16 h, and sodium triacetoxyborohydride (595.09 mg) was added. The mixture was stirred at 25° C. for 3 h. The reaction solution was concentrated to dryness, and 50 mL of water was added. The resulting mixture was extracted with dichloromethane (50 mL×2). The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-10%) to give compound 11-17.

MS-ESI calcd. $[M+H]^+$ 911, found 911.5.

Step 17: Synthesis of Compound 11

Compound 11-17 (110 mg) was dissolved in tetrahydrofuran (5 mL), and triethylamine trihydrofluoride (97.30 mg) was added. The mixture was stirred at 25° C. for 16 h. After the reaction was completed, the reaction solution was left to stand, and the supernatant was discarded. The solid was washed with 10 mL of tetrahydrofuran, and 5 mL of acetonitrile was added. The resulting mixture was stirred at 25° C. for 0.5 h. The reaction solution was filtered, and the filter cake was concentrated to dryness under reduced pressure to give compound 11.

$^1$H NMR (400 MHz, DMSO-$d_6$) δ: 8.30 (s, 1H), 8.21 (s, 1H), 8.11 (d, J=10.0 Hz, 1H), 7.65 (s, 1H), 7.50-7.43 (m, 3H), 7.23 (s, 1H), 7.08-7.03 (m, 4H), 7.00-6.95 (m, 3H), 6.89 (d, J=8.0 Hz, 1H), 6.39 (d, J=10.0 Hz, 1H), 5.14 (d, J=3.2 Hz, 1H), 5.05 (t, J=6.8 Hz, 2H), 4.77 (t, J=6.4 Hz, 1H), 4.66 (s, 1H), 4.49 (s, 3H), 4.34 (s, 1H), 4.20-4.15 (m, 2H), 2.98-2.90 (m, 1H), 2.82-2.77 (m, 2H), 2.20 (s, 2H), 2.17 (s, 3H), 1.93-1.85 (m, 2H), 1.68-1.60 (m, 2H), 1.40-1.25 (m, 4H).

MS-ESI calcd. $[M+H]^+$ 797.0, found 797.7.

Example 12

12

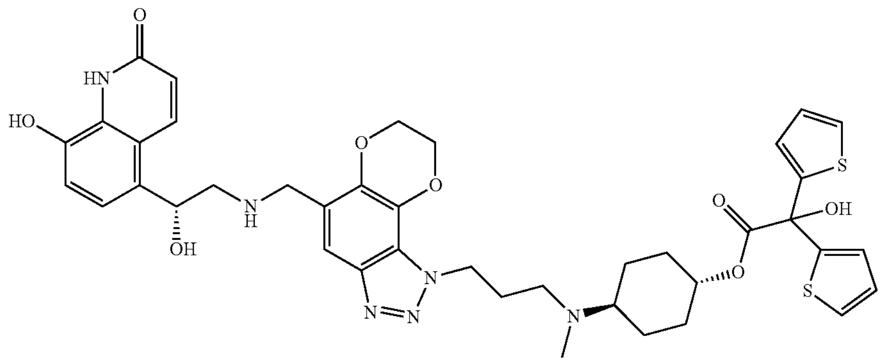

Synthetic Route:

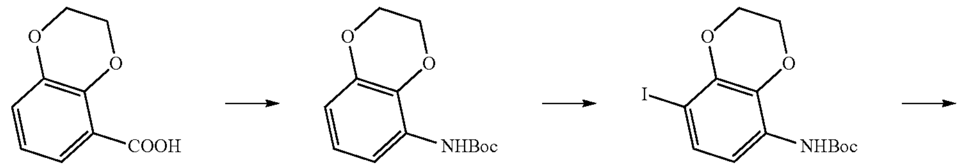

12-1 12-2 12-3

-continued
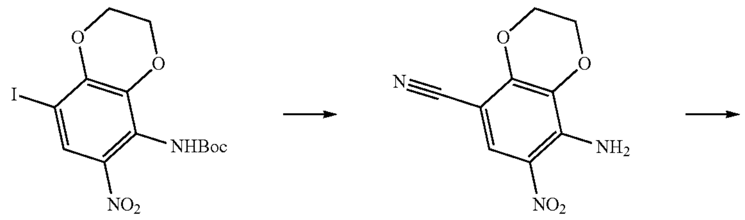
12-4 12-5
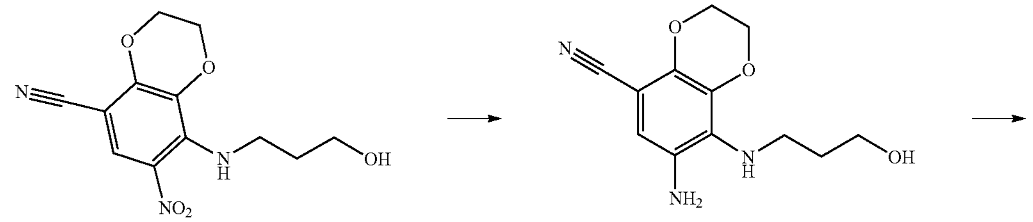
12-7 12-8
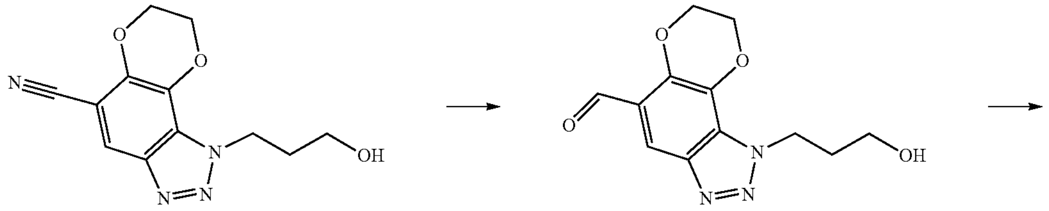
12-9 12-10
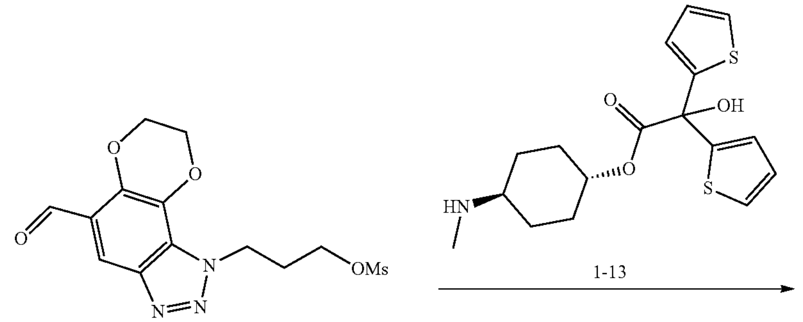
1-13
12-11
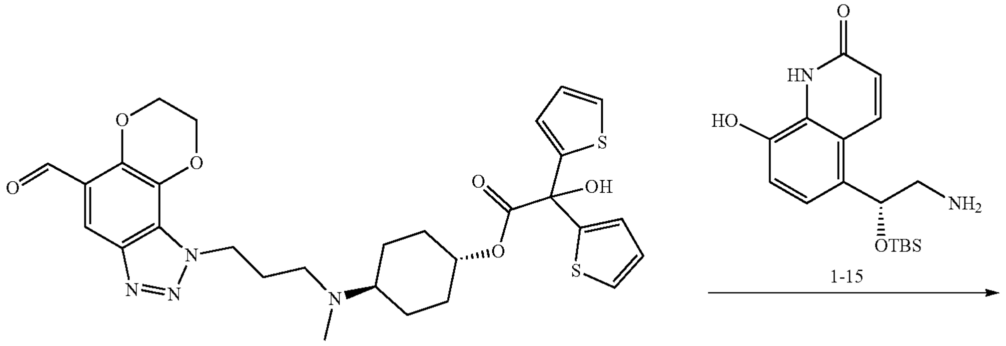
1-15
12-12

-continued

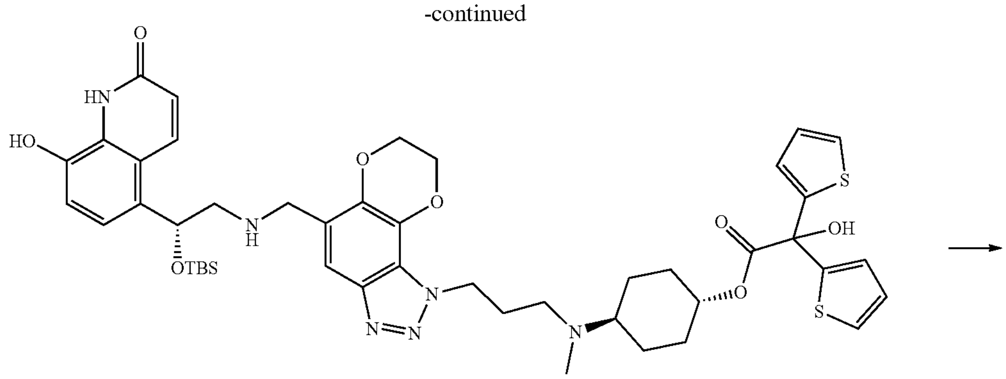

12-13

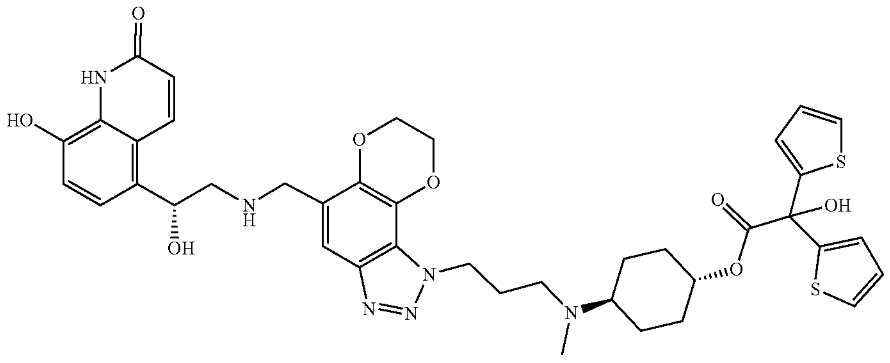

12

Step 1: Synthesis of Compound 12-2

Compound 12-1 (10 g) was dissolved in tert-butanol (60 mL), and triethylamine (11.23 g) was added. The mixture was heated to reflux. Diphenylphosphoryl azide (15.28 g) was slowly added dropwise, and the mixture was stirred at 90° C. for 16 h. After the reaction was completed, the reaction solution was concentrated to dryness, dissolved with 500 mL of ethyl acetate, and washed with 500 mL of 2 M sodium hydroxide solution, followed by liquid separation. The organic phase was concentrated to dryness under reduced pressure, and slurried with 600 mL of a mixed solvent of petroleum ether/ethyl acetate (v/v=5:1) at room temperature. The reaction solution was filtered, and the filtrate was collected and concentrated to dryness under reduced pressure to give compound 12-2.

MS-ESI calcd. $[M+H-100]^+$ 152, found 151.8; MS-ESI calcd. $[M+H-56]^+$ 196, found 195.9.

Step 2: Synthesis of Compound 12-3

Compound 12-2 (5.40 g) was dissolved in ethanol (150 mL), and sodium iodide (6.45 g) and bis(trifluoroacetoxy) iodobenzene (13.86 g) were added. The mixture was stirred at 50° C. for 14 h under air atmosphere. The reaction was quenched with a saturated aqueous sodium thiosulfate solution (120 mL), and the resulting mixture was extracted with ethyl acetate (150 mL×2). The organic phases were combined, dried over anhydrous sodium sulfate and concentrated under reduced pressure, and the residue was separated and purified by silica gel column chromatography (petroleum ether/ethyl acetate, 1:0-10:1) to give compound 12-3.

MS-ESI calcd. [M+H-100]+278, found 278.

Step 3: Synthesis of Compound 12-4

Acetic acid (200 mL) was added to a reaction flask, and concentrated nitric acid (3.86 g, content: 65%) was slowly added at -78° C. Compound 12-3 (10.0 g) was dissolved in acetic acid (100 mL), and the solution was slowly added dropwise to the reaction flask at -78° C. After the dropwise addition, the mixture was heated to 0° C. and stirred for 1 h. The reaction solution was slowly poured into ice water (3 L) under stirring, and the resulting mixture was stirred for 30 min. The reaction solution was filtered, and the filter cake was washed with water (500 mL) three times. The solid was dissolved with ethyl acetate (600 mL), washed with water (500 mL) twice, dried over anhydrous sodium sulfate, and concentrated under reduced pressure, and the residue was dissolved with ethyl acetate (50 mL) at 50° C. and then cooled to room temperature, whereupon a solid was precipitated. Then petroleum ether (200 mL) was added to the reaction flask, and the mixture was slurried for 30 min and filtered. The solid was collected to give compound 12-4.

$^1$H NMR (400 MHz, $CDCl_3$) δ: 8.05 (s, 1H), 7.07 (s, 1H), 4.48-4.45 (m, 2H), 4.37-4.34 (m, 2H), 1.49 (s, 9H).

Step 4: Synthesis of Compound 12-5

Compound 12-4 (6.00 g) was dissolved in dimethyl sulfoxide (90 mL), and cuprous oxide (508 mg) and acetonitrile (2.45 g) were added. The mixture was stirred at 130° C. for 14 h under nitrogen atmosphere. To the reaction solution were added water (150 mL) and ethyl acetate (150 mL). The resulting mixture was filtered, and the filtrate was extracted with ethyl acetate (100 mL×3). The organic phases were washed with saturated brine (300 mL×3), combined, dried over anhydrous sodium sulfate, and concentrated under reduced pressure to give crude compound 12-5.

$^1$H NMR (400 MHz, $CDCl_3$) δ: 8.14 (s, 1H), 4.50-4.47 (m, 2H), 4.43-4.41 (m, 2H).

Step 5: Synthesis of Compound 12-6

A mixture of copper chloride (2.43 g) and acetonitrile (40 mL) was heated to 60° C., tert-butyl nitrite (2.33 g) was added in one portion, and compound 12-5 (2.00 g) was added in portions. The mixture was stirred at 60° C. for 0.5 h. After the reaction was completed, the reaction solution was cooled to room temperature, and water (50 mL) was added. The resulting mixture was extracted with ethyl acetate (50 mL×2). The organic phase was washed with saturated brine (50 mL), dried over anhydrous sodium sulfate, filtered and concentrated to dryness under reduced pressure. The resulting crude compound was slurried with ethyl acetate (20 mL) and petroleum ether (10 mL) at room temperature for five minutes and filtered, and the filter cake was collected to give compound 12-6.

$^{1}$H NMR (400 MHz, $CDCl_3$) δ: 7.85 (s, 1H), 4.55-4.50 (m, 4H).

Step 6: Synthesis of Compound 12-7

Compound 12-6 (1.2 g) was dissolved in tetrahydrofuran (15 mL), and triethylamine (1.51 g) and 3-aminopropanol (1.12 g) were added. The mixture was heated to 60° C. and stirred for 14 h. After the reaction was completed, the reaction solution was cooled to room temperature, and water (30 mL) was added. The resulting mixture was extracted with ethyl acetate (40 mL×2). The organic phase was washed with saturated brine (30 mL×3), dried over anhydrous sodium sulfate, filtered and concentrated under reduced pressure to give crude compound 12-7.

MS-ESI calcd. $[M+H]^+$ 280, found 280.

Step 7: Synthesis of Compound 12-8

Compound 12-7 (1.25 g) was dissolved in ethanol (40 mL), and wet palladium on carbon (1 g, purity: 10%) was added. The mixture was stirred at room temperature for 14 h under hydrogen (15 psi) atmosphere. After the reaction was completed, the reaction solution was filtered, and the filter cake was washed with ethanol. The filtrate was collected and concentrated under reduced pressure to give crude compound 12-8.

$^{1}$H NMR (400 MHz, $CD_3OD$) δ: 6.56 (s, 1H), 4.31 (s, 4H), 3.70-3.65 (m, 2H), 3.32-3.27 (m, 2H), 1.78-1.71 (m, 2H).

Step 8: Synthesis of Compound 12-9

Compound 12-8 (1.1 g) was dissolved in an aqueous hydrochloric acid solution (6 M, 20 mL), and a solution of sodium nitrite (456.74 mg) in water (10 mL) was slowly added dropwise at 0° C. The mixture was stirred at 15° C. for 2 h. After the reaction was completed, the reaction solution was subjected to liquid separation in dichloromethane (20 mL) and water (20 mL). The organic phase was washed with saturated brine (50 mL), dried over anhydrous sodium sulfate, filtered and concentrated to dryness under reduced pressure to give compound 12-9, which was directly used in the next step.

MS-ESI calcd. $[M+H]^+$ 261, found 261.

Step 9: Synthesis of Compound 12-10

Compound 12-9 (760 mg) was dissolved in formic acid solution (40 mL, purity: 75%), and nickel-aluminum alloy (1.25 g) was added. The mixture was heated to 90° C. and stirred for 14 h. The reaction solution was supplemented with nickel-aluminum alloy (1.25 g), and heated to 90° C. and stirred for 20 h. The reaction solution was filtered, and the filtrate was collected and concentrated to dryness under reduced pressure. Ethanol (10 mL) and an aqueous sodium hydroxide solution (4 M, 10 mL) were added to the concentrate. The mixture was stirred at 15° C. for 1 h. After the reaction was completed, the reaction solution was extracted with dichloromethane (40 mL×2). The organic phase was washed with saturated brine (50 mL), dried over anhydrous sodium sulfate, filtered and concentrated to dryness under reduced pressure, and the residue was separated and purified by silica gel column chromatography (dichloromethane/methanol, 1:0-20:1) to give compound 12-10.

MS-ESI calcd. $[M+H]^+$ 264, found 264.

Step 10: Synthesis of Compound 12-11

Compound 12-10 (50 mg) was dissolved in dichloromethane (6 mL), and triethylamine (96.10 mg) and methanesulfonyl chloride (43.51 mg) were added. The mixture was stirred at 15° C. for 1 h. After the reaction was completed, the reaction solution was subjected to liquid separation in dichloromethane (10 mL) and water (10 mL). The organic phase was washed with saturated brine (20 mL), dried over anhydrous sodium sulfate, filtered and concentrated to dryness under reduced pressure, and the residue was separated and purified by silica gel column chromatography (dichloromethane/methanol, 1:0-20:1) to give compound 12-11.

MS-ESI calcd. $[M+H]^+$ 342, found 342.

Step 11: Synthesis of Compound 12-12

Compound 12-11 (52 mg) was dissolved in acetonitrile (15 mL), and diisopropylethylamine (59.07 mg), potassium iodide (126.44 mg) and compound 1-13 (53.55 mg) were added. The mixture was heated to 90° C. and stirred for 14 h. After the reaction was completed, the reaction solution was concentrated to dryness under reduced pressure, and the residue was separated and purified by silica gel column chromatography (dichloromethane/methanol, 1:0-20:1) to give compound 12-12.

MS-ESI calcd. $[M+H]^+$ 597, found 597.

Step 12: Synthesis of Compound 12-13

Compound 1-15 (50 mg, acetate) and compound 12-12 (74.87 mg) were dissolved in methanol (4 mL) and tetrahydrofuran (2 mL), and diisopropylethylamine (32.76 mg) and sodium triacetoxyborohydride (134.30 mg) were added. The mixture was stirred at 20° C. for 12 h, and sodium triacetoxyborohydride (134.30 mg) was added. The mixture was stirred at 20° C. for another 5 h. To the reaction solution was added a 5% aqueous sodium bicarbonate solution (10 mL), and the resulting mixture was extracted with ethyl acetate (15 mL×2). The organic phase was washed with saturated brine (15 mL), dried over anhydrous sodium sulfate, filtered and concentrated under reduced pressure to give crude compound 12-13.

MS-ESI calcd. [M+H]+ 915, found 915.

Step 13: Synthesis of Formate Salt of Compound 12

Compound 12-13 (90 mg) was dissolved in tetrahydrofuran (5 mL), and triethylamine trihydrofluoride (79.27 mg) was added. The mixture was stirred at 15° C. for 14 h. After the reaction was completed, the reaction solution was left to stand, and the supernatant was discarded. The solid was washed with 5 mL of tetrahydrofuran, and the residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 12.

$^{1}$H NMR (400 MHz, DMSO-$d_6$) δ: 8.28 (s, 2H), 8.15-8.10 (m, 1H), 7.48-7.44 (m, 3H), 7.08-7.03 (m, 3H), 6.99-6.95 (m, 2H), 6.93-6.90 (m, 1H), 6.45-6.40 (m, 1H), 5.08-5.03 (m, 1H), 4.71-4.63 (m, 3H), 4.42-4.34 (m, 4H), 3.78 (s, 2H), 2.81-2.62 (m, 3H), 2.13 (s, 3H), 1.99-1.89 (m, 4H), 1.69-1.61 (m, 3H), 1.39-1.29 (m, 5H). MS-ESI calcd. $[M+H]^+$ 801, found 801.

Example 13 and Example 14
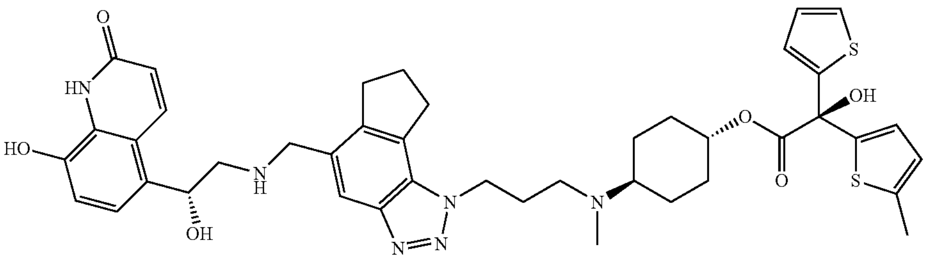
13 or 14
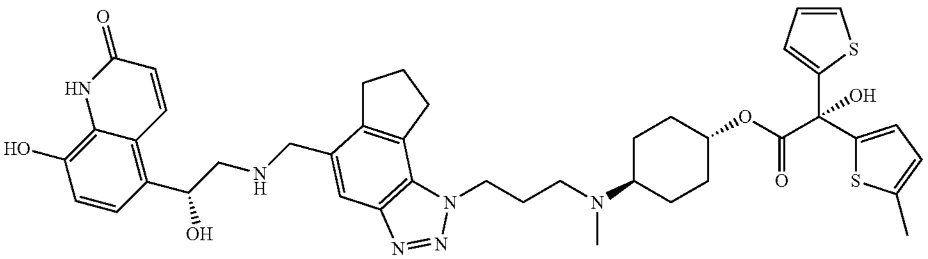
13 or 14
Synthetic Route:
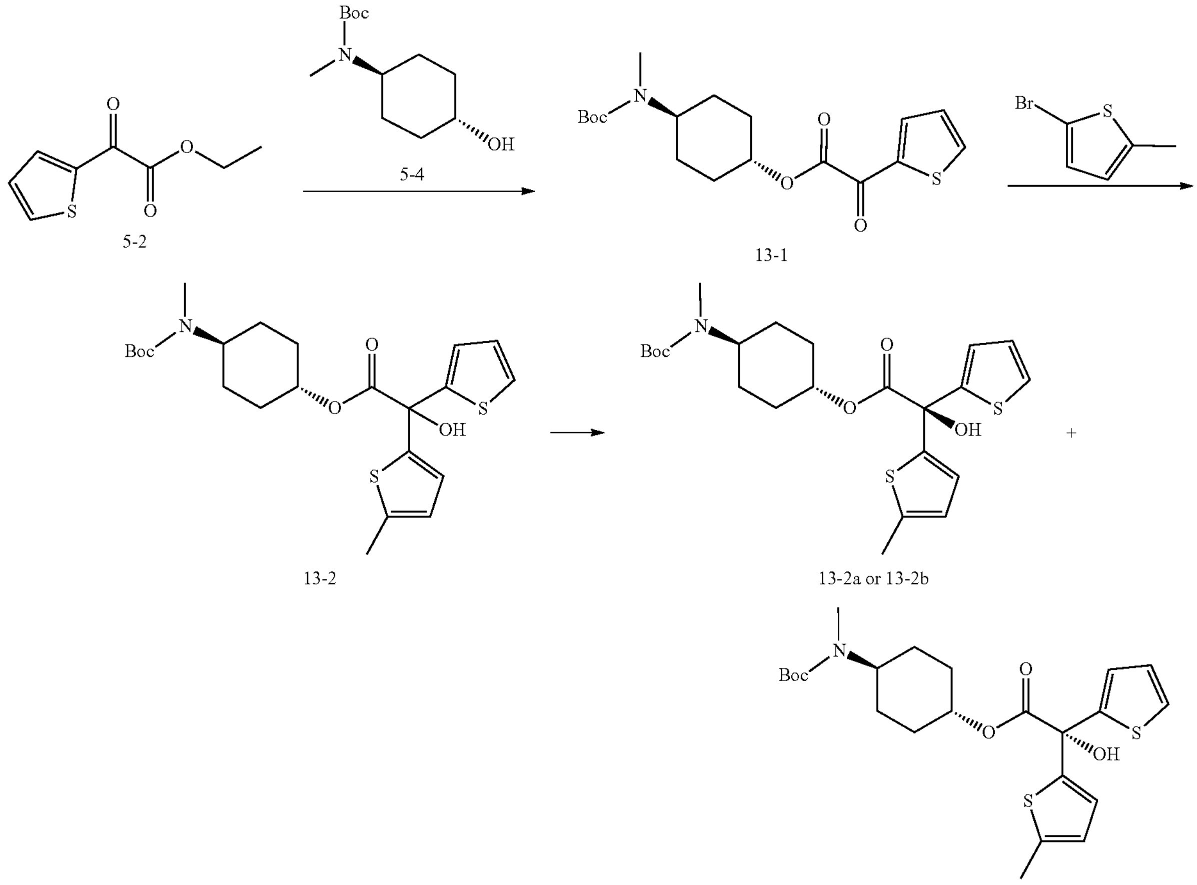
5-2
5-4
13-1
13-2
13-2a or 13-2b
+
13-2 a or 13-2b -continued
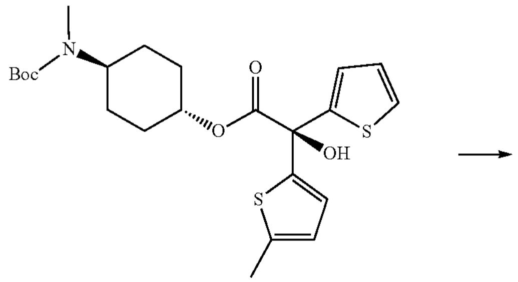
13-2a or 13-2b
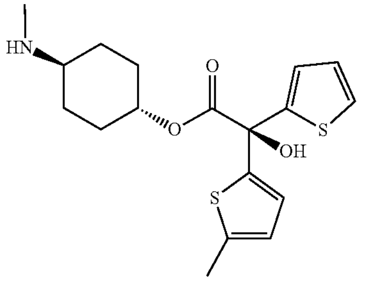
13-3 or 14-1
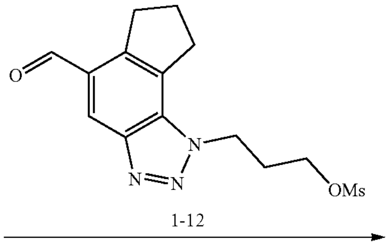
1-12
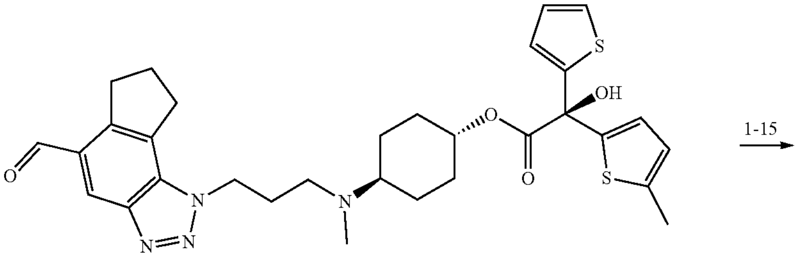
13-4 or 14-2
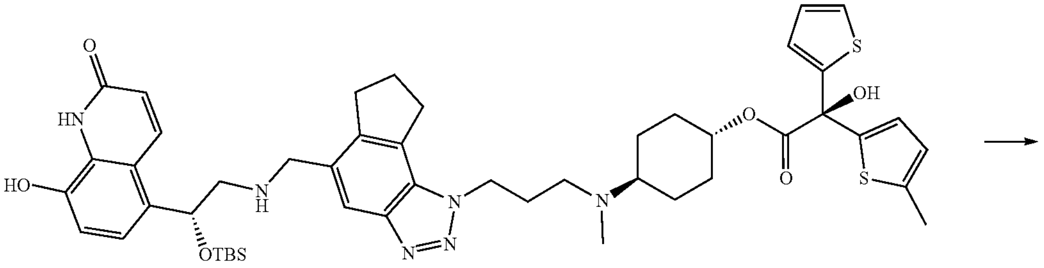
13-5 or 14-3
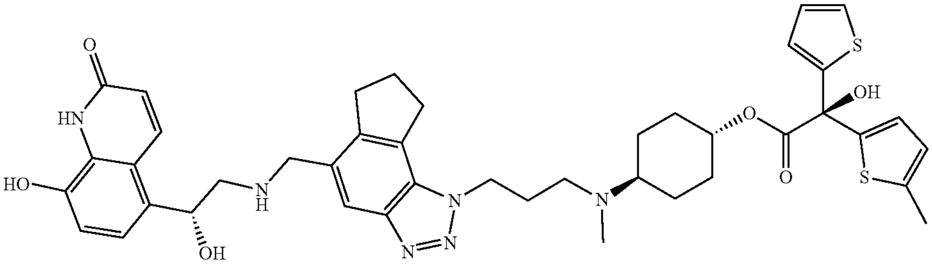
13 or 14

-continued

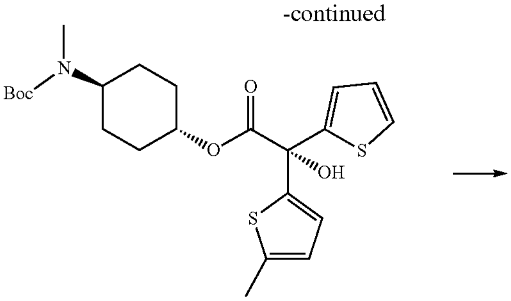

13-2a or 13-2b

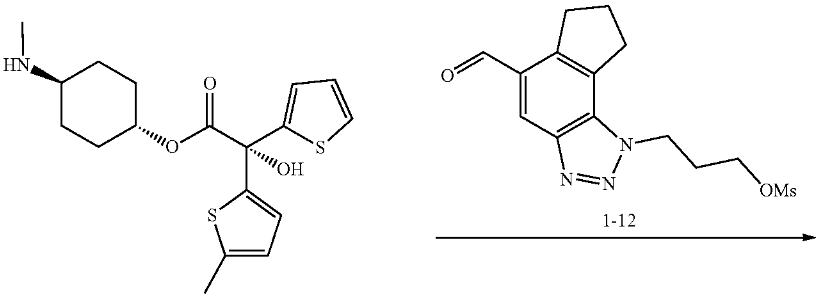

13-3 or 14-1

1-12

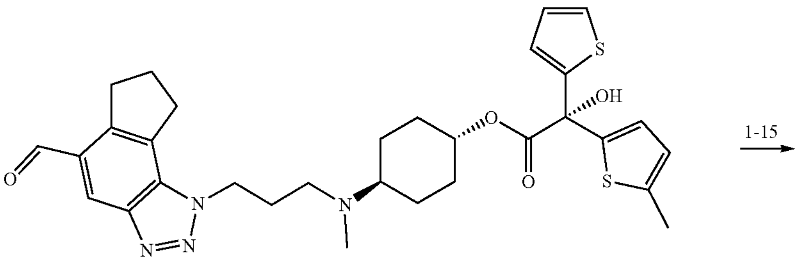

13-4 or 14-2

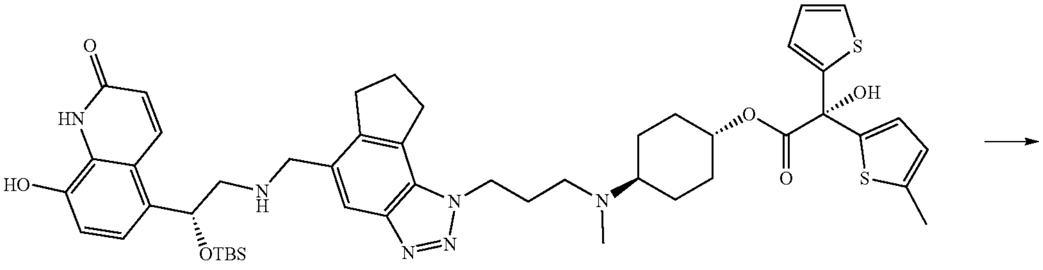

13-5 or 14-3

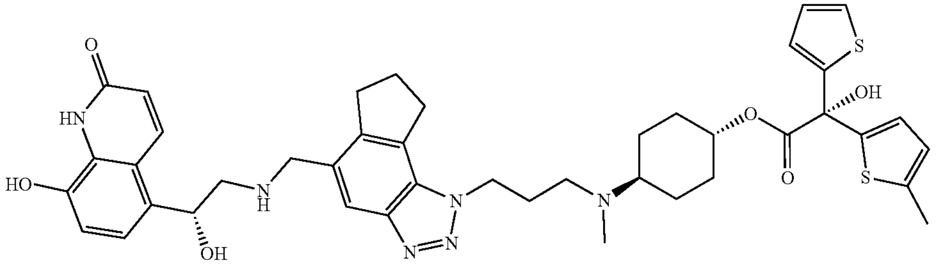

13 or 14

Step 1: Synthesis of Compound 13-1

Compound 5-2 (2 g) and compound 5-4 (2.24 g) were dissolved in anhydrous xylene (30 mL), and 4-dimethylaminopyridine (1.99 g) was added. The mixture was stirred at 140° C. for 14 h. The reaction solution was concentrated under reduced pressure, and the residue was separated and purified by silica gel column chromatography (petroleum ether/ethyl acetate, 1:0-3:1) to give compound 13-1.

MS-ESI calcd. $[M+H+23]^+$ 390, found 389.8.

Step 2: Synthesis of Compound 13-2

The compound 2-bromo-5-methylthiophene (250.6 mg) was dissolved in anhydrous tetrahydrofuran (2.7 mL), and n-butyllithium solution (2.5 M, 0.57 mL) was slowly added dropwise at −78° C. The mixture was stirred at this temperature for 1 h. Compound 13-1 (0.4 g) was dissolved in anhydrous tetrahydrofuran (2.7 mL), and the solution was added dropwise to the reaction solution at −78° C. The resulting mixture was stirred for 1 h.

A saturated aqueous ammonium chloride solution (30 mL) was added to the reaction solution at 0° C. to quench the reaction. The resulting mixture was extracted with ethyl acetate (30 mL×2). The organic phases were combined, dried over anhydrous sodium sulfate, filtered and concentrated under reduced pressure, and the residue was separated and purified by silica gel column chromatography (petroleum ether/ethyl acetate, 1:0-5:1) to give compound 13-2.

$^1$H NMR (400 MHz, $CDCl_3$) δ ppm: 6.69-6.59 (m, 1H), 6.58-6.57 (m, 1H), 6.39 (s, 1H), 6.38-6.33 (m, 1H), 6.03-6.02 (m, 1H), 4.23-4.16 (m, 1H), 4.06 (s, 1H), 3.41 (s, 1H), 2.13 (s, 3H), 1.86 (s, 3H), 1.51-1.49 (m, 2H), 1.17-1.16 (m, 2H), 1.04-0.91 (m, 4H), 0.88 (s, 9H).

MS-ESI calcd. [M+H+23]+488, found 488.2.

Step 3: Preparation of Compounds 13-2a and 13-2b

Compound 13-2 (520 mg) was separated and purified by chiral liquid chromatography to give compound 13-2a and compound 13-2b.

SFC separation method (chromatographic column: DAICEL CHIRALCEL IC (250 mm×30 mm, 10 μm); mobile phase: A: carbon dioxide, B: 40%-40% ethanol (containing 0.1% ammonium hydroxide); flow rate: 70 mL/min, column temperature: 40° C.).

The retention time of compound 13-2a: 5.757 min; MS-ESI calcd. $[M+H-18]^+$ 448, found 448.4. The retention time of compound 13-2b: 6.484 min; MS-ESI calcd. $[M+H-18]^+$ 448, found 448.3.

Step 4: Synthesis of Compound 13-3

Compound 13-2a (130 mg) was dissolved in anhydrous tetrahydrofuran solution (5 mL), and an aqueous hydrochloric acid solution (69.8 μL, 4 M) was added. The mixture was stirred at 25° C. for 18 h. The reaction solution was adjusted to about pH 8 with a saturated aqueous sodium carbonate solution and extracted with ethyl acetate (20 mL×3). The organic phases were combined, washed with saturated brine (20 mL), dried over anhydrous sodium sulfate, filtered and concentrated under reduced pressure to give crude compound 13-3.

MS-ESI calcd. $[M+H]^+$ 366, found 365.9.

Step 5: Synthesis of Compound 13-4

Compound 13-3 (85 mg) was dissolved in acetonitrile (4 mL), and compound 1-12 (75.2 mg), N,N-diisopropylethylamine (120 mg) and potassium iodide (154 mg) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 13-4.

MS-ESI calcd. $[M+H]^+$ 593, found 593.1.

Step 6: Synthesis of Compound 13-5

Compound 13-4 (86 mg) and compound 1-15 (48.5 mg, acetate) were dissolved in anhydrous methanol (4 mL) and anhydrous tetrahydrofuran (2 mL), and N,N-diisopropylethylamine (75 mg) and sodium triacetoxyborohydride (92.2 mg) were added. The mixture was stirred at 25° C. for 24 h, and sodium triacetoxyborohydride (92.2 mg) was added. The mixture was stirred for another 24 h, and sodium triacetoxyborohydride (92.2 mg) was added. The mixture was stirred for another 24 h. A saturated aqueous sodium bicarbonate solution (30 mL) was added to quench the reaction, and the resulting mixture was extracted with ethyl acetate (30 mL×3). The organic phases were combined, washed with brine (20 mL×2), dried over anhydrous sodium sulfate, filtered and concentrated under reduced pressure to give crude compound 13-5.

MS-ESI calcd. $[M+H]^+$ 912, found 911.6.

Step 7: Synthesis of Trifluoroacetate Salt of Compound 13

Compound 13-5 (120 mg) was dissolved in anhydrous tetrahydrofuran (4 mL), and triethylamine trihydrofluoride (120 mg) was added. The mixture was stirred at room temperature for 18 h. The reaction solution was concentrated under reduced pressure, and the residue was separated and purified by high performance liquid chromatography (column type: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 20% to 50% in 8 min) to give a trifluoroacetate salt of compound 13.

$^1$H NMR (400 MHz, DMSO-$d_6$) δ ppm: 10.53-10.49 (m, 2H), 9.74 (s, 1H), 9.22-9.16 (m, 2H), 8.15-8.08 (m, 2H), 7.47-7.46 (m, 1H), 7.16-7.14 (m, 2H), 7.07-7.06 (m, 1H), 7.00-6.96 (m, 2H), 6.83-6.82 (m, 1H), 6.65-6.64 (m, 1H), 6.55-6.53 (m, 1H), 6.26 (s, 1H), 5.43-5.41 (m, 1H), 4.81-4.71 (m, 3H), 4.39 (s, 2H), 3.38-3.34 (m, 4H), 3.18-3.08 (m, 4H), 2.72-2.70 (m, 3H), 2.55 (s, 1H), 2.38 (s, 3H), 2.32-2.21 (m, 1H), 2.00 (s, 4H), 1.68-1.60 (m, 2H), 1.48-1.45 (m, 2H).

MS-ESI calcd. $[M+H]^+$ 797, found 797.2.

The trifluoroacetate salt of compound 14 was prepared in a 4-step reaction with compound 13-2b as the starting material by referring to the synthetic route of the trifluoroacetate salt of compound 13, and the procedures were described in step 8-11.

Step 8: Synthesis of Compound 14-1

Compound 13-2b (140 mg, 300.7 μmol) was dissolved in anhydrous tetrahydrofuran (2 mL), and an aqueous hydrochloric acid solution (1 mL, 4.0 mmol, 4 M) was added. The mixture was stirred at 25° C. for 18 h. The reaction solution was adjusted to about pH 8 with a saturated aqueous sodium carbonate solution and extracted with ethyl acetate (20 mL×3). The organic phases were combined, washed with saturated brine (20 mL), dried over anhydrous sodium sulfate, filtered and concentrated under reduced pressure to give crude compound 14-1.

MS-ESI calcd. $[M+H]^+$ 366, found 365.9.

Step 9: Synthesis of Compound 14-2

Compound 14-1 (52.5 mg, 143.6 μmol) was dissolved in acetonitrile (6 mL), and compound 1-12 (46.4 mg, 143.6 μmol), N,N-diisopropylethylamine (74.2 mg, 574.5 μmol) and potassium iodide (95.3 mg, 574.5 μmol) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 14-2.

MS-ESI calcd. $[M+H]^+$ 593, found 593.

Step 10: Synthesis of Compound 14-3

Compound 14-2 (90 mg, 151.8 μmol) and compound 1-15 (50 mg, 149 μmol, acetate) were dissolved in anhydrous methanol (3 mL) and anhydrous tetrahydrofuran (1.5 mL), and N,N-diisopropylethylamine (78.4 mg, 607 μmol) and sodium triacetoxyborohydride (96.5 mg, 455.5 μmol) were added. The mixture was stirred at 25° C. for 24 h, and sodium triacetoxyborohydride (96.5 mg, 455.5 μmol) was added. The mixture was stirred for another 24 h. sodium triacetoxyborohydride (96.5 mg, 455.5 μmol) was added.

The mixture was stirred for another 24 h. A saturated aqueous sodium bicarbonate solution (30 mL) was added to quench the reaction, and the resulting mixture was extracted with ethyl acetate (30 mL×3). The organic phases were combined, washed with brine (20 mL×2), dried over anhydrous sodium sulfate, filtered and concentrated under reduced pressure to give crude compound 14-3.

MS-ESI calcd. $[M+H]^+$ 912, found 911.4.

Step 11: Synthesis of Trifluoroacetate Salt of Compound 14

Compound 14-3 (75 mg, 61.7 μmol) was dissolved in anhydrous tetrahydrofuran (4 mL), and triethylamine trihydrofluoride (56 mg, 348 μmol) was added. The mixture was stirred at room temperature for 18 h. The reaction solution was concentrated under reduced pressure, and the residue was separated and purified by high performance liquid chromatography (column type: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 22% to 52% in 8 min) to give a trifluoroacetate salt of compound 14.

Trifluoroacetate Salt of Compound 14:

$^1$H NMR (400 MHz, DMSO-$d_6$) δ ppm: 10.5 (s, 2H), 9.53 (s, 1H), 9.11 (s, 2H), 8.14-8.08 (m, 2H), 7.47-7.46 (m, 1H), 7.16-7.14 (m, 2H), 7.07-7.06 (m, 1H), 6.99-6.96 (m, 2H), 6.65-6.64 (m, 1H), 6.56-6.53 (m, 1H), 6.24 (s, 1H), 5.42-5.40 (m, 1H), 4.79-4.74 (m, 3H), 4.38 (s, 2H), 3.19-3.08 (m, 4H), 2.72-2.66 (m, 4H), 2.39 (s, 4H), 2.33-2.22 (m, 6H), 1.99 (s, 5H), 1.68-1.60 (m, 2H), 1.48-1.45 (m, 2H); MS-ESI calcd. $[M+H]^+$ 797, found 797.1.

Example 15 and Example 16

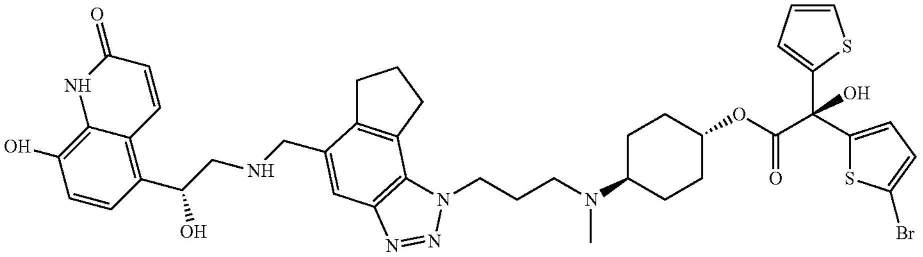

15 or 16

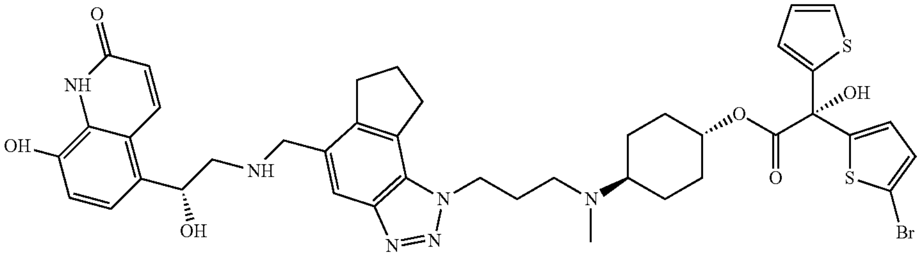

15 or 16

Synthetic Route:

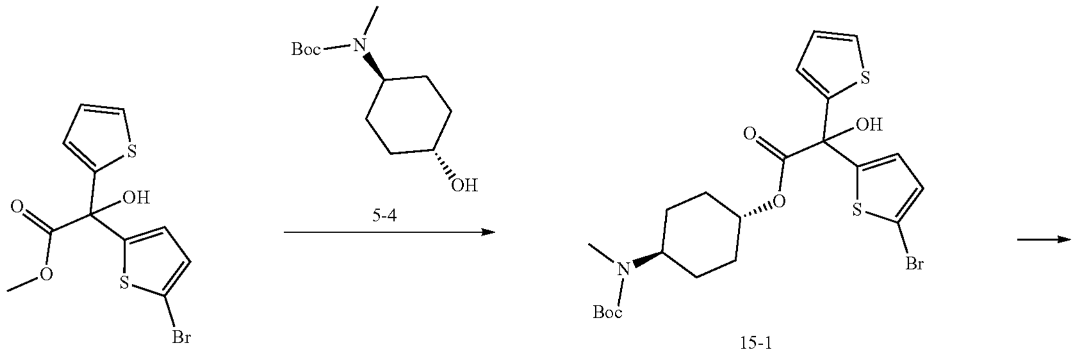

8-1

5-4

15-1

-continued
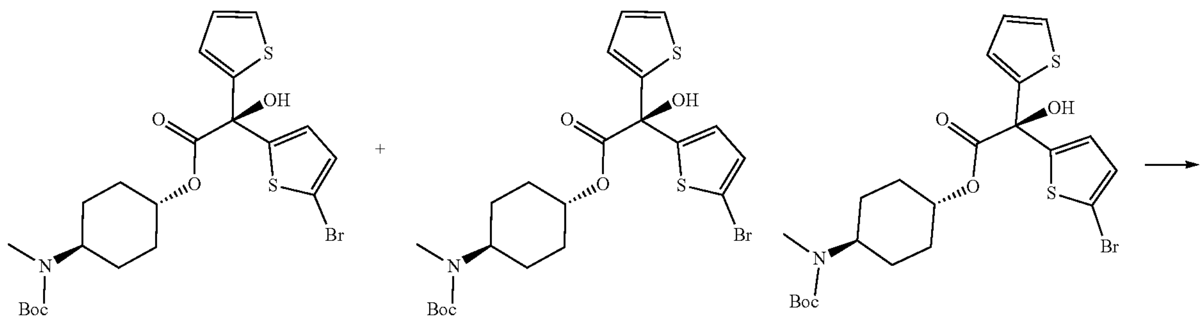
15-1a or 15-1b + 15-1a or 15-1b 15-1a or 15-1b
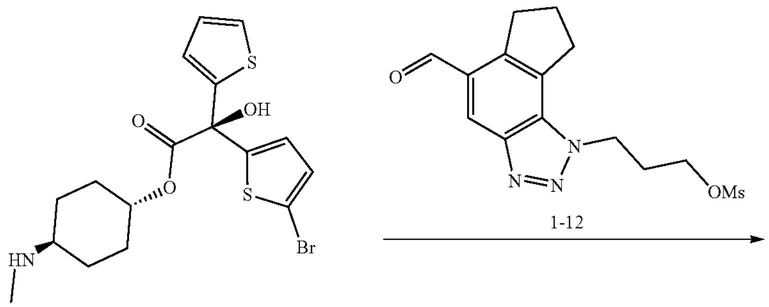
15-2 or 16-1
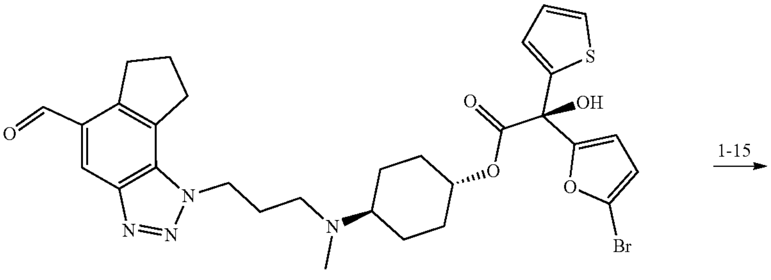
15-3 or 16-2
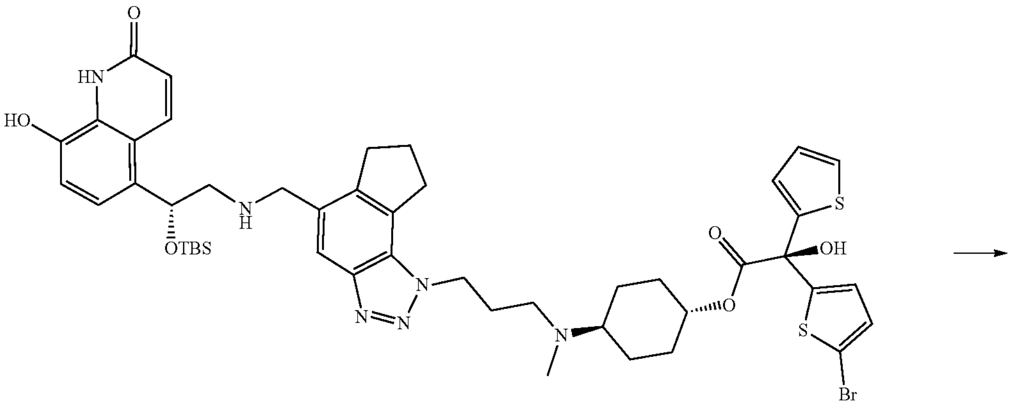
15-4 or 16-3

-continued
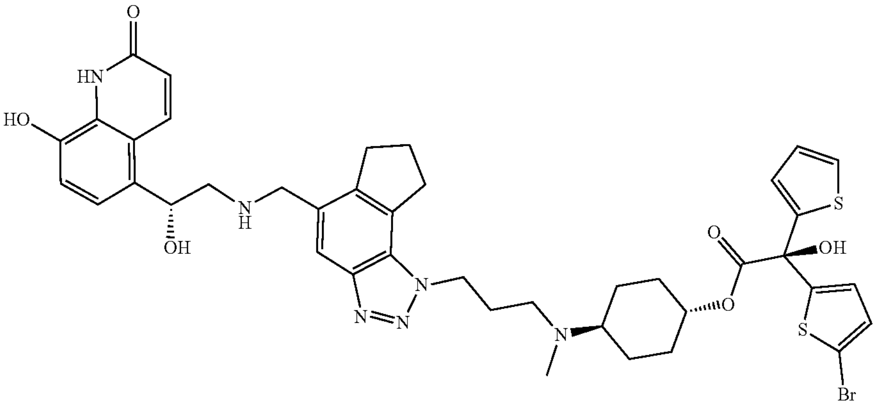
15 or 16
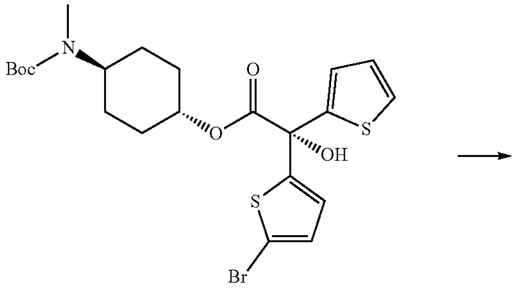
15-1a or 15-1b
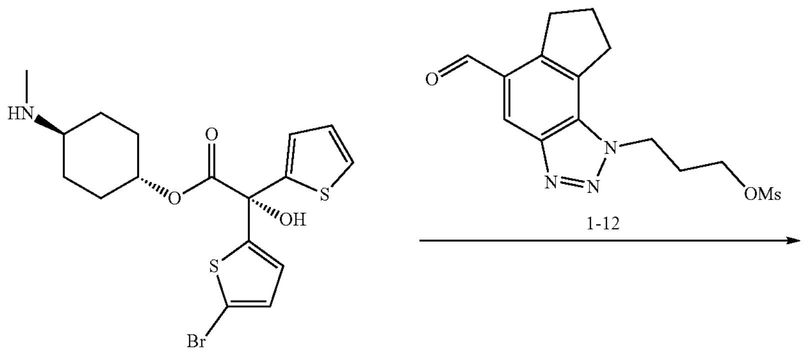
15-2 or 16-1
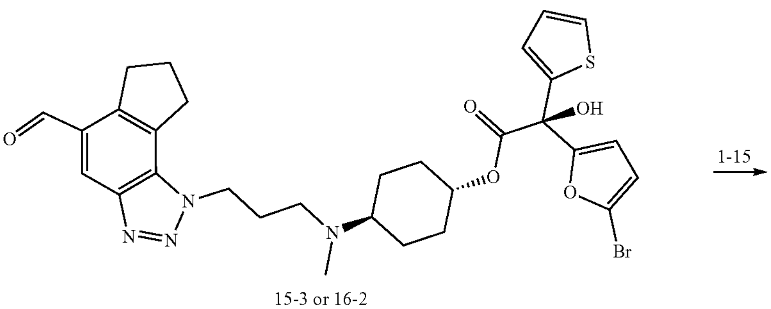
15-3 or 16-2

-continued

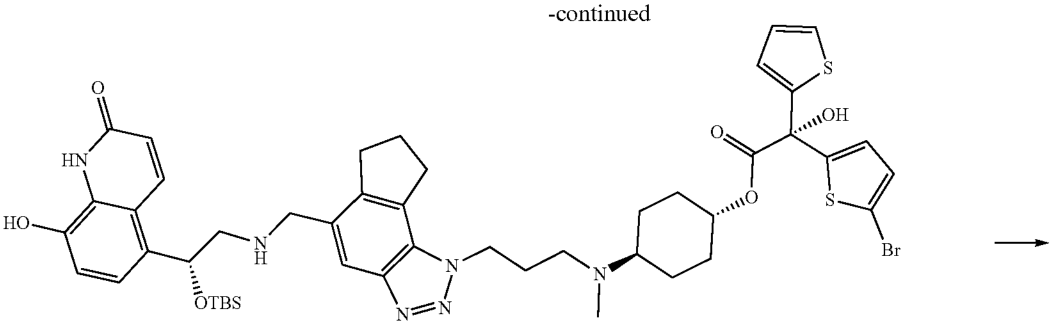

15-4 or 16-3

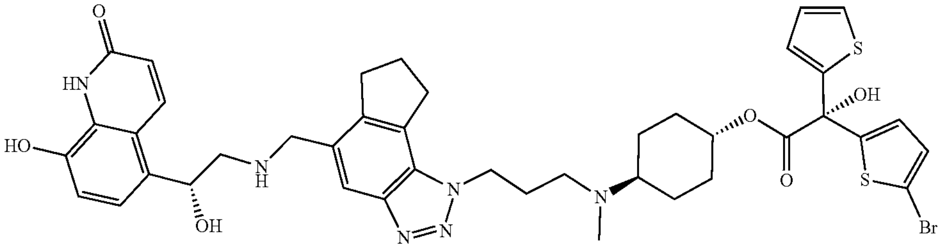

15 or 16

Step 1: Synthesis of Compound 15-1

Compound 8-1 (726 mg) and compound 5-4 (500 mg) were dissolved in anhydrous toluene (6 mL), and sodium hydride (87.2 mg, purity: 60%) was added. The mixture was stirred at 120° C. for 4 h. The reaction solution was cooled to 0° C., and a saturated aqueous ammonium chloride solution (20 mL) was added to quench the reaction. The resulting mixture was extracted with ethyl acetate (30 mL×3). The organic phases were combined, washed with saturated brine (30 mL), dried over anhydrous sodium sulfate, filtered and concentrated under reduced pressure, and the residue was separated and purified by silica gel column chromatography (petroleum ether/ethyl acetate, 1:0-5:1) to give compound 15-1.

MS-ESI calcd. $[M+H-18]^+$ 514, found 513.9.

Step 2: Preparation of Compounds 15-1a and 15-1b

Compound 15-1 (243 mg) was separated and purified by chiral liquid chromatography to give compound 15-1a and compound 15-1b.

SFC separation method (chromatographic column: DAICEL CHIRALPAK AD (250 mm×30 mm, 10 μm); mobile phase: A: carbon dioxide, B: 55%-55% ethanol (containing 0.1% ammonium hydroxide); flow rate: 70 mL/min, column temperature: 40° C.).

The retention time of compound 15-1a: 0.688 min; MS-ESI calcd. $[M+H-18]^+$ 514, found 513.9.

The retention time of compound 15-1b: 1.345 min; MS-ESI calcd. $[M+H-18]^+$ 514, found 513.8.

Step 3: Preparation of Compound 15-2

Compound 15-1a (120 mg) was dissolved in anhydrous dioxane (2 mL), and a dioxane solution of hydrochloric acid (4 mL, 4 M) was added. The mixture was stirred at 25° C. for 4 h. The reaction solution was adjusted to about pH 8 with a saturated aqueous sodium carbonate solution and extracted with ethyl acetate (20 mL×3). The organic phases were combined, washed with saturated brine (20 mL), dried over anhydrous sodium sulfate, filtered and concentrated under reduced pressure to give crude compound 15-2.

MS-ESI calcd. $[M+H]^+$ 430, found 429.8.

Step 4: Preparation of Compound 15-3

Compound 15-2 (79 mg) was dissolved in acetonitrile (4 mL), and compound 1-12 (59.3 mg), N,N-diisopropylethylamine (94.8 mg) and potassium iodide (121 mg) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 15-3.

MS-ESI calcd. $[M+H]^+$ 657 and 659, found 659.

Step 5: Preparation of Compound 15-4

Compound 15-3 (46 mg) and compound 1-15 (23.4 mg, acetate) were dissolved in anhydrous methanol (3 mL) and anhydrous tetrahydrofuran (1.5 mL), and N,N-diisopropylethylamine (27.1 mg) and sodium triacetoxyborohydride (44.4 mg) were added. The mixture was stirred at 25° C. for 24 h, and sodium triacetoxyborohydride (44.4 mg) was added. The mixture was stirred for another 24 h, and sodium triacetoxyborohydride (44.4 mg) was added. The mixture was stirred for another 24 h. A saturated aqueous sodium bicarbonate solution (30 mL) was added to quench the reaction, and the resulting mixture was extracted with ethyl acetate (30 mL×3). The organic phases were combined, washed with brine (20 mL×2), dried over anhydrous sodium sulfate, filtered and concentrated under reduced pressure to give crude compound 15-4.

MS-ESI calcd. $[M+H-42]^+$ 933, found 933.4.

Step 6: Preparation of Trifluoroacetate Salt of Compound 15

Compound 15-4 (102 mg) was dissolved in anhydrous tetrahydrofuran (4 mL), and triethylamine trihydrofluoride (100 mg) was added. The mixture was stirred at room temperature for 18 h. The reaction solution was concentrated under reduced pressure, and the residue was separated by high performance liquid chromatography (column type: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile from 25% to 55% in 8 min) to give a trifluoroacetate salt of compound 15.

$^1H$ NMR (400 MHz, DMSO-$d_6$) δ ppm: 10.50 (s, 2H), 9.68 (s, 1H), 9.16 (s, 2H), 8.15-8.08 (m, 2H), 7.52-7.50 (m, 2H), 7.17-7.14 (m, 1H), 7.10-7.08 (m, 1H), 7.00 (s, 2H), 6.94-6.90 (m, 1H), 6.55-6.53 (m, 1H), 6.25 (s, 1H), 5.43-5.41 (m, 1H), 4.79-4.77 (m, 3H), 4.38 (s, 2H), 3.37 (s, 4H), 3.19-3.10 (m, 4H), 2.72-2.67 (m, 3H), 2.33 (s, 3H), 2.25-2.21 (m, 3H), 2.01-1.99 (m, 4H), 1.65-1.63 (m, 2H), 1.49-1.46 (m, 2H).

MS-ESI calcd. $[M+H]^+$ 861, found 861.2.

The trifluoroacetate salt of compound 16 was prepared in a 4-step reaction with compound 15-1b as the starting material by referring to the synthetic route of the trifluoroacetate salt of compound 15.

Trifluoroacetate Salt of Compound 16:

$^1H$ NMR (400 MHz, DMSO-$d_6$) δ ppm: 10.54-10.50 (m, 2H), 9.74 (s, 1H), 9.21-9.15 (m, 2H), 8.15-8.07 (m, 2H), 7.51-7.50 (m, 2H), 7.16-7.14 (m, 1H), 7.08-7.07 (m, 1H), 7.00-6.97 (m, 3H), 6.93-6.92 (m, 1H), 6.55-6.52 (m, 1H), 6.26 (s, 1H), 5.43-5.40 (m, 1H), 4.78-4.77 (m, 3H), 4.38 (s, 2H), 3.38-3.36 (m, 4H), 3.18-3.07 (m, 4H), 2.71-2.67 (m, 3H), 2.54 (s, 1H), 2.32-2.20 (m, 4H), 2.00 (s, 4H), 1.68-1.57 (m, 2H), 1.52-1.46 (m, 2H);

MS-ESI calcd. $[M+H]^+$ 861, found 861.

Example 17 and Example 18

17 or 18

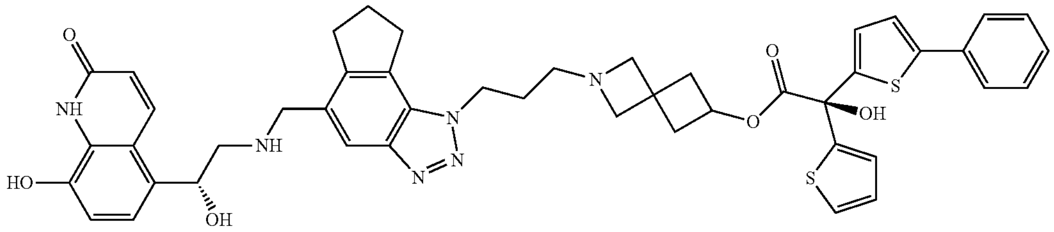

17 or 18

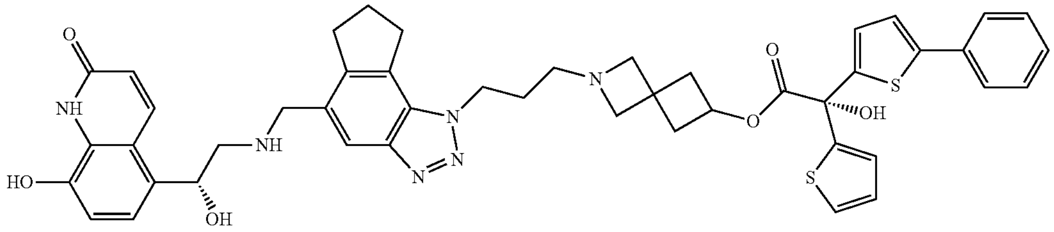

Synthetic Route:

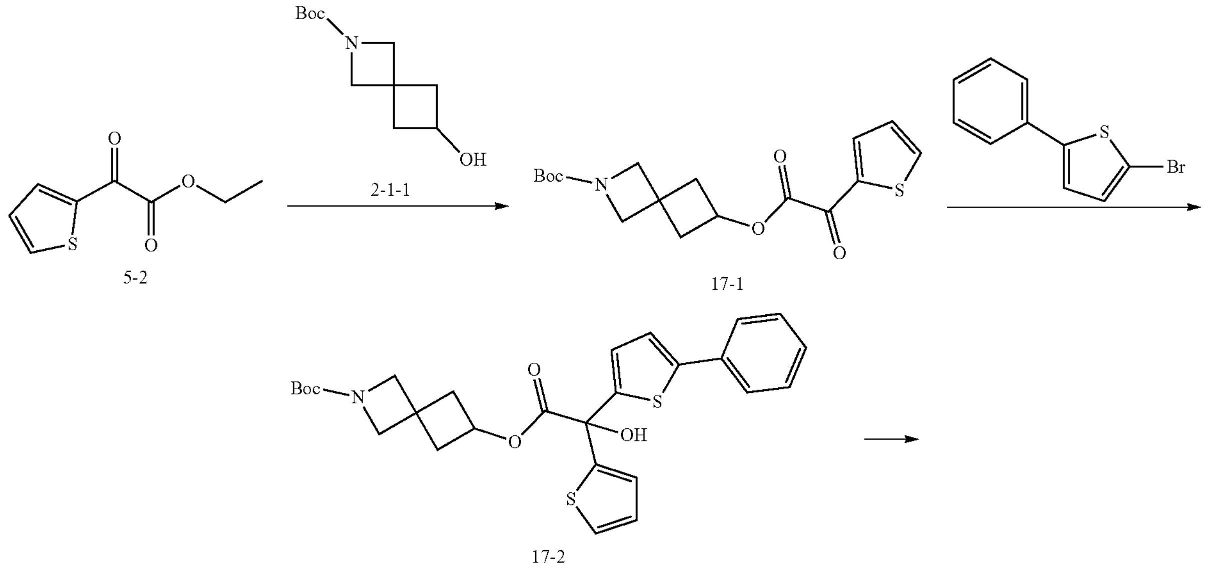

5-2

2-1-1

17-1

17-2

-continued
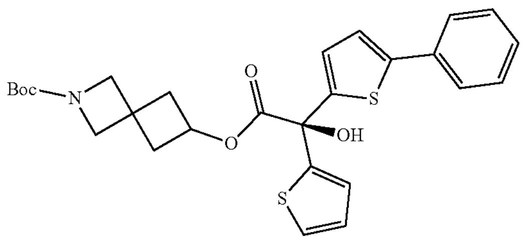
17-2a or 17-2b
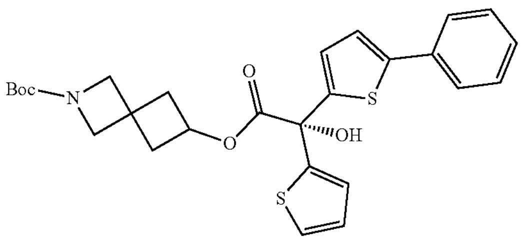
17-2a or 17-2b
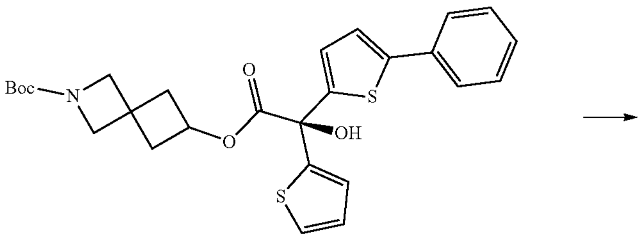
17-2a or 17-2b
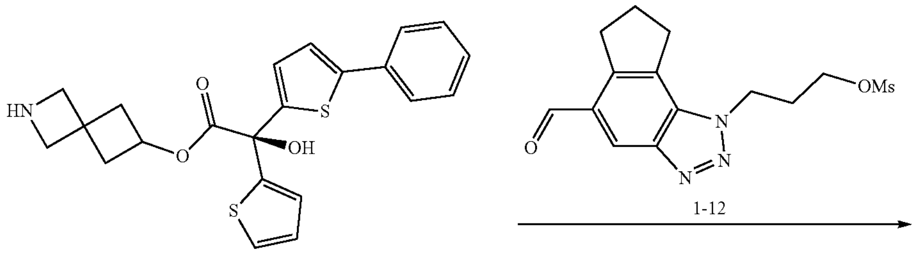
17-3 or 18-1
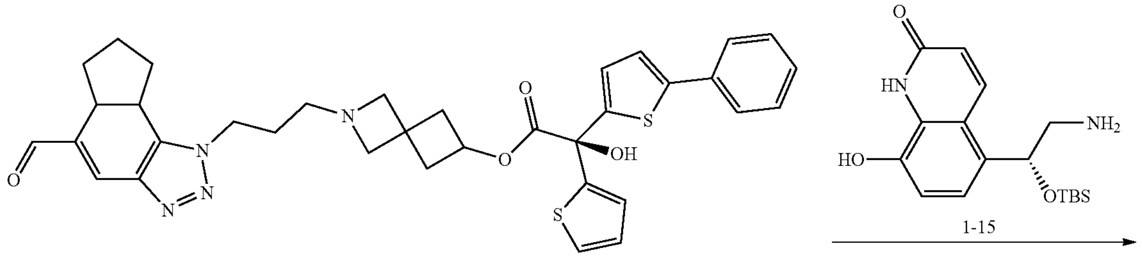
17-4 or 18-2
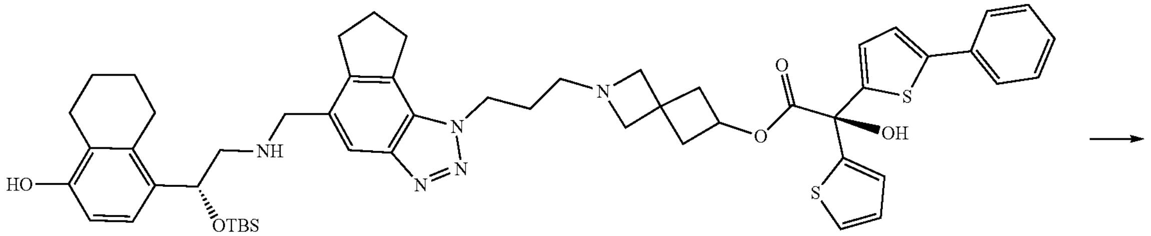
17-5 or 18-3
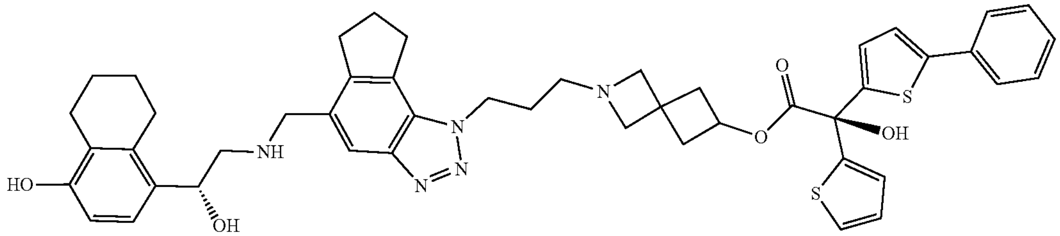
17 or 18

-continued

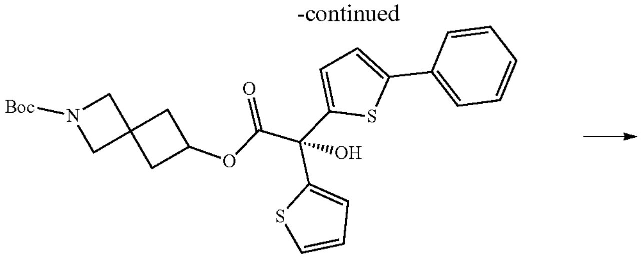

17-2a or 17-2b

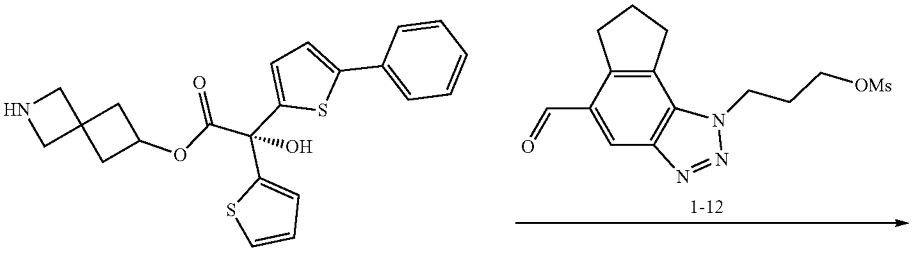

17-3 or 18-1

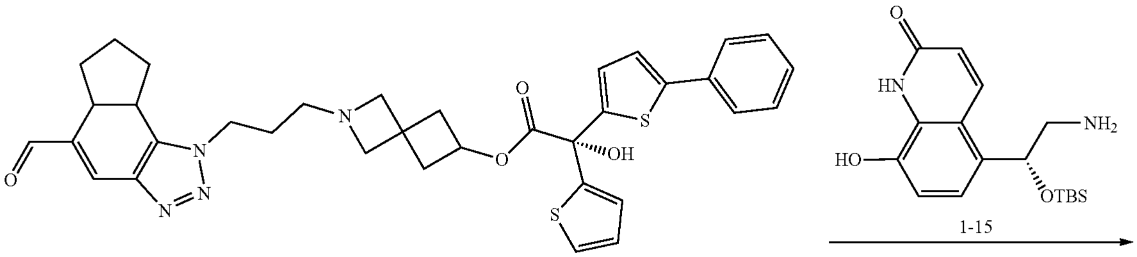

17-4 or 18-2

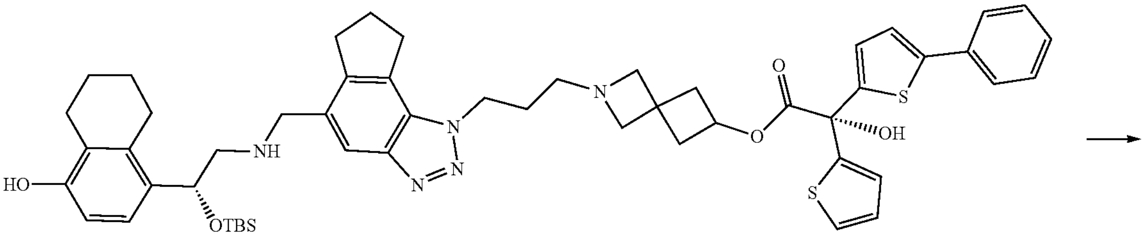

17-5 or 18-3

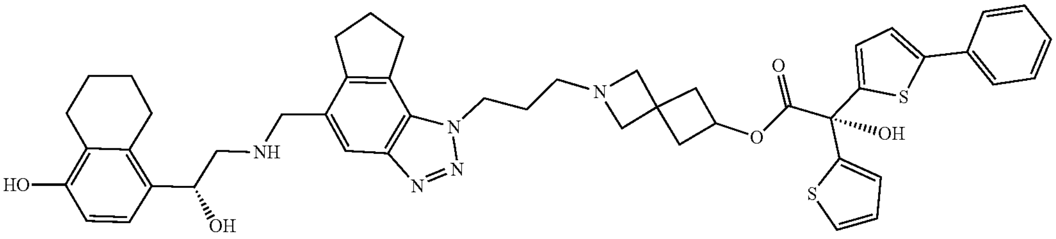

17 or 18

Step 1: Synthesis of Compound 17-1

Compound 5-2 (1.3 g) and compound 2-1-1 (1.00 g) were dissolved in anhydrous toluene (40 mL), and 4-dimethylaminopyridine (859 mg) was added at room temperature. The mixture was heated to 120° C. and stirred for 14 h. After the reaction was completed, the reaction solution was concentrated under reduced pressure, and the residue was separated and purified by flash silica gel column chromatography (eluent: ethyl acetate/petroleum ether, 0-25%) to give compound 17-1.

MS-ESI calcd. [M+H−56]+296, found 295.9.

Step 2: Synthesis of Compound 17-2

The compound 2-bromo-5-phenylthiophene (204 mg) was dissolved in tetrahydrofuran (8 mL) and n-butyllithium solution (2.5 M in tetrahydrofuran, 0.34 mL) was slowly added dropwise at −60° C. under nitrogen atmosphere. The mixture was stirred at −60° C. for 0.5 h. Compound 17-1 (200 mg) was dissolved in tetrahydrofuran (3 mL) and slowly added dropwise to the reaction solution at −60° C. After the dropwise addition, the mixture was stirred at −50° C. for 1 h. The reaction solution was heated to 0° C., and the reaction was quenched with a saturated aqueous ammonium chloride solution (10 mL). The resulting mixture was extracted with ethyl acetate (15 mL×2). The organic phase was washed with saturated brine (20 mL), dried over anhydrous sodium sulfate, and concentrated under reduced pressure, and the residue was separated and purified by flash silica gel column chromatography (eluent: ethyl acetate/petroleum ether, 0-25%) to give compound 17-2.

MS-ESI calcd. $[M+H-18]^+$ 494, found 494.4.

Step 3: Preparation of Compounds 17-2a and 17-2b by Chiral Resolution

Compound 17-2 was separated and purified by chiral liquid chromatography to give compound 17-2a and compound 17-2b.

SFC separation method: chromatographic column: DAICEL CHIRALPAK AD 250 mm×30 mm, 10 μm; mobile phase: A: carbon dioxide, B: ethanol (containing 0.1% ammonium hydroxide); flow rate: 70 mL/min, column temperature: 40° C.

The retention time of compound 17-2a: 0.889 min; MS-ESI calcd. $[M+H-18]^+$ 494, found 494.4.

The retention time of compound 17-2b: 1.302 min; MS-ESI calcd. $[M+H-18]^+$ 494, found 494.4.

Step 4: Synthesis of Compound 17-3

Compound 17-2a (250.0 mg) was dissolved in anhydrous tetrahydrofuran (10 mL), and an aqueous hydrochloric acid solution (10 mL, 4 M) was added. The mixture was stirred at room temperature for 14 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 17-3, which was directly used in the next step.

MS-ESI calcd. $[M+H]^+$ 412, found 411.9.

Step 5: Synthesis of Compound 17-4

Compound 17-3 (100 mg) was dissolved in acetonitrile (10 mL), and compound 1-12 (78.5 mg), potassium iodide (161 mg) and N,N-diisopropylethylamine (94.2 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 17-4.

MS-ESI calcd. $[M+H]^+$ 639, found 639.1.

Step 6: Synthesis of Compound 17-5

Compound 17-4 (77.7 mg) and compound 1-15 (40.0 mg, acetate) were dissolved in anhydrous methanol (4 mL) and anhydrous tetrahydrofuran (2 mL), and sodium triacetoxyborohydride (107 mg) and N,N-diisopropylethylamine (26.2 mg) were added. The mixture was stirred at 25° C. for 12 h, and sodium triacetoxyborohydride (107 mg) was added. The mixture was stirred for another 5 h. A 4% aqueous sodium bicarbonate solution (5 mL) was added to quench the reaction, and the resulting mixture was extracted with ethyl acetate (10 mL). The organic phases were combined, dried over anhydrous sodium sulfate, filtered and concentrated under reduced pressure to give compound 17-5, which was directly used in the next step.

MS-ESI calcd. $[M+H]^+$ 957, found 957.2.

Step 7: Synthesis of Formate Salt of Compound 17

Compound 17-5 (35 mg) was dissolved in tetrahydrofuran (3 mL), and triethylamine trihydrofluoride (29.5 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 17.

$^1H$ NMR (400 MHz, DMSO-$d_6$) δ: 8.36 (s, 1H), 8.15-8.10 (m, 1H), 7.70 (s, 1H), 7.61-7.57 (m, 2H), 7.50-7.48 (m, 1H), 7.40-7.33 (m, 3H), 7.31-7.27 (m, 1H), 7.13-7.12 (m, 1H), 7.06-7.03 (m, 2H), 7.02-6.98 (m, 1H), 6.90-6.86 (m, 1H), 6.42-6.37 (m, 1H), 5.08-5.04 (m, 1H), 4.95-4.91 (m, 1H), 4.67-4.61 (m, 2H), 3.80 (s, 2H), 3.06 (s, 2H), 2.99 (s, 2H), 2.93-2.87 (m, 2H), 2.82-2.66 (m, 4H), 2.35-2.31 (m, 1H), 2.29-2.25 (m, 2H), 2.17-2.07 (m, 5H), 1.82-1.78 (m, 2H).

MS-ESI calcd. $[M+H]^+$ 843, found 843.2.

The formate salt of compound 18 was prepared in a 4-step reaction with compound 17-2b as the starting material by referring to the synthetic route of the formate salt of compound 17.

Formate Salt of Compound 18:

$^1H$ NMR (400 MHz, DMSO-$d_6$) δ: 8.17 (s, 1H), 8.15-8.10 (m, 1H), 7.75 (s, 1H), 7.61-7.57 (m, 2H), 7.50-7.48 (m, 1H), 7.40-7.33 (m, 3H), 7.31-7.26 (m, 1H), 7.13-7.12 (m, 1H), 7.07-7.04 (m, 2H), 7.02-6.98 (m, 1H), 6.91-6.88 (m, 1H), 6.44-6.39 (m, 1H), 5.13-5.08 (m, 1H), 4.98-4.89 (m, 1H), 4.68-4.61 (m, 2H), 3.87 (s, 2H), 3.16 (s, 2H), 3.09 (s, 2H), 2.95-2.72 (m, 6H), 2.39-2.30 (m, 3H), 2.20-2.07 (m, 5H), 1.85-1.80 (m, 2H); MS-ESI calcd. $[M+H]^+$ 843, found 843.2.

Example 19

19

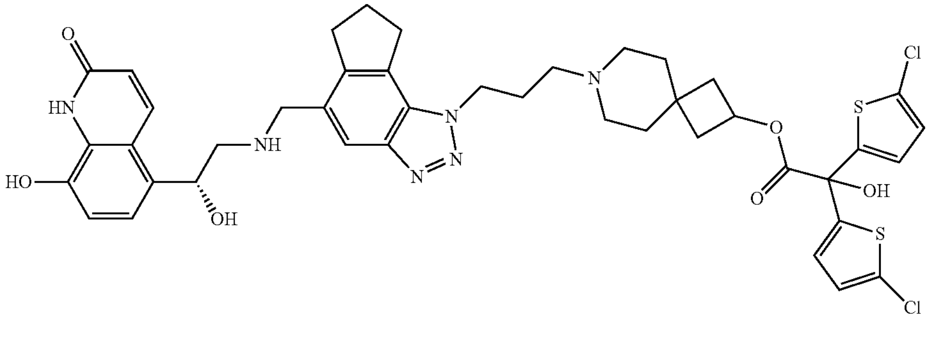

Synthetic Route:
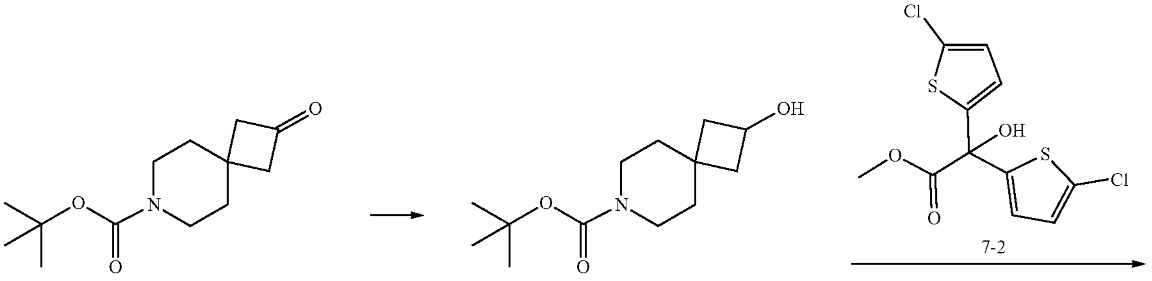
19-1 19-2
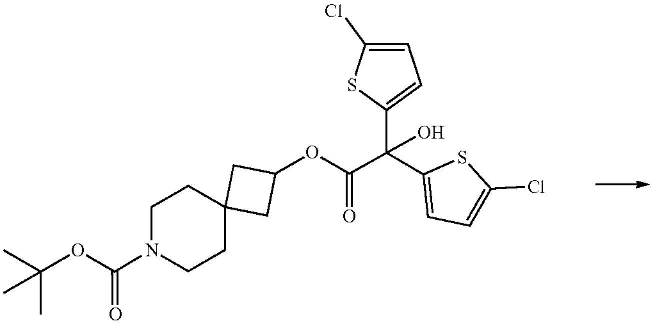
19-3
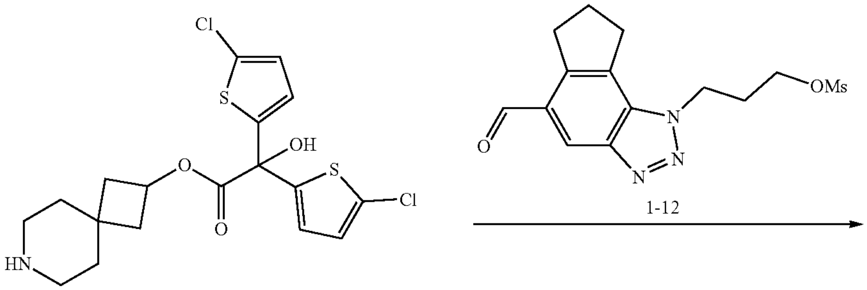
19-4
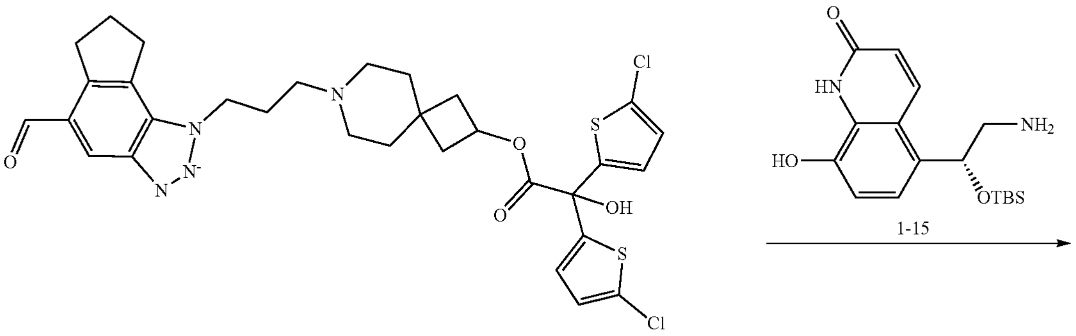
19-5

-continued

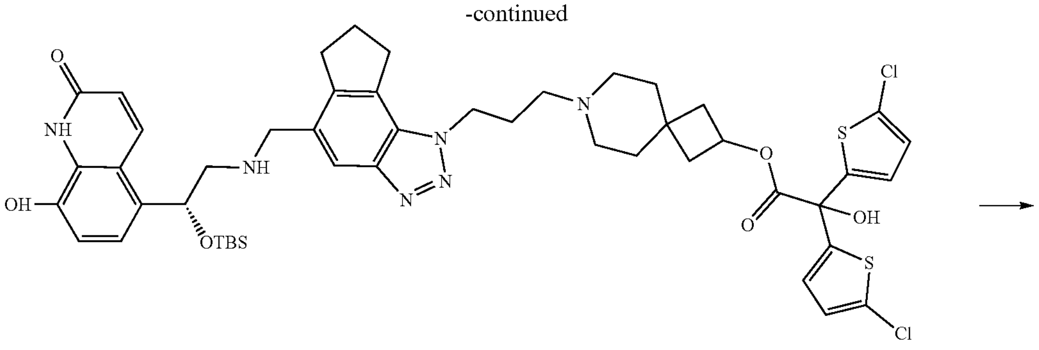

19-6

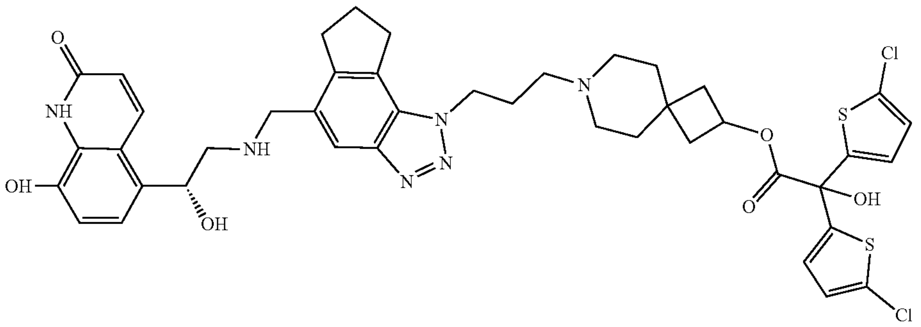

19

Step 1: Synthesis of Compound 19-2

Compound 19-1 (500 mg) was dissolved in methanol (10 mL), and sodium borohydride (158 mg) was added at 0° C. The mixture was stirred at 0° C. for 0.5 h. Water (15 mL) was added to quench the reaction, and the resulting mixture was extracted with ethyl acetate (20 mL×2). The organic phases were combined, dried over anhydrous sodium sulfate, filtered and concentrated under reduced pressure to give compound 19-2, which was directly used in the next step.

$^{1}$H NMR (400 MHz, $CDCl_3$) δ: 4.37-4.29 (m, 1H), 3.36-3.29 (m, 4H), 2.32-2.257 (m, 2H), 1.70-1.68 (m, 2H), 1.55-1.50 (m, 4H), 1.45 (s, 9H).

Step 2: Synthesis of Compound 19-3

Compound 7-2 (300.0 mg) and compound 19-2 (224 mg) were dissolved in anhydrous toluene (10 mL), and sodium hydride (18.5 mg, purity: 60%) was added in portions at room temperature. The mixture was heated to 120° C. and stirred for 2 h. Three batches were fed in parallel. After the reaction was completed, the reaction solution was cooled to room temperature, and slowly added to a saturated aqueous ammonium chloride solution (10 mL) under stirring in an ice-bath condition to quench the reaction. The resulting mixture was extracted with ethyl acetate (20 mL×2). The organic phases were combined, washed with saturated brine (50 mL), dried over anhydrous sodium sulfate, filtered and concentrated under reduced pressure, and the residue was separated and purified by flash silica gel column chromatography (eluent: ethyl acetate/petroleum ether, 0-25%) to give compound 19-3.

MS-ESI calcd. $[M+H-18-56]^+$ 458, found 457.8.

Step 3: Synthesis of Compound 19-4

Compound 19-3 (360.0 g) was dissolved in dioxane (2 mL), and hydrochloric acid/dioxane solution (10 mL, 4 M) was added. The mixture was stirred at room temperature for 2 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 19-4, which was directly used in the next step.

MS-ESI calcd. $[M+H]^+$ 432, found 431.9.

Step 4: Synthesis of Compound 19-5

Compound 19-4 (120.0 mg) was dissolved in acetonitrile (15 mL), and compound 1-12 (98.7 mg), potassium iodide (230 mg) and N,N-diisopropylethylamine (107.6 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 19-5.

MS-ESI calcd. $[M+H]^+$ 659, found 659.

Step 5: Synthesis of Compound 19-6

Compound 19-5 (83.6 mg) and compound 1-15 (50.0 mg, acetate) were dissolved in anhydrous methanol (4 mL) and anhydrous tetrahydrofuran (2 mL), and N,N-diisopropylethylamine (32.7 mg) and sodium triacetoxyborohydride (134 mg) were added. The mixture was stirred at 25° C. for 12 h, and sodium triacetoxyborohydride (134 mg) was added. The mixture was stirred for another 5 h. A 4% aqueous sodium bicarbonate solution (10 mL) was added to quench the reaction, and the resulting mixture was extracted with ethyl acetate (10 mL×2). The organic phases were combined, dried over anhydrous sodium sulfate, filtered and concentrated under reduced pressure to give compound 19-6, which was directly used in the next step.

MS-ESI calcd. $[M+H]^+$ 977, found 977.

Step 6: Synthesis of Formate Salt of Compound 19

Compound 19-6 (100 mg) was dissolved in tetrahydrofuran (5 mL), and triethylamine trihydrofluoride (82.4 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX $C_{18}$, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 19.

$^1$H NMR (400 MHz, DMSO-$d_6$) δ: 8.19 (s, 2H), 8.15-8.11 (m, 1H), 7.77 (s, 1H), 7.09-7.05 (m, 1H), 7.02-6.99 (m, 2H), 6.97-6.89 (m, 3H), 6.45-6.40 (m, 1H), 5.15-5.11 (m, 1H), 5.06-5.00 m, 1H), 4.71-4.66 (m, 2H), 3.90 (s, 2H), 3.32-3.27 (m, 2H), 2.97-2.90 (m 2H), 2.87-2.79 (m, 2H), 2.30-2.14 (m, 10H), 2.06-1.98 (m, 2H), 1.76-1.68 (m, 2H), 1.49-1.41 (m, 4H).

MS-ESI calcd. $[M+H]^+$ 863, found 863.1.

Example 20 and Example 21

20 or 21

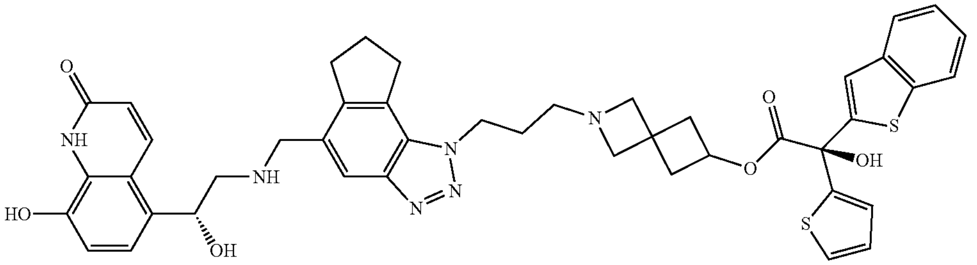

20 or 21

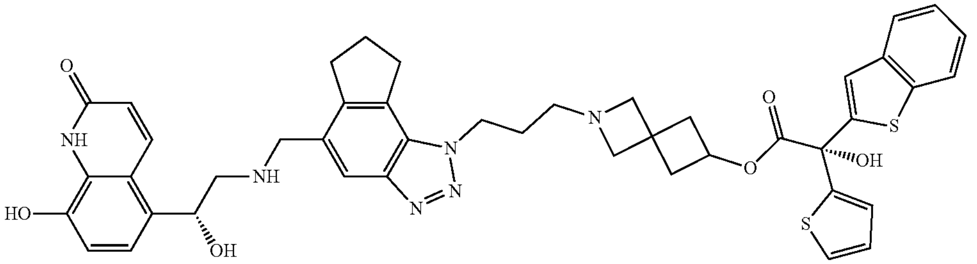

Synthetic Route:

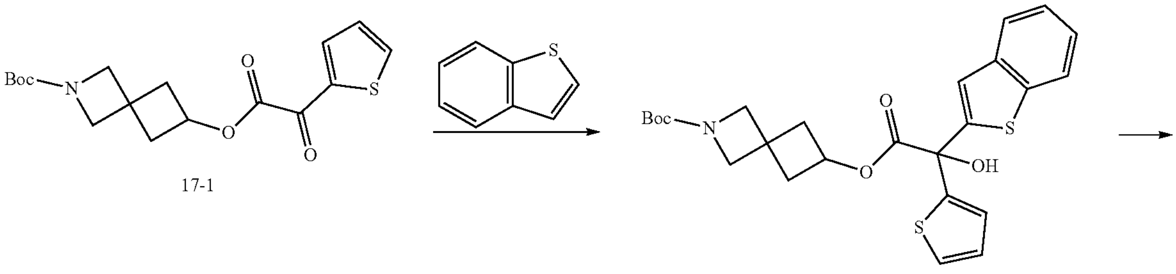

17-1

20-1

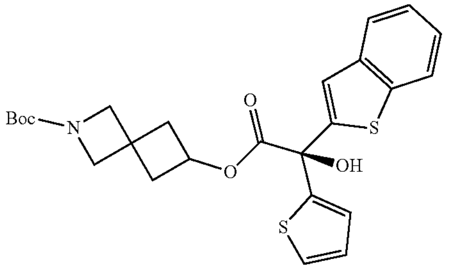

20-1A or 20-1B

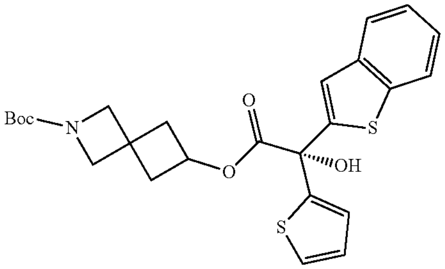

20-1A or 20-1B

-continued
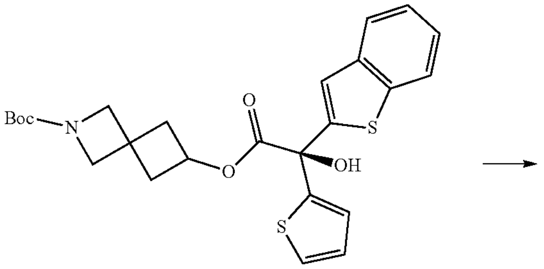
20-1A or 20-1B
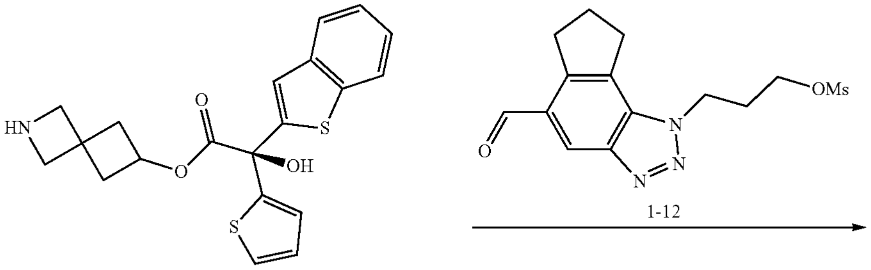
20-2 or 21-1
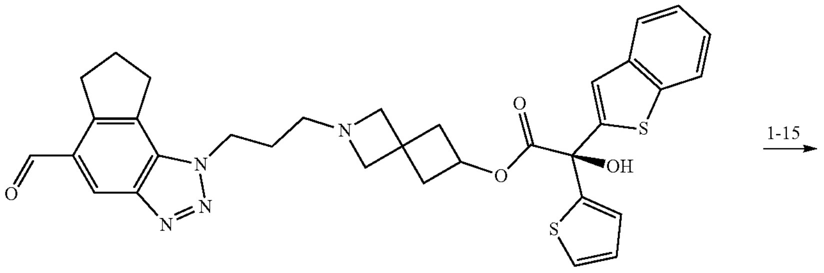
20-3 or 21-2
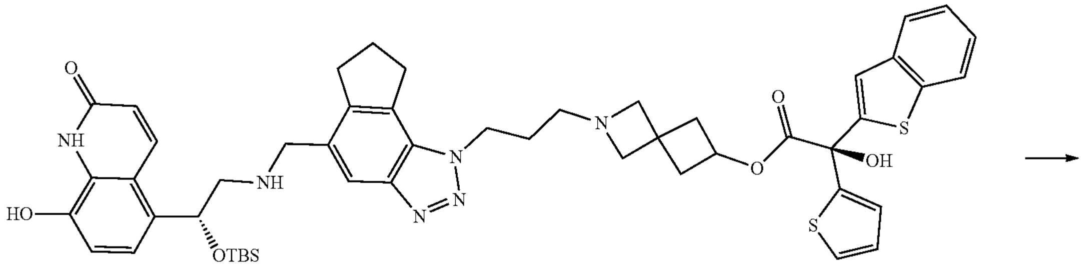
20-4 or 21-3
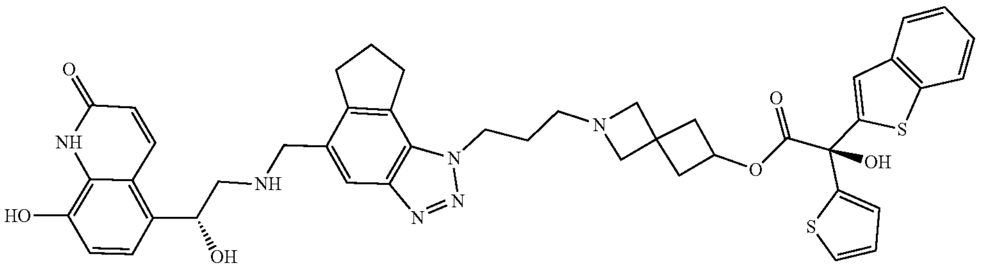
20 or 21

-continued

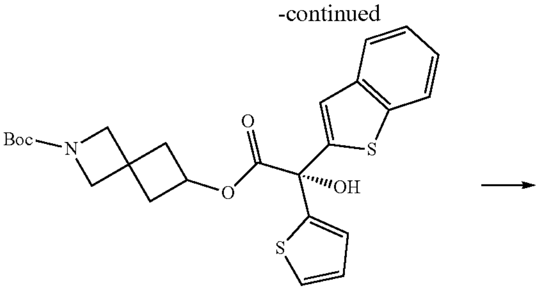

20-1A or 20-1B

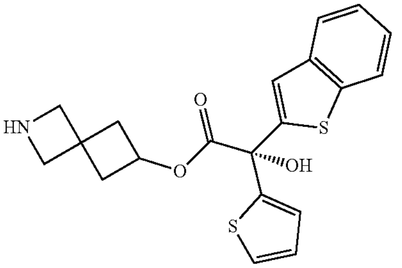

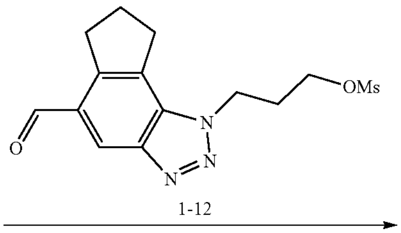

20-2 or 21-1

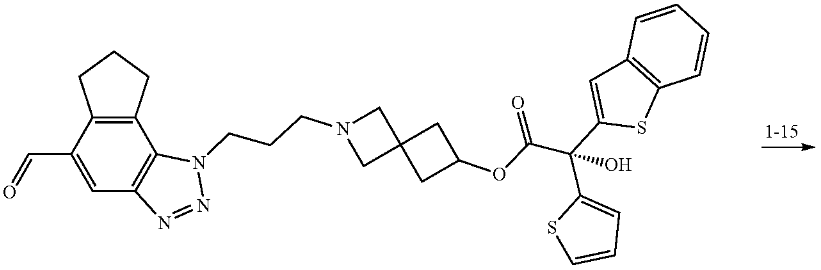

20-3 or 21-2

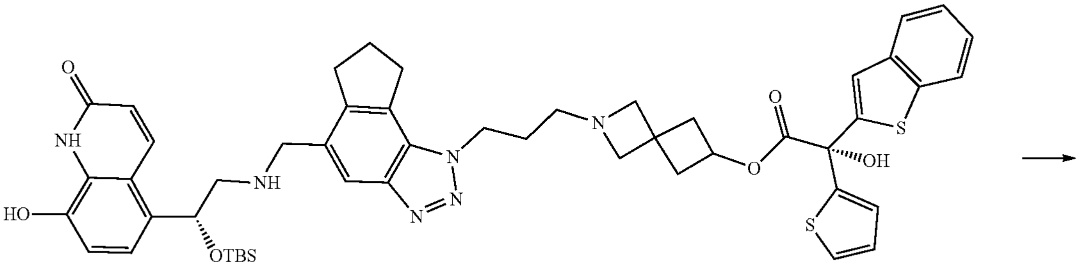

20-4 or 21-3

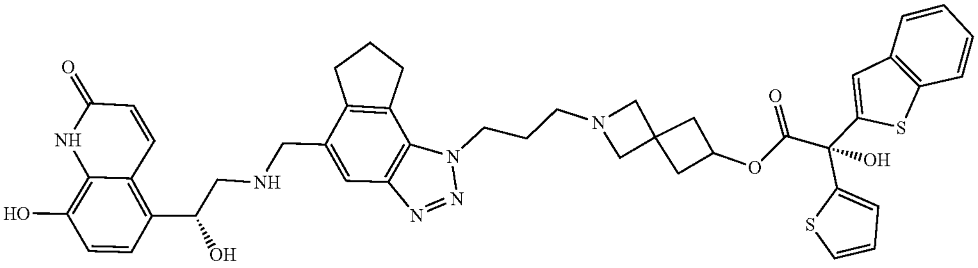

20 or 21

Step 1: Synthesis of Compound 20-1

The compound benzothiophene (198 mg) was dissolved in tetrahydrofuran (20 mL) and lithium diisopropylamide (2.0 M in tetrahydrofuran, 0.8 mL) was slowly added dropwise at −60° C. under nitrogen atmosphere. The mixture was stirred at −60° C. for 0.5 h. Compound 17-1 (400 mg) was dissolved in tetrahydrofuran (5 mL) and slowly added dropwise to the reaction solution at −60° C. After the dropwise addition, the mixture was stirred at −50° C. for 1 h. The reaction solution was heated to 0° C., and the reaction was quenched with a saturated aqueous ammonium chloride solution (10 mL). The resulting mixture was extracted with ethyl acetate (15 mL×2). The organic phase was washed with saturated brine (30 mL), dried over anhydrous sodium sulfate, and concentrated under reduced pressure, and the residue was separated and purified by flash silica gel column chromatography (eluent: ethyl acetate/petroleum ether, 0-25%) to give compound 20-1.

MS-ESI calcd. [M+H−56]+430, found 429.8.

Step 2: Preparation of Compounds 20-1A and 20-1B

Compound 20-1 was separated and purified by chiral liquid chromatography to give compound 20-1A and compound 20-1B.

SFC separation method: chromatographic column (DAICEL CHIRALPAK OJ 250 mm×30 mm, 10 μm); mobile phase: A: carbon dioxide, B: ethanol (containing 0.1% ammonium hydroxide); flow rate: 80 mL/min, column temperature: 40° C.

The retention time of compound 20-1A: 5.680 min; MS-ESI calcd. [M+H−56]+430, found 429.8.

The retention time of compound 20-1B: 6.705 min; MS-ESI calcd. [M+H−56]+430, found 429.8.

Step 3: Synthesis of Compound 20-2

Compound 20-1A (200.0 mg) was dissolved in anhydrous tetrahydrofuran (10 mL), and an aqueous hydrochloric acid solution (10 mL, 4 M) was added. The mixture was stirred at room temperature for 14 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 20-2, which was directly used in the next step.

MS-ESI calcd. $[M+H]^+$ 386, found 385.9.

Step 4: Synthesis of Compound 20-3

Compound 20-2 (83.9 mg) was dissolved in acetonitrile (20 mL), and compound 1-12 (100 mg), potassium iodide (215 mg) and N,N-diisopropylethylamine (100 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 20-3.

MS-ESI calcd. $[M+H]^+$ 613, found 613.

Step 5: Synthesis of Compound 20-4

Compound 20-3 (102.5 mg) and compound 1-15 (60.0 mg, acetate) were dissolved in anhydrous methanol (4 mL) and anhydrous tetrahydrofuran (2 mL), and sodium triacetoxyborohydride (161 mg) and N,N-diisopropylethylamine (39.3 mg) were added. The mixture was stirred at 25° C. for 12 h, and sodium triacetoxyborohydride (161 mg) was added. The mixture was stirred for another 5 h. A 4% aqueous sodium bicarbonate solution (5 mL) was added to quench the reaction, and the resulting mixture was extracted with ethyl acetate (8 mL×2). The organic phases were combined, dried over anhydrous sodium sulfate, filtered and concentrated under reduced pressure to give compound 20-4, which was directly used in the next step.

MS-ESI calcd. $[M+H]^+$ 931, found 931.3.

Step 7: Synthesis of Formate Salt of Compound 20

Compound 20-4 (125 mg) was dissolved in tetrahydrofuran (5 mL), and triethylamine trihydrofluoride (108 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX $C_{18}$, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 20.

$^1H$ NMR (400 MHz, DMSO-$d_6$) δ: 8.20 (s, 2H), 8.16-8.12 (m, 1H), 7.92-7.88 (m, 1H), 7.84-7.78 (m, 2H), 7.53-7.50 (m, 1H), 7.37 (s, 1H), 7.35-7.29 (m, 2H), 7.18-7.15 (m, 1H), 7.10-7.06 (m, 1H), 7.04-6.99 (m, 1H), 6.94-6.90 (m, 1H), 6.47-6.40 (m, 1H), 5.17-5.15 (m, 1H), 4.99-4.93 (m, 1H), 4.70-4.64 (m, 2H), 3.93 (s, 2H), 3.32-3.11 (m, 6H), 2.98-2.83 (m, 4H), 2.44-2.38 (m, 3H), 2.22-2.02 (m, 5H), 1.87-1.80 (m, 2H).

MS-ESI calcd. $[M+H]^+$ 817, found 817.2.

The formate salt of compound 21 was prepared in a 4-step reaction with compound 20-1B as the starting material by referring to the synthetic route of the formate salt of compound 20.

Formate Salt of Compound 21:

$^1H$ NMR (400 MHz, DMSO-$d_6$) δ: 8.20 (s, 2H), 8.16-8.11 (m, 1H), 7.91-7.87 (m, 1H), 7.82-7.78 (m, 2H), 7.52-7.49 (m, 1H), 7.38-7.29 (m, 3H), 7.17-7.14 (m, 1H), 7.10-7.05 (m, 1H), 7.04-6.99 (m, 1H), 6.94-6.89 (m, 1H), 6.46-6.40 (m, 1H), 5.17-5.15 (m, 1H), 4.99-4.92 (m, 1H), 4.68-4.63 (m, 2H), 3.93 (s, 2H), 3.32-3.11 (m, 6H), 2.98-2.83 (m, 4H), 2.44-2.38 (m, 3H), 2.22-2.05 (m, 5H), 1.87-1.80 (m, 2H);

MS-ESI calcd. $[M+H]^+$ 817, found 817.2.

Example 22 and Example 23

22 or 23

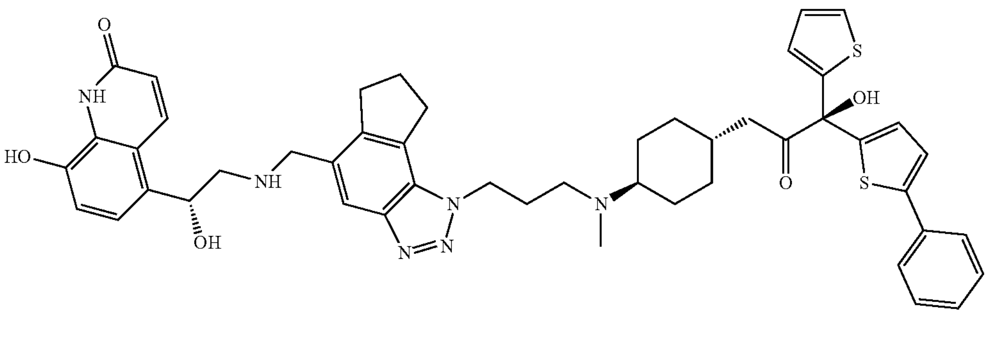

-continued
22 or 23
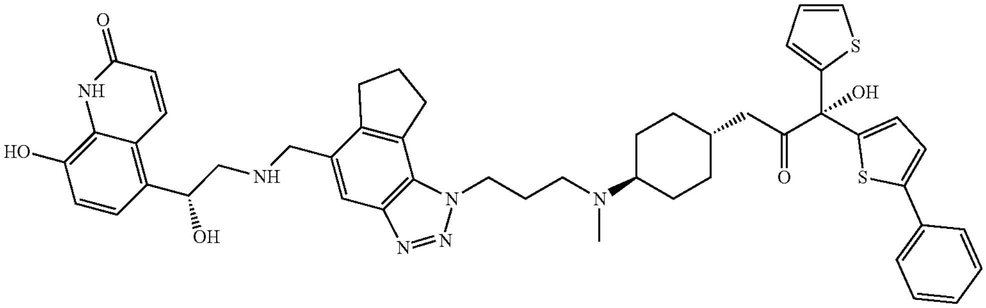
Synthetic Route:
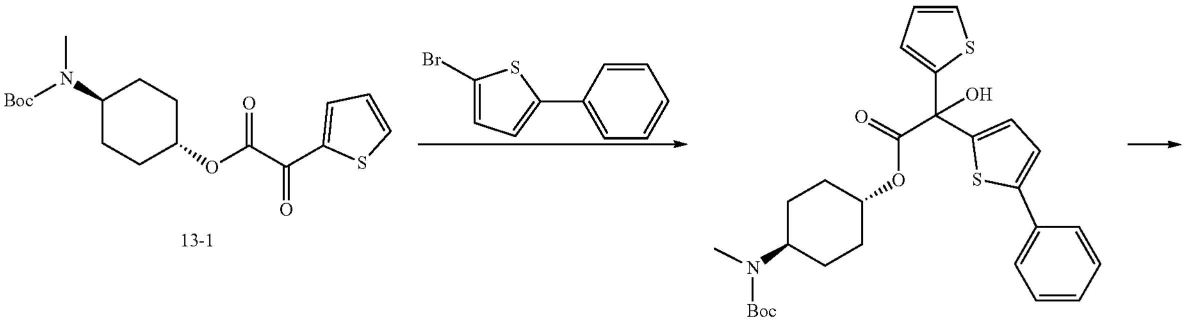
13-1
22-1
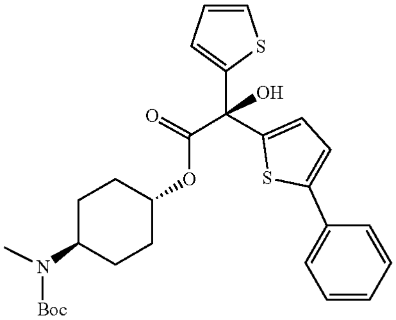
22-1a or 22-1b
+
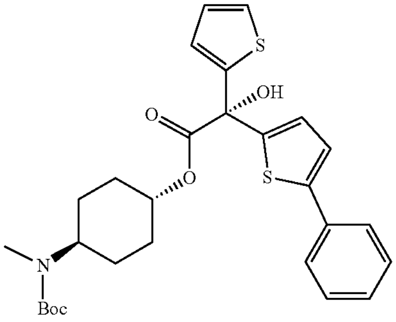
22-1a or 22-1b
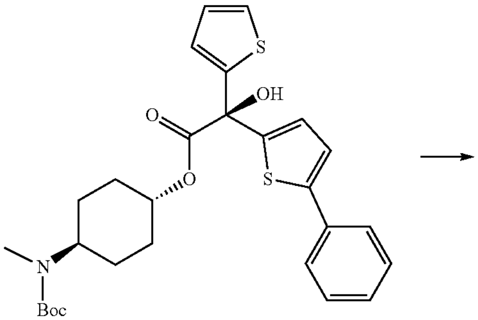
22-1a or 22-1b -continued
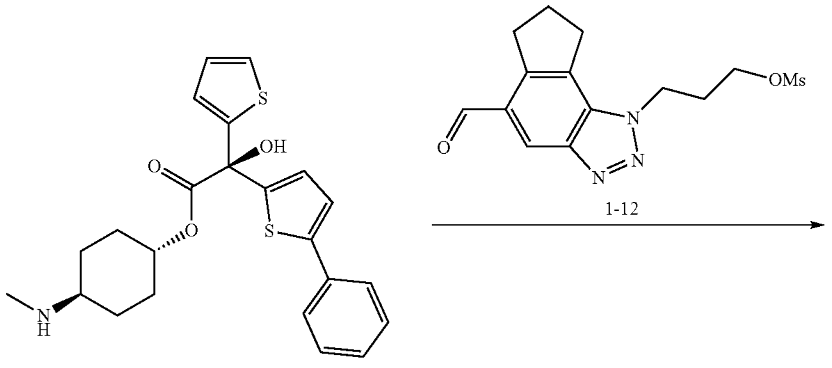
22-2 or 23-1
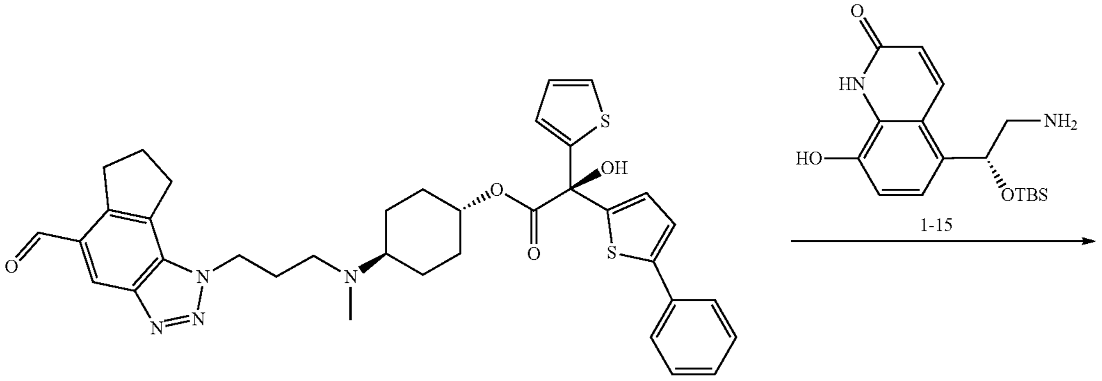
22-3 or 23-2
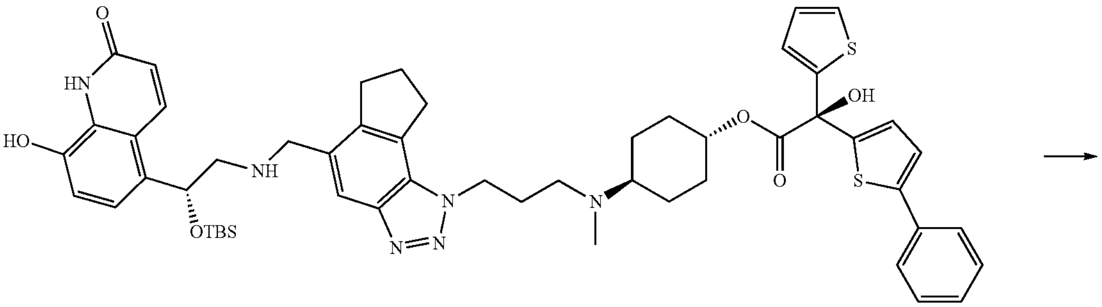
22-4 or 23-3
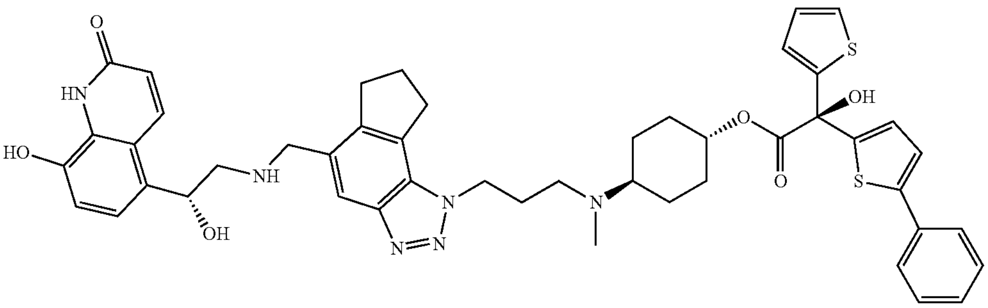
22 or 23

-continued
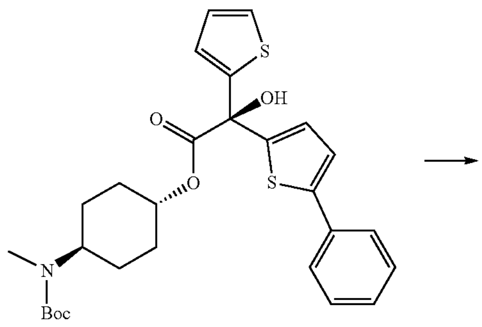
22-1a or 22-1b
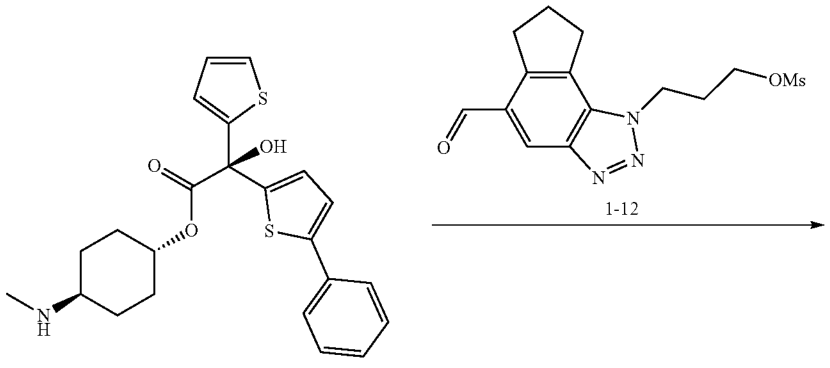
22-2 or 23-1
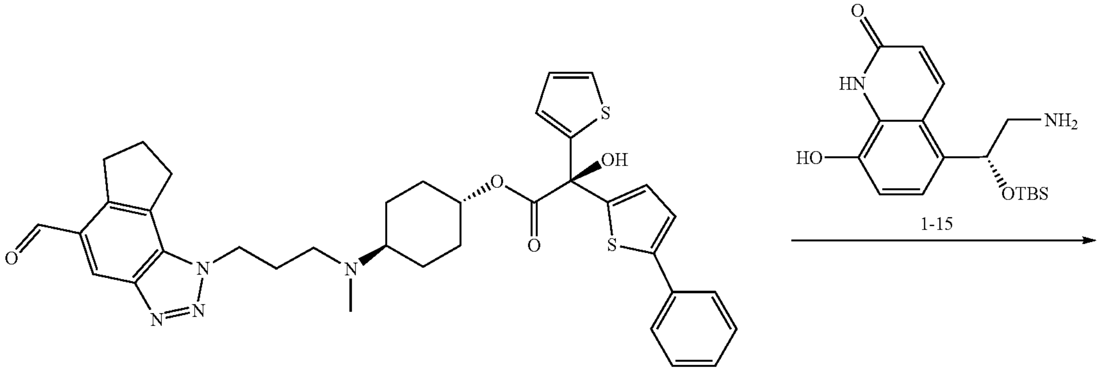
22-3 or 23-2
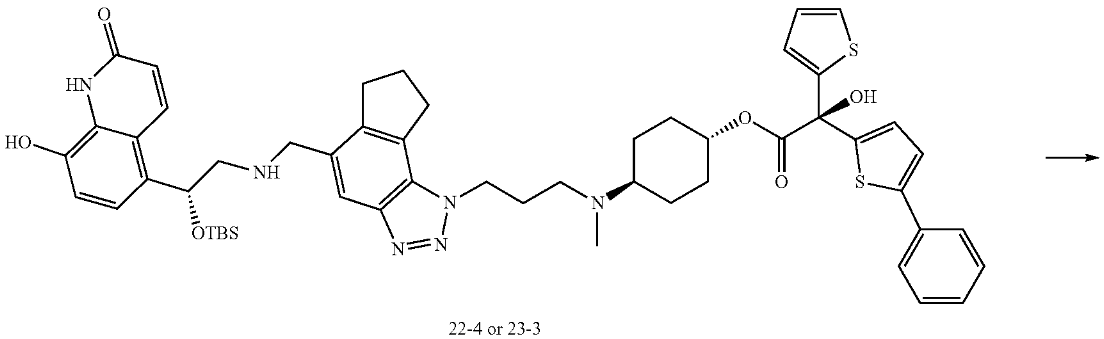
22-4 or 23-3

-continued

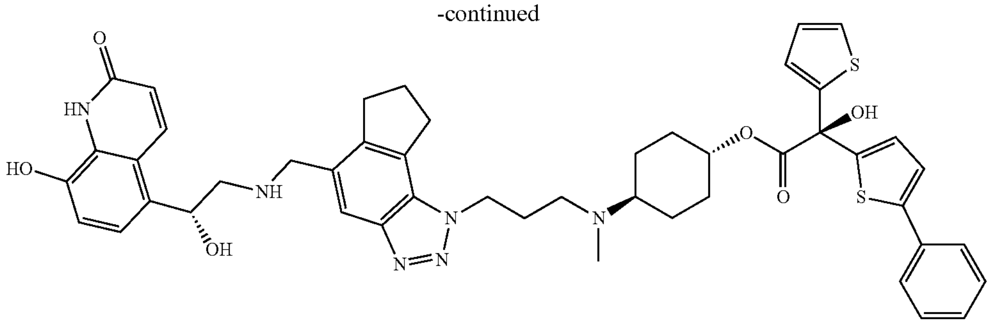

22 or 23

Step 1: Synthesis of Compound 22-1

The compound 2-bromo-5-phenylthiophene (273 mg) was dissolved in tetrahydrofuran (15 mL) and n-butyllithium solution (2.5 M in tetrahydrofuran, 0.49 mL) was slowly added dropwise at −60° C. under nitrogen atmosphere. The mixture was stirred at −60° C. for 0.5 h. Compound 13-1 (300 mg) was dissolved in tetrahydrofuran (4 mL) and slowly added dropwise to the reaction solution at −60° C. After the dropwise addition, the mixture was stirred at −50° C. for 1 h. The reaction solution was heated to 0° C., and the reaction was quenched with a saturated aqueous ammonium chloride solution (20 mL). The resulting mixture was extracted with ethyl acetate (30 mL×2). The organic phase was washed with saturated brine (50 mL), dried over anhydrous sodium sulfate, and concentrated under reduced pressure, and the residue was separated and purified by flash silica gel column chromatography (eluent: ethyl acetate/petroleum ether, 0-25%) to give compound 22-1.

MS-ESI calcd. $[M+H-18]^+$ 510, found 510.3.

Step 2: Preparation of Compounds 22-1a and 22-1b

Compound 22-1 was separated and purified by chiral liquid chromatography to give compound 22-1a and compound 22-1b.

SFC separation method: chromatographic column (DAICEL CHIRALPAK AD 250 mm×30 mm, 10 μm); mobile phase: A: carbon dioxide, B: ethanol (containing 0.1% ammonium hydroxide); flow rate: 50 mL/min, column temperature: 40° C.

The retention time of compound 22-1a: 2.290 min; MS-ESI calcd. $[M+H-18]^+$ 510, found 509.9.

The retention time of compound 22-1b: 2.724 min; MS-ESI calcd. $[M+H-18]^+$ 510, found 509.9.

Step 3: Synthesis of Compound 22-2

Compound 22-1a (260.0 g) was dissolved in dioxane (2 mL), and hydrochloric acid/dioxane solution (10 mL, 4 M) was added. The mixture was stirred at room temperature for 2 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 22-2, which was directly used in the next step.

MS-ESI calcd. $[M+H]^+$ 428, found 428.

Step 4: Synthesis of Compound 22-3

Compound 22-2 (99.2 mg) was dissolved in acetonitrile (15 mL), and compound 1-12 (75 mg), potassium iodide (192 mg) and N,N-diisopropylethylamine (89.9 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 22-3.

MS-ESI calcd. $[M+H]^+$ 655, found 655.1.

Step 5: Synthesis of Compound 22-4

Compound 22-3 (89.6 mg) and compound 1-15 (45.0 mg, acetate) were dissolved in anhydrous methanol (4 mL) and anhydrous tetrahydrofuran (2 mL), and sodium triacetoxyborohydride (36 mg) was added. The mixture was stirred at 25° C. for 12 h, and sodium triacetoxyborohydride (121 mg) was added. The mixture was stirred for another 5 h. A 4% aqueous sodium bicarbonate solution (5 mL) was added to quench the reaction, and the resulting mixture was extracted with ethyl acetate (10 mL×2). The organic phases were combined, dried over anhydrous sodium sulfate, filtered and concentrated under reduced pressure to give compound 22-4, which was directly used in the next step.

MS-ESI calcd. $[M+H]^+$ 973, found 973.2.

Step 6: Synthesis of Formate Salt of Compound 22

Compound 22-4 (85 mg) was dissolved in tetrahydrofuran (5 mL), and triethylamine trihydrofluoride (70.4 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 22.

$^1$H NMR (400 MHz, DMSO-$d_6$) δ: 8.19 (s, 2H), 8.15-8.11 (m, 1H), 7.77 (s, 1H), 7.62-7.58 (m, 2H), 7.51-7.46 (m, 1H), 7.41-7.29 (m, 4H), 7.14-7.11 (m, 1H), 7.08-7.04 (m, 2H), 7.01-6.97 (m, 1H), 6.93-6.89 (m, 1H), 6.44-6.40 (m, 1H), 5.15-5.11 (m, 1H), 4.70-4.66 (m, 2H), 3.89 (s, 3H), 3.32-3.25 (m, 3H), 2.98-2.75 (m, 5H), 2.21-2.11 (m, 6H), 2.01-1.91 (m, 4H), 1.70-1.65 (m, 2H), 1.41-1.30 (m, 4H).

MS-ESI calcd. $[M+H]^+$ 859, found 859.2.

The formate salt of compound 23 was prepared in a 4-step reaction with compound 22-1b as the starting material by referring to the synthetic route of the formate salt of compound 22.

Formate Salt of Compound 23:

$^1$H NMR (400 MHz, DMSO-$d_6$) δ: 8.19 (s, 2H), 8.15-8.11 (m, 1H), 7.78 (s, 1H), 7.62-7.58 (m, 2H), 7.51-7.46 (m, 1H), 7.41-7.29 (m, 4H), 7.14-7.11 (m, 1H), 7.09-7.04 (m, 2H), 7.01-6.97 (m, 1H), 6.93-6.89 (m, 1H), 6.45-6.40 (m, 1H), 5.16-5.11 (m, 1H), 4.71-4.66 (m, 2H), 3.91 (s, 3H), 3.32-3.25 (m, 3H), 2.98-2.77 (m, 5H), 2.21-2.11 (m, 6H), 2.02-1.91 (m, 4H), 1.70-1.65 (m, 2H), 1.39-1.29 (m, 4H); MS-ESI calcd. $[M+H]^+$ 859, found 859.2.

Example 24 and Example 25
24 or 25
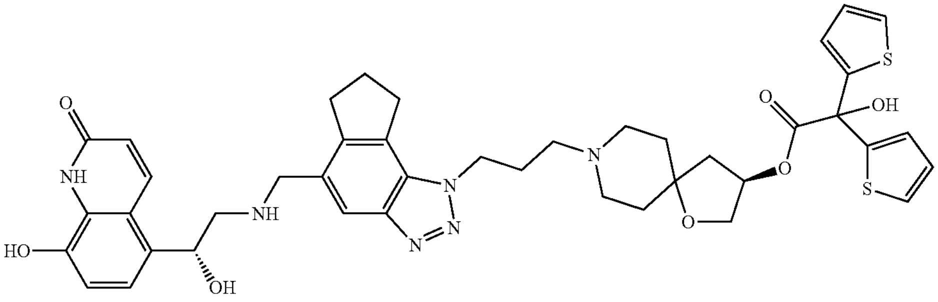
24 or 25
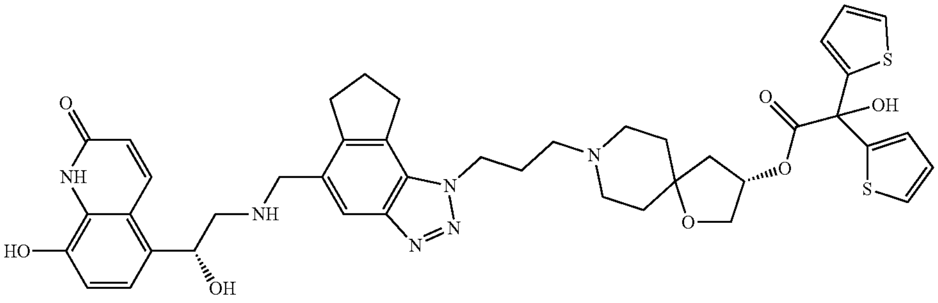
Synthetic Route:
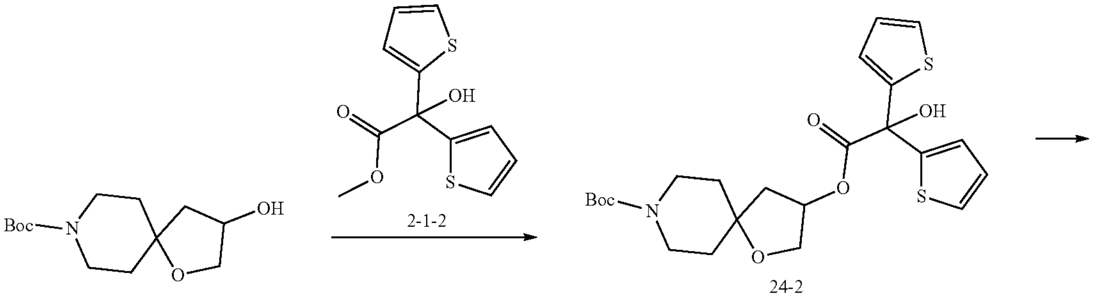
24-1 2-1-2 24-2
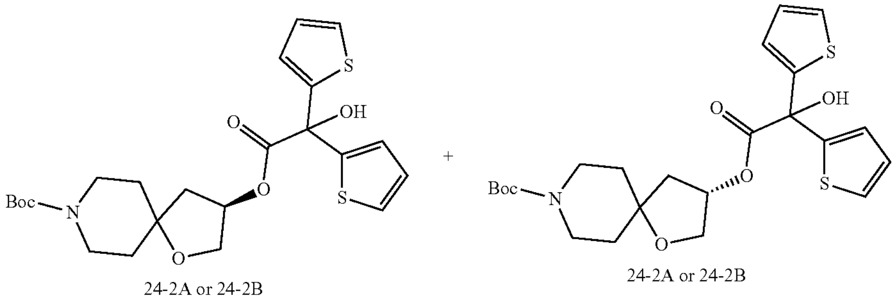
24-2A or 24-2B + 24-2A or 24-2B -continued
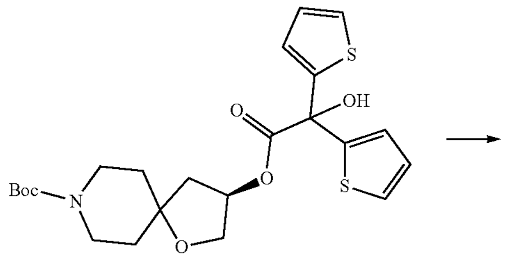
24-2A or 24-2B
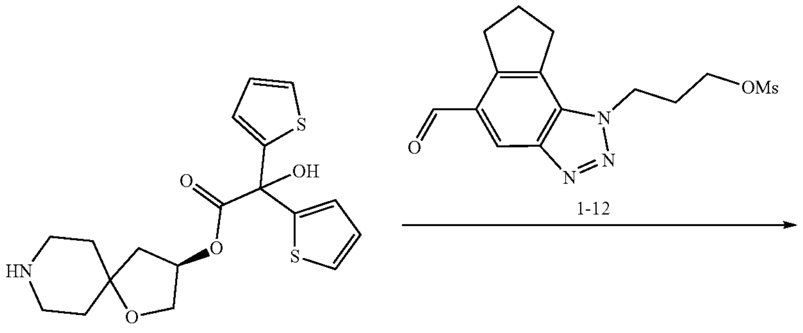
24-3 or 25-1
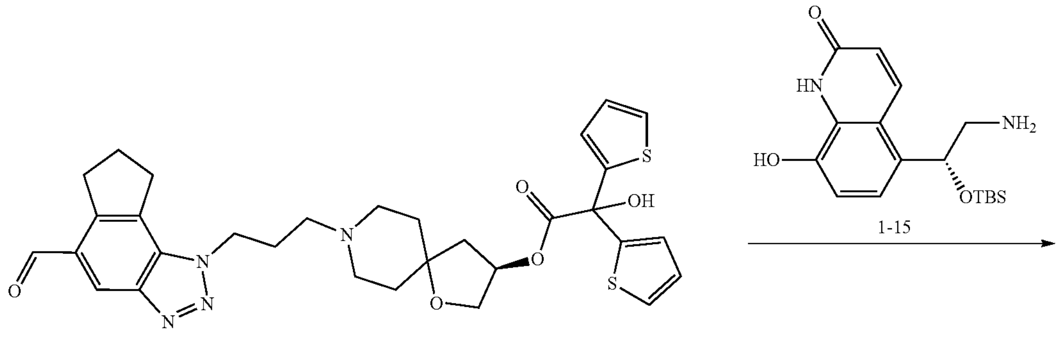
24-4 or 25-2
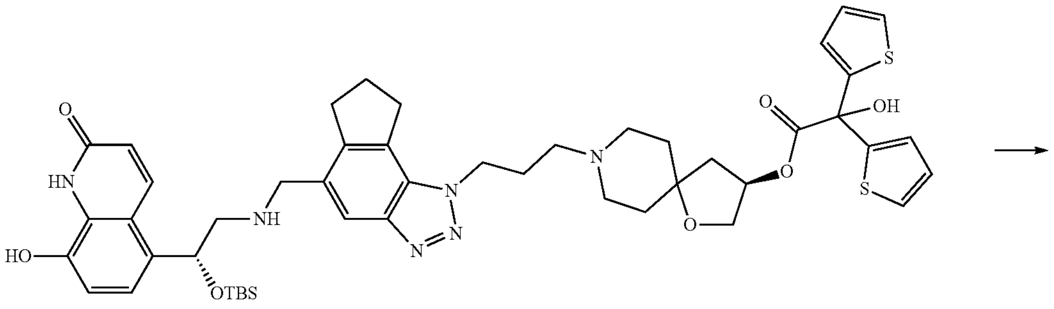
24-5 or 25-3
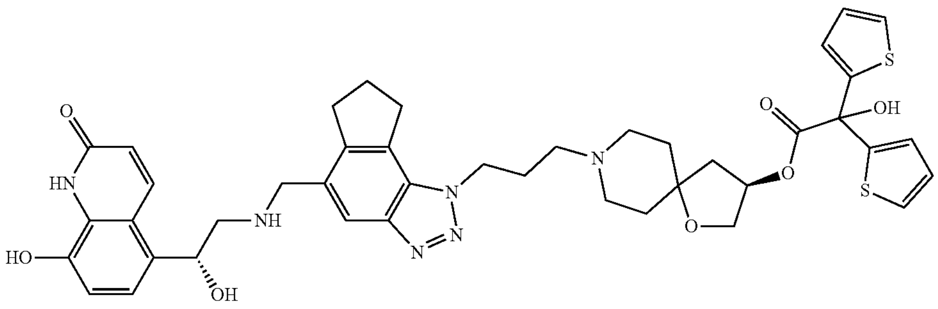
24 or 25

-continued
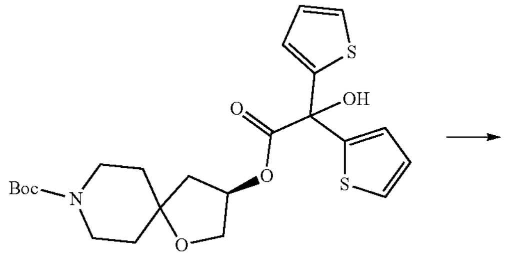
24-2A or 24-2B
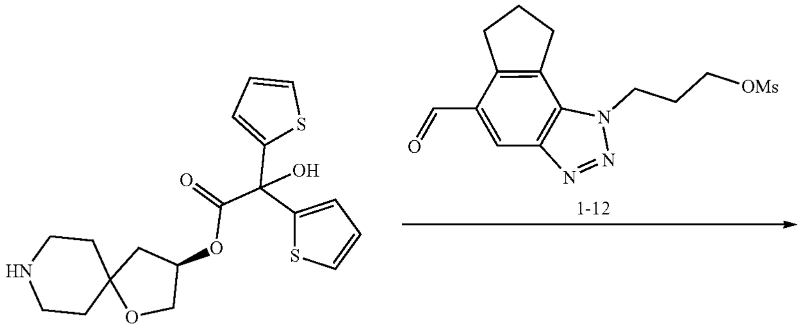
24-3 or 25-1
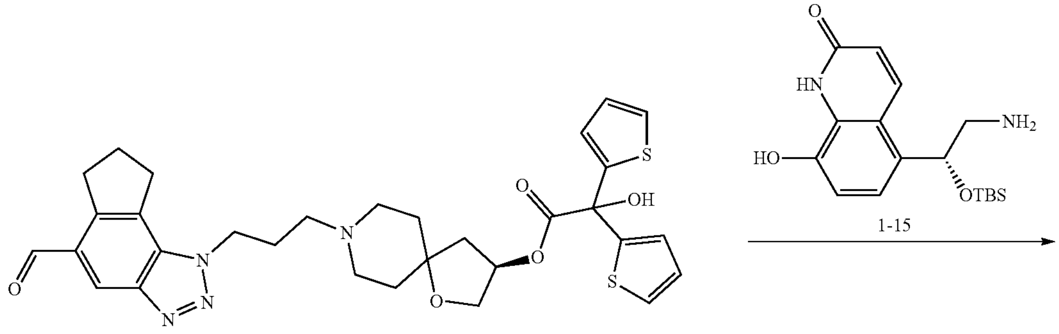
24-4 or 25-2
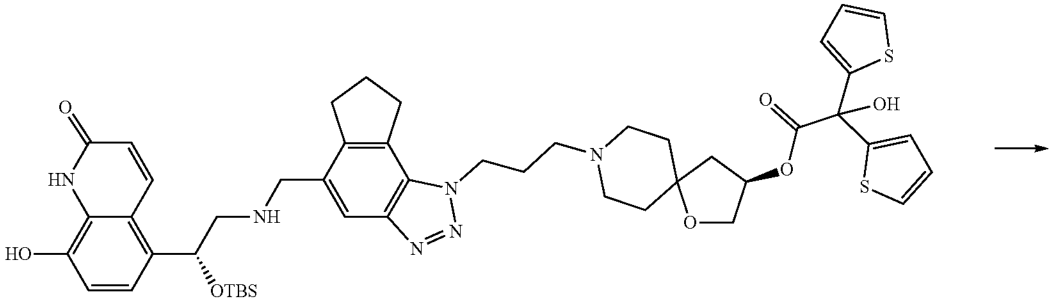
24-5 or 25-3
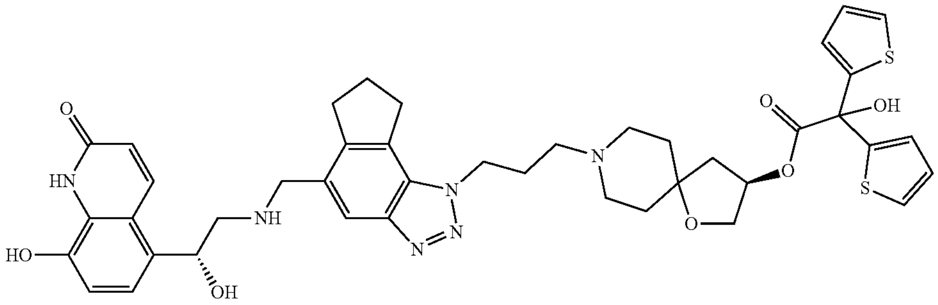
24 or 25

Step 1: Synthesis of Compound 24-2

Compound 2-1-2 (200.0 mg) and compound 24-1 (202 mg) were dissolved in anhydrous toluene (5 mL), and sodium hydride (15.7 mg, purity: 60%) was added in portions at room temperature. The mixture was heated to 120° C. and stirred for 2 h. Three batches were fed in parallel. After the reaction was completed, the reaction solution was cooled to room temperature, and slowly added to a saturated aqueous ammonium chloride solution (30 mL) under stirring in an ice-bath condition to quench the reaction. The resulting mixture was extracted with ethyl acetate (30 mL×2). The organic phases were combined, washed with saturated brine (50 mL), dried over anhydrous sodium sulfate, filtered and concentrated under reduced pressure, and the residue was separated and purified by flash silica gel column chromatography (eluent: ethyl acetate/petroleum ether, 0-25%) to give compound 24-2.

MS-ESI calcd. $[M+H-18-56]^+$ 406, found 405.8.

Step 2: Preparation of Compounds 24-2A and 24-2B

Compound 24-2 was separated and purified by chiral liquid chromatography to give compound 24-2A and compound 24-2B.

SFC separation method: chromatographic column (DAICEL CHIRALPAK AD 250 mm×30 mm, 10 μm); mobile phase: A: carbon dioxide, B: ethanol (containing 0.1% ammonium hydroxide); flow rate: 70 mL/min, column temperature: 40° C.

The retention time of compound 24-2A: 3.843 min; MS-ESI calcd. [M+H−18-56]+406, found 405.8.

The retention time of compound 24-2B: 4.425 min; MS-ESI calcd. [M+H−18-56]+406, found 405.8.

Step 3: Synthesis of Compound 24-3

Compound 24-2A (240.0 g) was dissolved in dioxane (3 mL), and hydrochloric acid/dioxane solution (6 mL, 4 M) was added. The mixture was stirred at room temperature for 2 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 24-3, which was directly used in the next step.

MS-ESI calcd. $[M+H]^+$ 380, found 380.

Step 4: Synthesis of Compound 24-4

Compound 24-3 (60.0 mg) was dissolved in acetonitrile (15 mL), and compound 1-12 (59.85 mg), potassium iodide (154 mg) and N,N-diisopropylethylamine (71.94 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 24-4.

MS-ESI calcd. $[M+H]^+$ 607, found 607.

Step 5: Synthesis of Compound 24-5

Compound 24-4 (89.5 mg) and compound 1-15 (60.0 mg, acetate) were dissolved in anhydrous methanol (6 mL) and anhydrous tetrahydrofuran (3 mL), and N,N-diisopropylethylamine (39.3 mg) and sodium triacetoxyborohydride (161 mg) were added. The mixture was stirred at 25° C. for 12 h, and sodium triacetoxyborohydride (161 mg) was added. The mixture was stirred for another 5 h. A 4% aqueous sodium bicarbonate solution (20 mL) was added to quench the reaction, and the resulting mixture was extracted with ethyl acetate (20 mL×2). The organic phases were combined, dried over anhydrous sodium sulfate, filtered and concentrated under reduced pressure to give compound 24-5, which was directly used in the next step.

MS-ESI calcd. $[M+H]^+$ 925, found 925.

Step 6: Synthesis of Formate Salt of Compound 24

Compound 24-5 (120 mg) was dissolved in tetrahydrofuran (6 mL), and triethylamine trihydrofluoride (104.5 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX $C_{18}$, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 24.

$^1$H NMR (400 MHz, DMSO-$d_6$) δ: 8.23 (s, 2H), 8.16 (d, J=12 Hz, 1H), 7.87 (s, 1H), 7.53-7.43 (m, 2H), 7.12-6.90 (m, 6H), 6.46 (d, J=12 Hz, 1H), 5.34-5.29 (m, 1H), 5.26-5.20 (m, 1H), 4.75-4.68 (m, 2H), 4.03 (s, 2H), 3.97-3.88 (m, 1H), 3.77-3.70 (m, 1H), 3.35-3.28 (m, 2H), 3.08-2.85 (m, 4H), 2.43-2.29 (m, 5H), 2.24-1.91 (m, 6H), 1.80-1.71 (m, 1H), 1.53-1.30 (m, 4H).

MS-ESI calcd. $[M+H]^+$ 811, found 811.

The formate salt of compound 25 was prepared in a 4-step reaction with compound 24-2B as the starting material by referring to the synthetic route of the formate salt of compound 24.

Formate Salt of Compound 25:

$^1$H NMR (400 MHz, DMSO-$d_6$) δ: 8.18 (s, 2H), 8.14 (d, J=8 Hz, 1H), 7.81 (s, 1H), 7.51-7.44 (m, 2H), 7.11-6.90 (m, 6H), 6.44 (d, J=8 Hz, 1H), 5.33-5.28 (m, 1H), 5.19-5.13 (m, 1H), 4.74-4.66 (m, 2H), 3.94 (s, 2H), 3.93-3.88 (m, 1H), 3.76-3.70 (m, 1H), 3.35-3.26 (m, 2H), 3.00-2.83 (m, 4H), 2.38-2.26 (m, 5H), 2.21-1.94 (m, 6H), 1.77-1.71 (m, 1H), 1.50-1.28 (m, 4H);

MS-ESI calcd. $[M+H]^+$ 811, found 811.

26 or 27

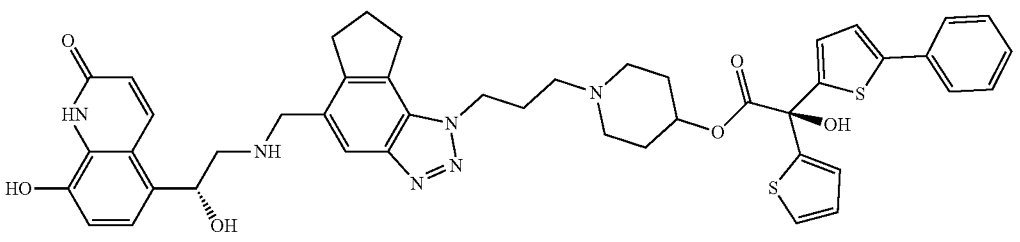

-continued
26 or 27
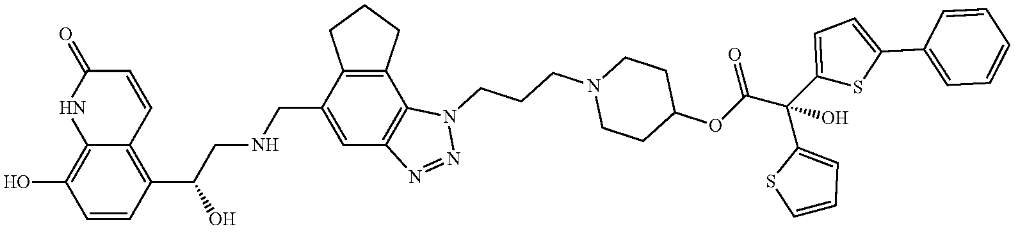
Example 26 and Example 27
Synthetic Route:
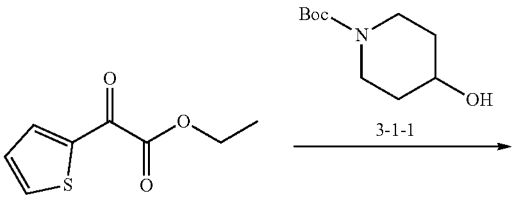
5-2
3-1-1
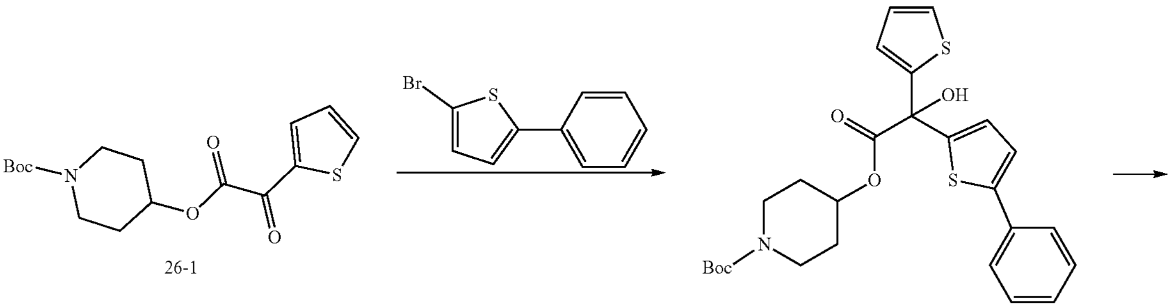
26-1
26-2
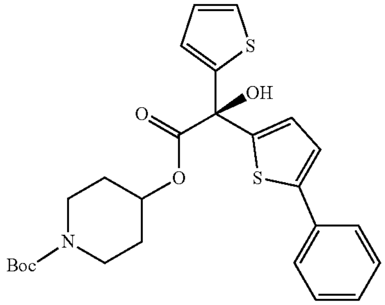
26-2a or 26-2b
+
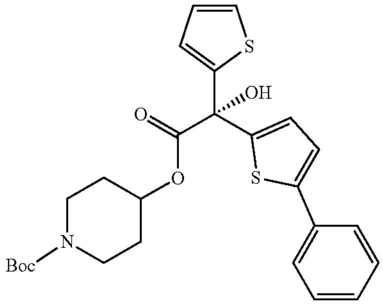
26-2a or 26-2b -continued
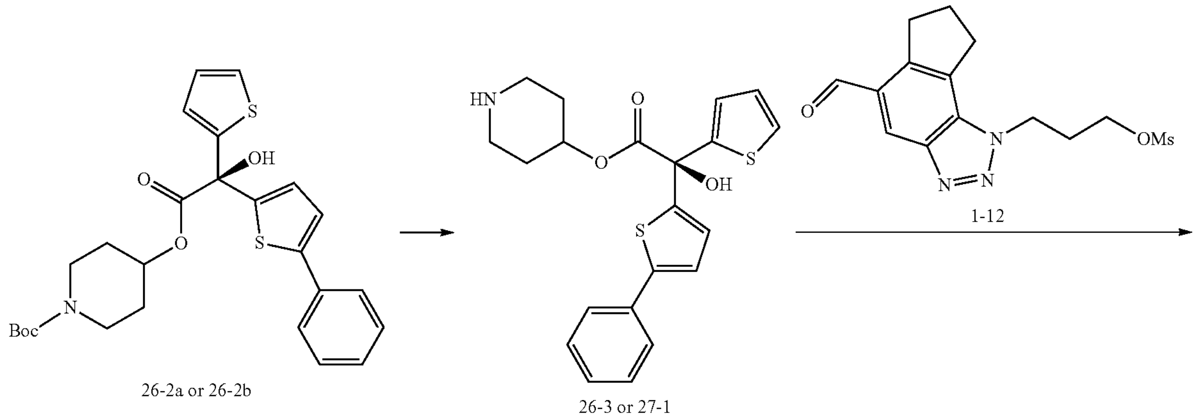
26-2a or 26-2b
26-3 or 27-1
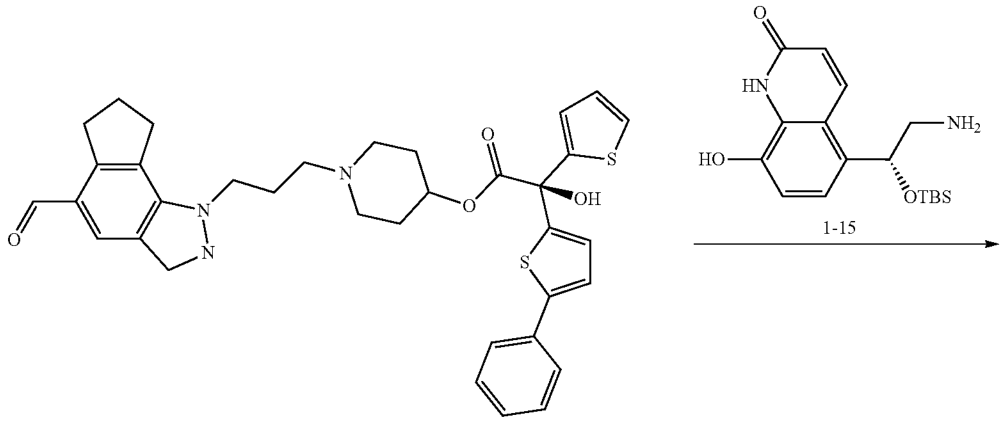
26-4 or 27-2
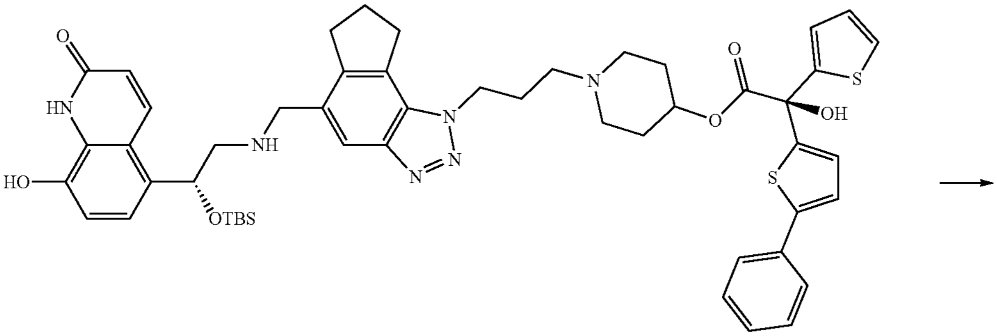
26-5 or 27-3
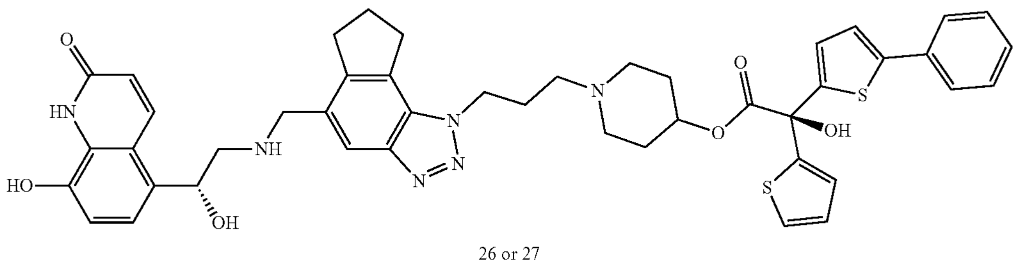
26 or 27

-continued
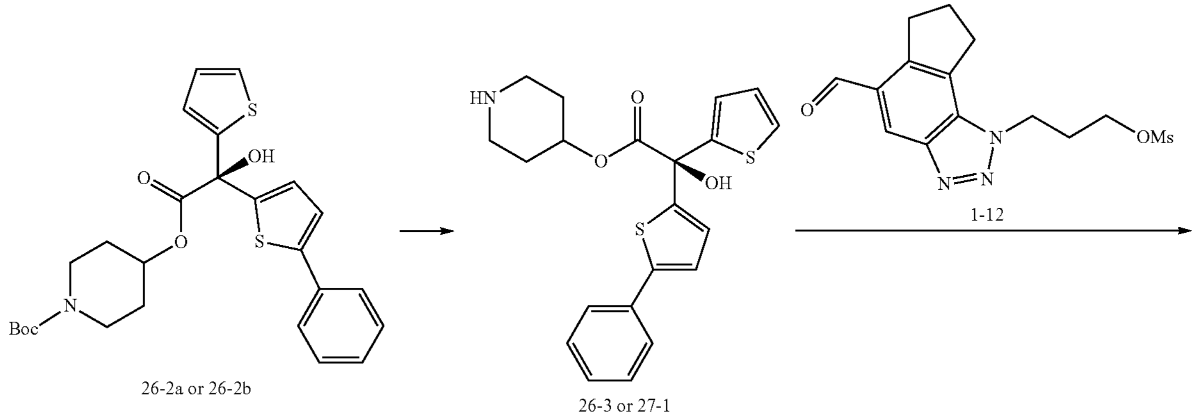
26-2a or 26-2b
26-3 or 27-1
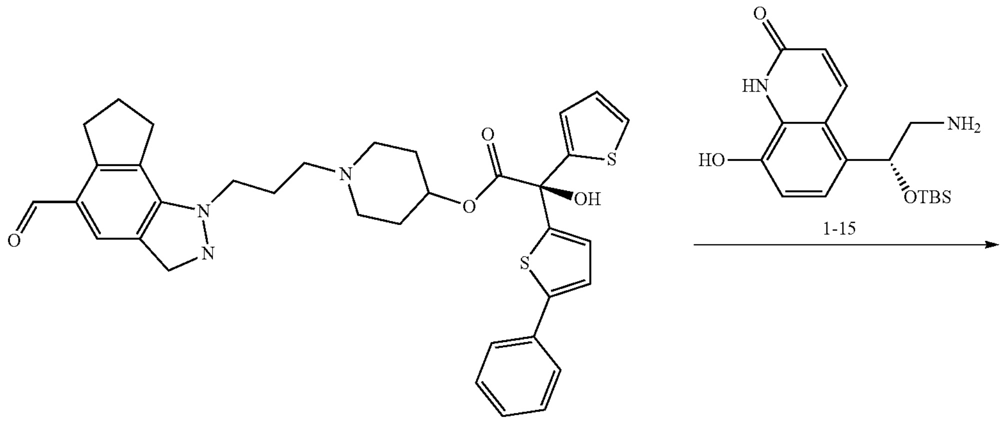
26-4 or 27-2
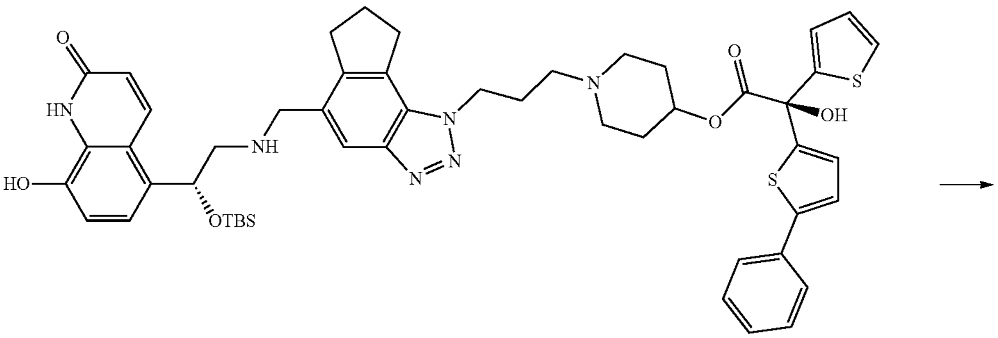
26-5 or 27-3
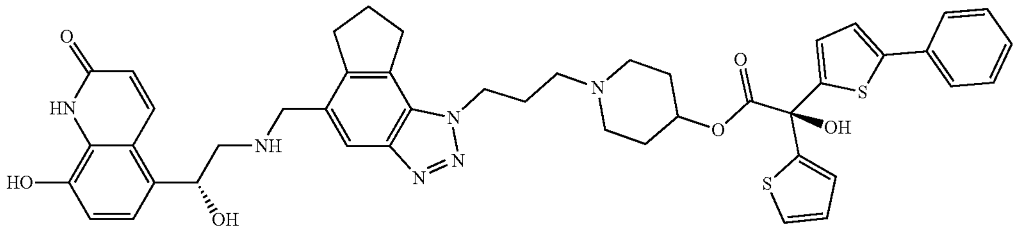
26 or 27

Step 1: Synthesis of Compound 26-1

Compound 5-2 (3 g) and compound 3-1-1 (2.98 g) were dissolved in anhydrous toluene (30 mL), and 4-dimethylaminopyridine (2.62 g) was added. The mixture was stirred at 120° C. for 18 h. The reaction solution was concentrated under reduced pressure, and the residue was separated and purified by silica gel column chromatography (petroleum ether/ethyl acetate, 1:0-5:1) to give compound 26-1.

$^1$H NMR (400 MHz, $CDCl_3$) δ ppm: 8.11-8.10 (m, 1H), 7.89-7.83 (m, 1H), 7.23-7.20 (m, 1H), 5.23-5.17 (m, 1H), 3.83-3.77 (m, 2H), 3.33-3.26 (m, 2H), 2.02-1.98 (m, 2H), 1.84-1.77 (m, 2H), 1.48 (s, 9H).

Step 2: Synthesis of Compound 26-2

The compound 2-bromo-5-phenylthiophene (986 mg) was dissolved in anhydrous tetrahydrofuran (30 mL), and n-butyllithium solution (2.5 M, 1.65 mL) was slowly added dropwise at −78° C. The mixture was stirred at this temperature for 0.5 h. Compound 26-1 (1 g) was dissolved in anhydrous tetrahydrofuran (30 mL), and the solution was added dropwise to the reaction solution at −50° C. The resulting mixture was stirred for 1 h. A saturated aqueous ammonium chloride solution (20 mL) was added to the reaction solution at −50° C. to quench the reaction. The resulting mixture was diluted with water (10 mL) and extracted with ethyl acetate (30 mL×3). The organic phases were combined, washed with saturated brine (30 mL), dried over anhydrous sodium sulfate, filtered and concentrated under reduced pressure, and the residue was separated and purified by silica gel column chromatography (petroleum ether/ethyl acetate, 1:0-4:1) to give compound 26-2.

$^1$H NMR (400 MHz, $CDCl_3$) δ ppm: 7.59-7.57 (m, 2H), 7.39-7.32 (m, 2H), 7.31-7.29 (m, 2H), 7.25-7.24 (m, 1H), 7.23-7.19 (m, 1H), 7.17-7.13 (m, 1H), 7.02-6.99 (m, 1H), 5.19-5.13 (m, 1H), 4.78 (s, 1H), 3.49-3.35 (m, 4H), 1.91-1.85 (m, 2H), 1.76-1.69 (m, 2H), 1.46 (s, 9H); MS-ESI calcd. $[M+H-18]^+$ 482, found 481.9.

Step 3: Preparation of Compounds 26-2a and 26-2b

Compound 26-2 (520 mg) was separated and purified by chiral liquid chromatography to give compound 26-2a and compound 26-2b.

SFC separation method (chromatographic column: DAICEL CHIRALCEL IC (250 mm×30 mm, 10 μm); mobile phase: A: carbon dioxide, B: 40%-40% ethanol (containing 0.1% ammonium hydroxide); flow rate: 70 mL/min, column temperature: 40° C.).

The retention time of compound 26-2a: 1.240 min; MS-ESI calcd. $[M+H]^+$ 482, found 481.9.

The retention time of compound 26-2b: 1.501 min; MS-ESI calcd. $[M+H]^+$ 482, found 481.9.

Step 4: Preparation of Compound 26-3

Compound 26-2a (210 mg) was dissolved in anhydrous dioxane (2 mL), and hydrochloric acid/dioxane solution (5.7 mL, 4 M) was added. The mixture was stirred at 25° C. for 3 h. The reaction solution was adjusted to about pH 8 with a saturated aqueous sodium carbonate solution and extracted with ethyl acetate (30 mL×3). The organic phases were combined, washed with saturated brine (20 mL), dried over anhydrous sodium sulfate, filtered and concentrated under reduced pressure to give crude compound 26-3.

MS-ESI calcd. $[M+H]^+$ 400, found 400.

Step 5: Preparation of Compound 26-4

Compound 26-3 (160 mg) was dissolved in acetonitrile (4 mL), and compound 1-12 (129.4 mg), N,N-diisopropylethylamine (155.2 mg) and potassium iodide (264 mg) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 26-4.

MS-ESI calcd. $[M+H]^+$ 627, found 627.1.

Step 6: Preparation of Compound 26-5

Compound 26-4 (210 mg) and compound 1-15 (112 mg, acetate) were dissolved in anhydrous methanol (4 mL) and anhydrous tetrahydrofuran (2 mL), and N,N-diisopropylethylamine (82.1 mg) and sodium triacetoxyborohydride (129 mg) were added. The mixture was stirred at 25° C. for 24 h, and sodium triacetoxyborohydride (129 mg) was added. The mixture was stirred for another 24 h, and sodium triacetoxyborohydride (129 mg) was added. The mixture was stirred for another 24 h. A saturated aqueous sodium bicarbonate solution (30 mL) was added to quench the reaction, and the resulting mixture was extracted with ethyl acetate (30 mL×3). The organic phases were combined, washed with water (20 mL×2), dried over anhydrous sodium sulfate, filtered and concentrated under reduced pressure to give crude compound 26-5.

MS-ESI calcd. $[M+H]^+$ 946, found 946.3.

Step 7: Preparation of Trifluoroacetate Salt of Compound 26

Compound 26-5 (249 mg) was dissolved in anhydrous tetrahydrofuran (2 mL), and triethylamine trihydrofluoride (300 mg) was added. The mixture was stirred at room temperature for 18 h. The reaction solution was concentrated under reduced pressure, and the residue was separated by high performance liquid chromatography (column type: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 24% to 54% in 8 min) to give a trifluoroacetate salt of compound 26.

$^1$H NMR (400 MHz, DMSO-$d_6$) δ ppm: 10.54-10.49 (m, 2H), 10.30-10.17 (m, 1H), 9.38 (s, 1H), 9.17 (m, 1H), 8.18-8.16 (m, 1H), 8.10 (s, 1H), 7.62-7.60 (m, 2H), 7.49 (s, 1H), 7.41-7.36 (m, 5H), 7.16-7.13 (m, 3H), 7.00-6.98 (m, 2H), 6.54-6.51 (m, 1H), 6.25 (s, 1H), 5.47-5.44 (m, 1H), 5.15-4.98 (m, 1H), 4.78 (s, 2H), 4.37 (s, 2H), 3.53 (s, 3H), 3.18 (s, 2H), 3.11-3.08 (m, 5H), 2.54 (s, 2H), 2.33 (s, 2H), 2.23-2.20 (m, 2H), 2.11 (s, 1H), 1.97 (s, 1H) 1.87-1.81 (m, 1H);

MS-ESI calcd. $[M+H]^+$ 831, found 831.

The trifluoroacetate salt of compound 27 was prepared in a 4-step reaction with compound 26-2b as the starting material by referring to the synthetic route of the trifluoroacetate salt of compound 26.

Trifluoroacetate Salt of Compound 27:

$^1$H NMR (400 MHz, DMSO-$d_6$) δ ppm: 10.51 (s, 2H), 9.75-9.62 (m, 1H), 9.14 (s, 2H), 8.14-8.09 (m, 2H), 7.63-7.61 (m, 2H), 7.50-7.48 (m, 2H), 7.43-7.37 (m, 3H), 7.33-7.30 (m, 1H), 7.18-7.08 (m, 3H), 6.99-6.97 (m, 2H), 6.56-6.53 (m, 1H), 6.25 (s, 1H), 5.42-5.40 (m, 1H), 5.16-4.99 (m, 1H), 4.78 (s, 2H), 4.38 (s, 2H), 3.36 (s, 3H), 3.19-3.08 (m, 7H), 2.82 (s, 1H), 2.33-2.20 (m, 3H), 2.25-2.21 (m, 2H), 2.15 (s, 1H), 1.98 (m, 2H), 1.78 (s, 1H); MS-ESI calcd. $[M+H]^+$ 831, found 831.

Example 28 and Example 29
28 or 29
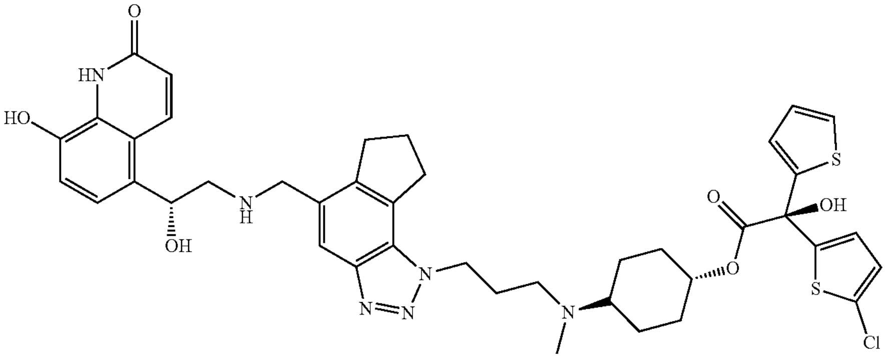
28 or 29
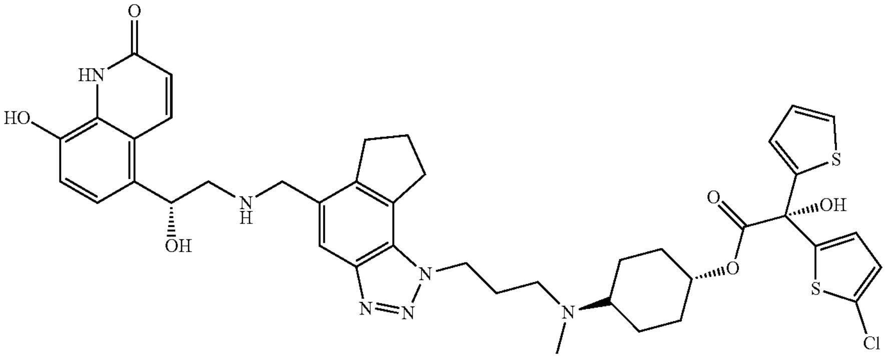
Synthetic Route:
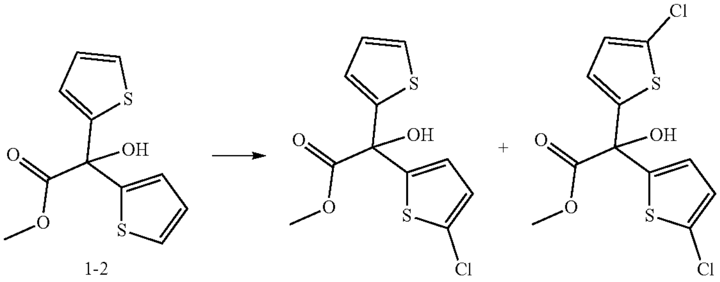
1-2
28-1
7-2
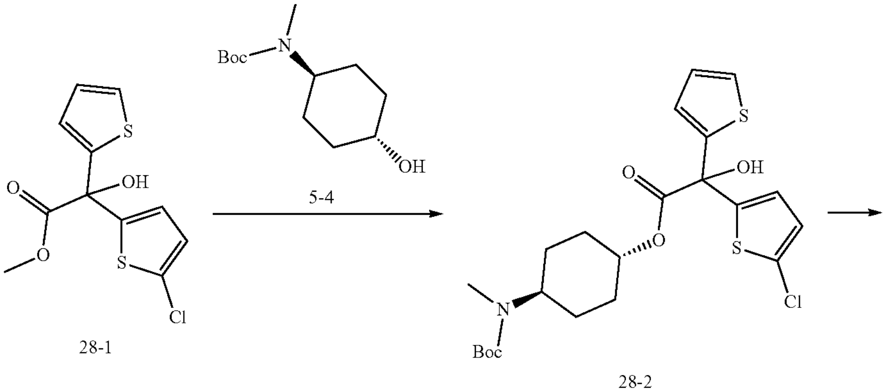
28-1
5-4
28-2

-continued
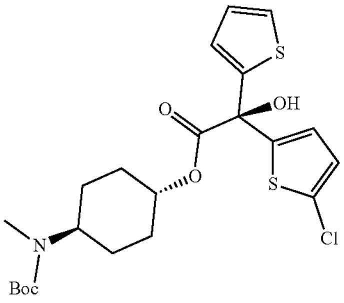
28-2a or 28-2b
+
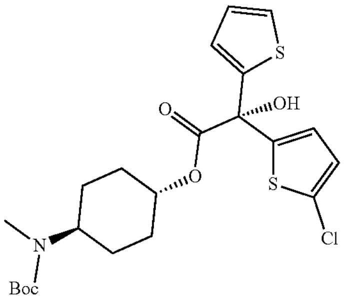
28-2a or 28-2b
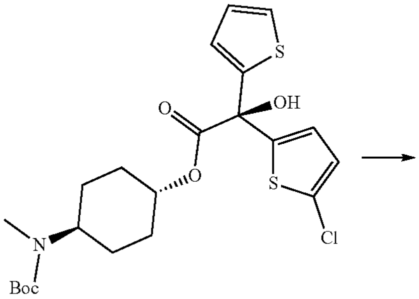
28-2a or 28-2b
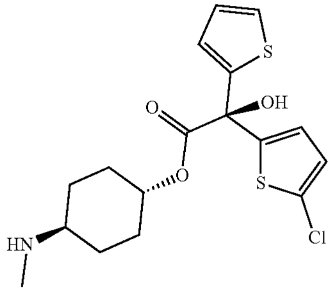
28-3 or 29-1
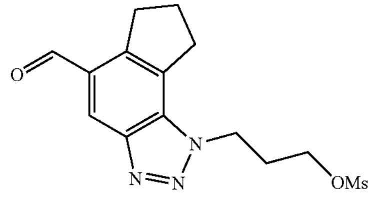
1-12
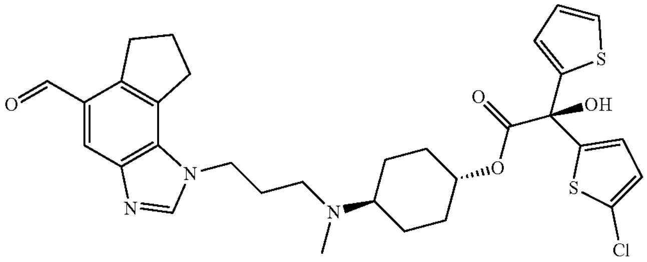
28-4 or 29-2
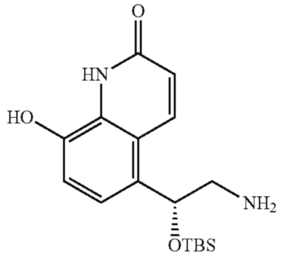
1-15
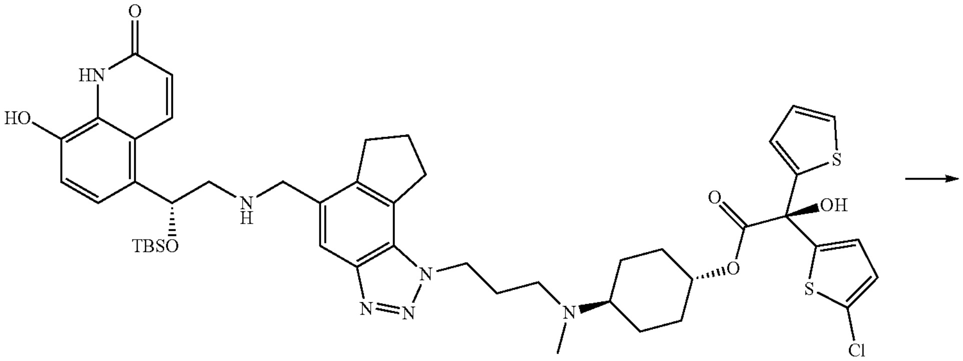
28-5 or 29-3

-continued
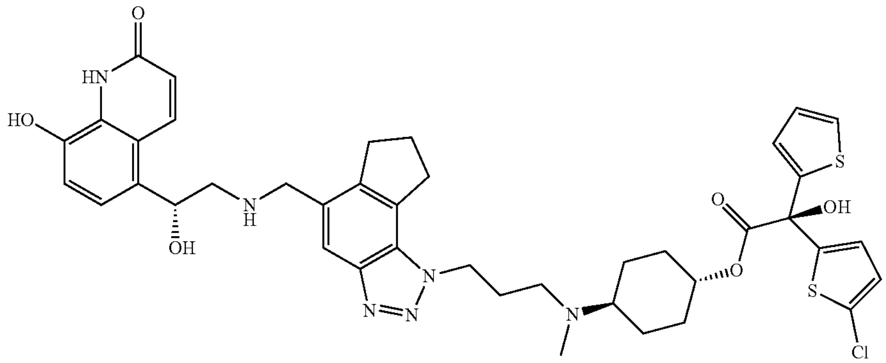
28 or 29
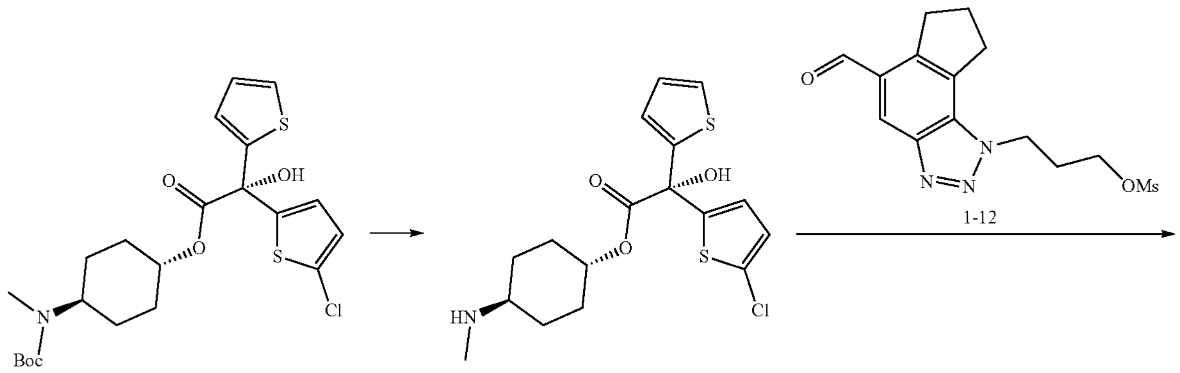
1-12
28-2a or 28-2b
28-3 or 29-1
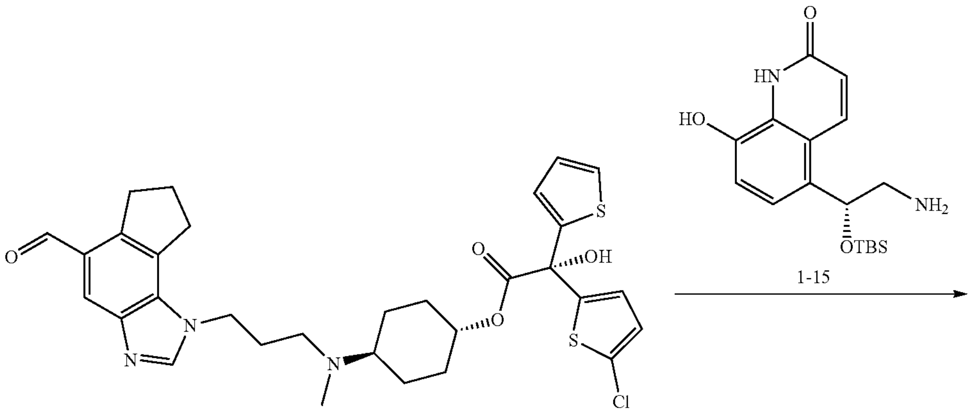
1-15
28-4 or 29-2
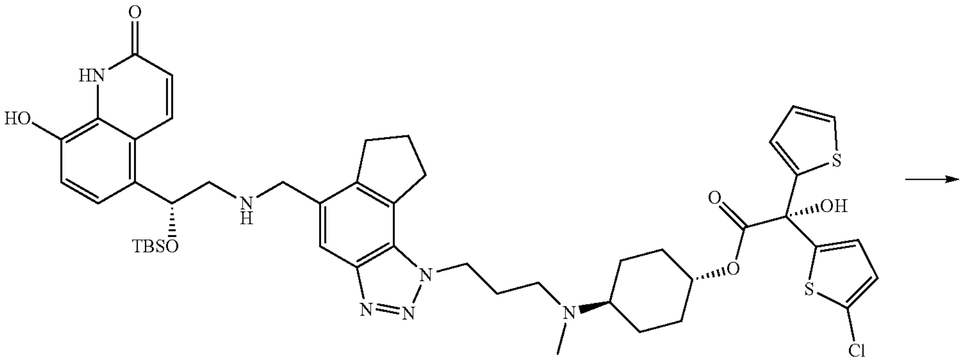
28-5 or 29-3

-continued

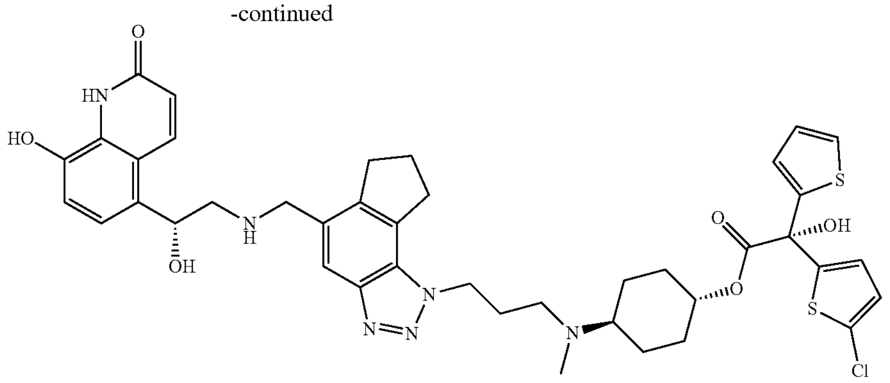

28 or 29

Step 1: Synthesis of Compound 28-1

Compound 1-2 (3 g) was dissolved in anhydrous dichloromethane (20 mL) and N-chlorosuccinimide (2.84 g) was added. The mixture was heated to 60° C. and stirred for 18 h. The reaction solution was cooled to room temperature and concentrated under reduced pressure, and the residue was separated and purified by high performance liquid chromatography to give compound 28-1 and compound 7-2.

MS-ESI calcd. $[M+H-18]^+$ 271, found 270.2.

Step 2: Synthesis of Compound 28-2

Compound 28-1 (630 mg) and compound 5-4 (500 mg) were dissolved in anhydrous xylene (6 mL), and sodium hydride (87.2 mg, purity: 60%) was added. The mixture was stirred at 120° C. for 4 h. The reaction solution was cooled to 0° C., and a saturated aqueous ammonium chloride solution (20 mL) was added to quench the reaction. The resulting mixture was extracted with ethyl acetate (30 mL×3). The organic phases were combined, washed with saturated brine (30 mL), dried over anhydrous sodium sulfate, filtered and concentrated under reduced pressure, and the residue was separated and purified by silica gel column chromatography (petroleum ether/ethyl acetate, 1:0-5:1) to give compound 28-2.

MS-ESI calcd. $[M+H-18]^+$ 468, found 467.9.

Step 3: preparation of compounds 28-2a and 28-2b Compound 28-2 (453 mg) was separated and purified by chiral liquid chromatography to give compound 28-2a and compound 28-2b.

SFC separation method (chromatographic column: DAICEL CHIRALPAK AD (250 mm×30 mm, 10 μm); mobile phase: A: carbon dioxide, B: 50%-50% ethanol (containing 0.1% ammonium hydroxide); flow rate: 70 mL/min, column temperature: 40° C.).

The retention time of compound 28-2a: 1.803 min; MS-ESI calcd. $[M+H-18]^+$ 468, found 468.

The retention time of compound 28-2b: 1.345 min; MS-ESI calcd. $[M+H-18]^+$ 468, found 467.9.

Step 4: Synthesis of Compound 28-3

Compound 28-2a (130 mg) was dissolved in anhydrous dioxane (3 mL), and a dioxane solution of hydrochloric acid (4 mL, 4 M) was added. The mixture was stirred at 25° C. for 4 h. The reaction solution was adjusted to about pH 8 with a saturated aqueous sodium carbonate solution and extracted with ethyl acetate (20 mL×3). The organic phases were combined, washed with saturated brine (20 mL), dried over anhydrous sodium sulfate, filtered and concentrated under reduced pressure to give crude compound 28-3.

MS-ESI calcd. $[M+H]^+$ 386, found 385.8.

Step 5: Synthesis of Compound 28-4

Compound 28-3 (90 mg) was dissolved in acetonitrile (5 mL), and compound 1-12 (75.4 mg), N,N-diisopropylethylamine (120.4 mg) and potassium iodide (154.8 mg) were added at room temperature. The mixture was stirred at 90° C. for 18 h. The reaction solution was concentrated under reduced pressure, and the residue was separated and purified by silica gel column chromatography (dichloromethane/methanol, 1:0-20:1) to give compound 28-4.

MS-ESI calcd. $[M+H]^+$ 613, found 613.

Step 6: Synthesis of Compound 28-5

Compound 28-4 (110 mg) and compound 1-15 (60 mg, acetate) were dissolved in anhydrous methanol (3 mL) and anhydrous tetrahydrofuran (1.5 mL), and N,N-diisopropylethylamine (2.7 mg) and sodium triacetoxyborohydride (114.1 mg) were added. The mixture was stirred at 25° C. for 24 h, and sodium triacetoxyborohydride (114.1 mg) was added. The mixture was stirred for another 24 h, and sodium triacetoxyborohydride (114.1 mg) was added. The mixture was stirred for another 24 h. A saturated aqueous sodium bicarbonate solution (30 mL) was added to quench the reaction, and the resulting mixture was extracted with ethyl acetate (30 mL×3). The organic phases were combined, washed with brine (20 mL×2), dried over anhydrous sodium sulfate, filtered and concentrated under reduced pressure to give crude compound 28-5.

MS-ESI calcd. $[M+H]^+$ 931, found 931.4.

Step 7: Synthesis of Trifluoroacetate Salt of Compound 28

Compound 28-5 (120 mg) was dissolved in anhydrous tetrahydrofuran (2 mL), and triethylamine trihydrofluoride (120.4 mg) was added. The mixture was stirred at room temperature for 18 h. The reaction solution was concentrated under reduced pressure, and the residue was separated by high performance liquid chromatography (column type: Welch Xitimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile from 22% to 52% in 8 min) to give a trifluoroacetate salt of compound 28.

$^1H$ NMR (400 MHz, DMSO-$d_6$) δ ppm: 10.51 (s, 2H), 9.60 (s, 1H), 9.14 (s, 2H), 8.14-8.07 (m, 2H), 7.51-7.50 (m, 2H), 7.17-7.08 (m, 2H), 7.00-6.97 (m, 3H), 6.93-6.92 (m, 1H), 6.55-6.52 (m, 1H), 6.25 (s, 1H), 5.42-5.40 (m, 1H), 4.78-4.77 (m, 3H), 4.38 (s, 2H), 3.38-3.36 (m, 3H), 3.18-

3.09 (m, 5H), 2.72-2.67 (m, 3H), 2.33-2.21 (m, 5H), 2.07-1.94 (m, 4H), 1.68-1.57 (m, 2H), 1.49-1.46 (m, 2H);

MS-ESI calcd. $[M+H]^+$ 817, found 817.3.

The trifluoroacetate salt of compound 29 was prepared in a 4-step reaction with compound 28-2b as the starting material by referring to the synthetic route of the trifluoroacetate salt of compound 28.

Trifluoroacetate Salt of Compound 29:

$^1H$ NMR (400 MHz, DMSO-$d_6$) δ ppm: 10.53-10.50 (m, 2H), 9.56 (s, 1H), 9.15 (s, 2H), 8.15-8.08 (m, 2H), 7.52-7.50 (m, 2H), 7.17-7.09 (m, 1H), 7.08-7.07 (m, 1H), 7.00-6.98 (m, 3H), 6.97-6.92 (m, 1H), 6.55-6.52 (m, 1H), 6.26 (s, 1H), 5.43-5.40 (m, 1H), 4.81-4.77 (m, 3H), 4.38 (s, 2H), 3.19-3.08 (m, 6H), 2.72-2.71 (m, 3H), 2.33-2.22 (m, 5H), 2.01-1.97 (m, 5H), 1.68-1.44 (m, 5H); MS-ESI calcd. $[M+H]^+$ 817, found 817.4.

Example 30

30

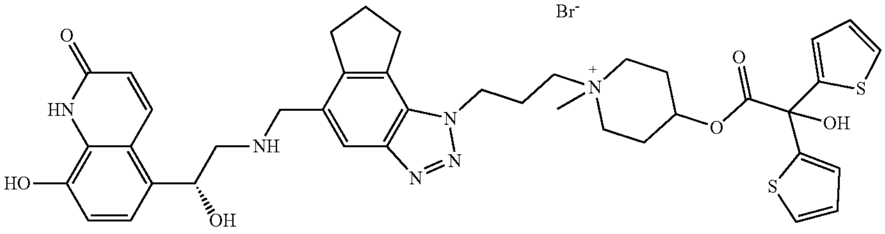

Synthetic Route:

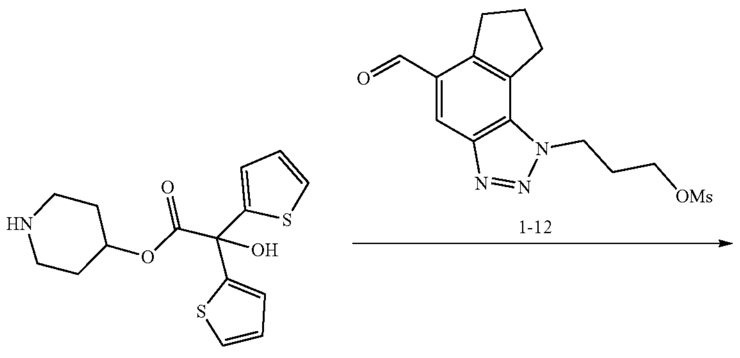

1-12

3-2

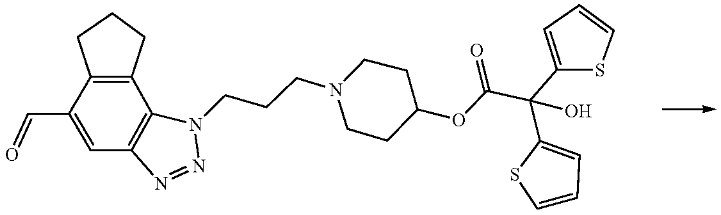

30-1

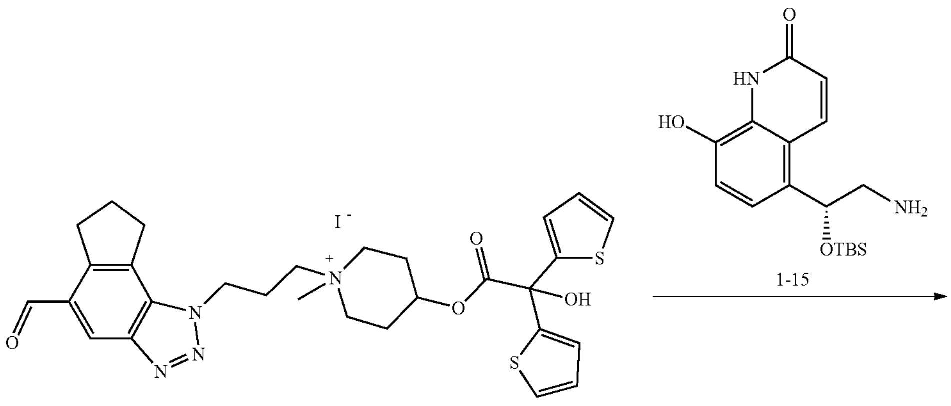

1-15

30-2

-continued

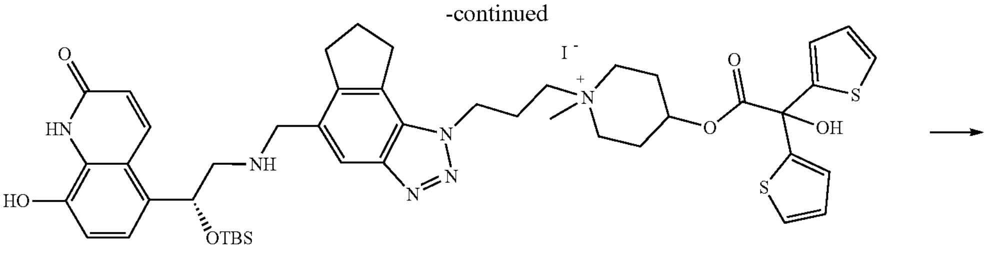

30-3

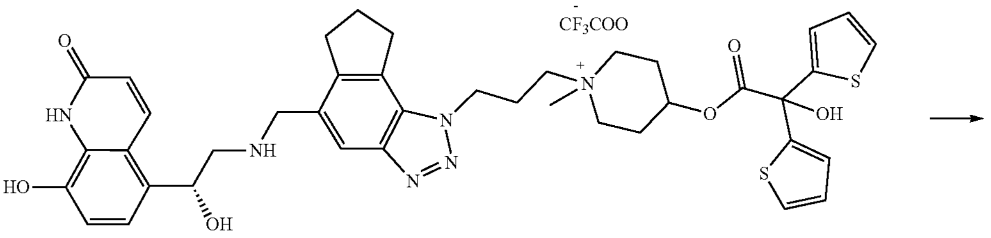

30-4

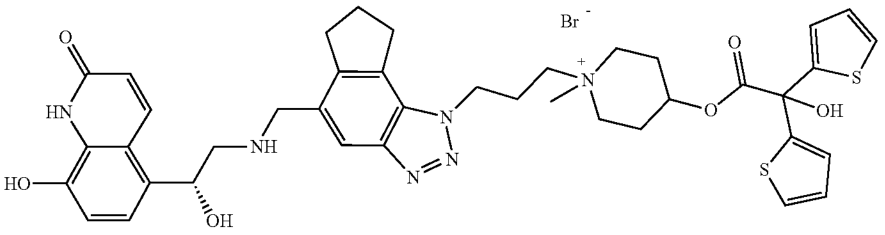

30

Step 1: Synthesis of Compound 30-1

Compound 3-2 (100 mg) was dissolved in acetonitrile (10 mL), and diisopropylethylamine (119.88 mg), potassium iodide (128.31 mg) and compound 1-12 (99.98 mg) were added. The mixture was heated to 90° C. and stirred for 16 h. After the reaction was completed, the reaction solution was poured into 30 mL of water, and the resulting mixture was extracted with dichloromethane (50 mL×2), followed by liquid separation. The organic phase was washed with saturated brine (50 mL), dried over anhydrous sodium sulfate, filtered, concentrated to dryness under reduced pressure, and separated and purified by a TLC preparative silica gel plate (eluent: methanol/dichloromethane=1/20) to give compound 30-1.

MS-ESI calcd. $[M+H]^+$ 551, found 551.2.

Step 2: Synthesis of Compound 30-2

Compound 30-1 (79 mg) was dissolved in a mixed solution of acetonitrile (10 mL), and iodomethane (101.81 mg) was added. The mixture was heated to 40° C. and stirred for 16 h. After the reaction was completed, the reaction solution was concentrated to dryness under reduced pressure to give crude compound 30-2.

MS-ESI calcd. $[M-127+H]^+$ 565, found 565.2.

Step 3: Synthesis of Compound 30-3

Compound 30-2 (99 mg) and compound 1-15 (47.81 mg) were dissolved in methanol (5 mL) and tetrahydrofuran (4 mL), and sodium triacetoxyborohydride (151.47 mg) was added. The mixture was stirred at 25° C. for 16 h, and sodium triacetoxyborohydride (151.47 mg) was added. The mixture was stirred at 25° C. for 72 h. The reaction solution was concentrated to dryness under reduced pressure to give crude compound 30-3.

MS-ESI calcd. $[M-127+H]^+$ 883, found 883.4.

Step 4: Synthesis of Compound 30-4

Compound 30-3 (144 mg) was dissolved in tetrahydrofuran (5 mL), and triethylamine trihydrofluoride (229.59 mg) was added. The mixture was stirred at 25° C. for 16 h. After the reaction was completed, the reaction solution was concentrated to dryness under reduced pressure, and separated and purified by high performance liquid chromatography (trifluoroacetic acid method, preparative column: Welch Xtimate C18, length×inner diameter: 100 mm×40 mm, 3 μm; preparation method: the crude product was dissolved in dimethyl sulfoxide and filtered through a 0.45 μm filter membrane to give a sample solution; mobile phase system: acetonitrile/water (containing 0.075% trifluoroacetic acid); gradient elution method: acetonitrile, from 15% to 45% in 9 min) to give compound 30-4.

MS-ESI calcd. $[M-114+H]^+$ 769, found 769.1.

Step 5: Synthesis of Hydrobromide Salt of Compound 30

Compound 30-4 (14.5 mg) was dissolved in water (1 mL), and an aqueous hydrobromic acid solution (16.61 mg, purity: 40%) was added. The mixture was stirred at 25° C. for 0.5 h. After the reaction was completed, the reaction solution was directly freeze-dried to give a hydrobromide salt of compound 30.

$^1$H NMR (400 MHz, DMSO-$d_6$) δ: 10.51 (s, 2H), 9.39-9.01 (m, 2H), 8.20-8.00 (m, 2H), 7.81-7.46 (m, 2H), 7.39 (s, 1H), 7.20-7.10 (m, 3H), 7.05-6.95 (m, 3H), 6.59-6.48 (m, 1H), 6.25 (s, 1H), 5.50-5.30 (m, 1H), 5.15-5.00 (m, 1H), 4.90-4.75 (m, 2H), 4.45-4.30 (m, 2H), 3.47-3.43 (m, 2H), 3.41-3.37 (m, 2H), 3.32-3.26 (m, 2H), 3.22-3.15 (m, 2H), 3.12-3.07 (m, 2H), 3.06-3.00 (m, 3H), 2.43-2.31 (m, 4H), 2.28-2.16 (m, 4H), 2.02-1.88 (m, 2H); MS-ESI calcd. [M−79+H]+769, found 769.2.

Example 31
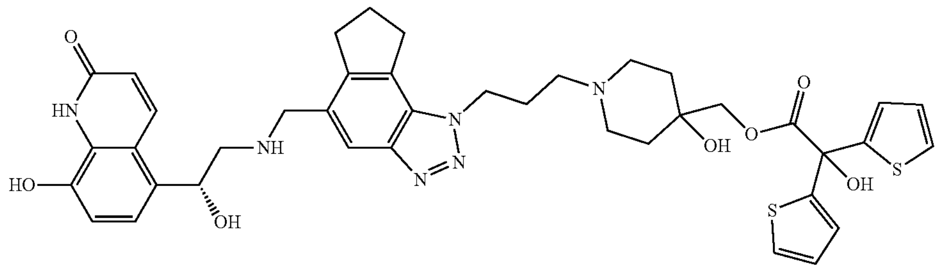
31
Synthetic Route:
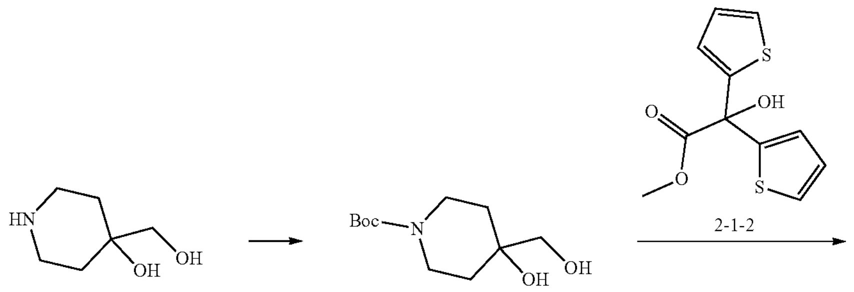
31 31-2
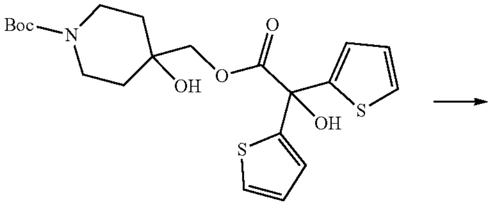
31-3
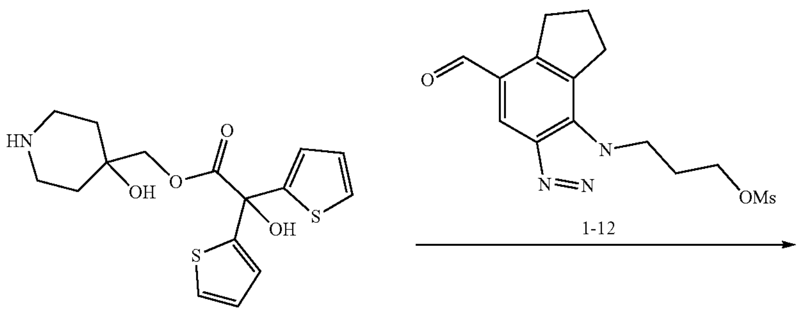
31-4

-continued

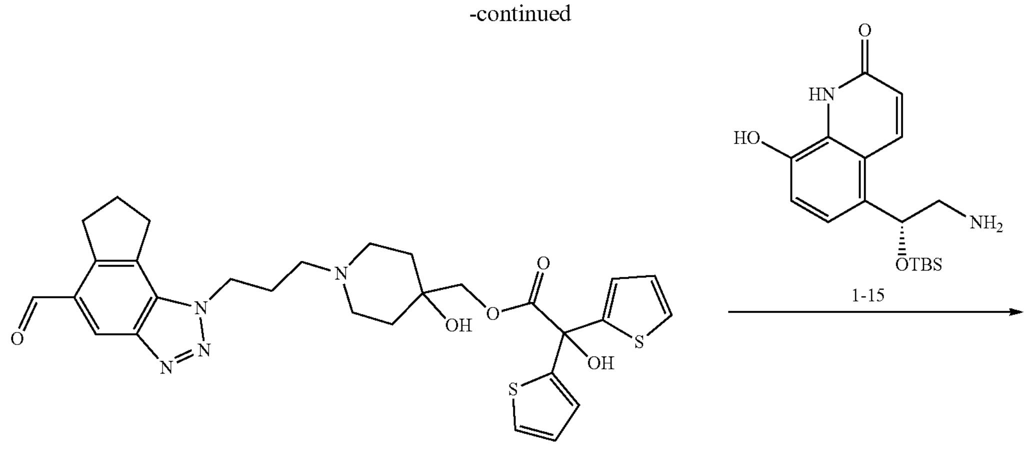

31-5

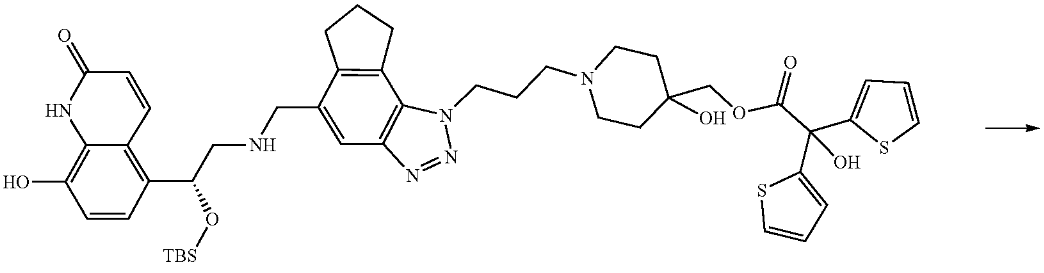

31-6

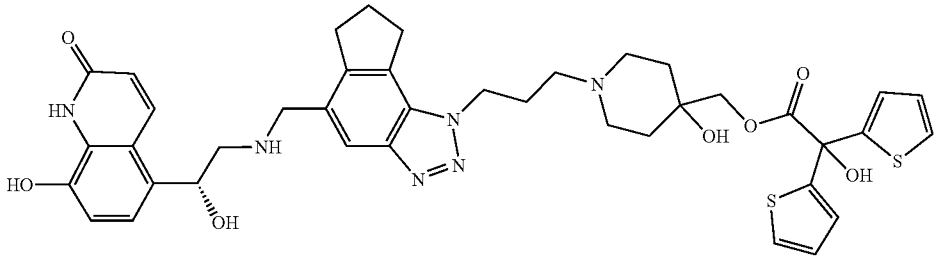

31

Step 1: Synthesis of Compound 31-2

Compound 31-1 (1.07 g) was dissolved in dichloromethane (10 mL), and sodium carbonate (2.59 g) and BOC anhydride (2.13 g) were added. The mixture was stirred at 20° C. for 12 h. After the reaction was completed, the reaction solution was poured into 50 mL of water, and the resulting mixture was extracted with ethyl acetate (50 mL×3). The organic phases were combined, dried over anhydrous sodium sulfate, filtered, and concentrated to dryness under reduced pressure. Additionally, the aqueous phase was extracted with a mixed solvent of dichloromethane/isopropanol (25 mL×4, v/v=3/1). The organic phases were combined, dried over anhydrous sodium sulfate, filtered, concentrated under reduced pressure. 20 mL of toluene was added, and the resulting mixture was concentrated to dryness under reduced pressure. The residues were combined to give compound 31-2.

$^1$H NMR (400 MHz, $CDCl_3$) δ: 3.90-3.80 (m, 2H), 3.48 (s, 2H), 3.25-3.15 (m, 2H), 1.95-1.70 (m, 2H), 1.65-1.55 (m, 2H), 1.54-1.48 (m, 2H), 1.47 (s, 9H).

Step 2: Synthesis of Compound 31-3

Compound 31-2 (250 mg) and compound 2-1-2 (274.9 mg) were dissolved in toluene (5 mL), and sodium hydride (21.62 mg, purity: 60%) was added. The mixture was heated to 120° C. and stirred for 2 h. After the reaction was completed, the reaction solution was cooled to room temperature and poured into 100 mL of cold saturated aqueous ammonium chloride solution to quench the reaction. The resulting mixture was extracted with ethyl acetate (50 mL×2). The organic phases were combined, washed with saturated brine (50 mL), dried over anhydrous sodium sulfate, filtered and concentrated to dryness under reduced pressure, and separated and purified by flash silica gel column chromatography (eluent: ethyl acetate/petroleum ether, 0-40%) to give compound 31-3.

MS-ESI calcd. $[M-100+H]^+$ 354, found 353.8.

Step 3: Synthesis of Compound 31-4

Compound 31-3 (260 mg) was dissolved in dioxane (2 mL), and a hydrogen chloride/dioxane solution (4 M, 7.17 mL) was added. The mixture was stirred at 25° C. for 2 h. After the reaction was completed, the reaction solution was adjusted to pH 11-12 with a saturated sodium carbonate solution, and extracted with ethyl acetate (100 mL×2). The organic phases were combined, dried over anhydrous sodium sulfate, filtered and concentrated to dryness under reduced pressure to give compound 31-4.

MS-ESI calcd. $[M+H]^+$ 354, found 353.8.

Step 4: Synthesis of Compound 31-5

Compound 31-4 (85.48 mg) was dissolved in acetonitrile (10 mL), and diisopropylethylamine (93.76 mg), potassium iodide (120.43 mg) and compound 1-12 (77.96 mg) were added. The mixture was heated to 90° C. and stirred for 16 h. After the reaction was completed, the reaction solution was poured into 50 mL of water, and the resulting mixture was extracted with dichloromethane (50 mL×2), followed by liquid separation. The organic phase was washed with saturated brine (50 mL), dried over anhydrous sodium sulfate, filtered, concentrated to dryness under reduced pressure, and separated and purified by a TLC preparative silica gel plate (eluent: methanol/dichloromethane=1/10) to give compound 31-5.

MS-ESI calcd. $[M+H]^+$ 581, found 580.9.

Step 5: Synthesis of Compound 31-6

Compound 31-5 (81 mg) and compound 1-15 (46.65 mg) were dissolved in methanol (5 mL) and tetrahydrofuran (4 mL), and sodium triacetoxyborohydride (147.81 mg) was added. The mixture was stirred at 25° C. for 16 h. The reaction solution was added to water (50 mL), and the resulting mixture was extracted with dichloromethane (50 mL×2). The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-10%) to give compound 31-6.

MS-ESI calcd. $[M+H]^+$ 899, found 899.2.

Step 6: Synthesis of Formate Salt of Compound 31

Compound 31-6 (60 mg) was dissolved in tetrahydrofuran (3 mL), and triethylamine trihydrofluoride (53.78 mg) was added. The mixture was stirred at 25° C. for 16 h. After the reaction was completed, the reaction solution was concentrated to dryness under reduced pressure, and separated and purified by high performance liquid chromatography (formic acid method, preparative column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (0.225% formic acid); gradient elution method: acetonitrile, from 0% to 30% in 7 min) to give a formate salt of compound 31.

$^1H$ NMR (400 MHz, DMSO-$d_6$) δ: 10.36 (s, 1H), 8.20 (s, 2H), 8.14 (d, J=10.0 Hz, 1H), 7.82 (s, 1H), 7.46 (d, J=4.8 Hz, 2H), 7.13 (d, J=3.2 Hz, 2H), 7.08 (d, J=8.0 Hz, 1H), 6.97 (t, J=4.4 Hz, 2H), 6.92 (d, J=8.0 Hz, 1H), 6.44 (d, J=10.0 Hz, 1H), 5.17 (t, J=6.0 Hz, 1H), 4.71 (t, J=6.4 Hz, 2H), 3.99-3.91 (m, 6H), 3.30 (t, J=6.8 Hz, 2H), 2.95 (t, J=7.2 Hz, 2H), 2.90-2.84 (m, 2H), 2.41-2.28 (m, 4H), 2.21-2.12 (m, 2H), 2.08-1.98 (m, 2H), 1.51-1.33 (m, 4H); MS-ESI calcd. $[M+H]^+$ 785, found 785.4.

Example 32

32

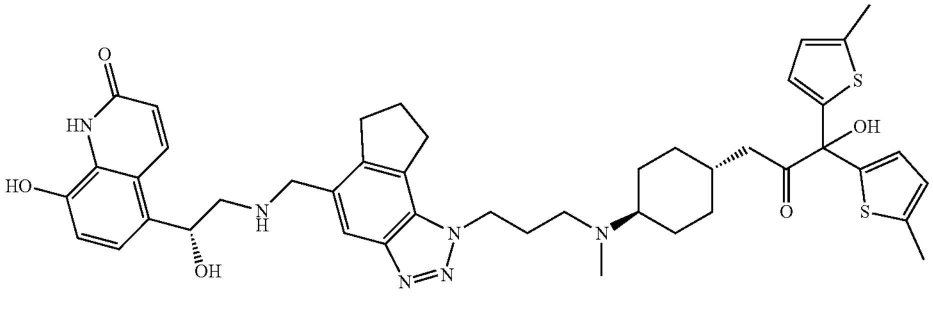

Synthetic Route:

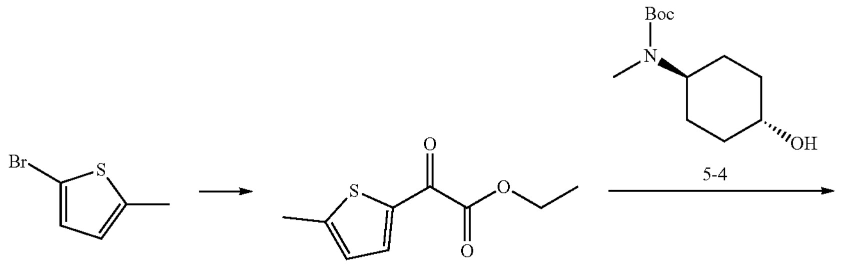

32-1

5-4

-continued
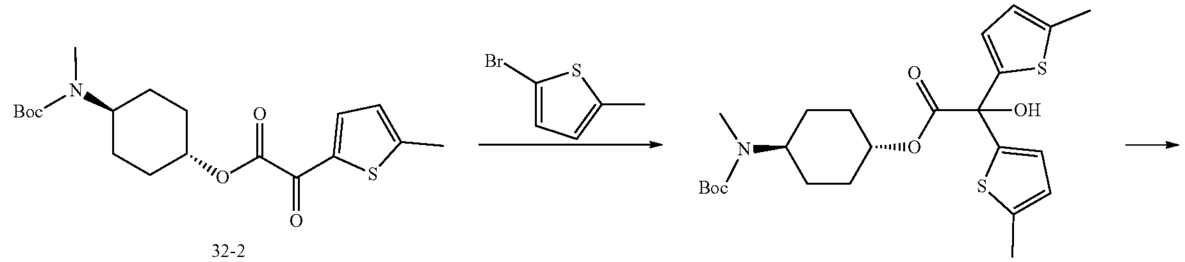
32-2
32-3
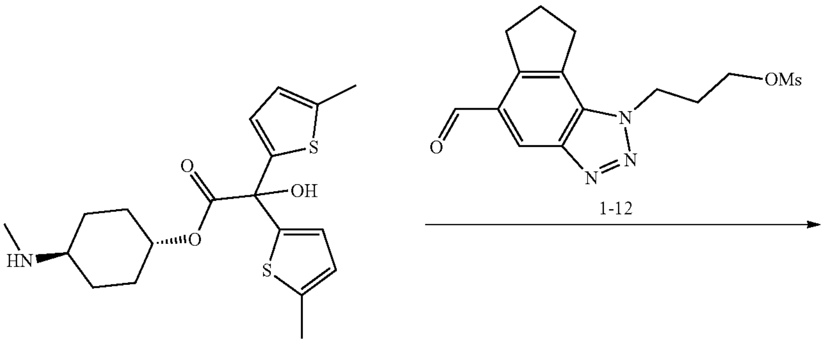
32-4
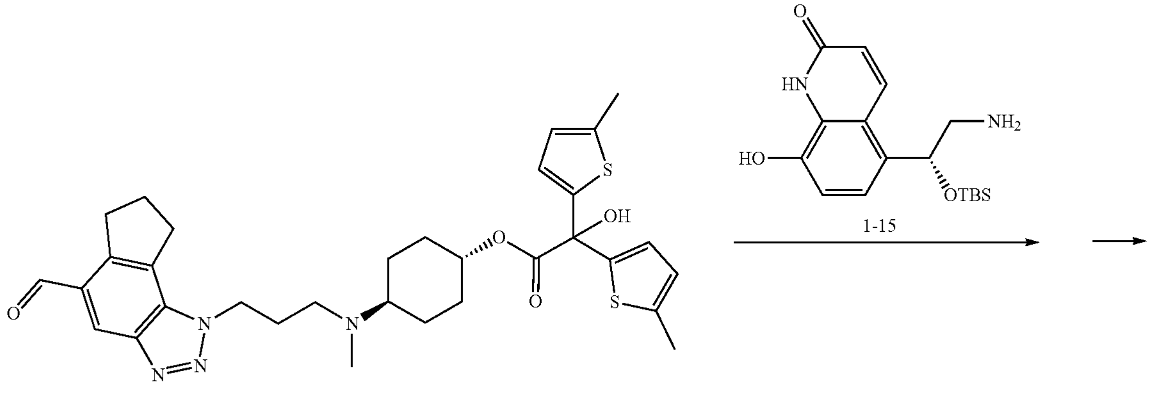
32-5
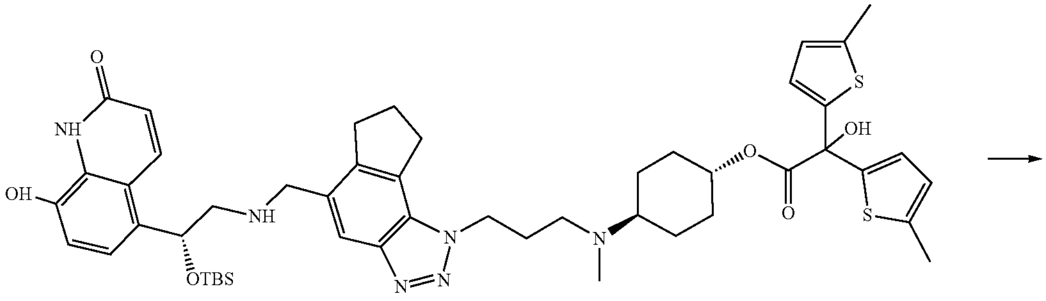
32-6

-continued

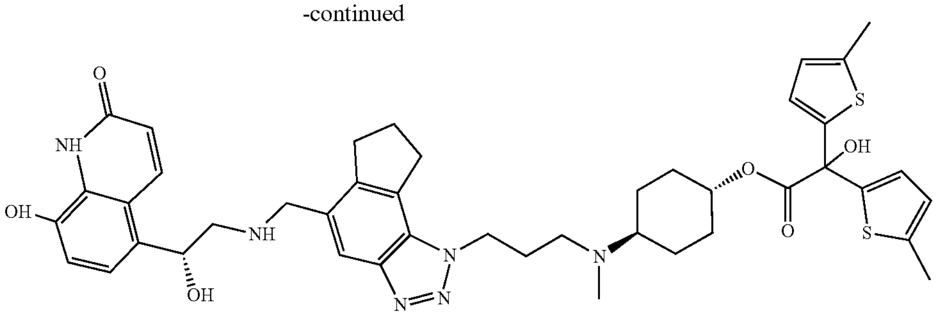

32

Step 1: Synthesis of Compound 32-1

Compound 2-bromo-5-methylthiophene (2.0 g) was dissolved in tetrahydrofuran (30 mL), and isopropylmagnesium chloride lithium chloride complex solution (1.3 M in tetrahydrofuran, 9.6 mL) was slowly added dropwise at 0° C. under nitrogen atmosphere. The mixture was stirred at 20° C. for 3 h. The reaction solution was cooled to −78° C. Diethyl oxalate (1.82 g) was dissolved in tetrahydrofuran (4 mL), and the solution was slowly added dropwise to the reaction solution at −78° C. After the dropwise addition, the mixture was stirred at −78° C. for 1 h. The reaction solution was heated to 0° C., and the reaction was quenched with a saturated aqueous ammonium chloride solution (100 mL). The resulting mixture was extracted with ethyl acetate (50 mL×2). The organic phase was washed with saturated brine (50 mL), dried over anhydrous sodium sulfate, and concentrated under reduced pressure. The residue was separated and purified by flash silica gel column chromatography (eluent: ethyl acetate/petroleum ether, 0-10%) and concentrated, and redundant diethyl oxalate was evaporated with an oil pump at 70° C. in a water bath to give compound 32-1.

$^1H$ NMR (400 MHz, $CDCl_3$) δ: 7.97-7.95 (m, 1H), 6.90-6.86 (m, 1H), 4.42 (q, J=8.0 Hz, 2H), 2.59 (s, 3H), 1.43 (t, J=8.0 Hz, 3H).

Step 2: Synthesis of Compound 32-2

Compound 32-1 (0.2 g) and compound 5-4 (462 mg) were dissolved in xylene (5 mL), and 4-dimethylaminopyridine (184 mg) was added at room temperature. The mixture was heated to 140° C. and stirred for 14 h. After the reaction was completed, the reaction solution was concentrated under reduced pressure, and the residue was separated and purified by flash silica gel column chromatography (eluent: ethyl acetate/petroleum ether, 0-25%) to give compound 32-2.

MS-ESI calcd. $[M+Na]^+$ 404, found 403.9.

Step 3: Synthesis of Compound 32-3 The compound 2-bromo-5-methylthiophene (169 mg) was dissolved in tetrahydrofuran (10 mL) and n-butyllithium solution (2.5 M in tetrahydrofuran, 0.41 mL) was slowly added dropwise at −60° C. under nitrogen atmosphere. The mixture was stirred at −60° C. for 0.5 h. Compound 32-2 (280 mg) was dissolved in tetrahydrofuran (4 mL) and slowly added dropwise to the reaction solution at −60° C. After the dropwise addition, the mixture was stirred at −50° C. for 2 h. The reaction solution was heated to 0° C., and the reaction was quenched with a saturated aqueous ammonium chloride solution (20 mL). The resulting mixture was extracted with ethyl acetate (30 mL×2). The organic phase was washed with saturated brine (50 mL), dried over anhydrous sodium sulfate, and concentrated under reduced pressure, and the residue was separated and purified by flash silica gel column chromatography (eluent: ethyl acetate/petroleum ether, 0-25%) to give compound 32-3.

MS-ESI calcd. $[M+H-18]^+$ 462, found 462.

Step 4: Synthesis of Compound 32-4

Compound 32-3 (70.0 mg) was dissolved in tetrahydrofuran (5 mL) and an aqueous hydrochloric acid solution (5 mL, 4 M) was added. The mixture was stirred at room temperature for 14 h. The reaction solution was adjusted to about pH 9 with a saturated aqueous sodium carbonate solution and extracted with ethyl acetate (20 mL×3). The organic phases were combined, dried over anhydrous sodium sulfate, and concentrated under reduced pressure to give compound 32-4, which was directly used in the next step.

MS-ESI calcd. $[M+H]^+$ 380, found 380.

Step 5: Synthesis of Compound 32-5

Compound 32-4 (45.8 mg) was dissolved in acetonitrile (20 mL), and compound 1-12 (39 mg), potassium iodide (100 mg) and N,N-diisopropylethylamine (46.7 mg) were added at room temperature. The mixture was stirred at 90° C. for 14 h. The reaction solution was concentrated under reduced pressure, and the residue was separated and purified by flash silica gel column chromatography (eluent: methanol/dichloromethane, 0-5%) to give compound 32-5.

MS-ESI calcd. $[M+H]^+$ 607, found 607.

Step 6: Synthesis of Compound 32-6

Compound 32-5 (36.9 mg) and compound 1-15 (24.0 mg, acetate) were dissolved in anhydrous methanol (4 mL) and anhydrous tetrahydrofuran (2 mL), and sodium triacetoxyborohydride (64.5 mg) and diisopropylethylamine (15.7 mg) were added. The mixture was stirred at 25° C. for 12 h, and sodium triacetoxyborohydride (64.5 mg) was added. The mixture was stirred for another 5 h. A 4% aqueous sodium bicarbonate solution (5 mL) was added to quench the reaction, and the resulting mixture was extracted with ethyl acetate (10 mL×2). The organic phases were combined, dried over anhydrous sodium sulfate, filtered and concentrated under reduced pressure to give compound 32-6, which was directly used in the next step.

MS-ESI calcd. $[M+H]^+$ 925, found 925.

Step 7: Synthesis of Formate Salt of Compound 32

Compound 32-6 (52 mg) was dissolved in tetrahydrofuran (4 mL), and triethylamine trihydrofluoride (45.3 mg) was added. The mixture was stirred at room temperature for 14 h. After the reaction was completed, the supernatant was discarded, and the solid precipitated at the bottom was concentrated under reduced pressure. The residue was separated by high performance liquid chromatography (column: Phenomenex Gemini-NX $C_{18}$, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 32.

$^1$H NMR (400 MHz, DMSO-$d_6$) δ: 8.19 (s, 1H), 8.15-8.10 (m, 1H), 7.73 (s, 1H), 7.08-7.04 (m, 1H), 6.97 (s, 1H), 6.92-6.88 (m, 1H), 6.82-6.79 (m, 2H), 6.64-6.60 (m, 2H), 6.43-6.37 (m, 1H), 5.10-5.05 (m, 1H), 4.72-4.61 (m, 3H), 3.83 (s, 2H), 2.95-2.89 (m, 2H), 2.82-2.63 (m, 4H), 2.42-2.35 (m, 9H), 2.18-2.12 (m, 5H), 2.01-1.95 (m, 2H), 1.93-1.86 (m, 2H), 1.68-1.62 (m, 2H), 1.87-1.29 (m, 4H); MS-ESI calcd. $[M+H]^+$ 811, found 811.

Example 33

33

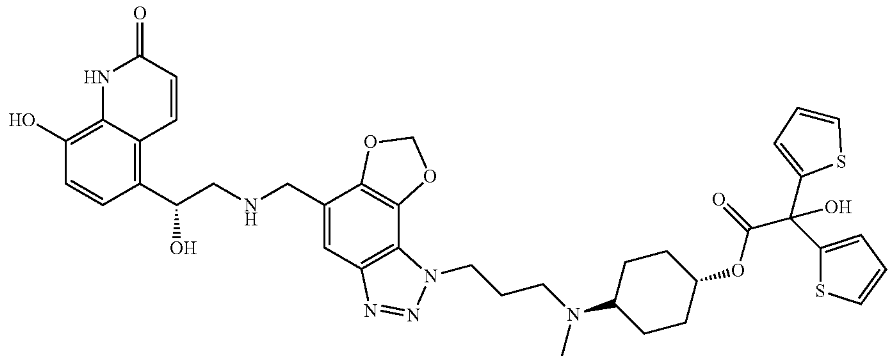

Synthetic Route:

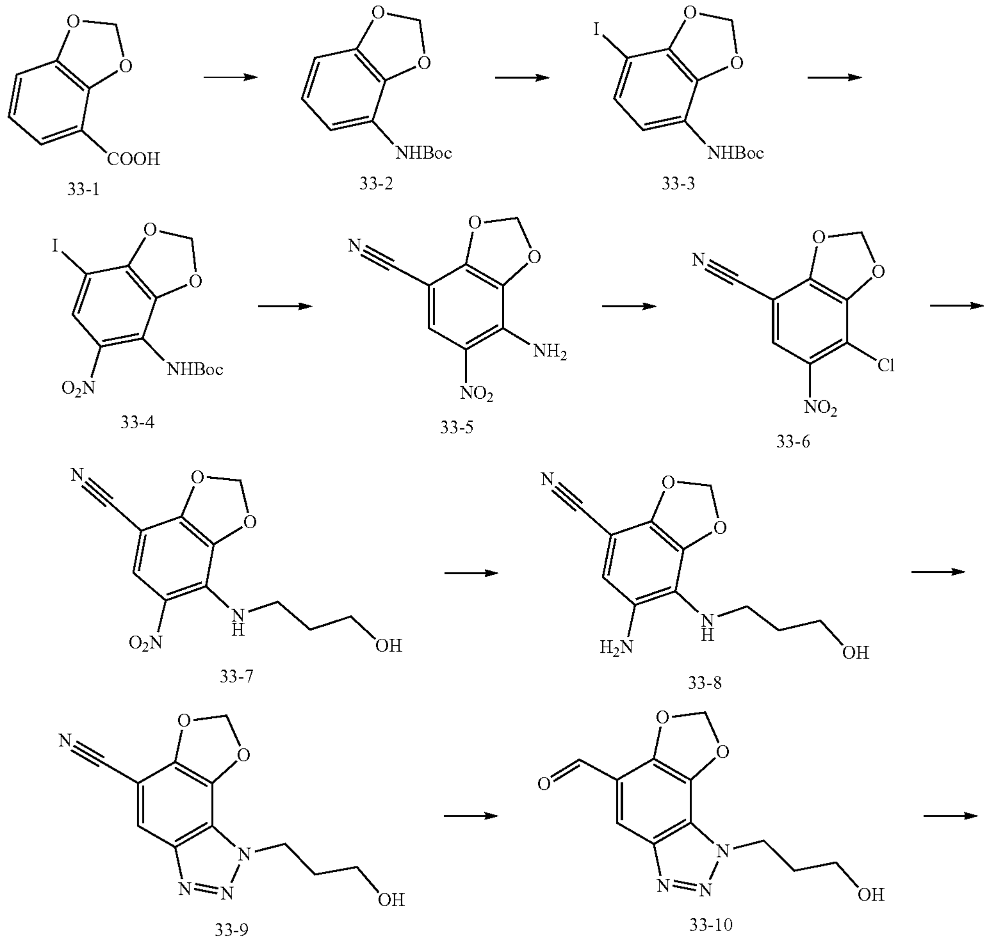

33-1 33-2 33-3 33-4 33-5 33-6 33-7 33-8 33-9 33-10

-continued
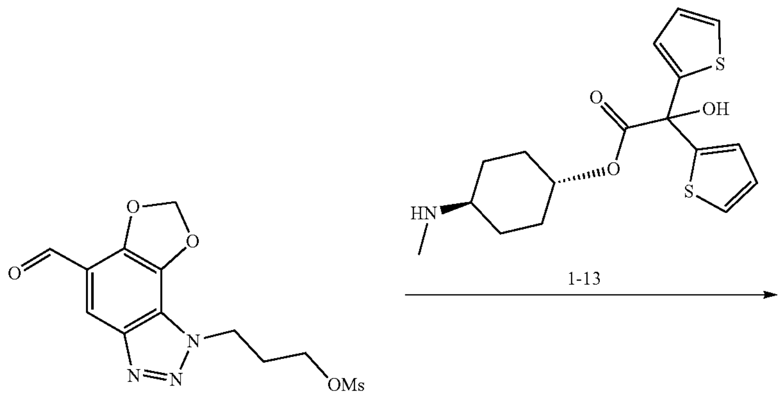
33-11
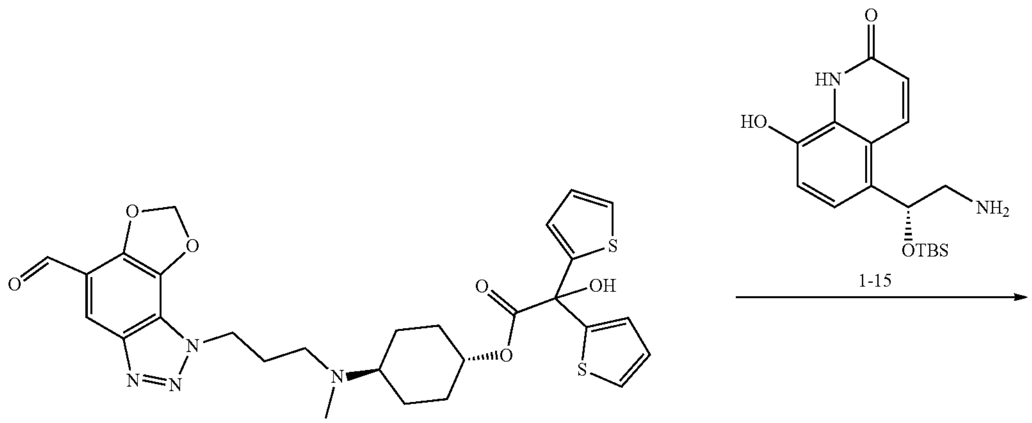
33-12
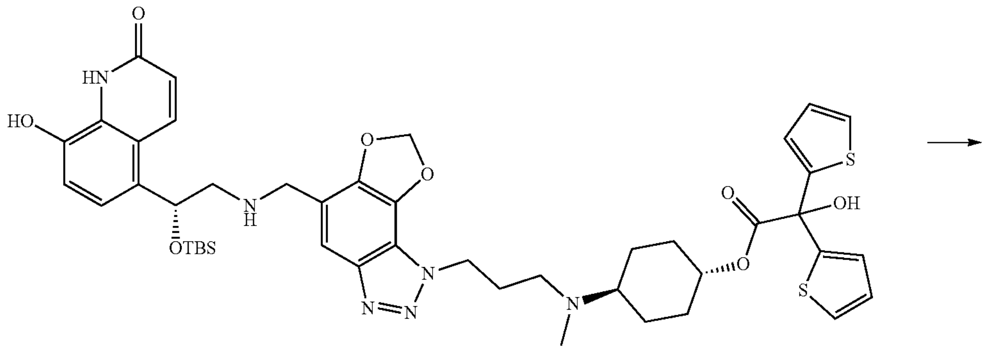
33-13
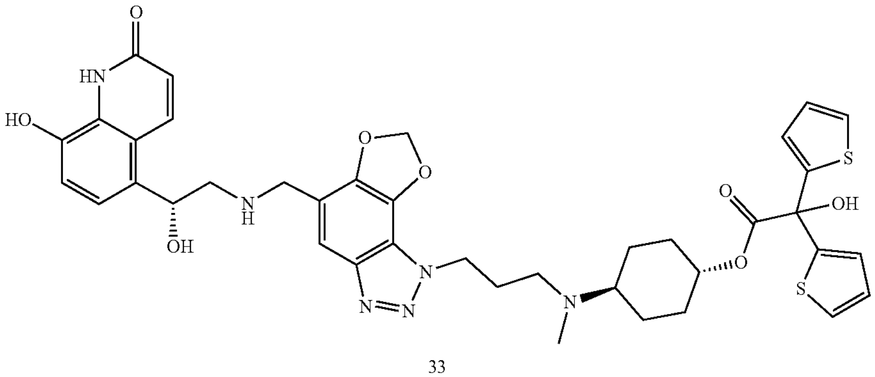
33

Step 1: Synthesis of Compound 33-2

Compound 33-1 (2.50 g) was dissolved in anhydrous tert-butanol (5 mL), and triethylamine (3.05 g) was added at room temperature. The mixture was heated to 90° C. Diphenylphosphoryl azide (4.14 g) was added in portions to the mixture under stirring. The resulting mixture was stirred at 90° C. for 14 h. After the reaction was completed, the reaction solution was filtered when it was still hot, concentrated under reduced pressure, and the residue was separated and purified by flash silica gel column chromatography (eluent: ethyl acetate/petroleum ether, 0-10%) to give compound 33-2.

$^1$H NMR (400 MHz, $CDCl_3$) δ: 7.48 (s, 1H), 6.83-6.77 (m, 1H), 6.59-6.55 (m, 1H), 6.44-6.42 (m, 1H), 5.94 (s, 2H), 1.52 (s, 9H).

Step 2: Synthesis of Compound 33-3

Compound 33-2 (250 mg) was dissolved in ethanol (10 mL), and sodium iodide (315 mg) and bis(trifluoroacetoxy) iodobenzene (679 mg) were added. The mixture was stirred at 50° C. for 14 h under air atmosphere. The reaction was quenched with a saturated aqueous sodium thiosulfate solution (15 mL), and the resulting mixture was extracted with ethyl acetate (20 mL×2). The organic phases were combined, dried over anhydrous sodium sulfate and concentrated under reduced pressure, and the residue was separated and purified by silica gel column chromatography (eluent: ethyl acetate/petroleum ether, 0-10%) to give compound 33-3.

MS-ESI calcd. $[M+H-56]^+$ 308, found 307.8.

Step 3: Synthesis of Compound 33-4 Acetic anhydride (8 mL) was added to a reaction flask, and concentrated nitric acid (200 mg, content: 65%) was slowly added at −78° C. Compound 33-3 (500 mg) was dissolved in acetic anhydride (5 mL), and the solution was slowly added dropwise to the reaction flask at −78° C. After the dropwise addition, the mixture was heated to 0° C. and stirred for 1 h. The reaction solution was slowly poured into ice water (100 mL) under stirring, and the resulting mixture was stirred for 10 min. The reaction solution was filtered, and the solid was dissolved in ethyl acetate (50 mL), washed with water (50 mL) twice, dried over anhydrous sodium sulfate, and concentrated under reduced pressure. The residue was separated and purified by silica gel column chromatography (eluent: ethyl acetate/petroleum ether, 0-30%) to give compound 33-4.

$^1$H NMR (400 MHz, DMSO-$d_6$) δ: 9.23 (s, 1H), 7.84 (s, 1H), 6.29 (s, 2H), 1.38 (s, 9H).

Step 4: Synthesis of Compound 33-5

Compound 33-4 (0.2 g) was dissolved in N,N-dimethylformamide (4 mL), and tris(dibenzylideneacetone)dipalladium (44.8 mg), 2-dicyclohexylphosphine-2,4,6-triisopropylbiphenyl (23.3 mg) and zinc cyanide (115 mg) were added. The mixture was stirred at 100° C. for 14 h under nitrogen atmosphere. Water (10 mL) and ethyl acetate (15 mL) were added to the reaction solution, and the resulting mixture was filtered. The filtrate was extracted with ethyl acetate (15 mL×2). The organic phases were washed with saturated brine (30 mL×3), combined, dried over anhydrous sodium sulfate, and concentrated under reduced pressure, and the residue was separated and purified by silica gel column chromatography (eluent: ethyl acetate/petroleum ether, 0-50%) to give compound 33-5.

$^1$H NMR (400 MHz, DMSO-$d_6$) δ: 8.21 (s, 1H), 7.55 (s, 2H), 6.34 (s, 2H).

Step 5: Synthesis of Compound 33-6

A mixture of copper chloride (90.8 mg) and acetonitrile (5 mL) was heated to 60° C., and tert-butyl nitrite (87.1 mg) was added in one portion. Compound 33-5 (70 mg) was dissolved in acetonitrile (5 mL), and the solution was added to the reaction solution in portions. The mixture was stirred at 60° C. for 0.5 h. After the reaction was completed, the reaction solution was cooled to room temperature, and water (10 mL) was added. The resulting mixture was extracted with ethyl acetate (15 mL×2). The organic phase was washed with saturated brine (30 mL), dried over anhydrous sodium sulfate, filtered and concentrated under reduced pressure, and the residue was separated and purified by silica gel column chromatography (eluent: ethyl acetate/petroleum ether, 0-30%) to give compound 33-6.

$^1$H NMR (400 MHz, DMSO-$d_6$) δ: 8.31 (s, 1H), 6.51 (s, 2H).

Step 6: Synthesis of Compound 33-7

Compound 33-6 (760 mg) was dissolved in tetrahydrofuran (15 mL), and triethylamine (1.02 g) and 3-aminopropanol (756 mg) were added. The mixture was heated to 60° C. and stirred for 14 h. After the reaction was completed, the reaction solution was cooled to room temperature, and water (30 mL) was added. The resulting mixture was extracted with ethyl acetate (35 mL×2). The organic phase was washed with saturated brine (50 mL×3), dried over anhydrous sodium sulfate, filtered and concentrated under reduced pressure, and the residue was separated and purified by silica gel column chromatography (eluent: methanol/dichloromethane, 0-5%) to give compound 33-7.

MS-ESI calcd. $[M+H]^+$ 266, found 266.

Step 7: Synthesis of Compound 33-8

Compound 33-7 (330 mg) was dissolved in ethanol (10 mL), and wet palladium on carbon (300 mg, purity: 10%) was added. The mixture was stirred at room temperature for 14 h under hydrogen (15 psi) atmosphere. After the reaction was completed, the reaction solution was filtered, and the filter cake was washed with ethanol. The filtrate was collected and concentrated under reduced pressure to give compound 33-8, which was directly used in the next step.

MS-ESI calcd. $[M+H]^+$ 236, found 235.9.

Step 8: Synthesis of Compound 33-9

Compound 33-8 (260 mg) was dissolved in an aqueous hydrochloric acid solution (6 M, 10 mL), and a solution of sodium nitrite (114 mg) in water (4 mL) was slowly added dropwise at 0° C. The mixture was stirred at 15° C. for 2 h. After the reaction was completed, the reaction solution was subjected to liquid separation in dichloromethane (20 mL) and water (15 mL). The organic phase was washed with saturated brine (20 mL), dried over anhydrous sodium sulfate, filtered and concentrated to dryness under reduced pressure to give compound 33-9, which was directly used in the next step.

MS-ESI calcd. $[M+H]^+$ 247, found 246.8.

Step 9: Synthesis of Compound 33-10

Compound 33-9 (250 mg) was dissolved in formic acid solution (20 mL, purity: 75%), and nickel-aluminum alloy (434 mg) was added. The mixture was heated to 90° C. and stirred for 14 h. The reaction solution was filtered, and the filtrate was collected and concentrated to dryness under reduced pressure. Ethanol (8 mL) and an aqueous sodium hydroxide solution (4 M, 8 mL) were added to the concentrate. The mixture was stirred at 15° C. for 1 h. After the reaction was completed, the reaction solution was extracted with dichloromethane (30 mL×2). The organic phase was washed with saturated brine (50 mL), dried over anhydrous sodium sulfate, filtered and concentrated to dryness under reduced pressure, and the residue was separated and purified by silica gel column chromatography (eluent: methanol/dichloromethane, 0-5%) to give compound 33-10.

MS-ESI calcd. $[M+H]^+$ 250, found 249.9.

Step 10: Synthesis of Compound 33-11

Compound 31-10 (110 mg) was dissolved in dichloromethane (6 mL), and triethylamine (223 mg) and methanesulfonyl chloride (101 mg) were added. The mixture was stirred at 15° C. for 1 h. After the reaction was completed, the reaction solution was subjected to liquid separation in dichloromethane (15 mL) and water (10 mL). The organic phase was washed with saturated brine (20 mL), dried over anhydrous sodium sulfate, filtered and concentrated to dryness under reduced pressure, and the residue was separated and purified by silica gel column chromatography (eluent: methanol/dichloromethane, 0-5%) to give compound 33-11.

MS-ESI calcd. $[M+H]^+$ 328, found 327.9.

Step 11: Synthesis of Compound 33-12

Compound 33-11 (50 mg) was dissolved in acetonitrile (20 mL), and diisopropylethylamine (59.2 mg), potassium iodide (126 mg) and compound 1-13 (53.7 mg) were added. The mixture was heated to 90° C. and stirred for 14 h. After the reaction was completed, the reaction solution was concentrated to dryness under reduced pressure, and the residue was separated and purified by silica gel column chromatography (eluent: methanol/dichloromethane, 0-5%) to give compound 33-12.

MS-ESI calcd. $[M+H]^+$ 583, found 583.

Step 12: Synthesis of Compound 33-13

Compound 1-15 (44 mg, acetate) and compound 33-12 (64.9 mg) were dissolved in methanol (4 mL) and tetrahydrofuran (2 mL), and diisopropylethylamine (28.8 mg) and sodium triacetoxyborohydride (118.2 mg) were added. The mixture was stirred at 20° C. for 12 h, and sodium triacetoxyborohydride (118.2 mg) was added. The mixture was stirred at 20° C. for another 5 h. To the reaction solution was added a 5% aqueous sodium bicarbonate solution (10 mL), and the resulting mixture was extracted with ethyl acetate (15 mL×2). The organic phase was washed with saturated brine (15 mL), dried over anhydrous sodium sulfate, filtered and concentrated under reduced pressure to give compound 33-13, which was directly used in the next step.

MS-ESI calcd. $[M+H]^+$ 901, found 901.

Step 13: Synthesis of Formate Salt of Compound 33

Compound 33-13 (62 mg) was dissolved in tetrahydrofuran (4 mL), and triethylamine trihydrofluoride (55.4 mg) was added. The mixture was stirred at 15° C. for 14 h. After the reaction was completed, the reaction solution was left to stand, and the supernatant was discarded. The solid was washed with 5 mL of tetrahydrofuran, and the residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 33.

$^1H$ NMR (400 MHz, DMSO-$d_6$) δ: 8.17 (s, 1H), 8.15-8.10 (m, 1H), 7.58 (s, 1H), 7.48-7.44 (m, 2H), 7.23 (s, 1H), 7.07-7.03 (m, 3H), 6.99-6.95 (m, 2H), 6.92-6.88 (m, 1H), 6.45-6.40 (m, 1H), 6.22-6.18 (m, 2H), 5.10-5.04 (m, 1H), 4.67-4.59 (m, 3H), 3.85 (s, 2H), 2.76-2.70 (m, 2H), 2.42-2.32 (m, 3H), 2.12 (s, 3H), 2.06-2.01 (m, 2H), 1.92-1.86 (m, 2H), 1.66-1.60 (m, 2H), 1.31-1.24 (m, 4H); MS-ESI calcd. $[M+H]^+$ 787, found 787.2.

Example 34 and Example 35

34 or 35

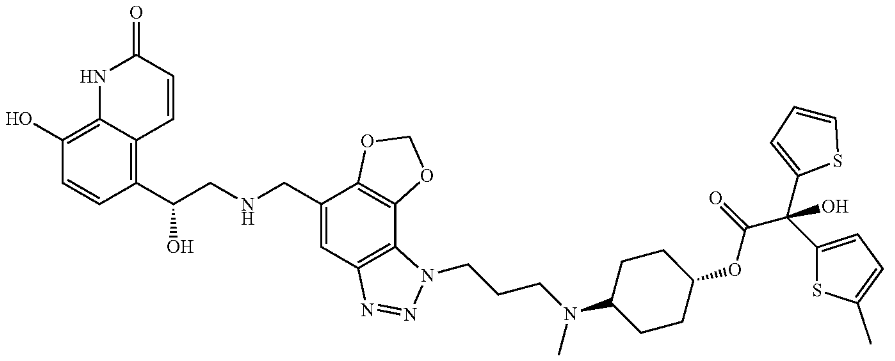

34 or 35

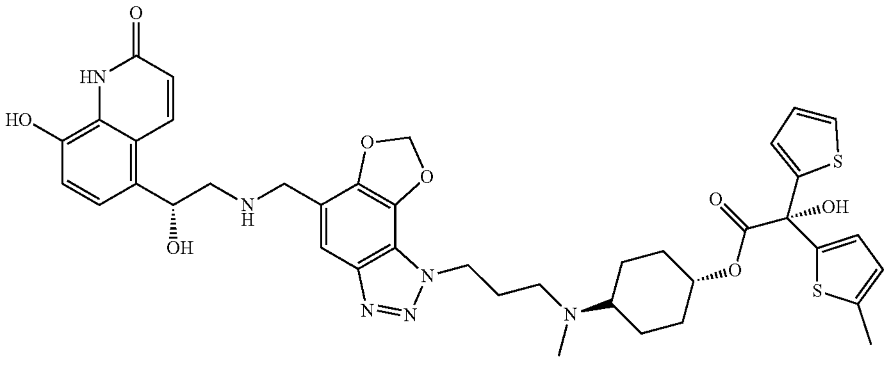

Synthetic Route:
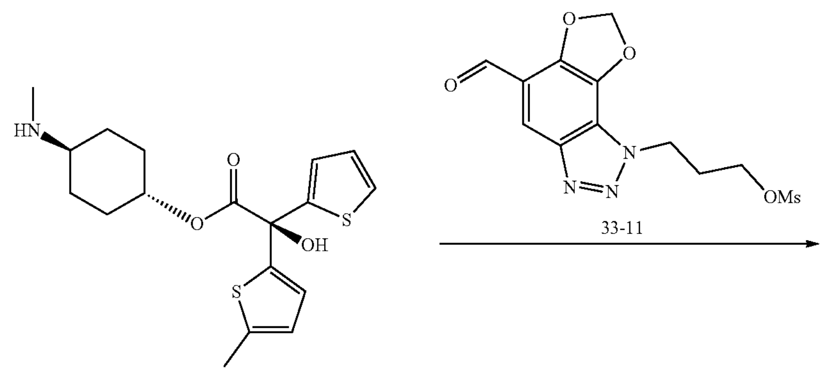
13-3 or 14-1
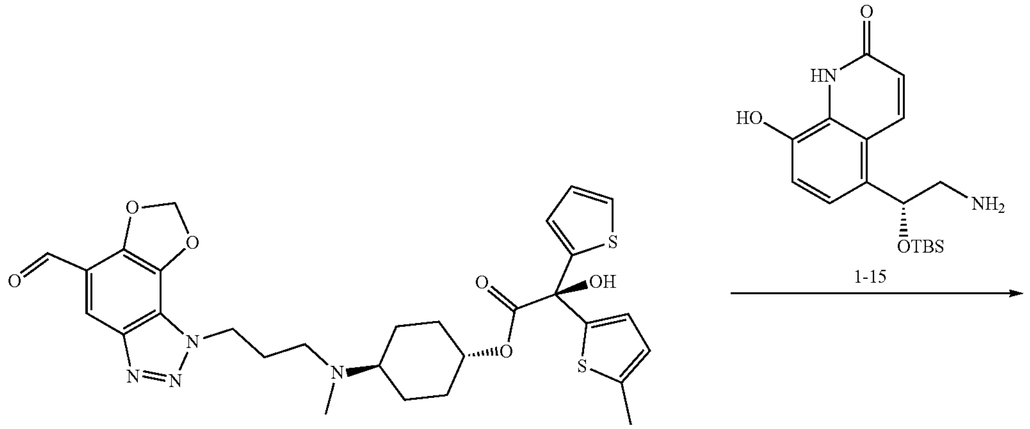
34-1 or 35-1
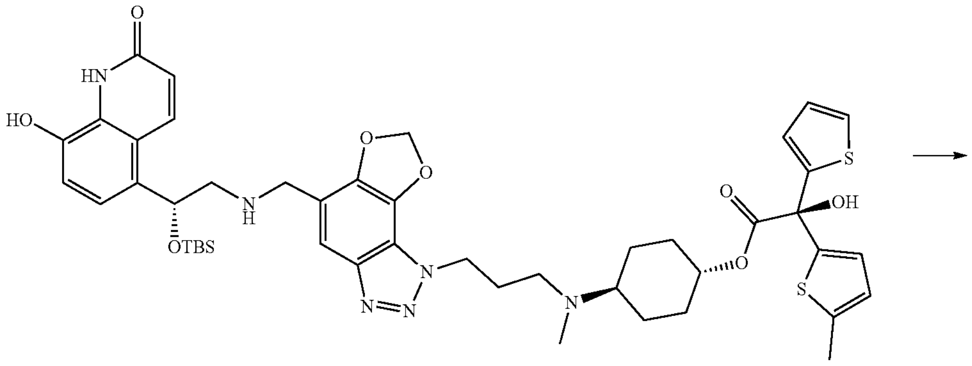
34-2 or 35-2
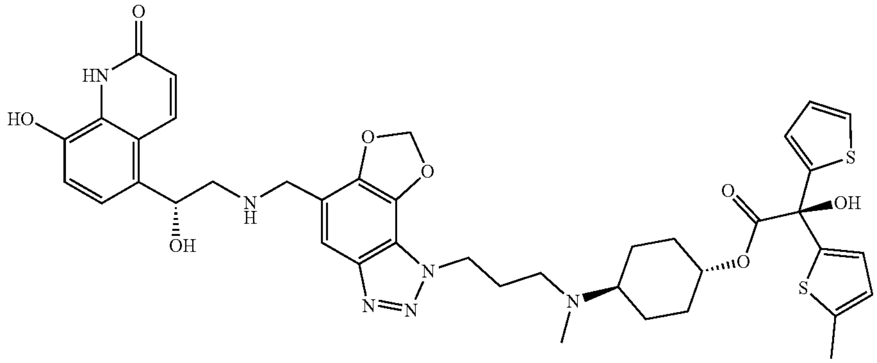
34 or 35

-continued
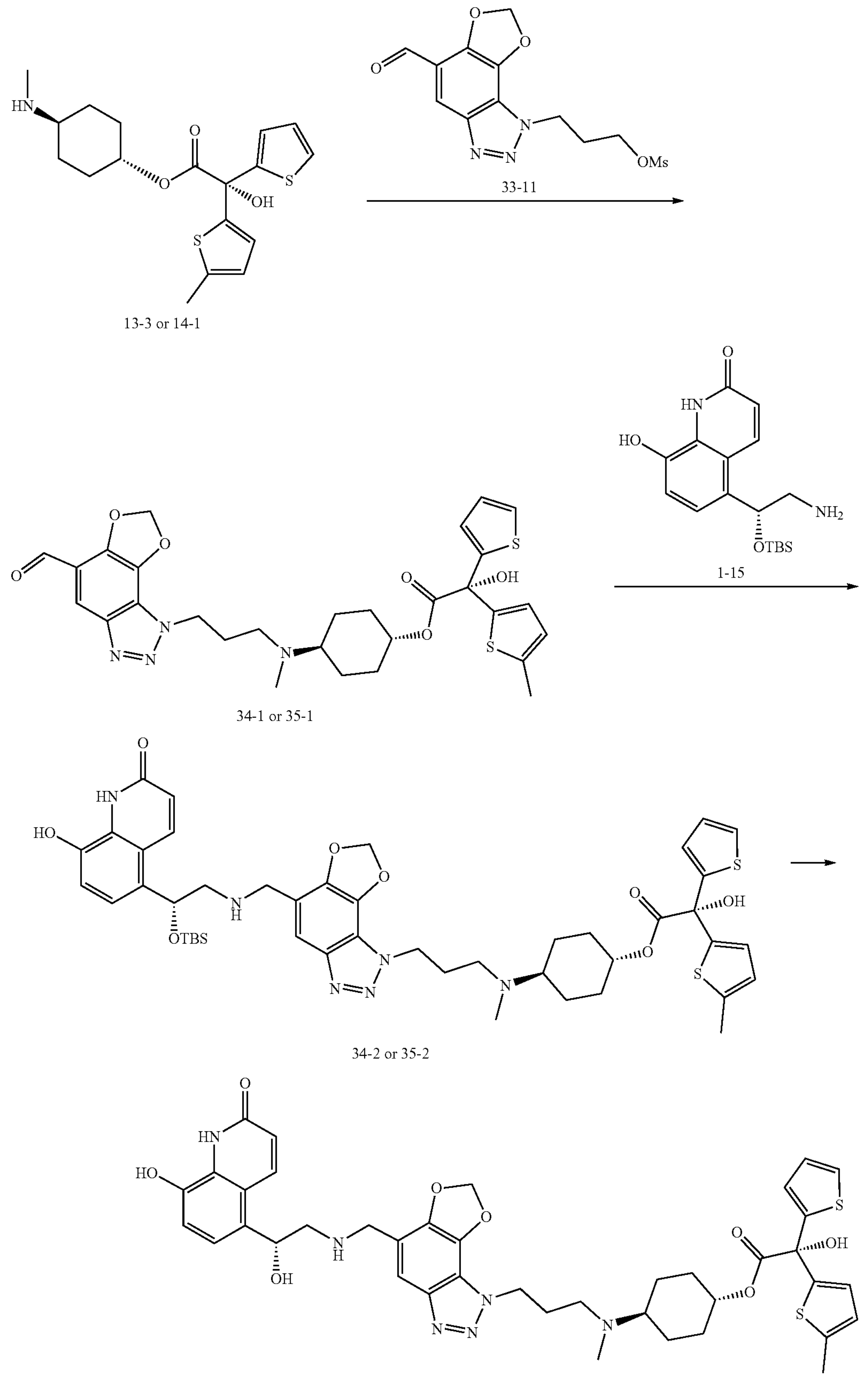
13-3 or 14-1
33-11
1-15
34-1 or 35-1
34-2 or 35-2
34 or 35

Step 1: Synthesis of Compound 34-1

Compound 33-11 (31 mg) was dissolved in acetonitrile (10 mL), and diisopropylethylamine (36.7 mg), potassium iodide (78.6 mg) and compound 13-3 (34.6 mg) were added. The mixture was heated to 90° C. and stirred for 14 h. After the reaction was completed, the reaction solution was concentrated to dryness under reduced pressure, and the residue was separated and purified by silica gel column chromatography (eluent: methanol/dichloromethane, 0-5%) to give compound 34-1.

MS-ESI calcd. $[M+H]^+$ 597, found 597.

Step 2: Synthesis of Compound 34-2

Compound 1-15 (30 mg, acetate) and compound 34-1 (45.3 mg) were dissolved in methanol (4 mL) and tetrahydrofuran (2 mL), and diisopropylethylamine (19.6 mg) and sodium triacetoxyborohydride (80.5 mg) were added. The mixture was stirred at 20° C. for 12 h, and sodium triacetoxyborohydride (80.5 mg) was added. The mixture was stirred at 20° C. for another 5 h. To the reaction solution was added a 5% aqueous sodium bicarbonate solution (10 mL), and the resulting mixture was extracted with ethyl acetate (15 mL×2). The organic phase was washed with saturated brine (15 mL), dried over anhydrous sodium sulfate, filtered and concentrated under reduced pressure to give compound 34-2, which was directly used in the next step.

MS-ESI calcd. $[M+H]^+$ 915, found 915.

Step 3: Synthesis of Formate Salt of Compound 34

Compound 34-2 (60 mg) was dissolved in tetrahydrofuran (4 mL), and triethylamine trihydrofluoride (52.8 mg) was added. The mixture was stirred at 15° C. for 14 h. After the reaction was completed, the reaction solution was left to stand, and the supernatant was discarded. The solid was washed with 5 mL of tetrahydrofuran, and the residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 34.

$^1H$ NMR (400 MHz, DMSO-$d_6$) δ: 8.18 (s, 1H), 8.15-8.10 (m, 1H), 7.57 (s, 1H), 7.46-7.42 (m, 2H), 7.07-7.04 (m, 2H), 6.98-6.94 (m, 1H), 6.92-6.88 (m, 1H), 6.83-6.80 (m, 1H), 6.64-6.62 (m, 1H), 6.45-6.40 (m, 1H), 6.22-6.19 (m, 2H), 5.08-5.05 (m, 1H), 4.66-4.60 (m, 3H), 3.85 (s, 2H), 2.76-2.68 (m, 2H), 2.42-2.33 (m, 6H), 2.11 (s, 3H), 2.06-2.00 (m, 2H), 1.90-1.86 (m, 2H), 1.66-1.61 (m, 2H), 1.35-1.26 (m, 4H);

MS-ESI calcd. $[M+H]^+$ 801, found 801.

The formate salt of compound 35 was prepared in a 3-step reaction with compounds 33-11 and 14-1 as the starting materials by referring to the synthetic route of the formate salt of compound 34.

Formate Salt of Compound 35:

$^1H$ NMR (400 MHz, DMSO-$d_6$) δ: 8.17 (s, 1H), 8.15-8.10 (m, 1H), 7.58 (s, 1H), 7.46-7.42 (m, 2H), 7.07-7.04 (m, 2H), 6.98-6.94 (m, 1H), 6.92-6.88 (m, 1H), 6.83-6.80 (m, 1H), 6.64-6.62 (m, 1H), 6.45-6.40 (m, 1H), 6.22-6.19 (m, 2H), 5.08-5.05 (m, 1H), 4.66-4.60 (m, 3H), 3.86 (s, 2H), 2.76-2.68 (m, 2H), 2.42-2.33 (m, 6H), 2.11 (s, 3H), 2.06-2.00 (m, 2H), 1.90-1.86 (m, 2H), 1.66-1.61 (m, 2H), 1.35-1.26 (m, 4H); MS-ESI calcd. $[M+H]^+$ 801, found 801.

Example 36 and Example 37

36 or 37

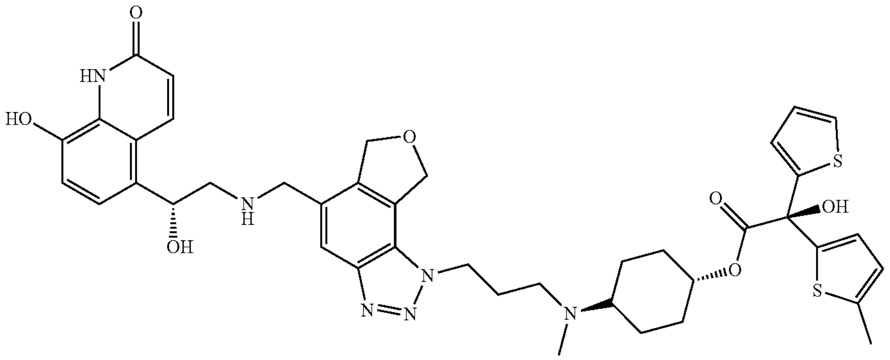

36 or 37

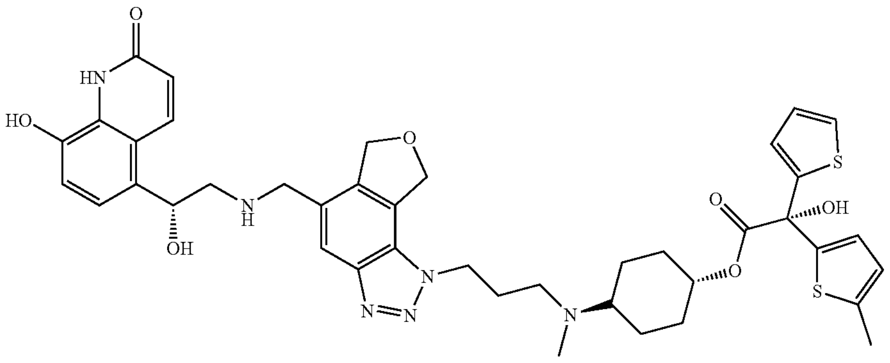

Synthetic Route:
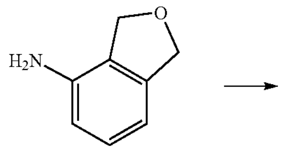
36-1
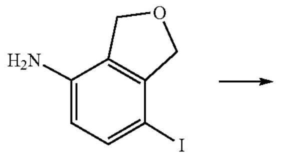
36-2
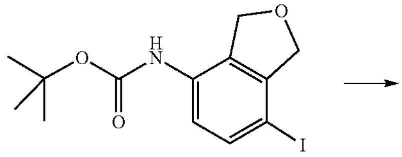
36-3
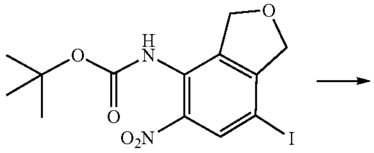
36-4
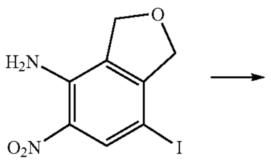
36-5
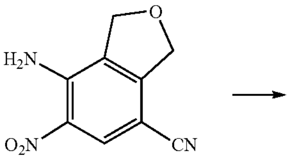
36-6
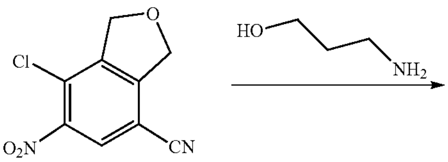
36-7
-continued
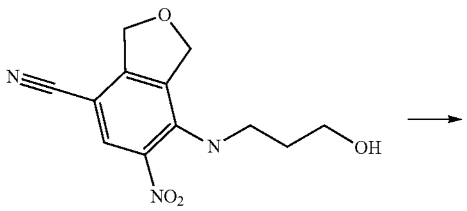
36-8
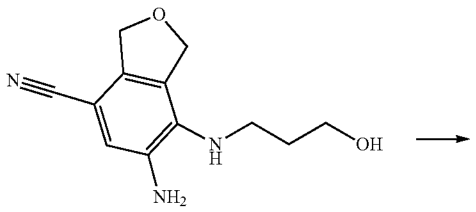
36-9
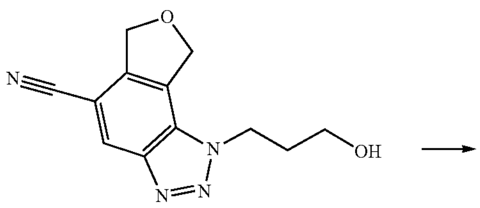
36-10
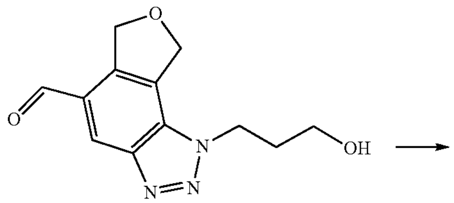
36-11
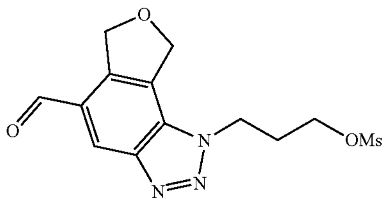
36-12

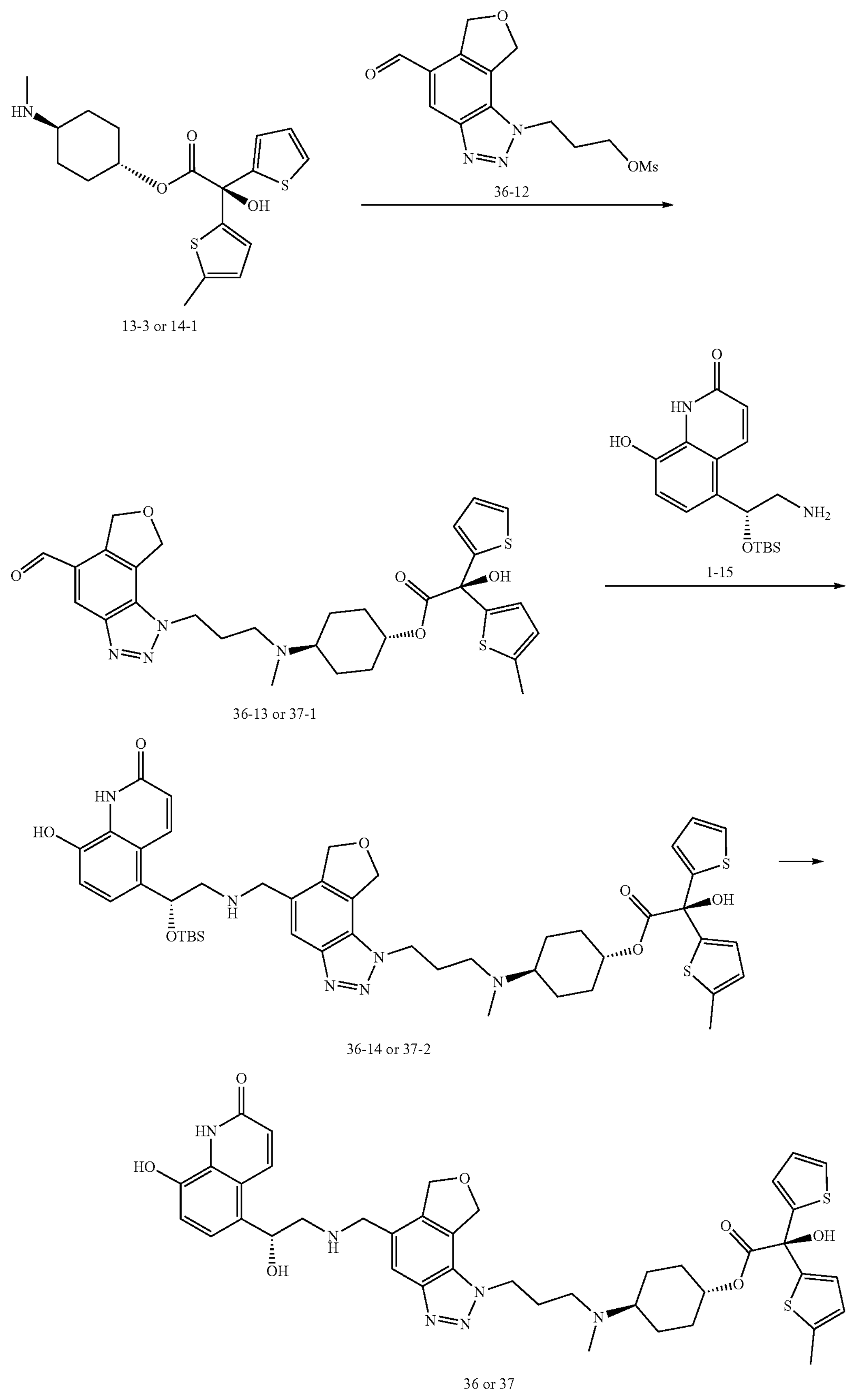
13-3 or 14-1
36-12
36-13 or 37-1
1-15
36-14 or 37-2
36 or 37

-continued
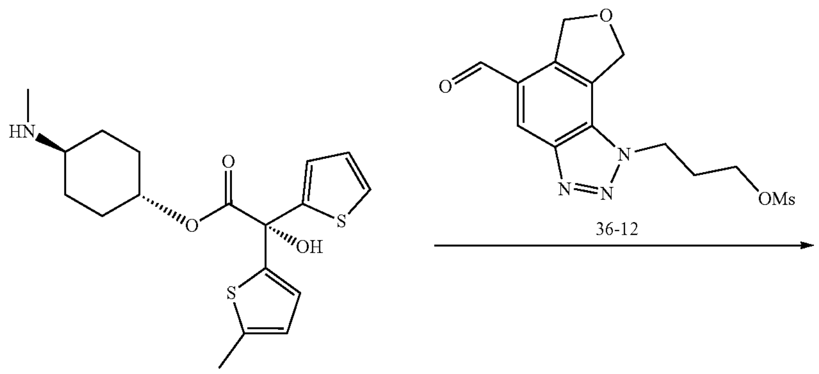
13-3 or 14-1
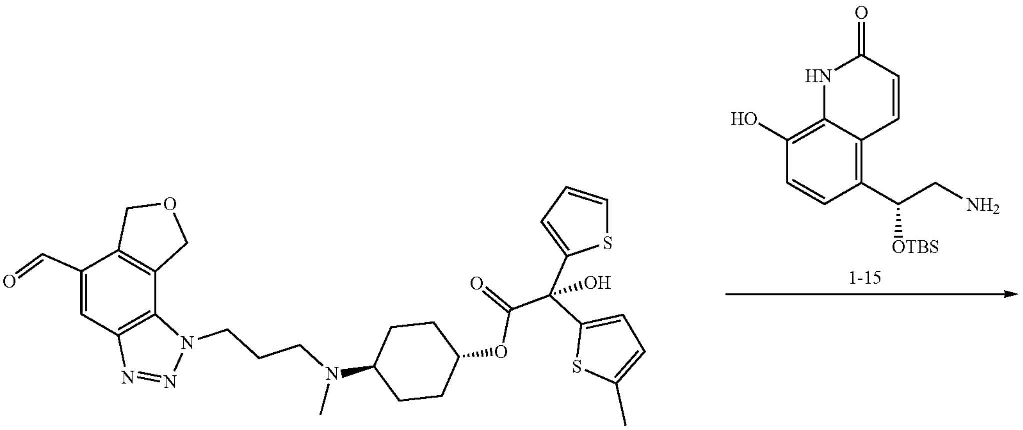
36-13 or 37-1
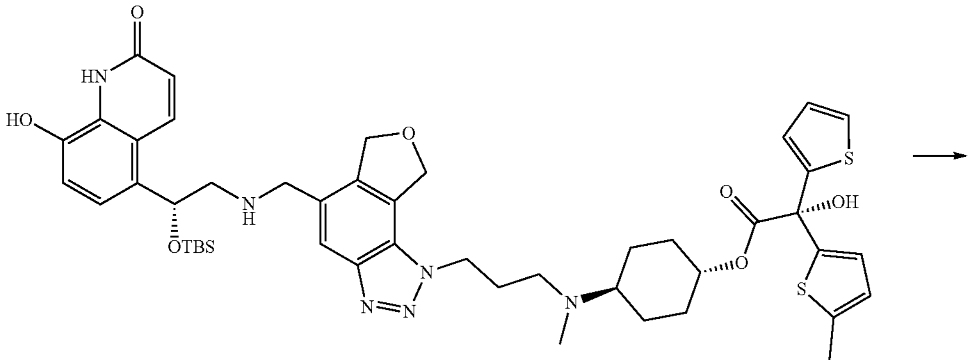
36-14 or 37-2
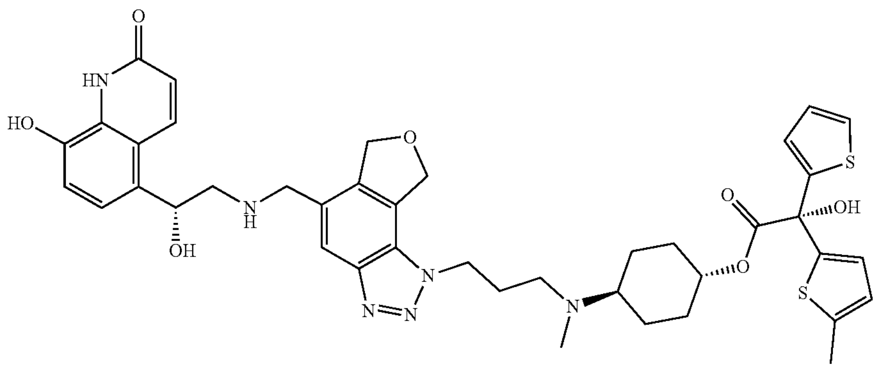
36 or 37

Step 1: Synthesis of Compound 36-2

Compound 36-1 (1 g) was dissolved in N,N-dimethylformamide (20 mL), and N-iodosuccinimide (7.22 g) was added at 0° C. The mixture was stirred at 25° C. for 1 h. After the reaction was completed, 200 mL of water was added to the reaction solution, and the resulting mixture was extracted with ethyl acetate (50 mL×2). The organic phases were combined, washed with saturated brine (100 mL×1), dried over anhydrous sodium sulfate, filtered and concentrated under reduced pressure, and separated and purified by flash silica gel column chromatography (eluent: ethyl acetate/petroleum ether, 0-20%) to give compound 36-2.

$^1H$ NMR (400 MHz, CHLOROFORM-d) δ: 7.37 (d, J=8.4 Hz, 1H), 6.38 (d, J=8.0 Hz, 1H), 5.15 (d, J=2.0 Hz, 2H), 5.00 (t, J=2.0 Hz, 2H), 3.55 (s, 2H).

Step 2: Synthesis of Compound 36-3

Compound 36-2 (3.25 g) was dissolved in tetrahydrofuran (60 mL), and triethylamine (3.15 g) and BOC anhydride (4.75 g) were added. The mixture was stirred at 70° C. for 2 h. After the reaction was completed, the reaction solution was poured into 500 mL of water, and the resulting mixture was extracted with ethyl acetate (500 mL×2). The organic phases were combined, washed with saturated brine (500 mL×1), dried over anhydrous sodium sulfate, filtered and concentrated under reduced pressure, and the residue was separated and purified by flash silica gel column chromatography (eluent: ethyl acetate/petroleum ether, 0-20%) to give compound 36-3.

$^1H$ NMR (400 MHz, DMSO-$d_6$) δ: 9.04 (s, 1H), 7.54 (d, J=8.4 Hz, 1H), 7.25 (d, J=8.4 Hz, 1H), 5.11 (s, 2H), 4.84 (s, 2H), 1.45 (s, 9H).

Step 3: Synthesis of Compound 36-4

Compound 36-3 (1 g) was dissolved in acetic anhydride (15 mL), and the solution was cooled to −78° C. Concentrated nitric acid (402.60 mg, purity: 65%) was added at this temperature. The mixture was stirred at 0° C. for 2 h. 10 reactions were set up in parallel. After the reaction was completed, the reaction mixture was poured into 2000 mL of water, and extracted with ethyl acetate (500 mL×2). The organic phases were combined, washed with saturated brine (500 mL×1), dried over anhydrous sodium sulfate, filtered and concentrated under reduced pressure, and the residue was separated and purified by flash silica gel column chromatography (eluent: ethyl acetate/petroleum ether, 0-5%) to give compound 36-4.

$^1H$ NMR (400 MHz, DMSO-$d_6$) δ: 9.46 (s, 1H), 8.15 (s, 1H), 5.18 (s, 2H), 4.95 (s, 2H), 1.40 (s, 9H).

Step 4: Synthesis of Compound 36-5

Compound 36-4 (1.02 g) was dissolved in ethyl acetate (10 mL), and hydrochloric acid/ethyl acetate solution (4 M, 31.39 mL) was added. The mixture was stirred at 20° C. for 4 h. After the reaction was completed, the reaction solution was concentrated to dryness under reduced pressure, and the residue was adjusted to pH 7 with a saturated aqueous sodium bicarbonate solution and extracted with ethyl acetate (100 mL×2). The organic phases were combined, washed with saturated brine (100 mL×1), dried over anhydrous sodium sulfate, filtered and concentrated under reduced pressure to give compound 36-5, which was directly used in the next step.

$^1H$ NMR (400 MHz, DMSO-$d_6$) δ: 8.23 (s, 1H), 7.35 (s, 2H), 5.11 (t, J=2.4 Hz, 2H), 4.89 (t, J=2.8 Hz, 2H).

Step 5: Synthesis of Compound 36-6

Compound 36-5 (1.12 g) was dissolved in N,N-dimethylformamide (25 mL), and tris(dibenzylideneacetone)dipalladium(0) (167.85 mg), 2-dicyclohexylphosphine-2',4',6'-triisopropylbiphenyl (174.77 mg) and zinc cyanide (516.60 mg) were added under nitrogen atmosphere. The mixture was heated to 80° C. under nitrogen atmosphere and stirred for 16 h. After the reaction was completed, the reaction solution was cooled to room temperature and poured into 250 mL of water, and the resulting mixture was extracted with ethyl acetate (100 mL×2). The organic phases were combined, washed with saturated brine (200 mL×1), dried over anhydrous sodium sulfate, filtered and concentrated under reduced pressure, and the residue was separated and purified by flash silica gel column chromatography (eluent: ethyl acetate/petroleum ether, 0-50%) to give compound 36-6.

Step 6: Synthesis of Compound 36-7

A mixture of cuprous chloride (897.78 mg) and acetonitrile (50 mL) was heated to 65° C., tert-butyl nitrite (860.72 mg) was added in one portion, and compound 36-6 (685 mg) was added in portions. The mixture was stirred at 65° C. for 0.5 h. After the reaction was completed, the reaction solution was cooled to room temperature and concentrated to dryness under reduced pressure. Ethyl acetate (75 mL) and hydrochloric acid solution (6 M, 30 mL) were added to the residue, followed by liquid separation. The organic phase was washed with saturated brine (50 mL), dried over anhydrous sodium sulfate, filtered and concentrated to dryness under reduced pressure to give compound 36-7, which was directly used in the next step.

Step 7: Synthesis of Compound 36-8

Compound 36-7 (750 mg) was dissolved in tetrahydrofuran (45 mL), and triethylamine (844.75 mg) and 3-aminopropanol (752.43 mg) were added. The mixture was heated to 65° C. and stirred for 16 h. After the reaction was completed, the reaction solution was cooled to room temperature and poured into 50 mL of water, and the resulting mixture was extracted with ethyl acetate (75 mL×2). The organic phase was washed with saturated brine (100 mL×1), dried over anhydrous sodium sulfate, filtered and concentrated under reduced pressure to give compound 36-8, which was directly used in the next step.

MS-ESI calcd. $[M+H]^+$ 264, found 263.9.

Step 8: Synthesis of Compound 36-9

Compound 36-8 (747 mg) was dissolved in ethanol (75 mL), and wet palladium on carbon (75 mg, purity: 10%) was added. The mixture was stirred at 25° C. for 16 h under hydrogen (15 psi) atmosphere. After the reaction was completed, the reaction solution was filtered, and the filter cake was washed with 100 mL of ethanol. The filtrate was collected and concentrated to dryness under reduced pressure to give compound 36-9.

MS-ESI calcd. $[M+H]^+$ 234, found 233.9.

Step 9: Synthesis of Compound 36-10

Compound 36-9 (660 mg) was dispersed in hydrochloric acid solution (6 M, 4.72 mL), and the system was cooled to 0° C. A solution of sodium nitrite (292.84 mg) in water (6 mL) was slowly added dropwise at 0° C. The mixture was stirred at 0-25° C. for 1 h. After the reaction was completed, the reaction solution was subjected to liquid separation in dichloromethane (500 mL) and water (50 mL). The organic phase was washed with saturated brine (100 mL), dried over anhydrous sodium sulfate, filtered, concentrated to dryness under reduced pressure, and separated and purified by flash silica gel column chromatography (eluent: methanol/dichloromethane, 0-5%) to give compound 36-10.

MS-ESI calcd. $[M+H]^+$ 245, found 244.9.

Step 10: Synthesis of Compound 36-11

Compound 36-10 (645.00 mg) was dissolved in formic acid solution (40 mL, purity: 75%), and nickel-aluminum alloy (1.13 g) was added. The mixture was heated to 90° C.

and stirred for 16 h. The reaction solution was filtered, and the filtrate was collected and concentrated to dryness under reduced pressure. The residue was dissolved in 30 mL of ethanol, and an aqueous sodium hydroxide solution (1 M, 13.22 mL) was added under stirring. The mixture was stirred at 15° C. for 1 h. After the reaction was completed, the reaction solution was concentrated under reduced pressure to remove most of the methanol, and extracted with ethyl acetate (250 mL×2). The organic phase was concentrated to dryness under reduced pressure to give compound 36-11, which was directly used in the next step.

MS-ESI calcd. $[M+H]^+$ 248, found 247.9.

Step 11: Synthesis of Compound 36-12

Compound 36-11 (650 mg) was dissolved in dichloromethane (50 mL), and triethylamine (1.33 g) and methanesulfonyl chloride (619.48 mg) were added. The mixture was stirred at 25° C. for 0.5 h. After the reaction was completed, the reaction solution was subjected to liquid separation in dichloromethane (100 mL) and water (50 mL). The organic phase was washed with saturated brine (100 mL), dried over anhydrous sodium sulfate, filtered, concentrated to dryness under reduced pressure, and separated and purified by flash silica gel column chromatography (eluent: methanol/dichloromethane, 0-5%) to give compound 36-12.

MS-ESI calcd. $[M+H]^+$ 326, found 325.8.

Step 12: Synthesis of Compound 36-13

Compound 13-3 (60 mg) was dissolved in acetonitrile (10 mL), and diisopropylethylamine (50.92 mg), potassium iodide (65.40 mg) and compound 36-12 (47.00 mg) were added. The mixture was heated to 90° C. and stirred for 16 h. After the reaction was completed, the reaction solution was poured into 50 mL of water, and the resulting mixture was extracted with dichloromethane (50 mL×2), followed by liquid separation. The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-5%) to give compound 36-13.

MS-ESI calcd. $[M+H]^+$ 595, found 595.1.

Step 13: Synthesis of Compound 36-14

Compound 36-13 (50.5 mg) and compound 1-15 (28.40 mg, acetate) were dissolved in methanol (3 mL) and tetrahydrofuran (2 mL). sodium triacetoxyborohydride (89.98 mg) was added. The mixture was stirred at 25° C. for 16 h. Then, sodium triacetoxyborohydride (89.98 mg) was added, and the mixture was stirred at 25° C. for 24 h. The reaction solution was added to water (50 mL), and the resulting mixture was extracted with dichloromethane (50 mL×2). The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-5%) to give compound 36-14.

MS-ESI calcd. $[M+H]^+$ 913, found 913.4.

Step 14: Synthesis of Formate Salt of Compound 36

Compound 36-14 (30 mg) was dissolved in tetrahydrofuran (5 mL), and triethylamine trihydrofluoride (26.48 mg) was added. The mixture was stirred at 25° C. for 16 h. After the reaction was completed, the reaction solution was left to stand, and the supernatant was discarded. The solid was washed with 10 mL of tetrahydrofuran, separated and purified by high performance liquid chromatography (formic acid method, preparative column type: Phenomenex C18, length×inner diameter: 150 mm×40 mm, 5 μm). preparation method: the crude product was dissolved in dimethyl sulfoxide and filtered through a 0.45 μm filter membrane to give a sample solution; mobile phase system: acetonitrile/water (containing formic acid); gradient elution method: acetonitrile, from 1% to 30% in 10 min), and freeze-dried to give a formate salt of compound 36.

$^1H$ NMR (400 MHz, DMSO-$d_6$) δ: 10.32 (s, 1H), 8.15 (s, 1H), 8.11 (d, J=10.0 Hz, 1H), 7.88 (s, 1H), 7.48-7.48 (m, 1H), 7.13 (s, 1H), 7.07-7.01 (m, 2H), 6.98-6.94 (m, 1H), 6.89 (d, J=8.4 Hz, 1H), 6.81 (d, J=3.6 Hz, 1H), 6.63 (d, J=2.4 Hz, 1H), 6.39 (d, J=10.0 Hz, 1H), 5.45 (s, 2H), 5.13 (s, 2H), 5.11-5.05 (m, 1H), 4.64 (s, 1H), 4.59 (t, J=6.8 Hz, 2H), 3.86 (s, 2H), 2.84-2.68 (m, 2H), 2.54 (s, 1H), 2.47-2.43 (m, 4H), 2.37 (s, 3H), 2.16 (s, 3H), 2.04-1.95 (m, 2H), 1.89 (s, 2H), 1.66 (s, 2H), 1.38-1.28 (m, 4H); MS-ESI calcd. $[M+H]^+$ 799, found 799.6.

The formate salt of compound 37 was prepared in a 3-step reaction with compounds 36-12 and 14-1 as the starting materials by referring to the synthetic route of the formate salt of compound 36.

Formate Salt of Compound 37:

$^1H$ NMR (400 MHz, DMSO-$d_6$) δ: 10.31 (s, 1H), 8.16 (s, 1H), 8.11 (d, J=10.0 Hz, 1H), 7.87 (s, 1H), 7.44 (d, J=5.2 Hz, 1H), 7.12 (s, 1H), 7.06-6.99 (m, 2H), 6.98-6.92 (m, 1H), 6.89 (d, J=8.0 Hz, 1H), 6.81 (d, J=3.2 Hz, 1H), 6.63 (d, J=2.8 Hz, 1H), 6.39 (d, J=10.0 Hz, 1H), 5.44 (s, 2H), 5.13 (s, 2H), 5.11-5.05 (m, 1H), 4.64 (s, 1H), 4.59 (t, J=6.8 Hz, 2H), 3.85 (s, 2H), 2.84-2.67 (m, 2H), 2.54 (s, 1H), 2.47-2.43 (m, 4H), 2.37 (s, 3H), 2.15 (s, 3H), 2.03-1.96 (m, 2H), 1.89 (s, 2H), 1.66 (s, 2H), 1.38-1.28 (m, 4H); MS-ESI calcd. $[M+H]^+$ 799, found 799.3.

Example 38 and Example 39

38 or 39

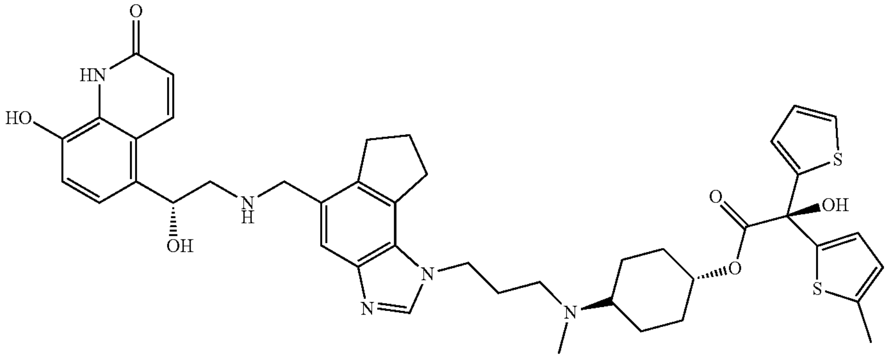

-continued
38 or 39
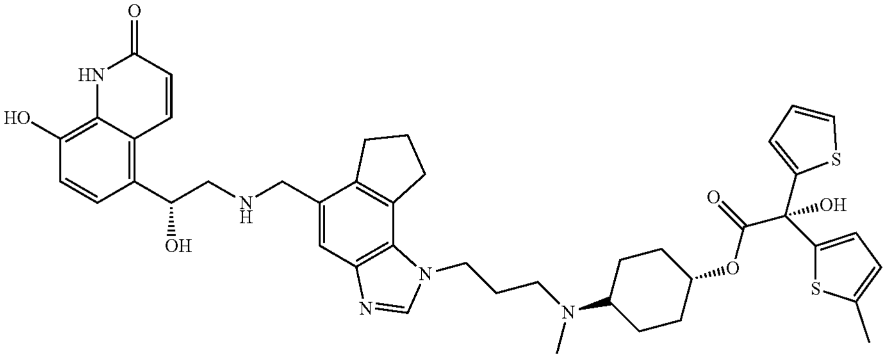
Synthetic Route:
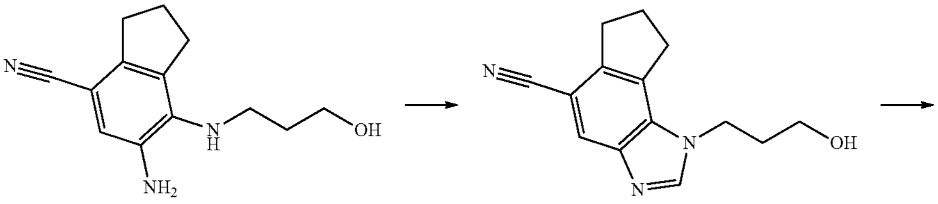
1-9
38-1
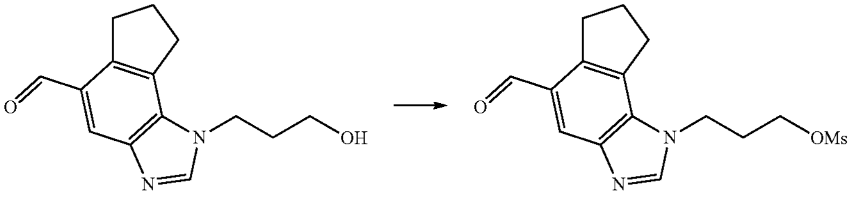
38-2
38-3
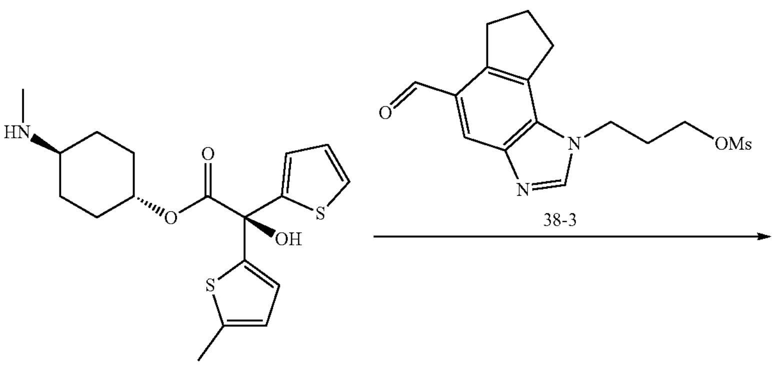
38-3
13-3 or 14-1

-continued
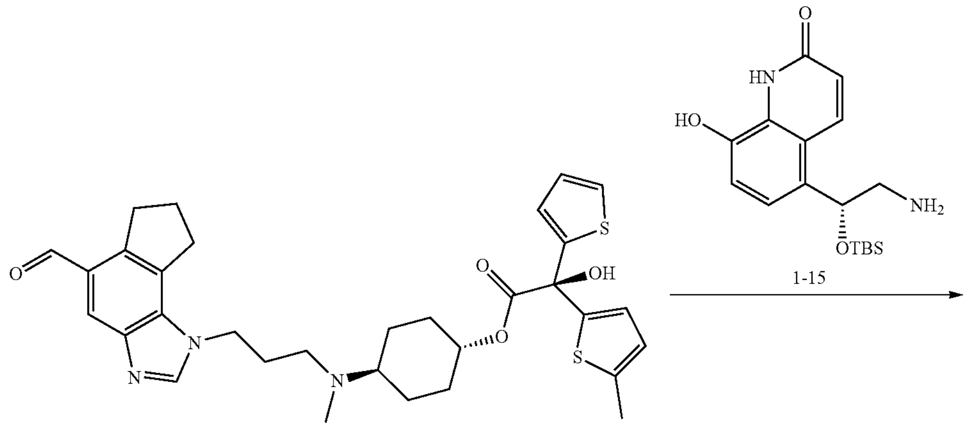
38-4 or 39-1
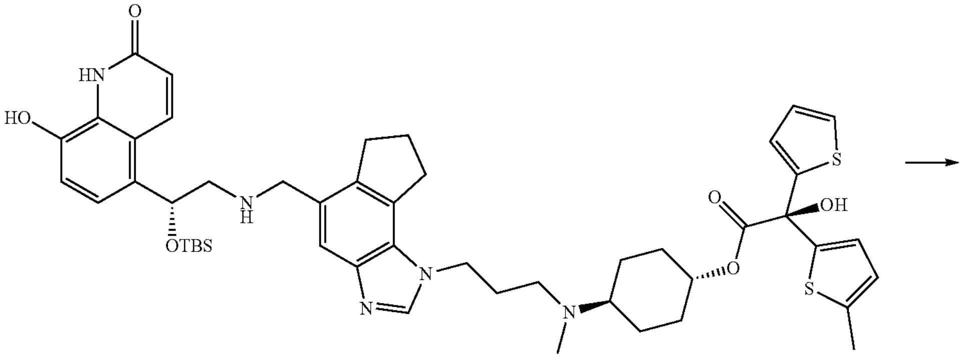
38-5 or 39-2
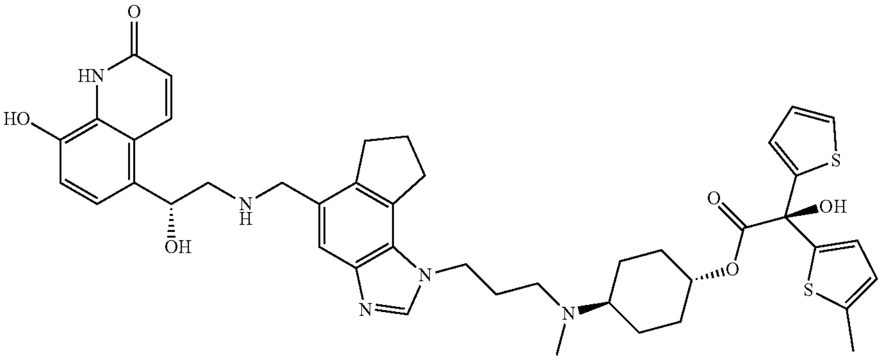
38 or 39
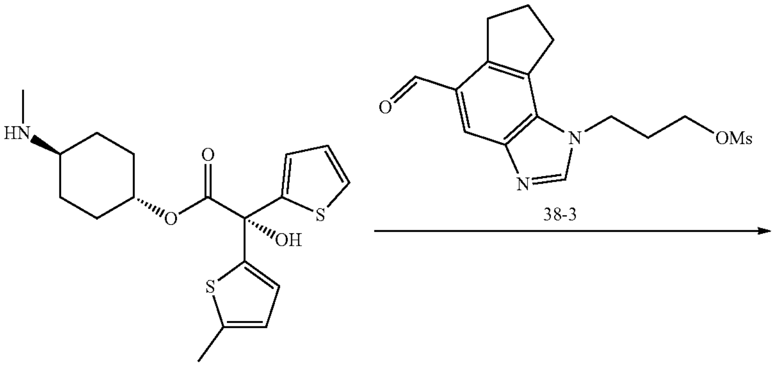
13-3 or 14-1

-continued

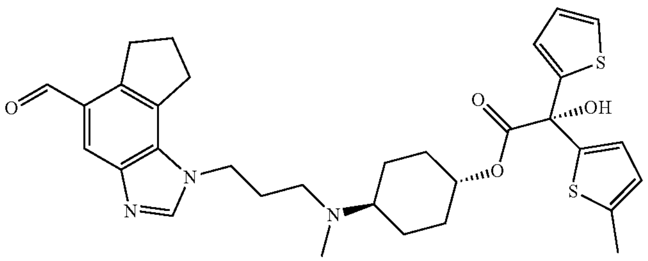

38-4 or 39-1

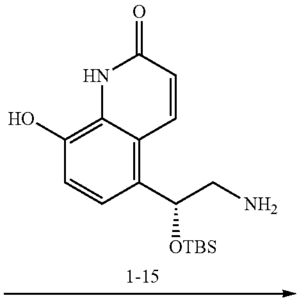

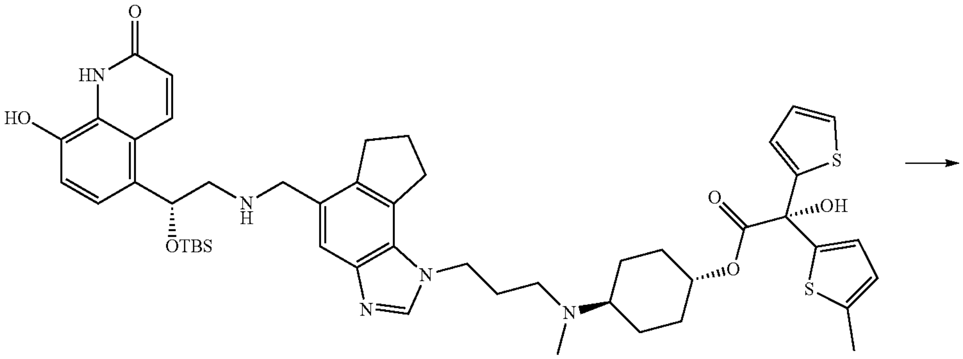

38-5 or 39-2

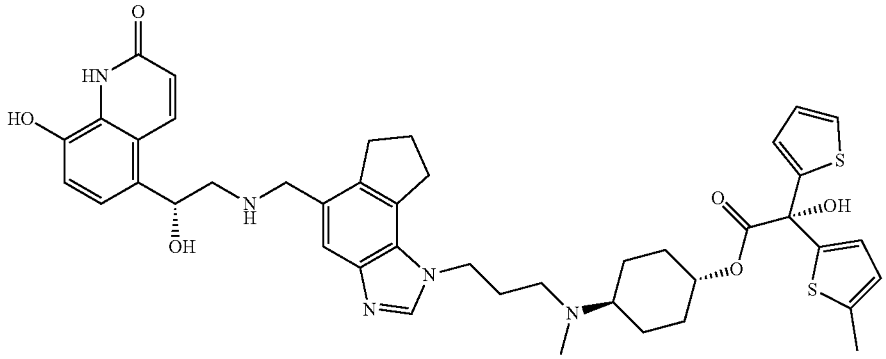

38 or 39

Step 1: Synthesis of Compound 38-1

Compound 1-9 (698 mg) was dissolved in toluene (25 mL), and trimethyl orthoformate (480.38 mg) and p-toluenesulfonic acid (77.95 mg) were added. The mixture was stirred at 120° C. for 16 h. After the reaction was completed, the reaction solution was concentrated to dryness under reduced pressure and dissolved with 50 mL of acetonitrile, and the solid was filtered off. The organic phase was concentrated to dryness under reduced pressure, and separated and purified by flash silica gel column chromatography (eluent: methanol/dichloromethane, 0-5%) to give compound 38-1.

MS-ESI calcd. $[M+H]^+$ 242, found 241.9.

Step 2: Synthesis of Compound 38-2

Compound 38-1 (304 mg) was dissolved in formic acid solution (50 mL, purity: 75%), and nickel-aluminum alloy (539.71 mg) was added. The mixture was heated to 90° C. and stirred for 16 h. The reaction solution was filtered, and the filtrate was collected and concentrated to dryness under reduced pressure. The residue was dissolved in 30 mL of ethanol, and an aqueous sodium hydroxide solution (1 M, 6.24 mL) was added under stirring. The mixture was stirred at 15° C. for 1 h. After the reaction was completed, the reaction solution was concentrated to dryness under reduced pressure and dissolved with 100 mL of methanol, and the solid was filtered off. The organic phase was concentrated to dryness under reduced pressure, and separated and purified by flash silica gel column chromatography (eluent: methanol/dichloromethane, 0-5%) to give compound 38-2.

MS-ESI calcd. $[M+H]^+$ 245, found 244.9.

Step 3: Synthesis of Compound 38-3

Compound 38-2 (138 mg) was dissolved in dichloromethane (25 mL), and triethylamine (285.81 mg) and methanesulfonyl chloride (133.11 mg) were added. The mixture was stirred at 25° C. for 0.5 h. After the reaction was completed, the reaction solution was subjected to liquid separation in dichloromethane (50 mL) and water (50 mL). The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-5%) to give compound 38-3.

MS-ESI calcd. $[M+H]^+$ 323, found 322.9.

Step 4: Synthesis of Compound 38-4

Compound 13-3 (60 mg) was dissolved in acetonitrile (10 mL), and diisopropylethylamine (50.92 mg), potassium iodide (65.40 mg) and compound 38-3 (46.57 mg) were added. The mixture was heated to 90° C. and stirred for 16 h. After the reaction was completed, the reaction solution was poured into 50 mL of water, and the resulting mixture was extracted with dichloromethane (50 mL×2), followed by liquid separation. The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-5%) to give compound 38-4.

MS-ESI calcd. [M+Na]+614, found 614.1.

Step 5: Synthesis of Compound 38-5

Compound 38-4 (46.9 mg) and compound 1-15 (26.51 mg, acetate) were dissolved in methanol (3 mL) and tetrahydrofuran (2 mL). sodium triacetoxyborohydride (83.98 mg) was added. The mixture was stirred at 25° C. for 16 h. Then, sodium triacetoxyborohydride (83.98 mg) was added, and the mixture was stirred at 25° C. for 24 h. The reaction solution was added to water (50 mL), and the resulting mixture was extracted with dichloromethane (50 mL×2). The organic phase was washed with saturated brine (50 mL), dried over anhydrous sodium sulfate, filtered, concentrated to dryness under reduced pressure, and separated and purified by flash silica gel column chromatography (eluent: methanol/dichloromethane, 0-5%) to give compound 38-5.

MS-ESI calcd. $[M+H]^+$ 910, found 910.5.

Step 6: Synthesis of Formate Salt of Compound 38

Compound 38-5 (33.5 mg) was dissolved in tetrahydrofuran (5 mL), and triethylamine trihydrofluoride (29.66 mg) was added. The mixture was stirred at 25° C. for 16 h. After the reaction was completed, the reaction solution was left to stand, and the supernatant was discarded. The solid was washed with 10 mL of tetrahydrofuran, separated and purified by high performance liquid chromatography (formic acid method, preparative column type: Phenomenex C18, length×inner diameter: 150 mm×40 mm, 5 μm); preparation method: the crude product was dissolved in dimethyl sulfoxide and filtered through a 0.45 μm filter membrane to give a sample solution; mobile phase system: acetonitrile/water (containing formic acid); gradient elution method: acetonitrile, from 1% to 30% in 10 min), and freeze-dried to give a formate salt of compound 38.

$^1$H NMR (400 MHz, DMSO-$d_6$) δ: 10.39 (s, 1H), 8.20 (s, 2H), 8.09 (d, J=10.0 Hz, 1H), 8.06 (s, 1H), 7.48 (s, 1H), 7.44 (dd, J=1.2, 5.2 Hz, 1H), 7.11-7.03 (m, 2H), 6.98-6.94 (m, 1H), 6.91 (d, J=8.0 Hz, 1H), 6.81 (d, J=3.6 Hz, 1H), 6.63 (d, J=2.4 Hz, 1H), 6.44 (d, J=9.6 Hz, 1H), 5.16 (s, 1H), 4.66 (s, 1H), 4.26 (t, J=6.8 Hz, 2H), 3.94 (s, 2H), 3.24 (t, J=7.2 Hz, 2H), 2.92 (t, J=7.2 Hz, 2H), 2.86 (s, 2H), 2.54 (s, 1H), 2.46-2.38 (m, 4H), 2.37 (s, 3H), 2.14 (s, 3H), 2.12-2.05 (s, 2H), 1.91 (s, 2H), 1.88-1.82 (m, 2H), 1.69 (s, 2H), 1.40-1.31 (m, 4H).

MS-ESI calcd. $[M+H]^+$ 796, found 796.5.

The formate salt of compound 39 was prepared in a 3-step reaction with compounds 38-3 and 14-1 as the starting materials by referring to the synthetic route of the formate salt of compound 38.

Formate Salt of Compound 39:

$^1$H NMR (400 MHz, DMSO-$d_6$) δ: 10.35 (s, 1H), 8.19 (s, 1H), 8.09 (d, J=10.0 Hz, 1H), 8.04 (s, 1H), 7.48-7.42 (m, 2H), 7.12 (s, 1H), 7.08-7.04 (m, 2H), 6.96 (dd, J=3.6, 5.2 Hz, 1H), 6.91 (d, J=8.4 Hz, 1H), 6.82 (d, J=3.6 Hz, 1H), 6.64 (d, J=2.4 Hz, 1H), 6.43 (d, J=10.0 Hz, 1H), 5.12 (s, 1H), 4.66 (s, 1H), 4.30-4.22 (m, 2H), 3.92-3.85 (m, 2H), 3.28-3.06 (m, 2H), 2.90 (t, J=7.2 Hz, 2H), 2.84-2.78 (m, 2H), 2.54 (s, 1H), 2.45-2.39 (m, 2H), 2.38 (s, 3H), 2.37-2.34 (m, 2H), 2.13 (s, 3H), 2.10 (s, 2H), 1.91 (s, 2H), 1.88-1.81 (m, 2H), 1.70 (s, 2H), 1.41-1.31 (m, 4H);

MS-ESI calcd. $[M+H]^+$ 796, found 796.4.

Example 40

40

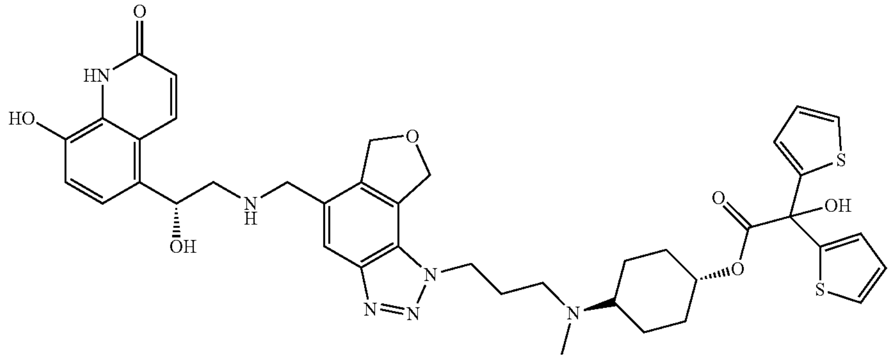

Synthetic Route:
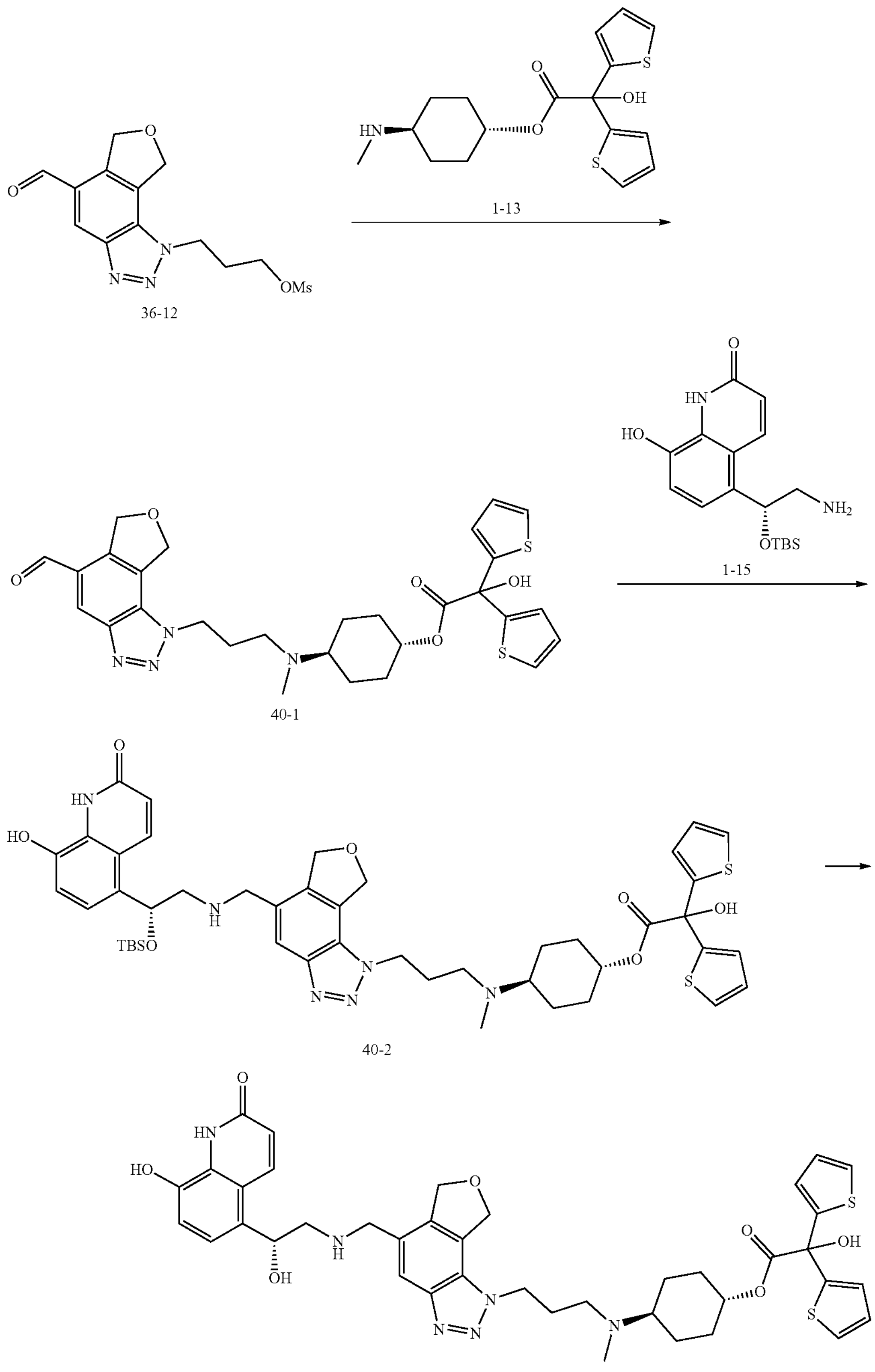
40

Step 1: Synthesis of Compound 40-1

Compound 36-12 (40 mg) was dissolved in acetonitrile (10 mL), and diisopropylethylamine (47.7 mg), potassium iodide (102 mg) and compound 1-13 (43.2 mg) were added. The mixture was heated to 90° C. and stirred for 14 h. After the reaction was completed, the reaction solution was concentrated under reduced pressure, and separated and purified by silica gel column chromatography (eluent: methanol/dichloromethane, 0-5%) to give compound 40-1.

MS-ESI calcd. $[M+H]^+$ 581, found 581.

Step 2: Synthesis of Compound 40-2

Compound 1-15 (27 mg, acetate) and compound 40-1 (39.7 mg) were dissolved in methanol (4 mL) and tetrahydrofuran (2 mL), and diisopropylethylamine (17.7 mg) and sodium triacetoxyborohydride (72.5 mg) were added. The mixture was stirred at 20° C. for 12 h, and sodium triacetoxyborohydride (72.5 mg) was added. The mixture was stirred at 20° C. for another 5 h. To the reaction solution was added a 5% aqueous sodium bicarbonate solution (10 mL), and the resulting mixture was extracted with ethyl acetate (15 mL×2). The organic phase was washed with saturated brine (15 mL), dried over anhydrous sodium sulfate, filtered and concentrated under reduced pressure to give compound 40-2, which was directly used in the next step.

MS-ESI calcd. $[M+H]^+$ 899, found 899.

Step 3: Synthesis of Formate Salt of Compound 40

Compound 40-2 (60 mg) was dissolved in tetrahydrofuran (4 mL), and triethylamine trihydrofluoride (53.8 mg) was added. The mixture was stirred at 15° C. for 14 h. After the reaction was completed, the reaction solution was left to stand, and the supernatant was discarded. The solid precipitated at the bottom was washed with 5 mL of tetrahydrofuran and concentrated under reduced pressure, and the residue was separated by high performance liquid chromatography (column: Phenomenex Gemini-NX C18, length×inner diameter: 75 mm×30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 40.

$^1H$ NMR (400 MHz, DMSO-$d_6$) δ: 8.18 (s, 2H), 8.13-8.08 (m, 1H), 7.87 (s, 1H), 7.47-7.44 (m, 2H), 7.09-7.00 (m, 3H), 6.99-6.95 (m, 2H), 6.91-6.87 (m, 1H), 6.41-6.37 (m, 1H), 5.48-5.41 (m, 2H), 5.16-5.05 (m, 3H), 4.68-4.56 (m, 3H), 3.91-3.77 (m, 2H), 2.81-2.66 (m, 2H), 2.46-2.41 (m, 3H), 2.15 (s, 3H), 2.05-1.96 (m, 2H), 1.92-1.85 (m, 2H), 1.69-1.63 (m, 2H), 1.37-1.28 (m, 4H); MS-ESI calcd. $[M+H]^+$ 785, found 785.

Example 41

41

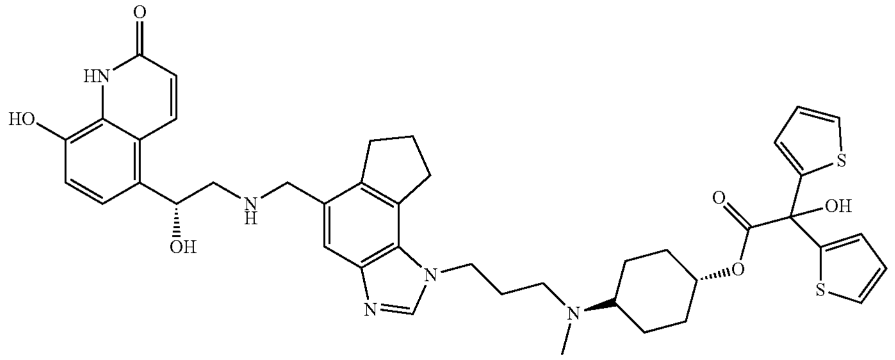

Synthetic Route:

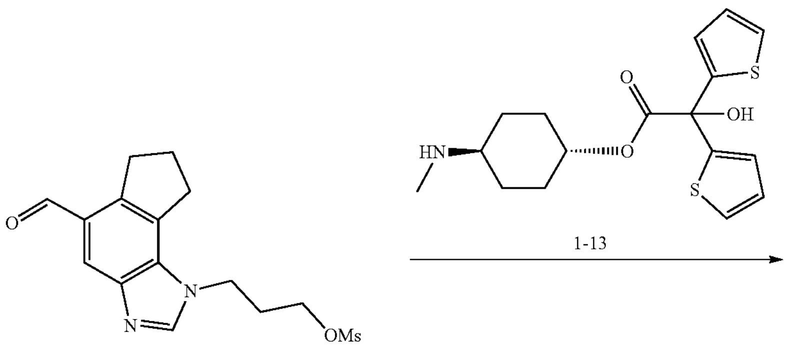

38-3

-continued

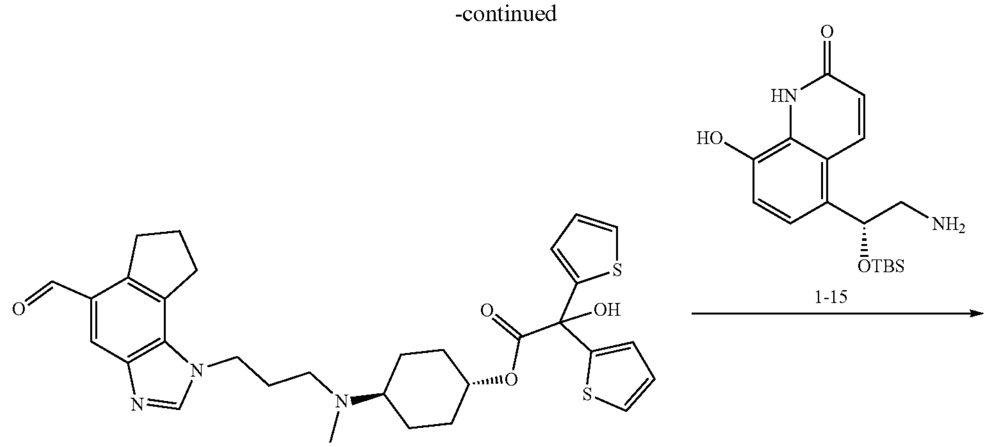

1-15

41-1

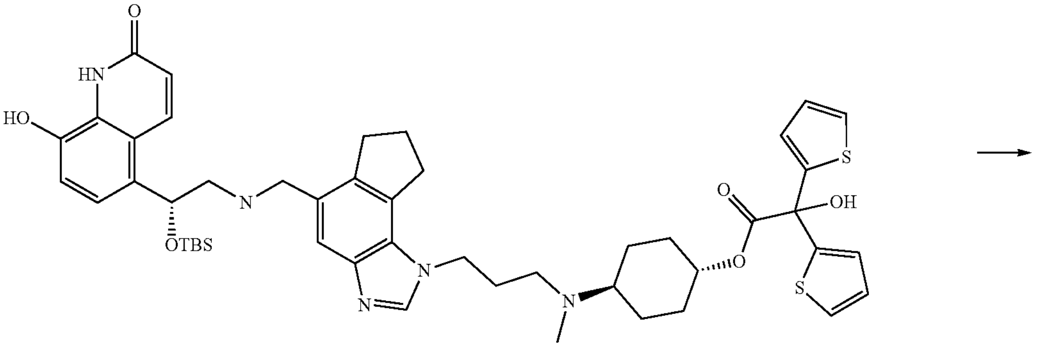

41-2

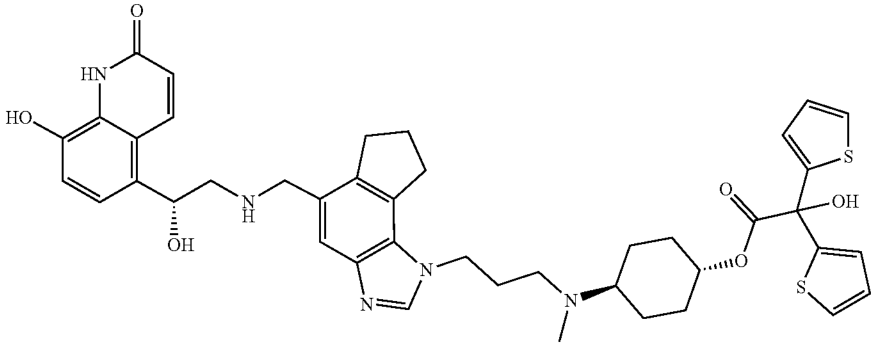

41

Step 1: Synthesis of Compound 41-1

Compound 38-3 (40 mg) was dissolved in acetonitrile (10 mL), and diisopropylethylamine (48.1 mg), potassium iodide (103 mg) and compound 1-13 (43.6 mg) were added. The mixture was heated to 90° C. and stirred for 14 h. After the reaction was completed, the reaction solution was concentrated under reduced pressure, and separated and purified by silica gel column chromatography (eluent: methanol/dichloromethane, 0-5%) to give compound 41-1.

MS-ESI calcd. $[M+H]^+$ 578, found 578.

Step 2: Synthesis of Compound 41-2

Compound 1-15 (30 mg, acetate) and compound 41-1 (43.9 mg) were dissolved in methanol (4 mL) and tetrahydrofuran (2 mL), and diisopropylethylamine (19.6 mg) and sodium triacetoxyborohydride (80.6 mg) were added. The mixture was stirred at 20° C. for 12 h, and sodium triacetoxyborohydride (80.6 mg) was added. The mixture was stirred at 20° C. for another 5 h. To the reaction solution was added a 5% aqueous sodium bicarbonate solution (10 mL), and the resulting mixture was extracted with ethyl acetate (15 mL×2). The organic phase was washed with saturated brine (15 mL), dried over anhydrous sodium sulfate, filtered and concentrated under reduced pressure to give compound 41-2, which was directly used in the next step.

MS-ESI calcd. $[M+H]^+$ 896, found 896.

Step 3: Synthesis of Formate Salt of Compound 41

Compound 41-2 (65 mg) was dissolved in tetrahydrofuran (4 mL), and triethylamine trihydrofluoride (58.5 mg) was added. The mixture was stirred at 15° C. for 14 h. After the reaction was completed, the reaction solution was left to stand, and the supernatant was discarded. The solid precipitated at the bottom was washed with 5 mL of tetrahydrofuran and concentrated under reduced pressure, and the residue was separated by high performance liquid chromatography (column: Phenomenex Gemini-NX C18, length×inner diameter: 75 mm× 30 mm, 3 μm; preparation method: the crude product was dissolved in dimethyl sulfoxide and filtered through a 0.45 μm filter membrane to give a sample solution; mobile phase system: acetonitrile/water (containing 0.225% formic acid), gradient elution method: acetonitrile, from 0% to 30% in 7 min) to give a formate salt of compound 41.

$^1$H NMR (400 MHz, DMSO-$d_6$) δ: 8.24 (s, 2H), 8.13-8.06 (m, 2H), 7.50-7.45 (m, 3H), 7.09-7.06 (m, 3H), 6.99-6.95 (m, 2H), 6.95-6.91 (m, 1H), 6.47-6.43 (m, 1H), 5.20-5.15 (m, 1H), 4.71-4.67 (m, 1H), 4.31-4.22 (m, 2H), 3.95 (s, 2H), 3.29-3.21 (m, 2H), 2.96-2.84 (m, 4H), 2.42-2.37 (m, 3H), 2.17-2.10 (m, 5H), 1.96-1.83 (m, 4H), 1.74-1.68 (m, 2H), 1.42-1.31 (m, 4H);

MS-ESI calcd. $[M+H]^+$ 782, found 782.

Bioactivity Assay

Test Example 1. Assay on Agonistic Effect of Compounds on β1 Receptor by HTRF cAMP Method Experimental Objective:

β1 receptor is a G protein-coupled receptor, which is mainly coupled with Gs protein, and can activate adenylate cyclase activity through the Gs protein after being activated by binding to the ligand, thereby increasing the level of intracellular cAMP. In this experiment, the agonistic activity of the compounds against the β1 receptor in vitro was assayed by the cAMP kit.

Experimental Method:

β1 cells (expressing human ADRB1 gene) from ICE Bioscience Inc. were grown under standard conditions. The cells were collected and diluted with 1× Stimulation Buffer, and 9 μL of the cell dilution was added to a white low-volume 384-well plate with 4000 cells seeded in each well. Compounds were serially diluted in DMSO in a 5-fold gradient to obtain 10 concentrations. Before testing, compounds that had been serially diluted in DMSO were subjected to 100-fold dilution with 1× Stimulation Buffer to obtain compound working solutions. The concentration of the vehicle DMSO was 0.1%. Eu-cAMP and ULight™-anti-cAMP were diluted to the working concentration with Detection buffer. 5 μL of Eu-cAMP diluent and 5 μL of ULight™-anti-cAMP diluent were sequentially added into corresponding experiment wells. After 1 h of incubation at room temperature, readings at 665 nm and 620 nm were measured under the excitation wavelength of 330 nm using a Biotek microplate reader. The activity of the compounds was obtained by plotting through Ratio (665/620) against the concentration of the compounds, fitting the curve by a nonlinear regression method using GraphPad Prism 7 software and calculating $EC_{50}$.

The experimental results are shown in Table 1.

TABLE 1

Agonistic activity of the compounds of the present application against the β1 receptor in vitro

| Compound No. | $EC_{50}$ (nM) |
|---|---|
| Trifluoroacetate salt of compound 1 | 84.54 |
| Formate salt of compound 2 | 157.1 |
| Formate salt of compound 4 | 303.9 |
| Formate salt of compound 5 | 231.2 |
| Formate salt of compound 6 | 277.6 |
| Trifluoroacetate salt of compound 8 | 394.9 |
| Trifluoroacetate salt of compound 9 | 696.3 |
| Trifluoroacetate salt of compound 10 | 269.0 |
| Compound 11 | 33.7 |
| Formate salt of compound 12 | 127.2 |
| Trifluoroacetate salt of compound 13 | 141.7 |
| Trifluoroacetate salt of compound 14 | 127.2 |
| Trifluoroacetate salt of compound 15 | 381.5 |
| Trifluoroacetate salt of compound 16 | 276.1 |
| Formate salt of compound 19 | 1436 |
| Formate salt of compound 21 | 275.8 |
| Formate salt of compound 24 | 155.1 |
| Formate salt of compound 25 | 193.3 |
| Trifluoroacetate salt of compound 28 | 253.2 |
| Trifluoroacetate salt of compound 29 | 432.2 |
| Hydrobromide salt of compound 30 | 94.9 |
| Formate salt of compound 32 | 145.2 |
| Formate salt of compound 33 | 53.13 |
| Formate salt of compound 34 | 37.31 |
| Formate salt of compound 35 | 55.58 |
| Formate salt of compound 36 | 50.49 |
| Formate salt of compound 37 | 48.02 |
| Formate salt of compound 38 | 337.6 |
| Formate salt of compound 39 | 299.5 |
| Formate salt of compound 40 | 56.67 |
| Formate salt of compound 41 | 228.9 |

Conclusion: the compounds of the present application have a certain agonistic effect on the β1 receptor.

Test Example 2. Assay on Agonistic Effect of Compounds on β2 Receptor by HTRF cAMP Method Experimental Objective:

β2 receptor is a G protein-coupled receptor, which is mainly coupled with Gs protein, and can activate adenylate cyclase activity through the Gs protein after being activated by binding to the ligand, thereby increasing the level of intracellular cAMP. In this experiment, the agonistic activity of the compounds against the β2 receptor in vitro was assayed by the cAMP kit.

Experimental Method:

β2 cells (expressing human ADRB2 gene) from ICE Bioscience Inc. were grown under standard conditions. The cells were collected and diluted with 1× Stimulation Buffer, and 9 μL of the cell dilution was added to a white low-volume 384-well plate with 1000 cells seeded in each well. Compounds were serially diluted in DMSO in a 5-fold gradient to obtain 10 concentrations. Before testing, compounds that had been serially diluted in DMSO were subjected to 100-fold dilution with 1× Stimulation Buffer to obtain compound working solutions. The concentration of the vehicle DMSO was 0.1%. Eu-cAMP and ULight™-anti-cAMP were diluted to the working concentration with Detection buffer. 5 μL of Eu-cAMP diluent and 5 μL of ULight™-anti-cAMP diluent were sequentially added into corresponding experiment wells. After 1 h of incubation at room temperature, readings at 665 nm and 620 nm were measured under the excitation wavelength of 330 nm using a Biotek microplate reader. The activity of the compounds was obtained by plotting through Ratio (665/620) against the concentration of the compounds, fitting the curve by a nonlinear regression method using GraphPad Prism 7 software and calculating $EC_{50}$.

The experimental results are shown in Table 2.

TABLE 2

Agonistic activity of the compounds of the present application against the β2 receptor in vitro

| Compound No. | $EC_{50}$ (nM) |
|---|---|
| Trifluoroacetate salt of compound 1 | 3.472 |
| Formate salt of compound 2 | 0.8889 |
| Formate salt of compound 4 | 2.148 |
| Formate salt of compound 5 | 2.635 |
| Formate salt of compound 6 | 0.6244 |
| Trifluoroacetate salt of compound 8 | 1.618 |
| Trifluoroacetate salt of compound 9 | 6.736 |
| Trifluoroacetate salt of compound 10 | 1.357 |
| Compound 11 | 1.122 |
| Formate salt of compound 12 | 2.038 |
| Trifluoroacetate salt of compound 13 | 1.726 |
| Trifluoroacetate salt of compound 14 | 1.397 |
| Trifluoroacetate salt of compound 15 | 1.892 |
| Trifluoroacetate salt of compound 16 | 2.161 |
| Formate salt of compound 19 | 5.139 |
| Formate salt of compound 21 | 2.113 |
| Formate salt of compound 22 | 20.82 |
| Formate salt of compound 23 | 16.77 |
| Formate salt of compound 24 | 157.6 |
| Formate salt of compound 25 | 0.3881 |
| Trifluoroacetate salt of compound 28 | 1.411 |
| Trifluoroacetate salt of compound 29 | 2.73 |
| Hydrobromide salt of compound 30 | 1.714 |
| Formate salt of compound 32 | 1.571 |
| Formate salt of compound 33 | 0.7418 |
| Formate salt of compound 34 | 0.4045 |
| Formate salt of compound 35 | 0.6714 |
| Formate salt of compound 36 | 2.452 |
| Formate salt of compound 37 | 1.933 |
| Formate salt of compound 38 | 13.52 |
| Formate salt of compound 39 | 21.9 |
| Formate salt of compound 40 | 2.802 |
| Formate salt of compound 41 | 13.76 |

Conclusion: the compounds of the present application have a strong or very strong agonistic effect on the β2 receptor.

Test Example 3. M3 Receptor Affinity Test

Experimental Objective:

M3 receptor is a G protein-coupled receptor. In this experiment, the activity of test compounds against the M3 receptor in vitro was assayed by the competition of radioisotope labeled NMS and non-isotope labeled test compounds for an M3 binding site.

Experimental Method:

The experiment was performed by a radioisotope affinity assay. The M3 receptor membrane protein was prepared at 10 μg/mL by Biology Department of WuXi AppTec, and compounds were serially diluted in a 2.5-fold gradient in DMSO to obtain 10 concentrations. Radioisotope 3H-NMS was prepared at 0.2 nM in an assay buffer (10 mM HEPES, 1 mM $MgCl_2$, pH 7.40). In formal testing, the experimental system comprising 1 of the test compound, 100 μL of M3 receptor membrane protein and 100 μL of radioisotope was shaken in a shaker at 300 RPM for 2 h at room temperature. A GF/C plate (Perkin Elmer, Cat No. 6055690) was pre-foamed with 0.3% PEI, and the membrane proteins in the reaction solution were collected by filtration onto the GF/C plate. The signal values were read by a Perkin Elmer Microbeta2 instrument and the inhibition rate for each concentration point was shown as a percentage.

The experimental results are shown in Table 3.

TABLE 3

Activity of the compounds of the present application against the M3 receptor in vitro

| Compound No. | $IC_{50}$ (nM) |
|---|---|
| Trifluoroacetate salt of compound 1 | 0.384 |
| Formate salt of compound 2 | 0.347 |
| Formate salt of compound 3 | 1.113 |
| Formate salt of compound 4 | 0.3426 |
| Formate salt of compound 5 | 13.78 |
| Formate salt of compound 6 | 3.861 |
| Trifluoroacetate salt of compound 7 | 5.572 |
| Trifluoroacetate salt of compound 8 | 2.77 |
| Trifluoroacetate salt of compound 9 | 4.162 |
| Trifluoroacetate salt of compound 10 | 1.267 |
| Compound 11 | 0.6384 |
| Trifluoroacetate salt of compound 13 | 0.6873 |
| Trifluoroacetate salt of compound 14 | 0.6606 |
| Trifluoroacetate salt of compound 15 | 0.1977 |
| Trifluoroacetate salt of compound 16 | 0.255 |
| Formate salt of compound 18 | 9.361 |
| Formate salt of compound 19 | 0.281 |
| Formate salt of compound 20 | 31.07 |
| Formate salt of compound 21 | 1.529 |
| Formate salt of compound 24 | 0.22 |
| Formate salt of compound 25 | 0.1787 |
| Trifluoroacetate salt of compound 28 | 0.136 |
| Trifluoroacetate salt of compound 29 | 0.324 |
| Hydrobromide salt of compound 30 | 1.102 |
| Formate salt of compound 31 | 0.6547 |
| Formate salt of compound 32 | 1.197 |
| Formate salt of compound 33 | 0.4938 |
| Formate salt of compound 34 | 0.6572 |
| Formate salt of compound 35 | 0.2126 |
| Formate salt of compound 36 | 0.7921 |
| Formate salt of compound 37 | 0.8714 |
| Formate salt of compound 38 | 0.5552 |
| Formate salt of compound 39 | 0.5333 |
| Formate salt of compound 40 | 0.3627 |
| Formate salt of compound 41 | 0.2013 |

Conclusion: the compounds of the present application have a strong or very strong binding effect on the M3 receptor.

Test Example 4. M2 Receptor Affinity Test

Experimental Objective:

M2 receptor is a G protein-coupled receptor. In this experiment, the activity of test compounds against the M2 receptor in vitro was assayed by the competition of radioisotope labeled NMS and non-isotope labeled test compounds for an M2 binding site.

Experimental Method:

The M2 receptor membrane protein was prepared at 100 μg/mL by Biology Department of WuXi AppTec, and compounds were serially diluted in a 2.5-fold gradient in DMSO to obtain 10 concentrations. Radioisotope 3H-NMS was prepared at 0.2 nM in an assay buffer (10 mM HEPES, 1 mM $MgCl_2$, pH 7.40). In formal testing, the experimental system comprising 1 μL of the test compound, 100 μL of M2 receptor membrane protein and 100 μL of radioisotope was shaken in a shaker at 300 RPM for 2 h at room temperature. A GF/C plate (Perkin Elmer, Cat No. 6055690) was pre-foamed with 0.3% PEI, and the membrane proteins in the reaction solution were collected by filtration onto the GF/C plate. The signal values were read by a Perkin Elmer Microbeta2 instrument and the inhibition rate for each concentration point was shown as a percentage.

The experimental results are shown in Table 4.

TABLE 4

Activity of the compounds of the present application against the M2 receptor in vitro

| Compound No. | $IC_{50}$ (nM) |
|---|---|
| Trifluoroacetate salt of compound 1 | 0.06196 |
| Trifluoroacetate salt of compound 13 | 0.2403 |
| Trifluoroacetate salt of compound 14 | 0.3754 |
| Trifluoroacetate salt of compound 15 | 0.1303 |
| Trifluoroacetate salt of compound 16 | 0.104 |
| Formate salt of compound 24 | 0.014 |
| Formate salt of compound 25 | 0.03 |
| Trifluoroacetate salt of compound 28 | 0.0825 |
| Trifluoroacetate salt of compound 29 | 0.146 |
| Formate salt of compound 32 | 0.8137 |
| Formate salt of compound 33 | 0.1535 |
| Formate salt of compound 34 | 0.2481 |
| Formate salt of compound 35 | 0.5879 |
| Formate salt of compound 36 | 1.742 |
| Formate salt of compound 37 | 2.012 |
| Formate salt of compound 38 | 0.8423 |

TABLE 4-continued

Activity of the compounds of the present application against the M2 receptor in vitro

| Compound No. | $IC_{50}$ (nM) |
|---|---|
| Formate salt of compound 39 | 1.245 |
| Formate salt of compound 40 | 0.2282 |
| Formate salt of compound 41 | 0.2676 |

Conclusion: the compounds of the present application have a strong binding effect on the M2 receptor.

Test Example 5. Pharmacokinetic Evaluation of Compounds

Experimental Objective:

To test pharmacokinetics of test compounds in SD rats

Experimental Materials:

SD rats (male, 200-250 g, 7-9 weeks old, Beijing Vital River Laboratory Animal Technology Co., Ltd.)

Procedures:

A formulation containing 10% aqueous HPβCD solution as a vehicle was administered by intravenous injection (2 mpk), and a formulation containing 10% aqueous HPβCD solution as a vehicle was administered by intra-tracheal administration (5 mpk) with a nebulizer needle. Before the animal experiment, all animals were fed normally; and all animals were given free access to water. Blood collection time points were as follows: intravenous administration group: 0.083 h, 0.25 h, 0.5 h, 1 h, 2 h, 4 h, 8 h, and 24 h; nebulizer needle administration group: 0.083 h, 0.25 h, 0.5 h, 1 h, 2 h, 4 h, 8 h, and 24 h.

Whole blood samples (0.25 mL) were collected via the jugular vein (or other suitable collection site) at prescribed time points, and all blood samples were added to labeled plastic centrifuge tubes containing a K2-EDTA anticoagulant. After blood collection, plasma was separated by centrifugation and placed in dry ice rapidly, and the samples were stored at low temperature. All samples were analyzed by LC-MS/MS with a limit of detection of 4 nM. The mean concentration of plasma was processed using a non-compartmental model of the pharmacokinetic software WinNonlin™ Version 6.3 (Pharsight, Mountain View, CA), and pharmacokinetic parameters were calculated by a linear log-trapezoidal method. The experimental results are shown in FIG. 5:

TABLE 5

Pharmacokinetic test results

| Test sample (compounds prepared in examples) | Clearance rate (mL/min/kg) for administration by intravenous injection | Concentration integration AUC (nM · hr) for administration by intravenous injection | Half life $T_{1/2}$ (h) for intra-tracheal administration with a nebulizer needle | Concentration integration AUC (nM · hr) for intra-tracheal administration with a nebulizer needle | Bioavailability F (%) for intra-tracheal administration with a nebulizer needle |
|---|---|---|---|---|---|
| Hydrofluoride salt of AZD8871 | 35 | 1271 | 0.515 | 2437 | 76.7 |
| Trifluoroacetate salt of compound 1 | 62.8 | 681 | 1.38 | 2611 | 153 |

Conclusion: the compounds of the present application can significantly improve a single index or part of indices of pharmacokinetics in mice.

The invention claimed is:

1. A compound of formula (III) or a pharmaceutically acceptable salt thereof, (III)

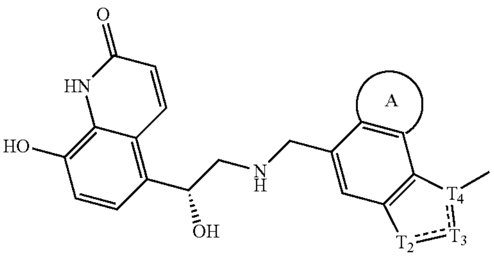

-continued

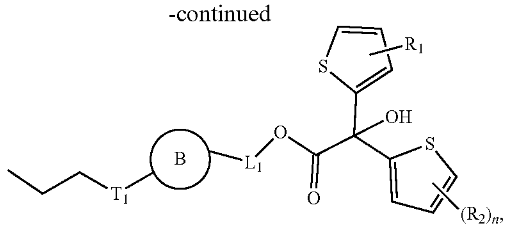

wherein, $R_1$ is selected from the group consisting of H, halogen, $C_{1-4}$ alkyl and phenyl;

$R_2$ is each independently selected from the group consisting of H, halogen and $C_{1-4}$ alkyl;

or two $R_2$, together with the thiophene ring to which they are connected, form benzothiophene;

n is selected from the group consisting of 1 and 2;

$T_1$ is selected from the group consisting of a single bond, —NH— and —$N(CH_3)$—;

$L_1$ is selected from the group consisting of a single bond and —$CH_2$—;

the structural unit

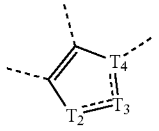

is selected from the group consisting of

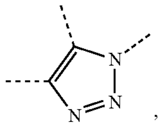

,

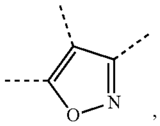

,

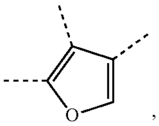

,

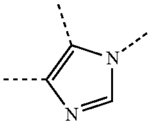

and

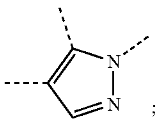

;

ring A is selected from the group consisting of the following groups optionally substituted with 1 or 2 $R_b$: $C_{4-6}$ cycloalkenyl, 4- to 6-membered heterocycloalkenyl, 5- to 6-membered heteroaryl,

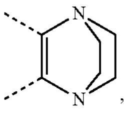

,

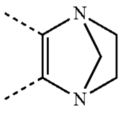

and phenyl;

$R_b$ is each independently selected from the group consisting of —F, —Cl, —Br, —I, —$CH_3$ and —$CH_2CH_3$;

ring B is selected from the group consisting of cyclopentyl, cyclohexyl and 6- to 10-membered heterocycloalkyl, wherein the 6- to 10-membered heterocycloalkyl is optionally substituted with 1 $R_a$;

$R_a$ is selected from the group consisting of —F, —Cl, methyl, —OH and —CN;

wherein "hetero" of the "6- to 10-membered heterocycloalkyl" comprises 1, 2 or 3 heteroatoms or heteroatom groups independently selected from the group consisting of O, S, NH and N, wherein the nitrogen atom is optionally quaternized with methyl halide.

2. The compound or the pharmaceutically acceptable salt thereof according to claim 1, wherein $R_1$ is selected from the group consisting of H, —Cl, —Br, methyl, tert-butyl and phenyl.

3. The compound or the pharmaceutically acceptable salt thereof according to claim 1, wherein $R_2$ is each independently selected from the group consisting of H, —Cl, —Br, methyl and tert-butyl.

4. The compound or the pharmaceutically acceptable salt thereof according to claim 1, wherein $T_1$ is selected from the group consisting of a single bond and —$N(CH_3)$—.

5. The compound or the pharmaceutically acceptable salt thereof according to claim 1, wherein ring B is selected from the group consisting of cyclohexyl and 6- to 10-membered heterocycloalkyl, wherein the 6- to 10-membered heterocycloalkyl is optionally substituted with 1 $R_a$.

6. The compound or the pharmaceutically acceptable salt thereof according to claim 5, wherein ring B is selected from the group consisting of cyclohexyl and the following groups optionally substituted with 1 $R_a$: piperidinyl, piperazinyl, morpholinyl, dioxanyl, dithianyl, tetrahydrooxazinyl, tetrahydrothiazinyl, hexahydropyridazinyl, homopiperazinyl, homopiperidinyl, dioxepanyl,

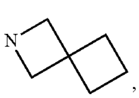

,

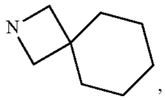

,

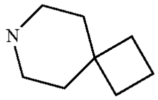

and

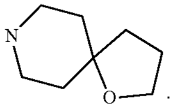

.

7. The compound or the pharmaceutically acceptable salt thereof according to claim 6, wherein ring B is selected from the group consisting of cyclohexyl and the following groups optionally substituted with 1 $R_a$: piperidinyl, piperazinyl,

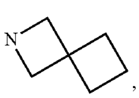

,

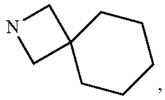

,

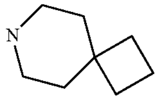

and

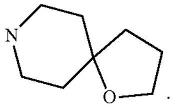

.

8. The compound or the pharmaceutically acceptable salt thereof according to claim 1, wherein the structural unit

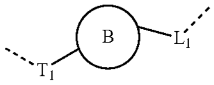

is selected from the group consisting of

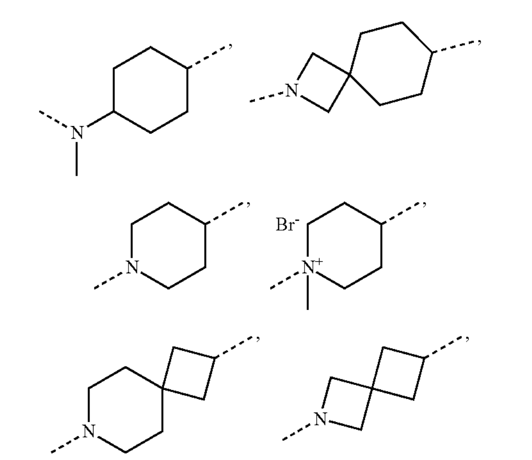

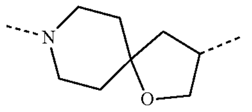

and

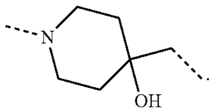

9. The compound or the pharmaceutically acceptable salt thereof according to claim 1, wherein the structural unit

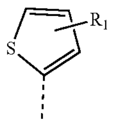

is selected from the group consisting of

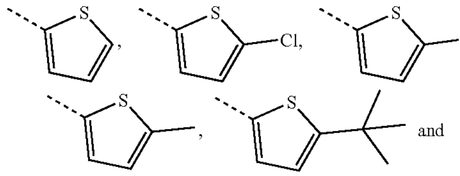

and

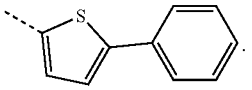

10. The compound or the pharmaceutically acceptable salt thereof according to claim 1, wherein the structural unit

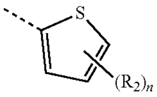

is selected from the group consisting of

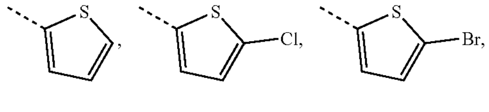

-continued

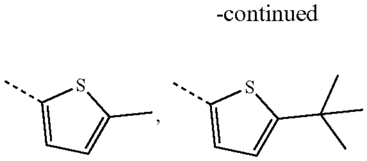

and

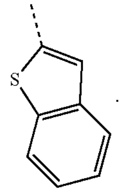

11. The compound or the pharmaceutically acceptable salt thereof according to claim 1, wherein $R_a$ is selected from the group consisting of —F, —$CH_3$, —OH and —CN.

12. The compound or the pharmaceutically acceptable salt thereof according to claim 1, wherein $R_b$ is each independently selected from the group consisting of —F, —Cl, —Br, —I and —$CH_3$.

13. The compound or the pharmaceutically acceptable salt thereof according to claim 1, wherein ring A is selected from the group consisting of the following groups optionally substituted with 1 or 2 $R_b$:

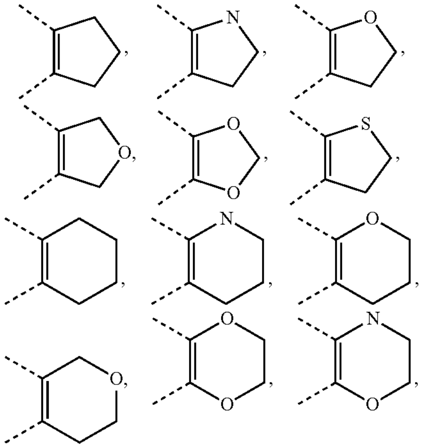

pyrrolyl, thienyl, furanyl, pyrazolyl, imidazolyl, oxazolyl, thiazolyl, triazolyl, pyridinyl, pyrimidinyl, pyrazinyl, pyridazinyl,

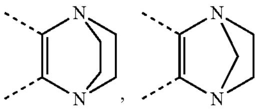

and phenyl.

14. The compound or the pharmaceutically acceptable salt thereof according to claim 1, wherein ring A is selected from the group consisting of the following groups optionally substituted with 1 or 2 $R_b$:

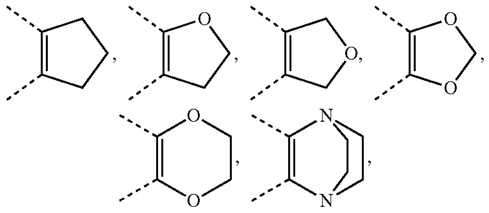

pyrazolyl and phenyl.

15. The compound or the pharmaceutically acceptable salt thereof according to claim 1, wherein the compound is selected from the group consisting of structures of (III-1), (III-2), (III-3), (IV-1), (IV-2) and (V-1),
(III-1)
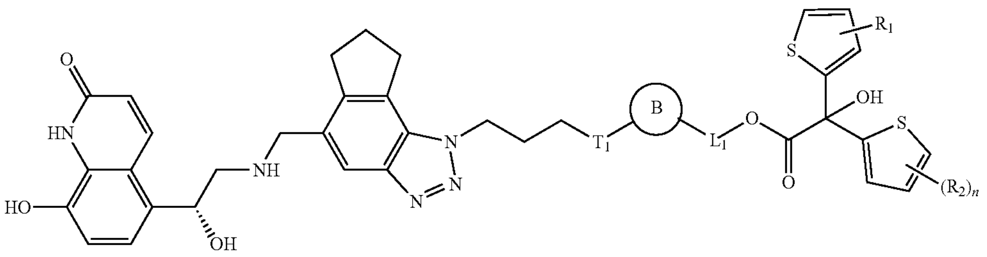
(III-2)
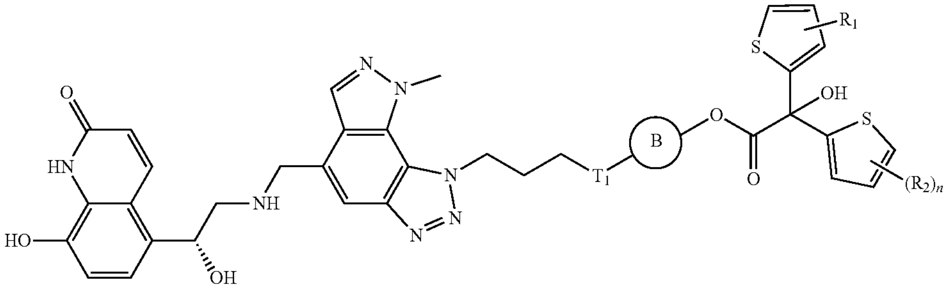
(III-3)
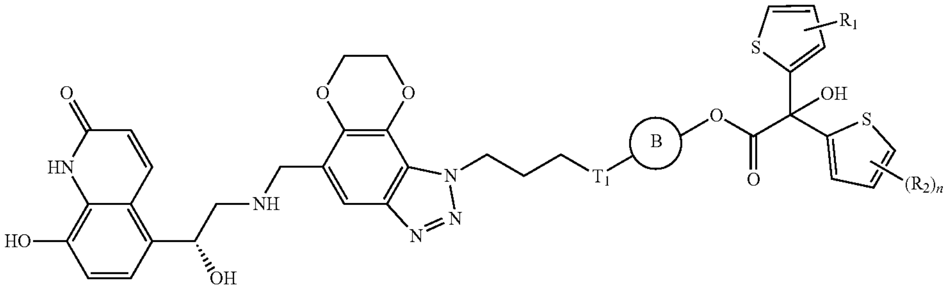
(IV-1)
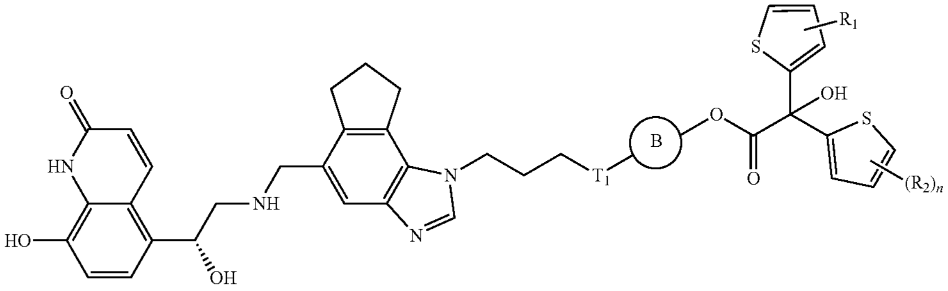
(IV-2)
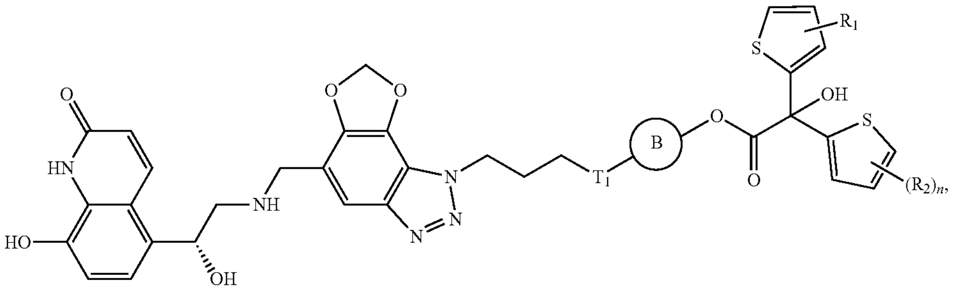

-continued
(V-1)
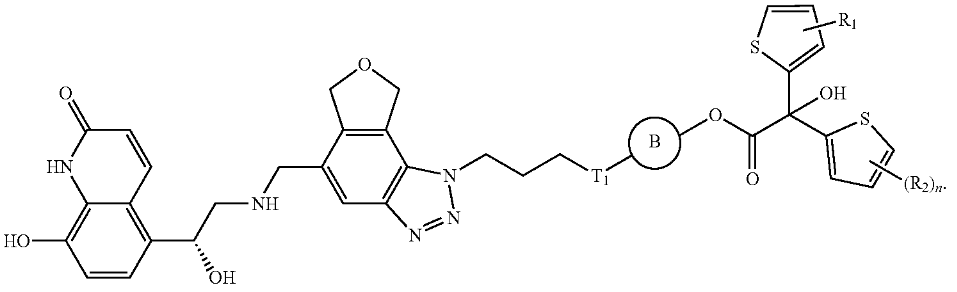
16. Compounds as shown below or pharmaceutically acceptable salts thereof,
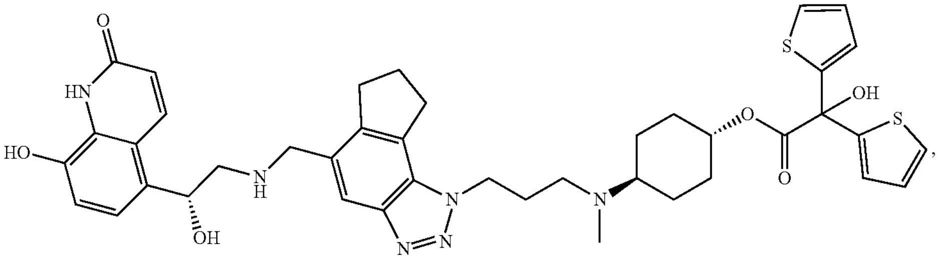
,
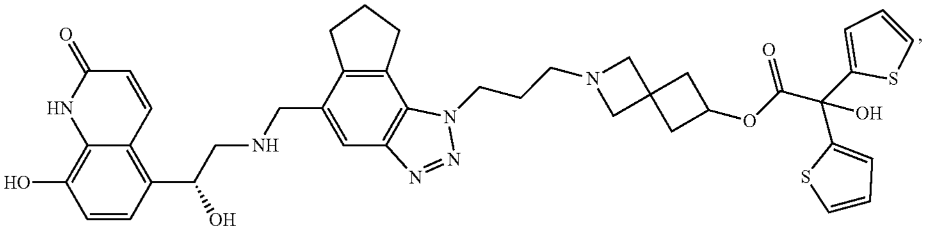
,
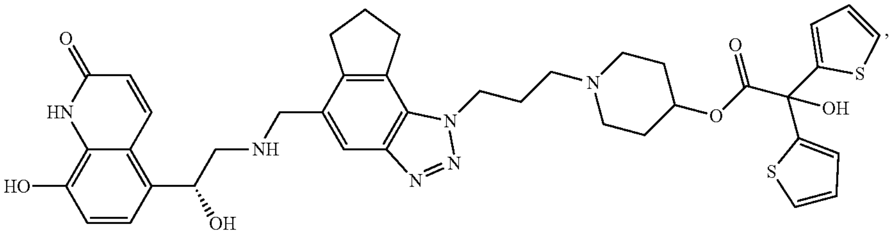
,
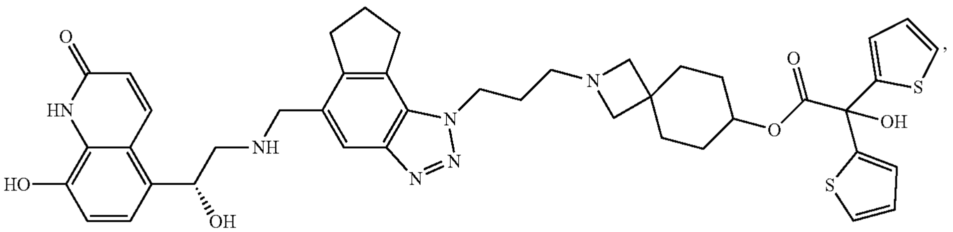
,
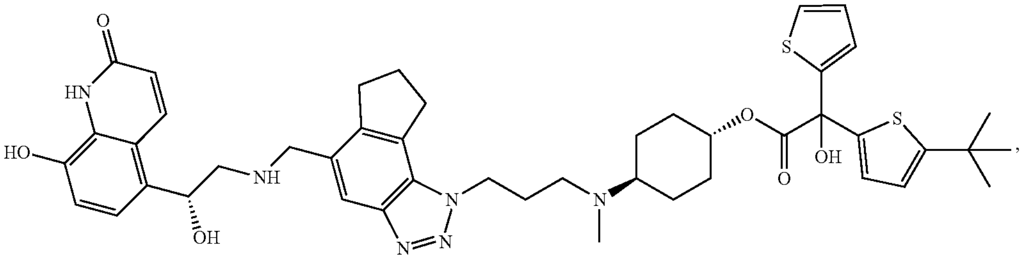
, -continued
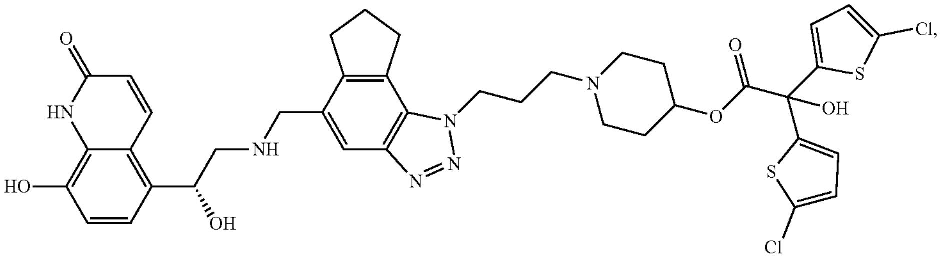
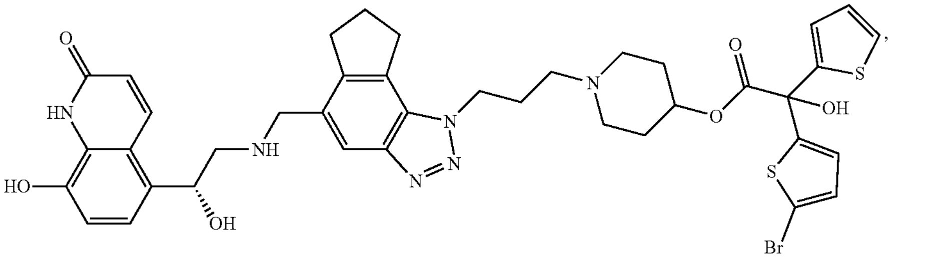
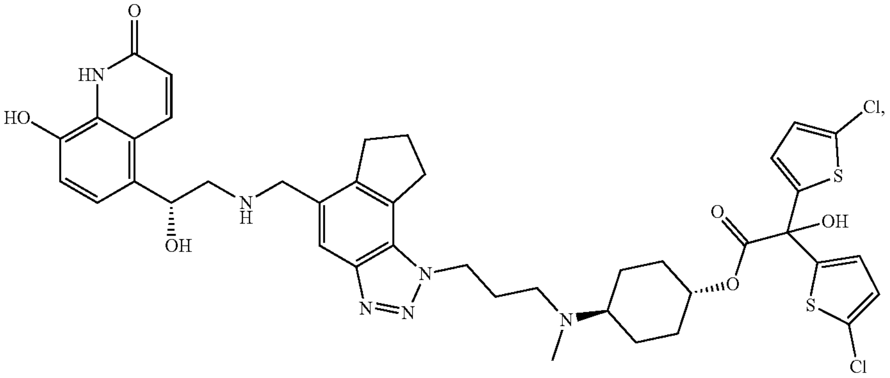
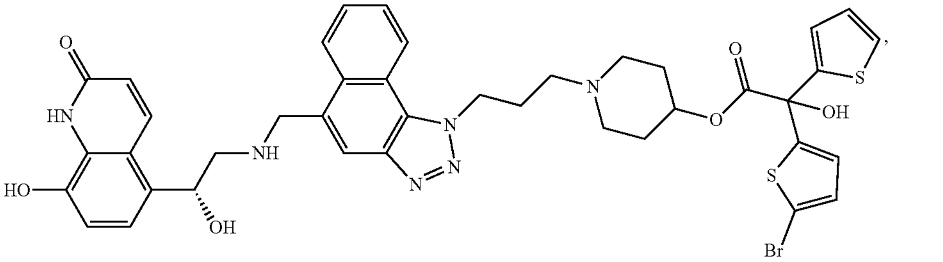
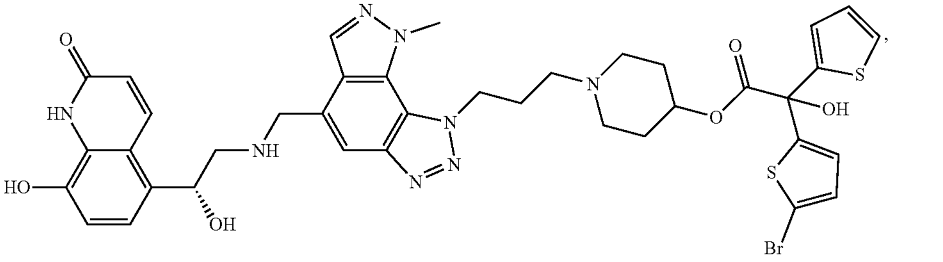
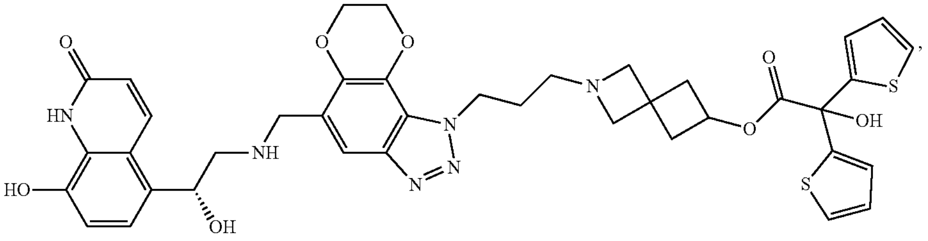

-continued
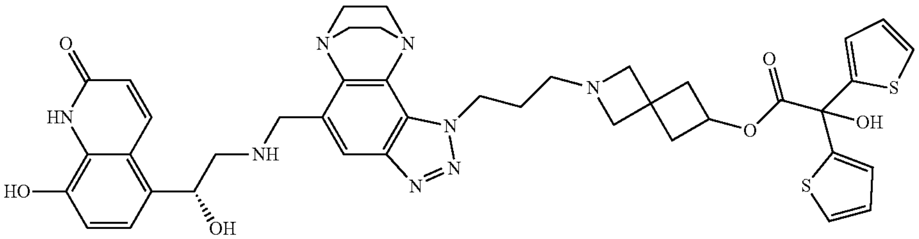
,
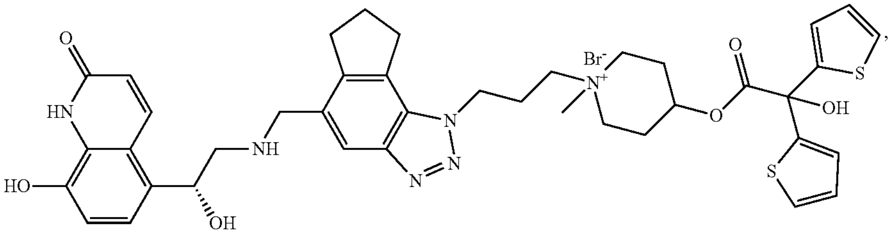
,
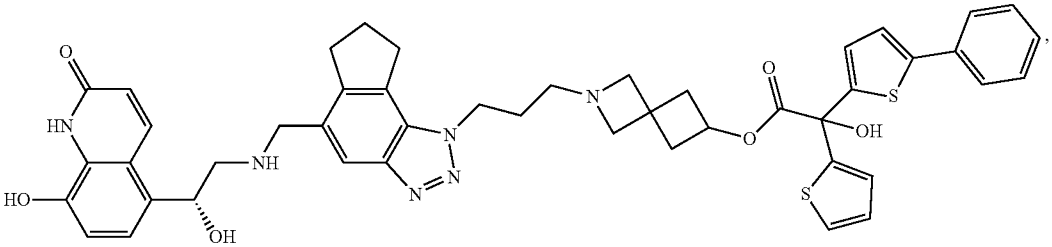
,
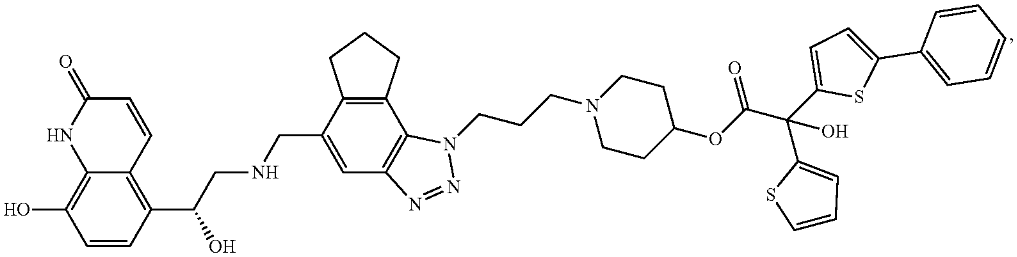
,
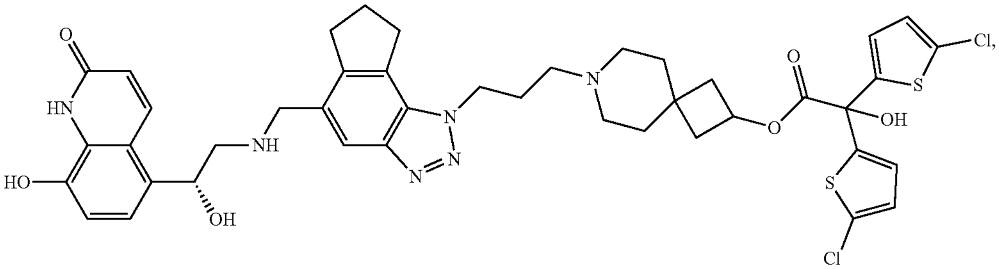
,
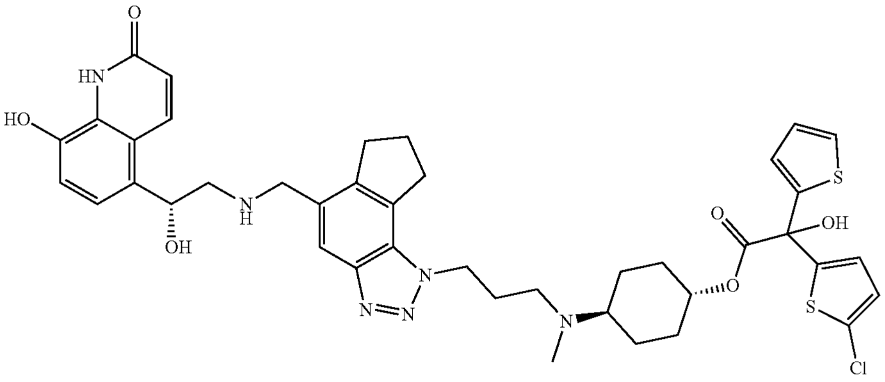
, -continued
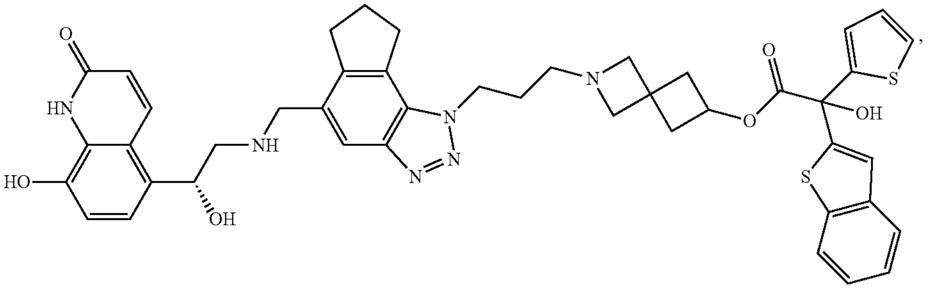
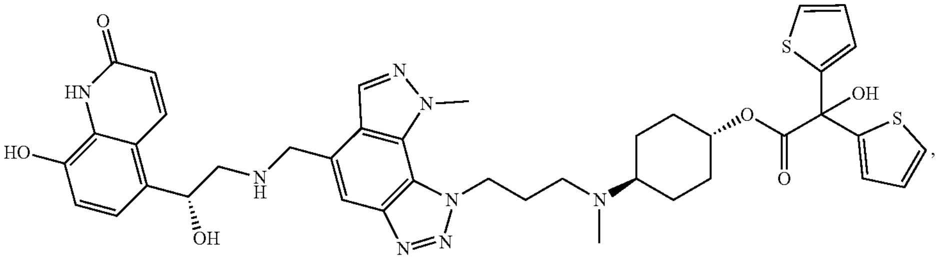
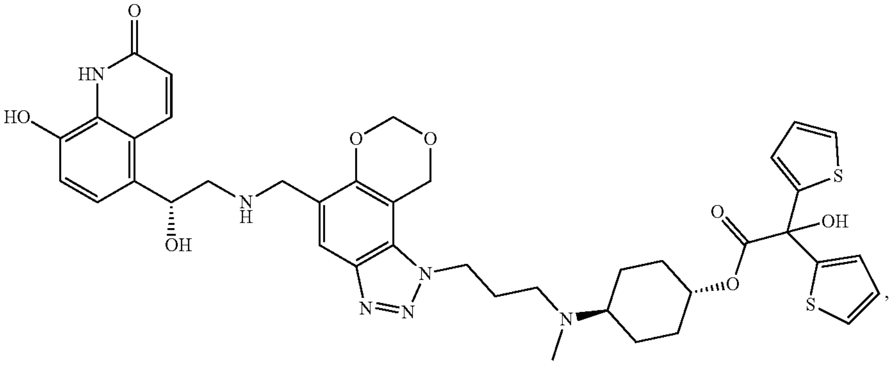
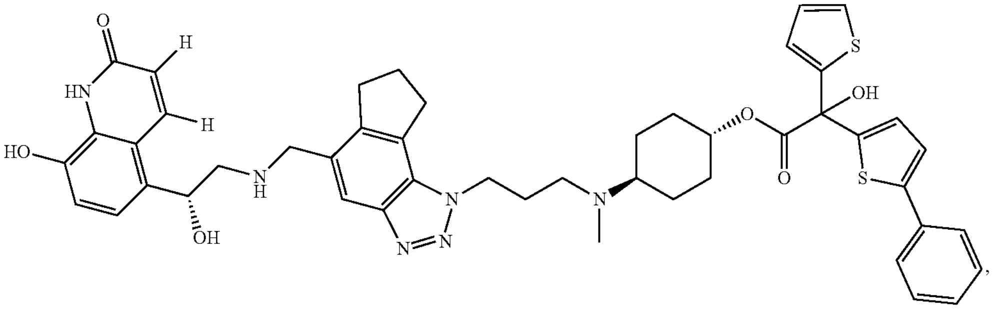
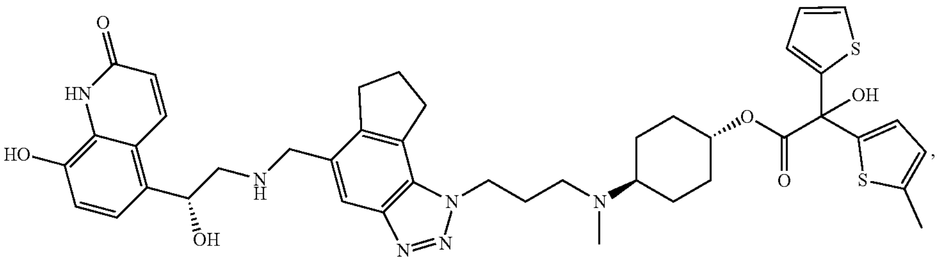

-continued
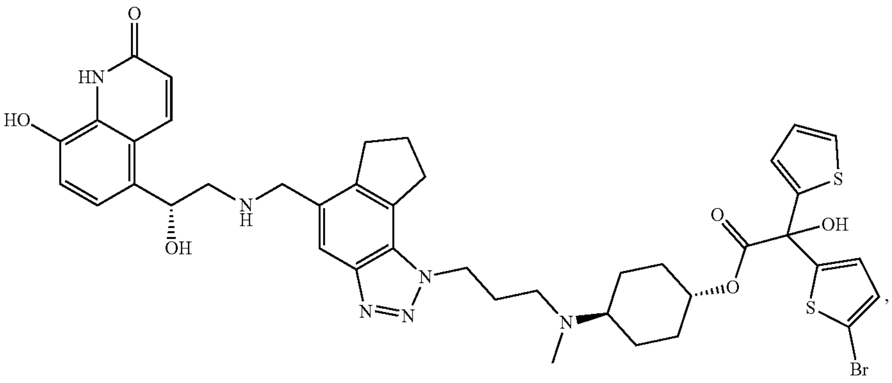
,
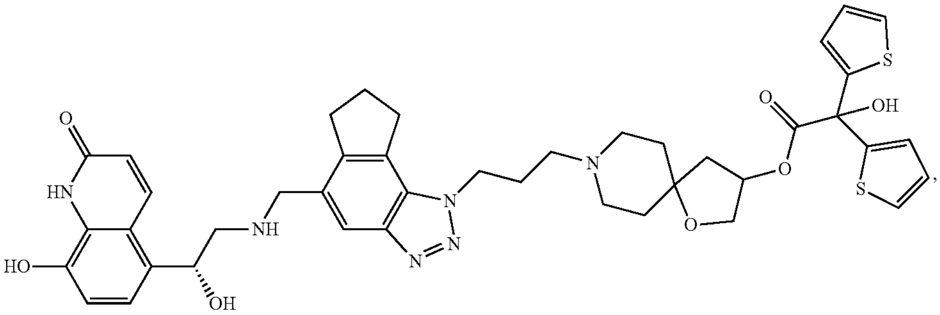
,
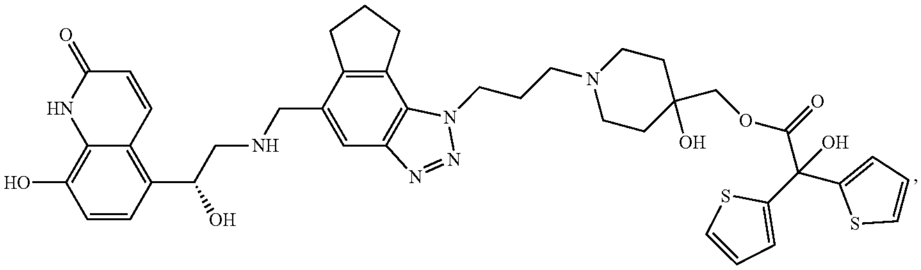
,
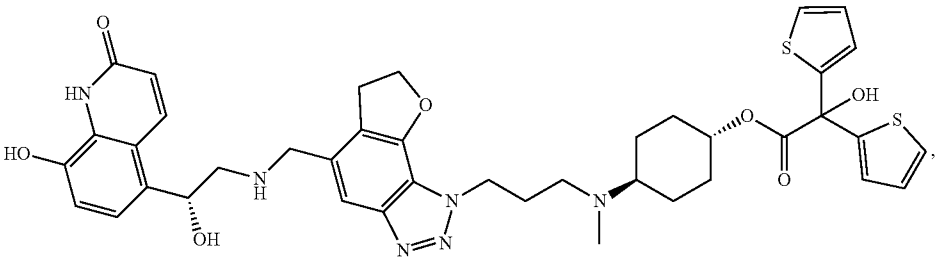
,
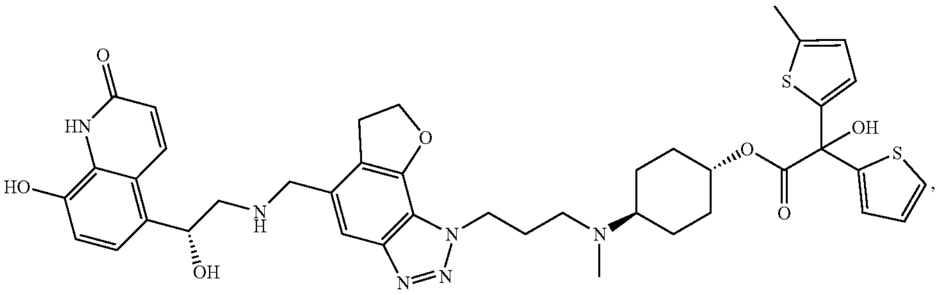
, -continued
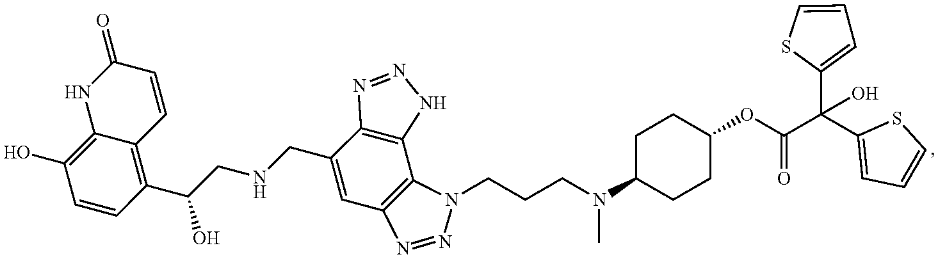
,
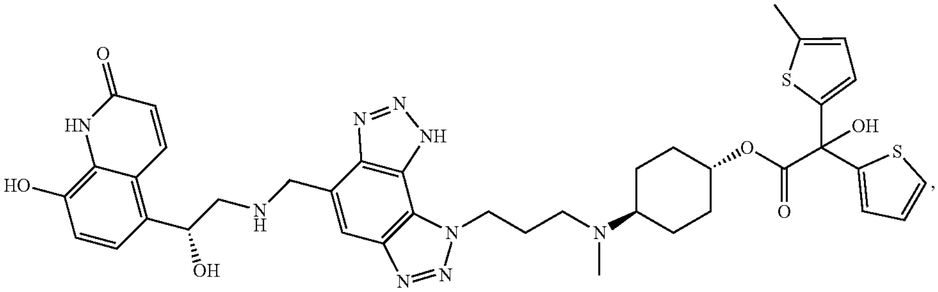
,
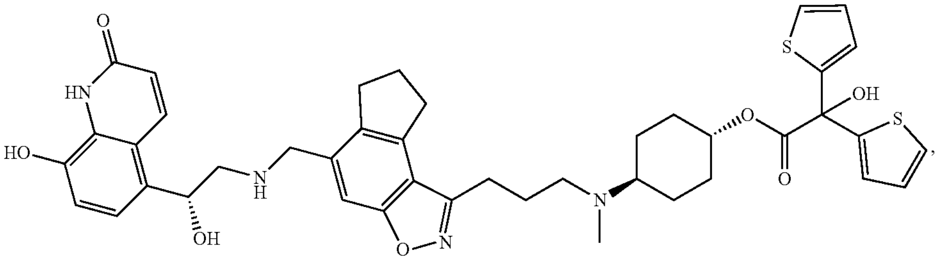
,
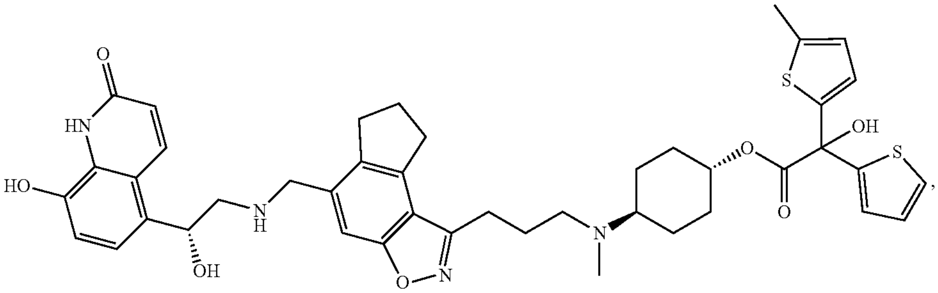
,
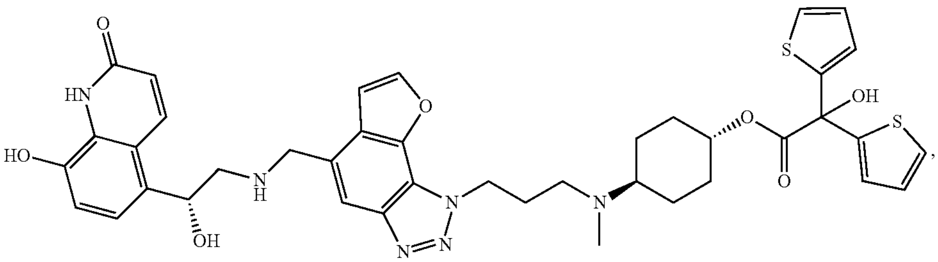
,
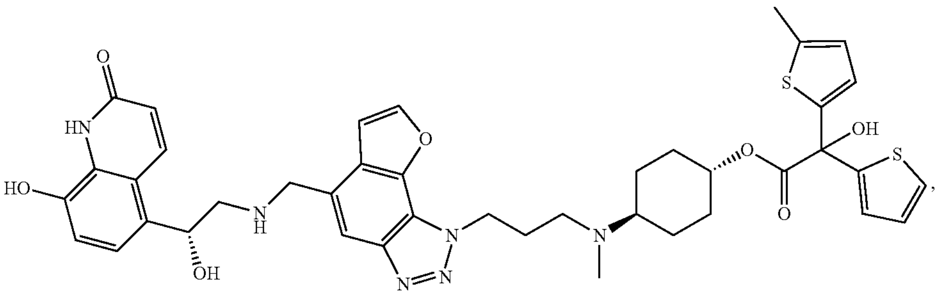
, -continued
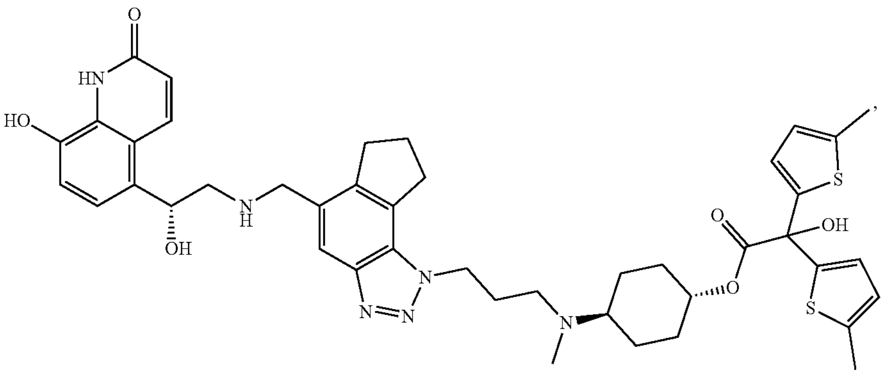
,
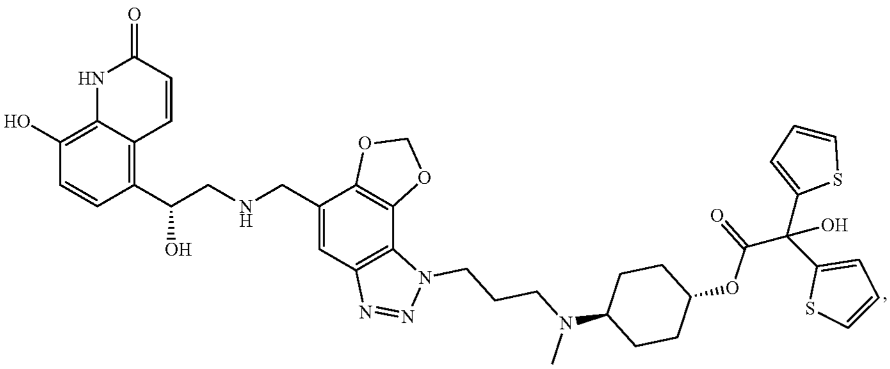
,
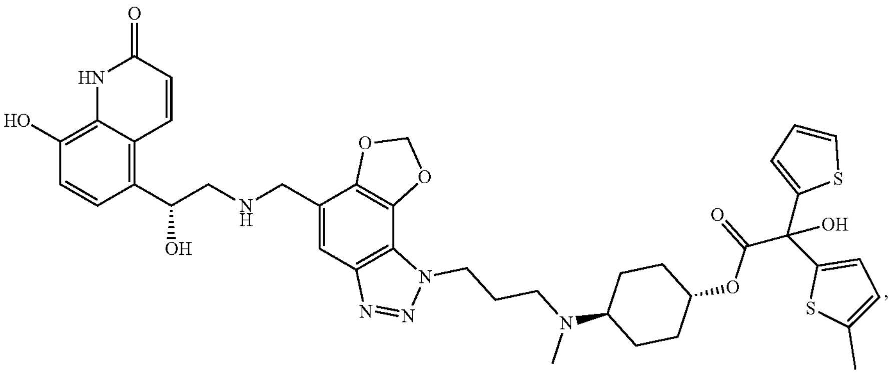
,
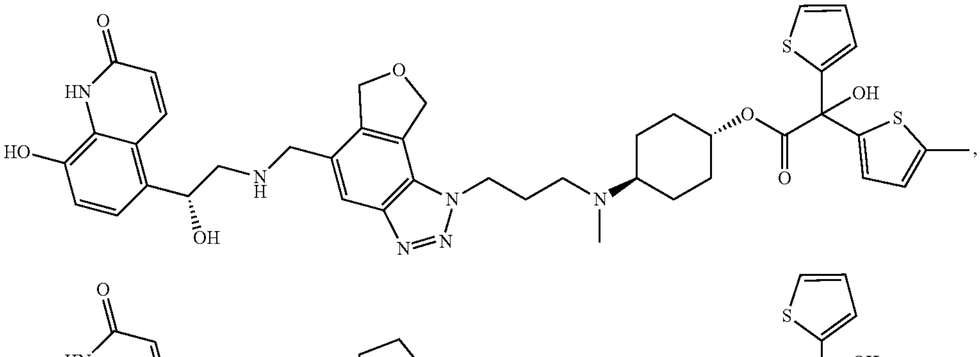
,
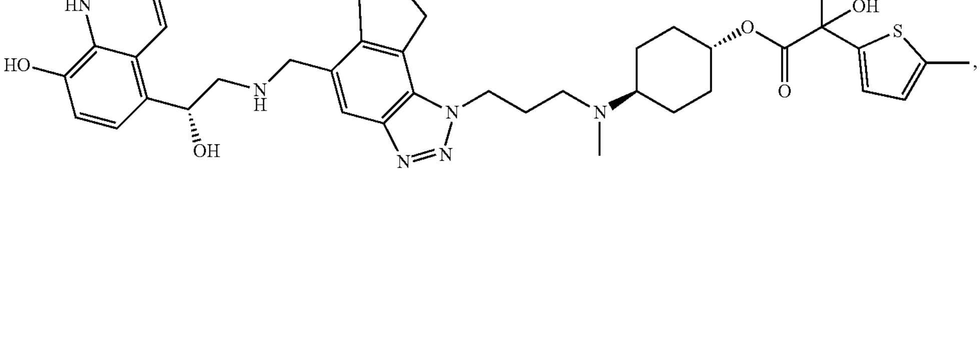
, -continued
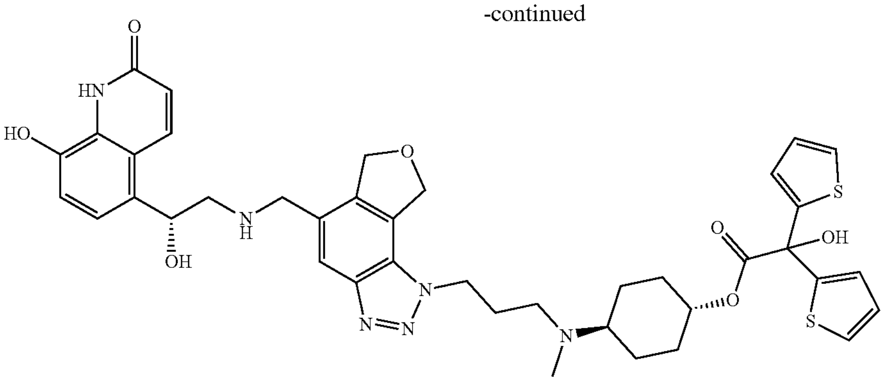
and
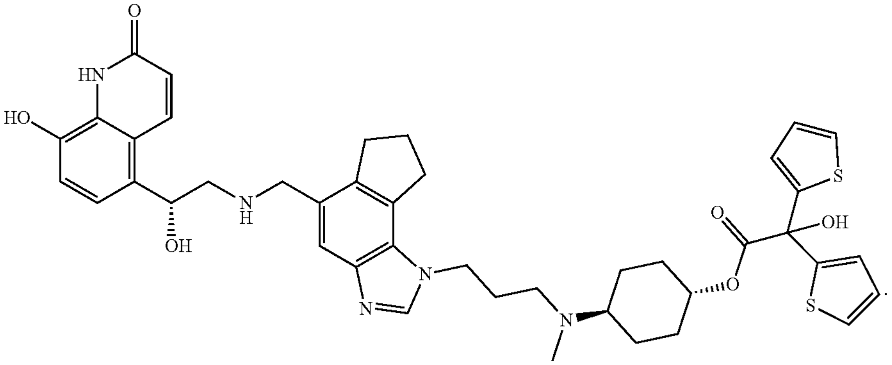
17. The compounds or the pharmaceutically acceptable salts thereof according to claim 16, wherein the compounds are selected from the group consisting of:
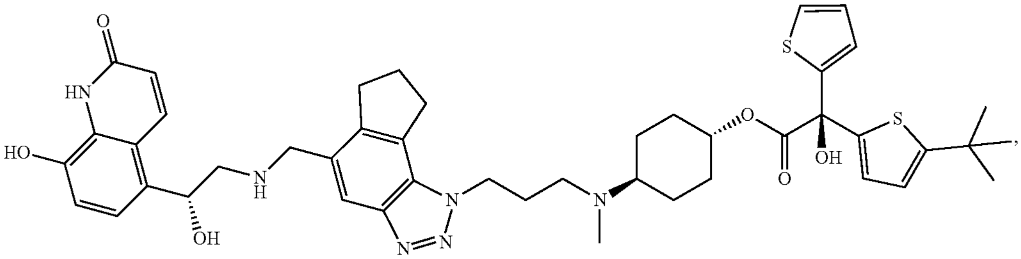
,
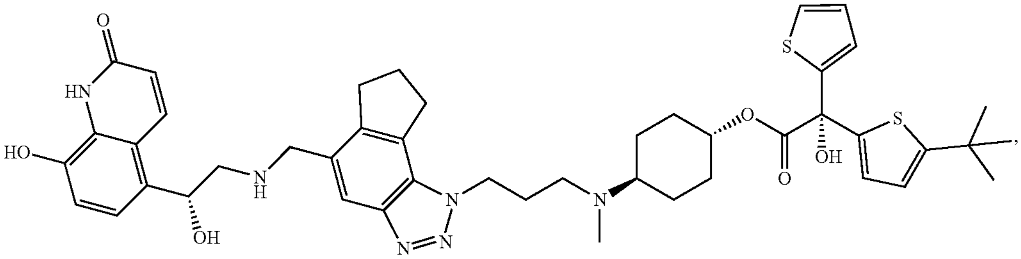
,
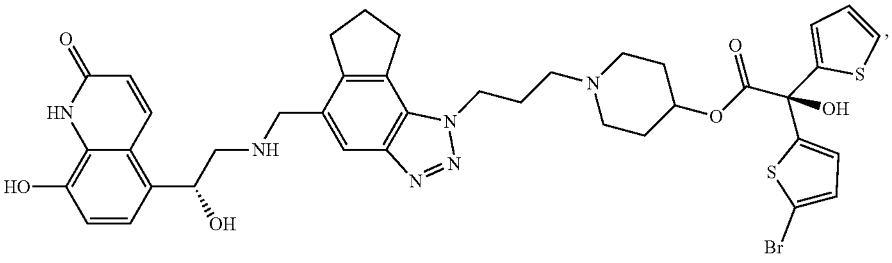
, -continued
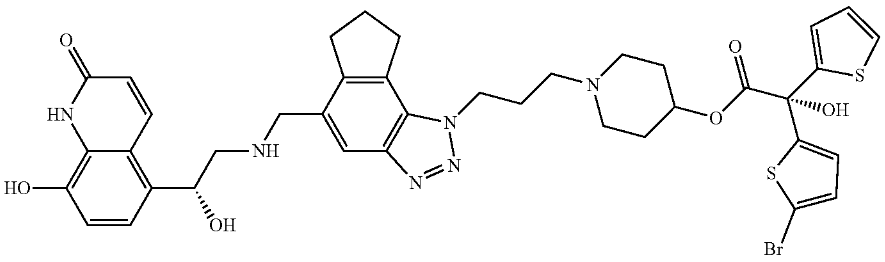
,
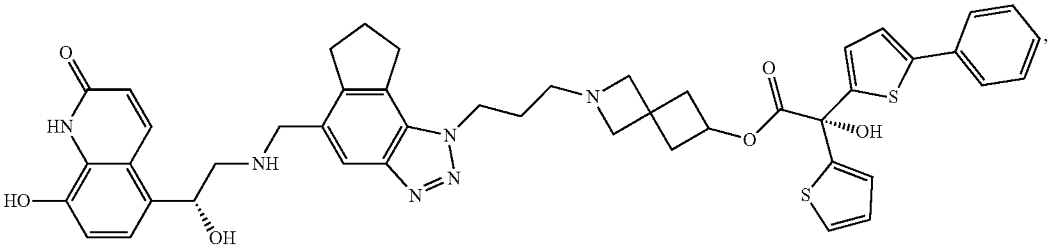
,
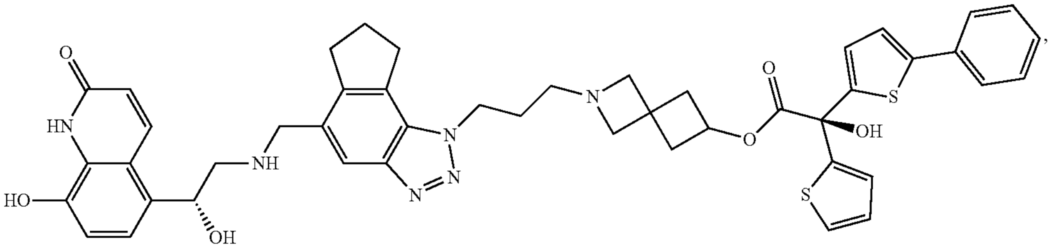
,
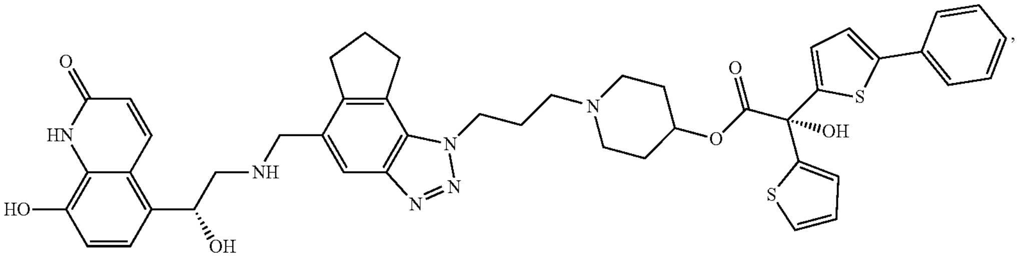
,
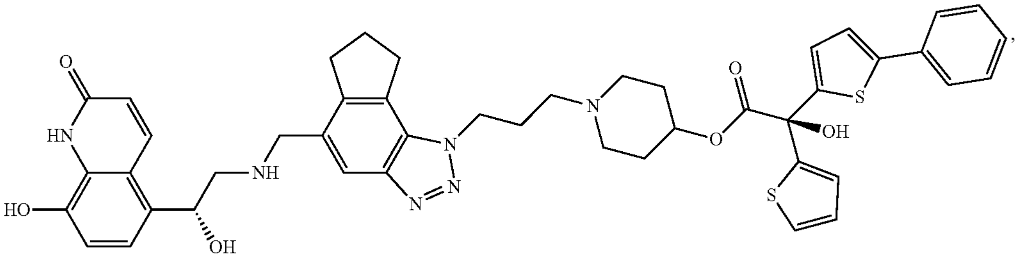
,
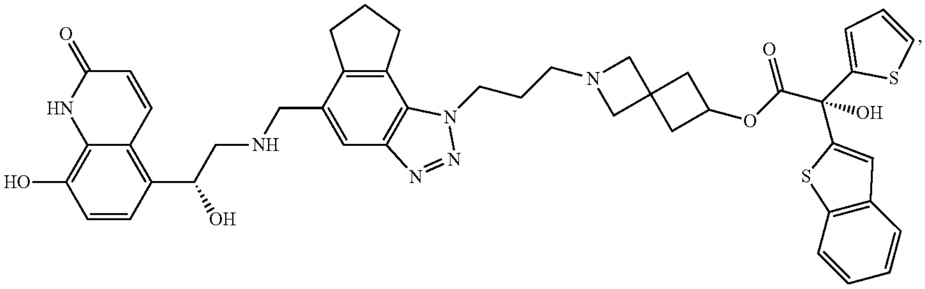
, -continued
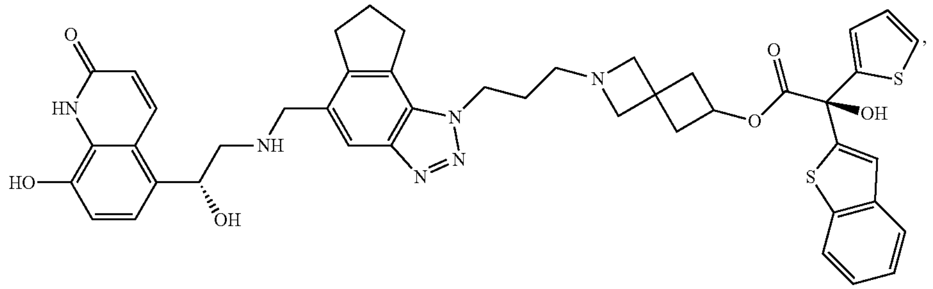
,
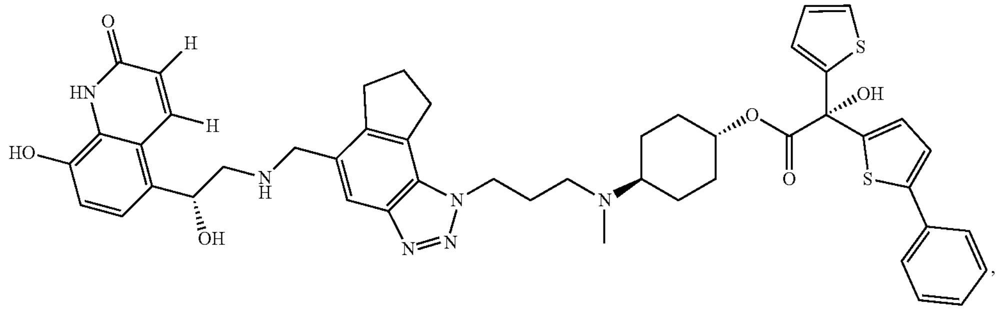
,
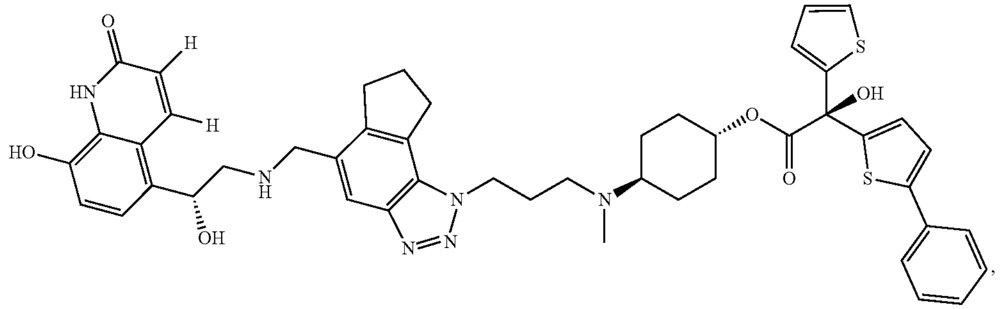
,
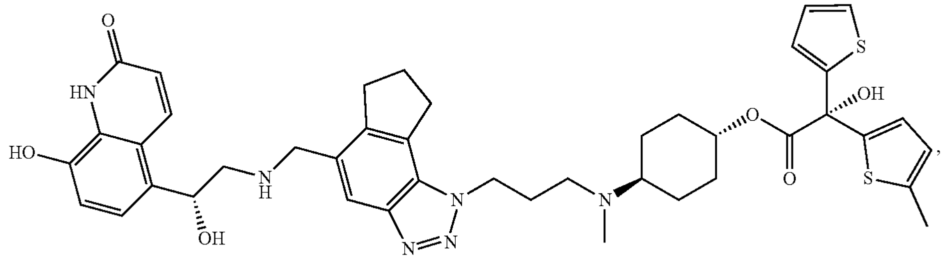
,
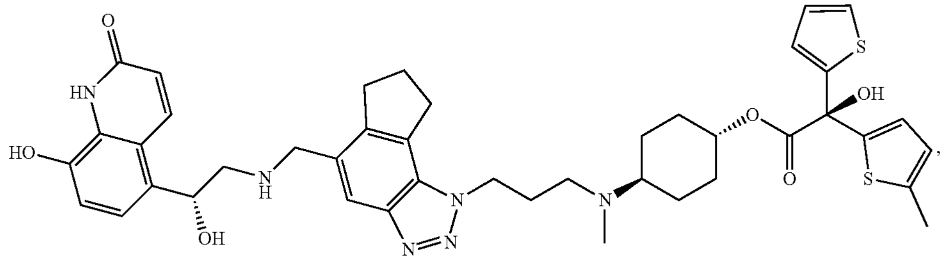
, -continued
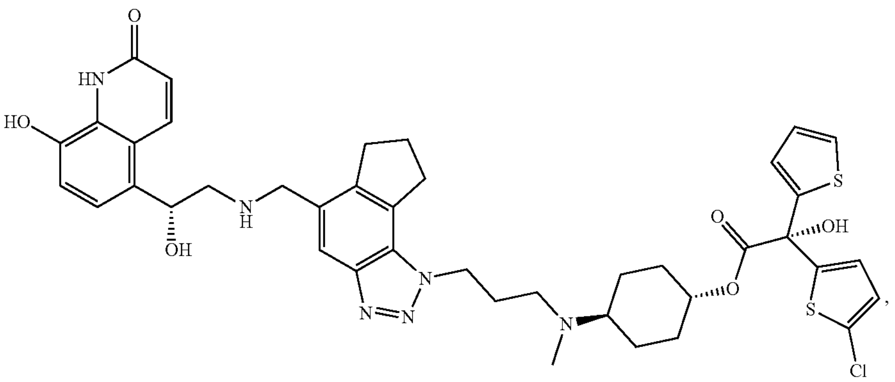
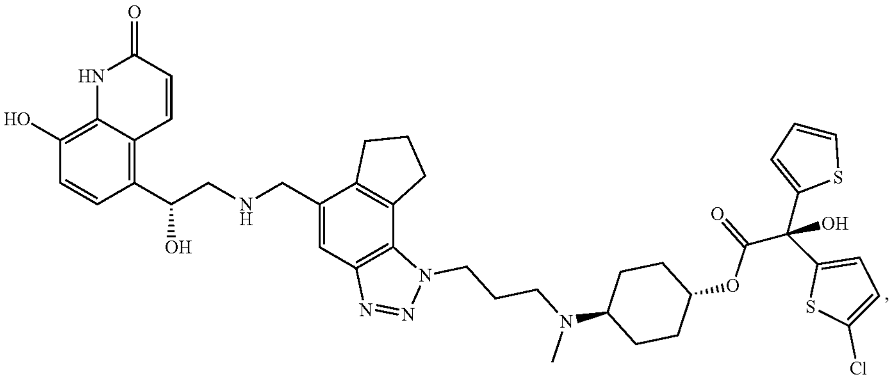
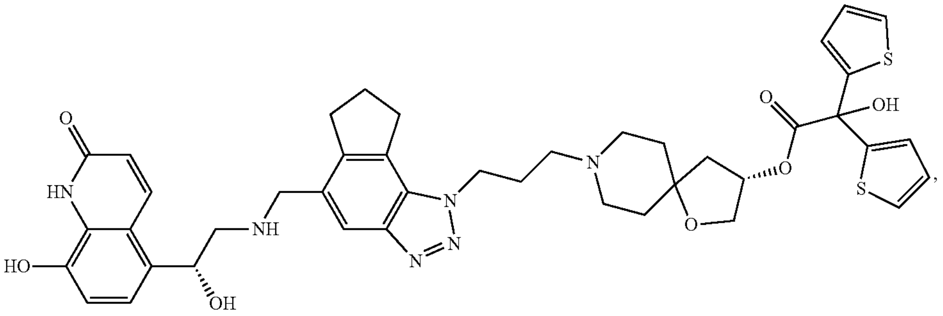
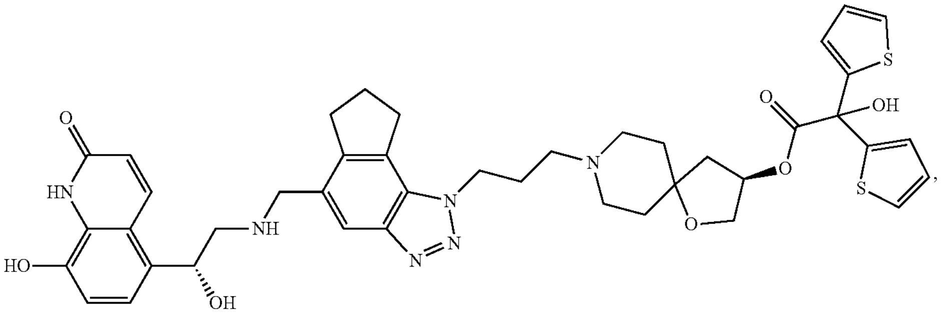

-continued
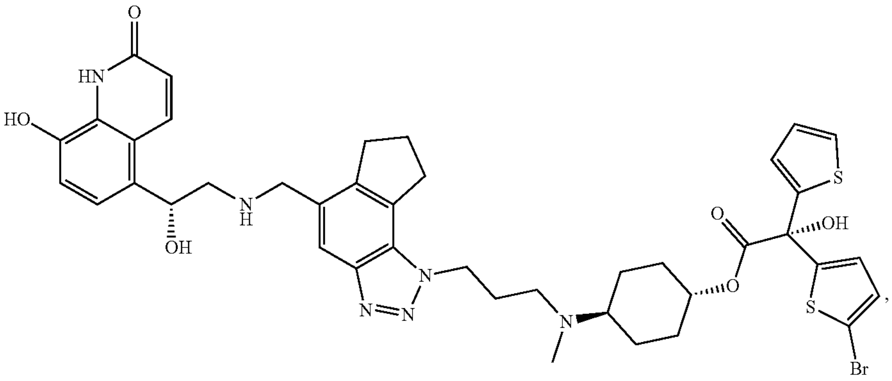
,
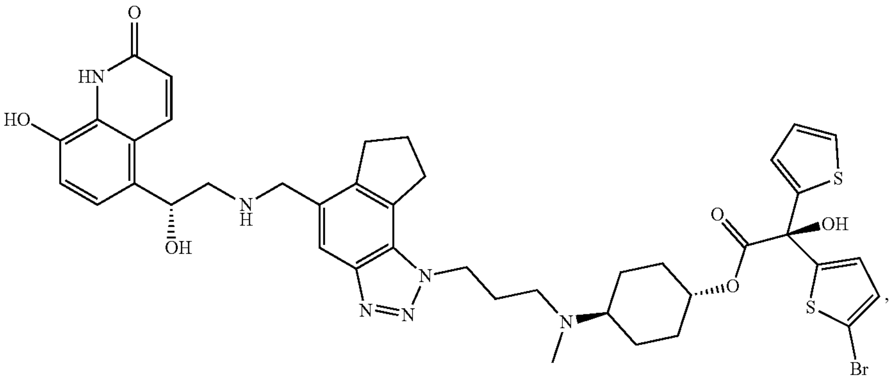
,
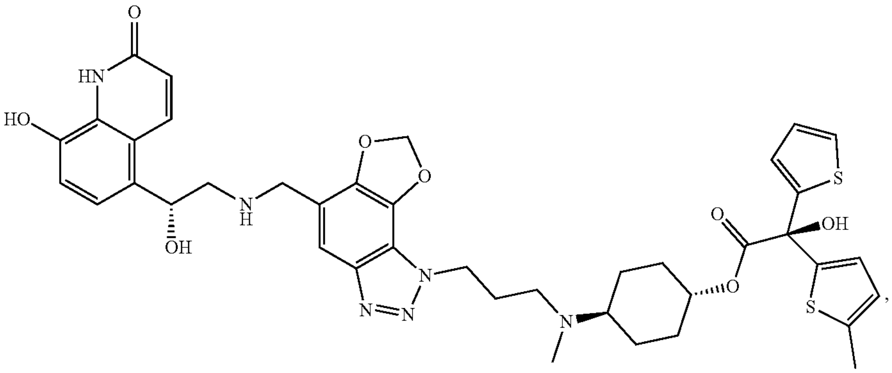
,
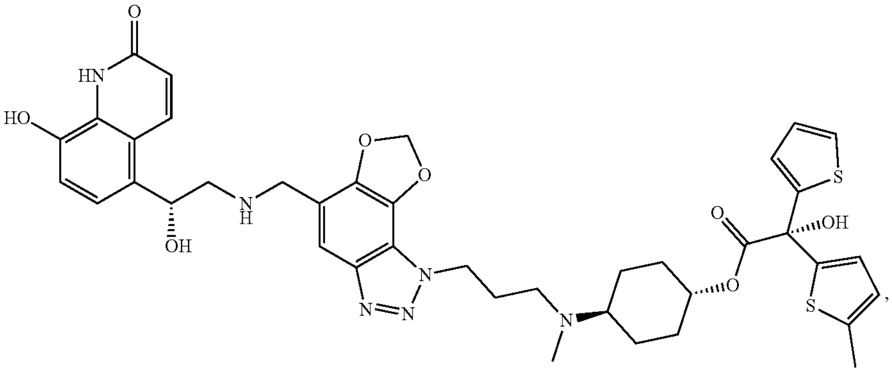
,

-continued

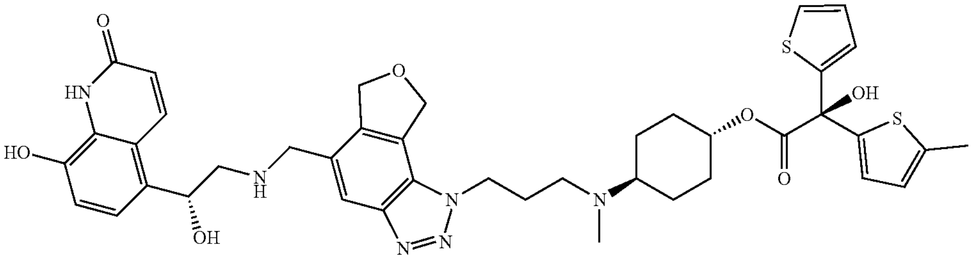

,

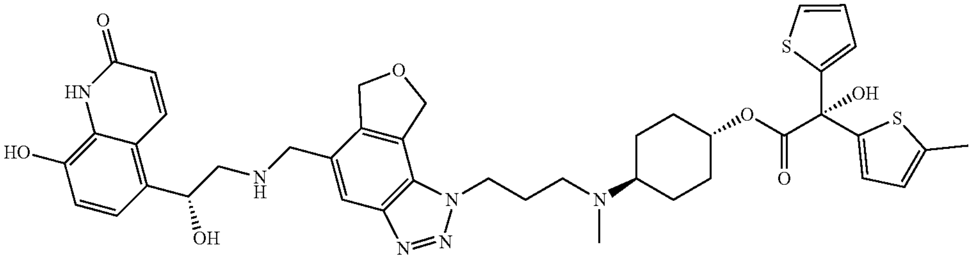

,

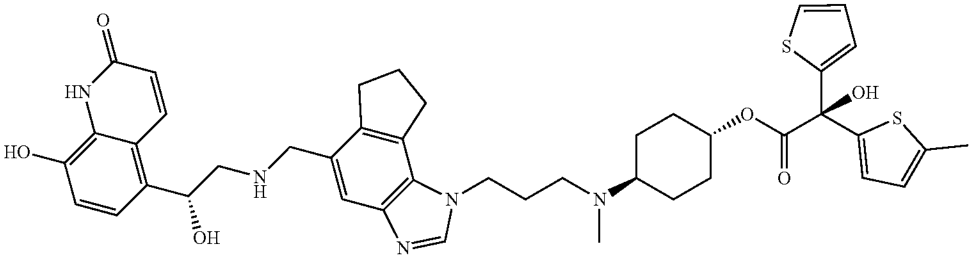

,

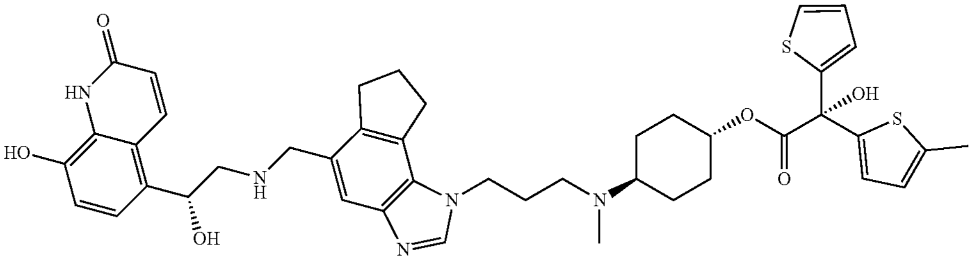

.

18. A pharmaceutical composition comprising the compound or the pharmaceutically acceptable salt thereof according to claim 1; and optionally the pharmaceutical composition comprising a pharmaceutically acceptable excipient.

19. A method for treating chronic obstructive pulmonary disease, comprising administering to a subject in need thereof a therapeutically effective amount of the compound or the pharmaceutically acceptable salt thereof according to claim 1.

20. The method for treating chronic obstructive pulmonary disease according to claim 19, wherein the compound is in the form of the pharmaceutical composition according to claim 18.

* * * * *